US008491869B2

(12) United States Patent
Gangadharmath et al.

(10) Patent No.: US 8,491,869 B2
(45) Date of Patent: Jul. 23, 2013

(54) IMAGING AGENTS FOR DETECTING NEUROLOGICAL DISORDERS

(75) Inventors: Umesh B. Gangadharmath, Los Angeles, CA (US); Hartmuth C. Kolb, Playa Del Rey, CA (US); Peter J. H. Scott, Ypsilanti, MI (US); Joseph C. Walsh, Pacific Palisades, CA (US); Wei Zhang, Los Angeles, CA (US); Anna Katrin Szardenings, Torrance, CA (US); Anjana Sinha, San Diego, CA (US); Gang Chen, Los Angeles, CA (US); Eric Wang, San Diego, CA (US); Vani P. Mocharia, Los Angeles, CA (US); Chul Yu, Los Angeles, CA (US); Changhui Liu, Los Angeles, CA (US); Daniel Kurt Cashion, Manhattan Beach, CA (US); Dhanalakshmi Kasi, Los Angeles, CA (US)

(73) Assignee: Eli Lilly and Company, Indianapolis, IN (US)

( * ) Notice: Subject to any disclaimer, the term of this patent is extended or adjusted under 35 U.S.C. 154(b) by 352 days.

(21) Appl. No.: 12/661,777

(22) Filed: Mar. 23, 2010

(65) Prior Publication Data

US 2010/0239496 A1 Sep. 23, 2010

Related U.S. Application Data

(60) Provisional application No. 61/162,421, filed on Mar. 23, 2009.

(51) Int. Cl.
*A61K 51/00* (2006.01)
*A61M 36/14* (2006.01)

(52) U.S. Cl.
USPC ....... 424/1.89; 424/1.11; 424/1.65; 424/1.81; 424/1.85

(58) Field of Classification Search
USPC .................... 424/1.11, 1.65, 1.81, 1.85, 1.89, 424/9.1, 9.3, 9.4, 9.5, 9.6, 9.7, 9.8; 544/1, 544/3, 63, 180, 224; 546/1, 152, 184, 249; 548/100, 146, 215, 255, 300.1, 400; 549/1, 549/200; 552/1; 568/18, 300
See application file for complete search history.

(56) References Cited

U.S. PATENT DOCUMENTS

| | | | |
|---|---|---|---|
| 5,871,934 | A | 2/1999 | Lee et al. |
| 6,562,319 | B2 | 5/2003 | Mishani et al. |
| 2003/0149250 | A1 | 8/2003 | Kung et al. |
| 2006/0110787 | A1 | 5/2006 | Walker |
| 2007/0060618 | A1 | 3/2007 | Cosford et al. |
| 2007/0258887 | A1 | 11/2007 | Tamagnan et al. |
| 2008/0166299 | A1 | 7/2008 | Kung et al. |

FOREIGN PATENT DOCUMENTS

| | | | |
|---|---|---|---|
| EP | 1655287 | | 5/2006 |
| EP | 1 815 872 | A | 8/2007 |
| EP | 1944281 | | 7/2008 |
| EP | 2218464 | | 8/2010 |
| JP | 9165378 | A | 6/1997 |
| JP | 2001048786 | | 2/2001 |
| JP | 2006100537 | | 4/2006 |
| JP | 2007223952 | A | 9/2007 |
| WO | WO 94/14477 | A | 7/1994 |
| WO | WO 97/14679 | A | 4/1997 |
| WO | 02085903 | A2 | 10/2002 |
| WO | WO 2004/043496 | A | 5/2004 |
| WO | 2004056399 | A2 | 7/2004 |
| WO | WO 2004087139 | A1 | 10/2004 |
| WO | WO 2006116736 | A2 | 11/2006 |
| WO | WO 2007/014467 | | 2/2007 |
| WO | WO 2007/057705 | A | 5/2007 |
| WO | WO 2007063946 | A1 | 6/2007 |
| WO | WO 2007/094718 | A | 8/2007 |
| WO | WO 2008027162 | A2 | 3/2008 |
| WO | 2008073350 | A2 | 6/2008 |
| WO | WO 2008/083454 | A | 7/2008 |
| WO | 2008124812 | A1 | 10/2008 |
| WO | WO 2008/131148 | A | 10/2008 |
| WO | WO 2008/132454 | A | 11/2008 |
| WO | 2009004914 | A1 | 1/2009 |
| WO | 2009045535 | A2 | 4/2009 |
| WO | 2009055401 | | 4/2009 |
| WO | 2010011964 | | 1/2010 |
| WO | 20010073719 | | 7/2010 |

OTHER PUBLICATIONS

Tseng et al, J. Heterocyclic Chem., 1987, vol. 24, pp. 837-843.*
Qu, et al., Radioiodinated Aza-Diphenylacetylenes As Potential SPECT Imaging Agents for Beta-Amyloid Plaque Detection, Published in Bioorganic & Medicinal Chemistry Letters, vol. 17, No. 13, 1 Jul. 2007 (pp. 3581-3584). Science Direct, Elsevier.
Invitation to Pay Additional Fees in PCT/US2010/028360.
Aoyama, et al., "Polynnethylated .gamma.-carbolines with potent anti-bovine viral diarrhea virus (BVDV) activity", Heterocycles (2009), 77(2), 779-785.
Sako, et al., "Gamma-carboline derivatives with anti-bovine viral diarrhea virus (BVDV) activity", Bioorg Med Chem 2008 Apr. 1, 16(7), 3780-3790.
Chen, et al., "Microwave-enhanced Fischer reaction: an efficient one-pot synthesis of y-carbolines", Synlett (2008), (1), 77-82.

(Continued)

*Primary Examiner* — D L Jones
(74) *Attorney, Agent, or Firm* — Manisha A. Desai

(57) ABSTRACT

Imaging agents of formula (I) and methods for detecting neurological disorders comprising administering ti a patient in need compounds of formula (I) capable of binding to tau proteins and β-amyloid peptides are presented herein. The invention also relates to methods of imaging Aβ and tau aggregates comprising introducing a detectable quantity of pharmaceutical formulation comprising a radiolabeled compound of formula (I) and detecting the labeled compound associated with amyloid deposits and/or tau proteins in a patient. These methods and compositions enable preclinical diagnosis and monitoring progression of AD and other neurological disorders.

20 Claims, 30 Drawing Sheets
(27 of 30 Drawing Sheet(s) Filed in Color)

OTHER PUBLICATIONS

Engler, et al., "Lewis Acid-Directed Cyclocondensation of Piperidone Enol Ethers with 2-Methoxy-4-(Nphenylsulfonyl)-1,4-benzoquinoneimine: A New Regioselective Synthesis of Oxygenated Carbolines", Journal of Organic Chemistry (2000), 65(8), 2444-2457.

Mehta, et al., "The elimination of an alkoxy group in the photo-Graebe—Ullmann conversion of 1-(2,5-dialkoxyphenyl) triazolopyridines into carbolines, and the preparation of $\alpha$-, $\gamma$- and $\delta$-carboline quinones", J. Chem. Soc., Perkin Trans. 1, 1993, 1261-1267.

Patrick, et al., "Some carbazole and carboline quinones and an unexpected demethoxylation reaction", Journal of Chemical Research, Synopses (1990), (1), 1.

Molina, et al., "Novel DNA Intercalators Based on the Pyridazino [1',6':1,2] pyrido [4,3-b] indol-5-inium System", J. Org. Chem, 1999, 64, 3907-3915.

Molina, et al., "Synthesis and DNA Binding Properties of y-Carbolinium Derivatives and Benzologues", J. Org. Chem, 1996, 61, 5587-5599.

PCT/US2010/028360 Search Report issued Nov. 22, 2010.

Kruglenko, et al.; "Condensed Imidazo-1,2,4-azines. 31. Synthesis and Chemical Transformations of Substituted 1,2,4-Triazepino[2,3-a]benzimidaloses"; Chemistry of Heterocyclic Compounds, vol. 38, No. 5, 2002- pp. 598-606.

Tseng, et al., "A Simple Regioselective Synthesis of Pyrimido[1,2-a]benzimidazoles"; vol. 24, May 1, 1987; Jun. 1, 1987, pp. 837-843.

Yousefi, et al., "Synthesis and Evaluation of 11C-Labeled Imidazo [2,1-b] benzothiazoles (IBTs) as PET Tracers for Imaging $\beta$-Amyloid Plaques in Alzheimer's Disease", J. Med. Chem., Article ASAP, DOI: 10.1021/jm101129a Publication Date (Web): Jan. 28, 2011.

Nobuyuki Okamura, et al., Quinoline and Benzimidazole Derivatives: Candidate Probes for in Vivo Imaging of Tau Pathology in Alzheimer's Disease, Journal of Neuroscience, Nov. 23, 2005, 25(47); pp. 10857-10862.

Rex Boyd, "New reactor needed for medical imaging—why cyclotrons cannot do the job", Radiotopes in Medicine; Article from May 1999 edition Australasian Science Magazine; Jun. 1999, pp. 10-11.

Hank F. Kung, et al., "F Stilbenes and Styrylpyridines for PET Imaging of A$\beta$Plaques in Alzheimer's Disease: A Miniperspective", J. Med. Chem., 2010, vol. 53, pp. 933-941.

M.N. Sabbagh, "Drug Development for Alzheimer's Disease: Where are we now and where are we headed?", American Journal of Geriatric Phamacotherapy, vol. 7, No. 3, Jun. 2009, pp. 167-185.

Dr. Richard A. Houghten and Michael Lebl, "Peptides: The Wave of the Future", 2nd International Peptide Symposium in conjunction with the 17th American Peptide Symposium, Jun. 9-14, 2001, San Diego, California.

Nordberg, A., "PET imaging of amyloid in Alzheimer's disease", Lancet Neurology, Lancet Publ. Group, London, GB, vol. 3, No. 9, Sep. 1, 2004, pp. 519-527.

Brizel, et al., "Tumor oxygenation predicts the likelihood of distant metastases in human soft tissue sarcoma", Cancer Res. (1996) 56:941-943.

Kolb, et al., "Click Chemistry: Diverse Chemical Function from a Few Good Reactions", Angewandte Chemie, International Edition (2001), 40:2004-2021.

Kolb, et al., "The growing impact of click chemistry on drug discovery", Drug Discovery Today (2003), 8:1128-1137.

Mocharla, et al., "In Situ Click Chemistry: Enzyme-Generated Inhibitors of Carbonic Anhydrase II", Agnew Andte Chemie. Intl. Edition, VCH Verlag, Weinheim, DE, vol. 44, No. 1, Dec. 17, 2004, pp. 116-120.

Tornoe, et al., "Peptidotriazoles on Solid Phase: [1,2,3]-Triazoles by Regiospecific Copper(I)-Catalyzed 1,3-Dipolar Cycloadditions of Terminal Alkynes to Azides", Journal of Organic Chemistry (2002), 67:3057-3064.

Wang, et al., "Bioconjugation by Copper(I)-Catalyzed Azide-Alkyne [3+2] Cycloaddition", Journal of the American Cancer Society (2003), 125:3192-3193.

Wang, et al., "Positron Emission Tomography: Application in Drug Discovery and Drug Development", Curr. Top. Med. Chem. (2005), 5:1053-1075.

Bergstrom, Mats et al.: "Synthesis of some 11C-labeled MAO-A inhibitors and their in vivo uptake kinetics in rhesus monkey brain", Nuclear Medicine and Biology, 24(5), 381-388 Coden: Nimbieo; ISSN: 0883-2897, 1997.

Sintas, Jose A. et al.: "Iodination, radioiodination and spectroscopic identification of beta.-carboline derivatives", Journal of Labelled Compounds & Radiopharmaceuticals, 42(5), 409-413 Coden: JLCRD4; ISSN: 0362-4803, 1999.

Karimi, Farhad et al.: "Synthesis of 11c-labelled amides by palladium-mediated carboxamination using [11C]carbon.monoxide, in situ activated amines and 1,2,2,6,6-pentamethylpiperidine", European Journal of Organic Chemistry, (11), 2132-2137 Coden: Ejocfk; ISSN: 1434-193X, 2003.

Baranowska-Kortylewicz J et al.: "Radioiodination of 7-Methoxy-and6,7-Dimethoxy-4-.Bromomethylcoumarins", Journal of Labelled Compounds and Radiopharmaceuticals, John Wiley, Chichester, DB, vol. 29, No. 12, Jan. 1, 1991, pp. 1301-1307, ISSN: 0362-4803.

Heike Radeke et al.: "Synthesis and biological evaluation of the mitochondrial complex 1 inhibitor 2-[4-(4-fluorobutyl). benzylsulfanyl]-3-meth ylchromene-4-one as a potential cardiac positron emission tomography tracer", J. Med. Chem., vol. 50, 2007, pp. 4304-4315.

Maria Graciela Barolli et al.: "Synthesis of [1311]-iodinated quercetin", J. Label. Compds. Radiopharm., vol. 32, No. 11, 1997, pp. 297-933.

Hollie I. Swanson et al.: "Use of [1251]4'-iodoflavone as a tool to characterize ligand-dependent differences in Ah receptor behavior", J. Biochem. Molecular Toxicology, vol. 16, No. 6, 2002, pp. 298-310.

Takahashi K et al.: "Imaging of aromatase distribution in rat and rhesus monkey brains with [<11>C]vorozole".Nuclear Medicine and Biology, Elsevier, NY, US, vol. 33, No. 5, Jul. 1, 2006, pp. 599-605, XP025103506 ISSN: 0969-8051.

Wenchao Qu et al.: "Quick Assembly of 2,24-diphenyltriazoles as probes targeting beta-amyloid aggregates in alzheimer's disease", J. Med. Chem., vol. 50, 2007, pp. 3380-3387.

Glaser M et al.: "Click Labeling with 2-[18F]Fluoroethylazide for Positron Emission Tomography" Bioconjugate Chemistry, ACS, Washington, DC, US, vol. 18, Apr. 13, 2007, pp. 989-993, ISSN: 1043-1802.

Sirion et al.: "An efficient F-18 labeling method for PET study: Huisgen 1,3-dipolar cycloaddition of bioactive.substances and F-18-labeled compounds" Tetrahenron Letters, Elsevier, Amsterdam, vol. 48, No. 23, 2007-06-04, pp. 3953-3957, ISSN: 0040-4039.

Mathias C. J. et al.: "Radiolebeled hypoxic cell sensitizers: Tracers for assessment of ischemia" Life Sciences, Pergamon Press, Oxford, GB, vol. 41, No. 2, 13 Jul. 1987, pp. 199-206, ISSN: 0024-3205.

Jerabek P.A. et al.: "Synthesis and biodistrubtion of <18>F-labeled fluoronitroimidazoles: Potential in vivo markers of hypoxic tissue", Applied Radiation and Isotopes, International Journal of Radiation Applications and Instrumentation, Part A, Pergamon Press, Ltd., GB, vol. 37, No. 7, Jan. 1, 1986, pp. 599-605, ISSN: 0883-2889.

Visser G.W. M. et al.: "THe preparation and stability of <211>At-astato-imidazoles" International Journal of Applied Radiation and Isotops, Pergamon Press, New York, Ny, US, vol. 31, No. 5, May 1, 1980, pp. 275-278, ISSN: 0020-708X.

Miriko Tanaka et al.: "radiosynthesis and evaluation of 11C-labeled diaryl-substituted imidazole and indole derivatives for mapping cyclooxygenase-2" Biological & Pharmaceutical Bulletin (Of Japan)., vol. 29, No. 10, 2006, pp. 2087-2094, Pharmaceutical Society of Japan, Tokyo.

Gareth Getvoldsen et al.: Microwave-assisted cyclocondensation of 1,2-diaminobenzene with [4-18F]fluorobenzoic acid: microwave synthesis of 2-([4-18F]fluorophenyl) benzimidazole, Journal of Labelled Compounds and Radiopharmaceuticals, research article, J. Label Compd Radiopharm 2004; 47: 139-145.

Piotr Garnuszek et al.: "Synthesis and characterisation of platinum(II) complexes with histamine and iodohistamine", Inorganica Chimica Acta, vol. 338 (2002) 119-126.

Fumihiko Yamamoto et al.: “Synthesis and Evaluation of 4-Bromo-1-(3[8F]fluoropropy1)-2-nitroimidazole with a Low Entergy LUMO Orbital Designed as Brain Hypoxia-Targeting Imaging Agent”, Biol. Pharm. Bull. 25(5) 616-621 (2002), vol. 25, No. 5.

Fumihiko Yamamoto et al.: “Synthesis and Characterization of Lipohilic 1-[18F]Fluoralky1-21nitroimidazoles for Imaging Hypoxia”, Biol. Pharm. Bull. 22(6) 590-597 (1999), vol. 22, No. 6.

Blom, Elisabeth et al.: “Synthesis and in vitro evaluation of 18F-. beta.-carboline alkaloids as PET ligands” Journal of Labelled Compounds and Radiophaarmaceuticlas, 51(6), 277-282 Coden: JLCRD4, May 2008.

Dumont F. et al.: “Synthesis and in Vivo Evaluation of 7-chloro-5-[<123>I]iodo-4-oxo-1,4 dihydroquinoline-2- carboxylic Acid” Applied Radiation and Isotopes, Elsevier, Oxford, GB, vol. 48, No. 9, Sep. 1, 1997, pp. 1173-1177.

Livni E. et al.: “Synthesis and biodistribution of <18>F-labeled Fleroxacin” Nuclear Medicine and Biology, Elsevier, Ny, US, vol. 20, No. 1, Jan. 1, 1993, pp. 81-87.

Zijlstra Set al.: “Synthesis and evaluation of fluorine-18 labelled compounds for imaging of bacterial infections with pet” Applied Radiation and Isotopes, Elsevier, Oxford, GB, vol. 64, No. 7, Jul. 1, 2006, pp. 802-807.

Choi, Osaku Wataru et al.: “Preparation of F-18 labeling benzyl N-containing heterocyclyl compounds as PET diagnostic remedies”, Chemical Abstracts Service, Columbus, Ohio, US: Database accession No. 127:65770 abstract & JP 09 165378 A, Jun. 24, 1997.

Zheng, et al., “Biological Characters of [18F]0-FEt-PIB In A Rat Model of Alzheimer’s Disease Using Micro-PET Imaging”, Published in Acta Pharmacologica Sinica, vol. 29, No. 5, May 1, 2008 (pp. 548-554).

Wang, et al., “PET Imaging and Optical Imaging With D-Luciferin [<11>C]methyl Ester and D-Luciferin [11C]methyl Ether Of Luciferase Gene Expression in Tumor Xenografts Of Living Mice”, Published in Bioorganic & Medicinal Chemistry Letters, vol. 16, No. 2, Jan. 15, 2006 (pp. 331-337).

Solbach, et al., “Efficient Radiosynthesis of Carbon-11 Labelled Uncharged Thioflavin T Derivatives Using [110] methyl Triflate for Beta-Amyloid Imaging in Alzheimer’s Disease With PET”, Published in Applied Radiation and Isotopes, vol. 62, No. 4, Apr. 1, 2005 (pp. 591-595).

Mathis, et al., “Synthesis and Evaluation of 11C-Labeled 6-Substituted 2-Arylbenzothiazoles As Amyloid Imaging Agents”, Published in Journal of Medicinal Chemistry, American Chemical Society, vol. 46, Jun. 19, 2003 (pp. 2740-2754).

Serdons, et al., “Synthesis and Evaluation of 18F-Labeled 2-Phenylbenzothiazoles As Positron Emission Tomography Imaging Agents for Amyloid Plaques in Alzheimer’s Disease”, Published in Journal of Medicinal Chemistry, American Cancer Society, vol. 52, Feb. 13, 2009 (pp. 1428-1437).

Johnson, et al., “AZD2184: A Radioligand for Sensitive Detection of Beta-Amyloid Deposits”, Published in Journal of Neurochemistry, vol. 108, Mar. 1, 2009 (pp. 1177-1186).

Seneca, et al., “Brain and Whole-Body Imaging in Nonhuman Primates With [11C]MeS-IMPY, a Candidate Radioligand for Beta-Amyloid Plaques”, Published in Nuclear Medicine and Biology, vol. 34, Aug. 6, 2007 (pp. 681-689).

Vasdev, et al., “Synthesis and Ex Vivo Evaluation of Carbon-11 Labelled N-(4-methoxybenzyI)-N’-(5-nitro-1,3- thiazol-2-yl)urea([11C]Ar-A014418): A Radiolabelled Glycogen Synthase Kinase-3beta Specific Inhibitor for PET Studies”, Published in Bioorganic & Medicinal Chemistry Letters, vol. 15, No. 23, Dec. 1, 2005 (pp. 5270-5273).

* cited by examiner

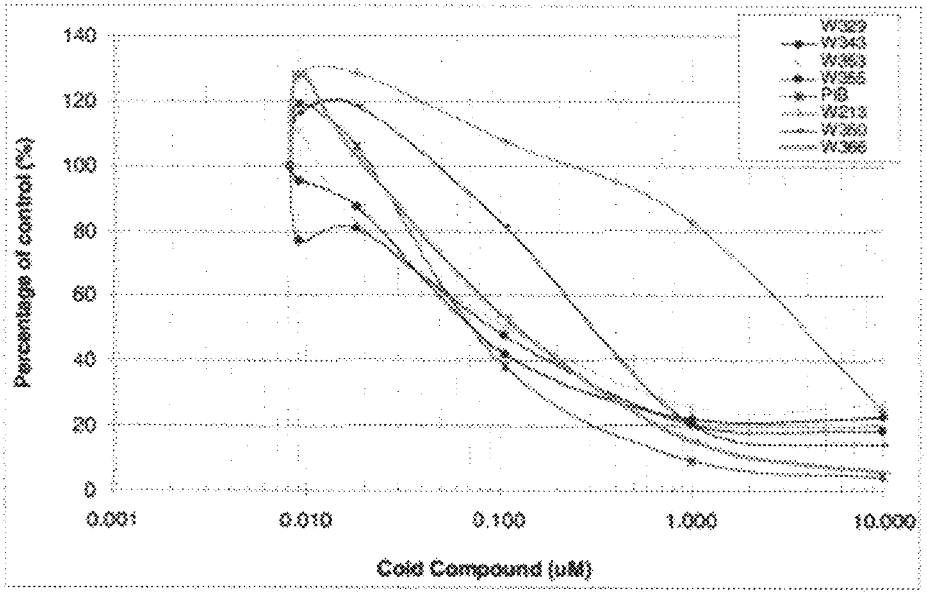
| Compound | IC50 [nM] |
|---|---|
| PIB | 72 |
| W343 | 72 |
| W355 | 80 |
| W353 | 102 |
| W366 | 103 |
Figure 1a. $IC_{50}$ determination of W366 and related compounds

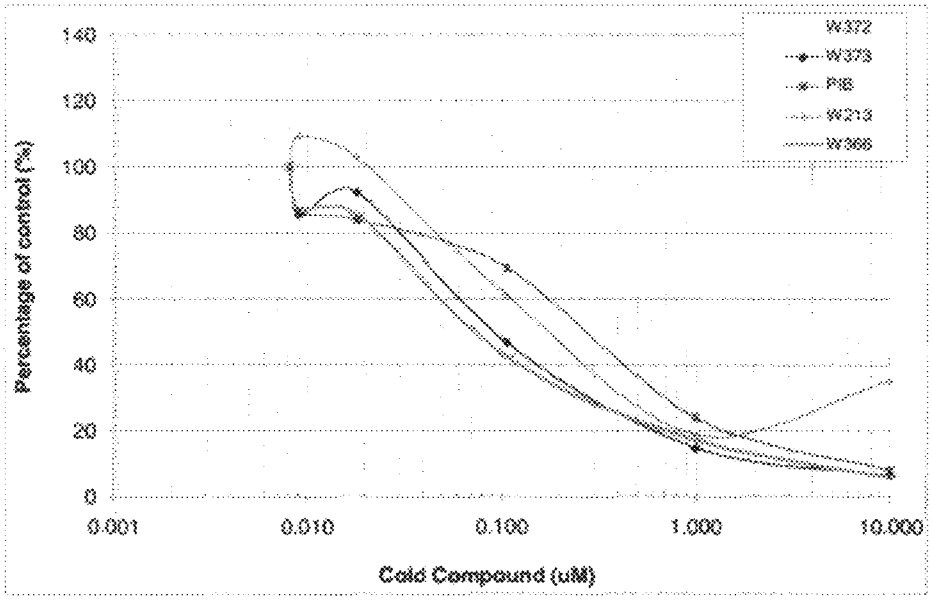
| Compound | IC50 [nM] |
|---|---|
| W366 | 69 |
| W373 | 85 |
| W372 | 120 |
| W213 | 120 |
| PiB | 230 |
Figure 1b. $IC_{50}$ determination of W366 and related compounds

Double labeling of Compound T482 (100uM) and
Total-tau IHC Staining on Human Brain Section #0185(40x)
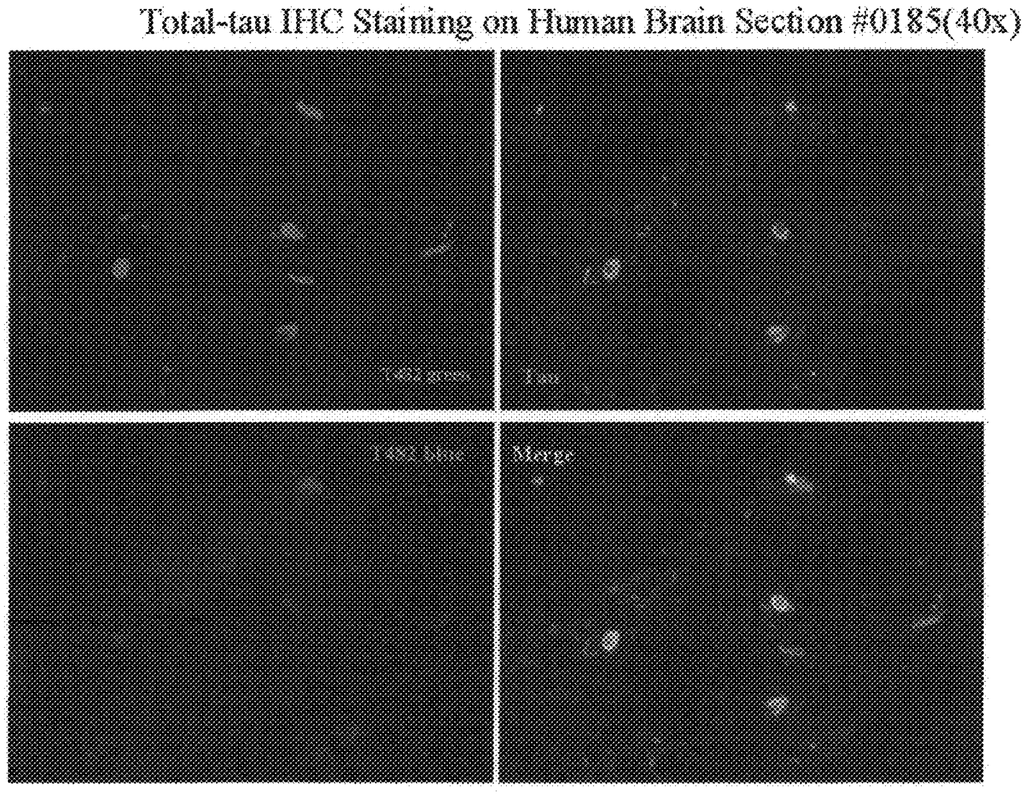
Figure 2

Double labeling of Compound T540 (100uM) and

Total+AD-tau IHC Staining on Human Brain Section #0185(10x)

Double labeling of Compound T540 (100uM) and

Total+AD-tau IHC Staining on Human Brain Section #0185(60x)

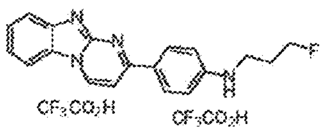
Double labeling of Compound T542 (100uM) and
Total+AD-tau IHC Staining on Human Brain Section #0185(10x)
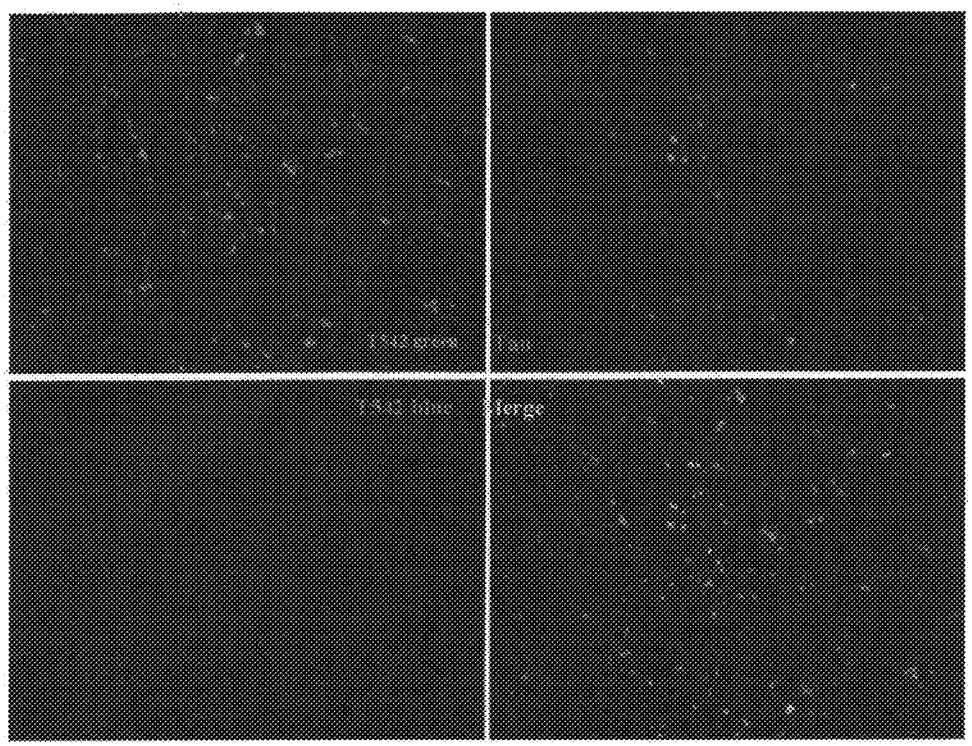
Figure 6a Double labeling of Compound T542 (100uM) and Total+AD-tau IHC Staining on Human Brain Section #0185(10x)

Double Labeling of Compound T542 (100uM) and Total+AD-tau IHC

Staining on Human Brain Section White Matter #0185(60x)

Note: It seems that in white matter T542 stains cell membrane.

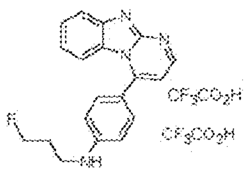
Double labeling of Compound T544 (100uM) and
Total+AD-tau IHC Staining on Human Brain Section #0185(60x)
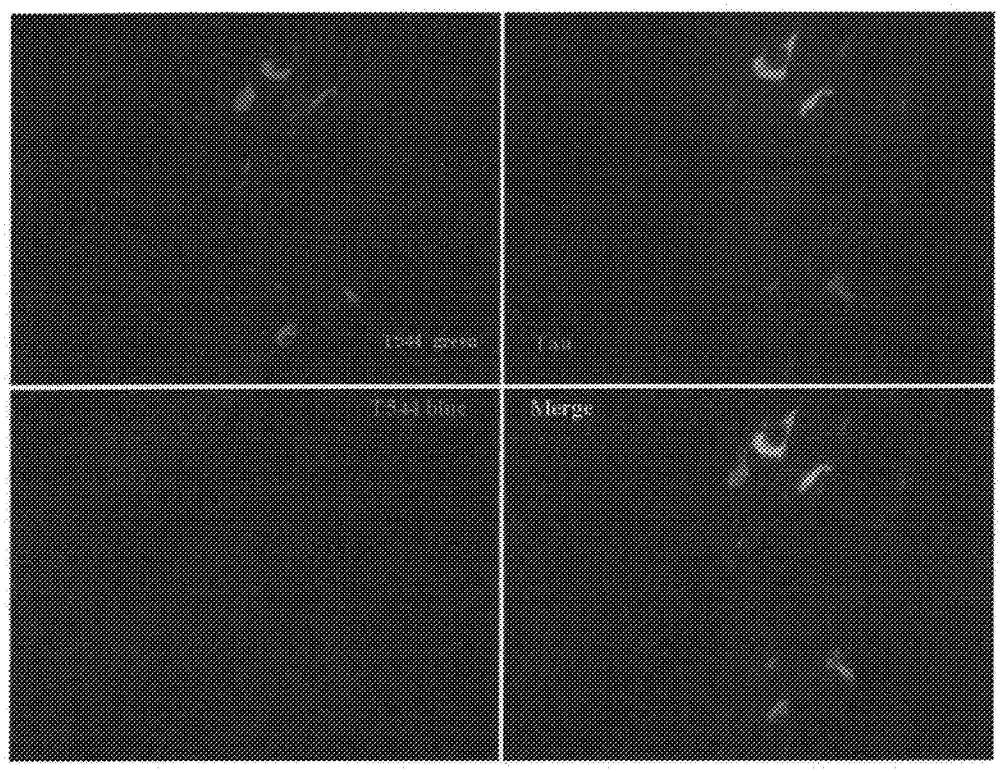
Figure 7

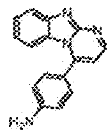
Double labeling of Compound T520 (100uM) and
Total-tau IHC Staining on Human Brain Section #0185(10x)
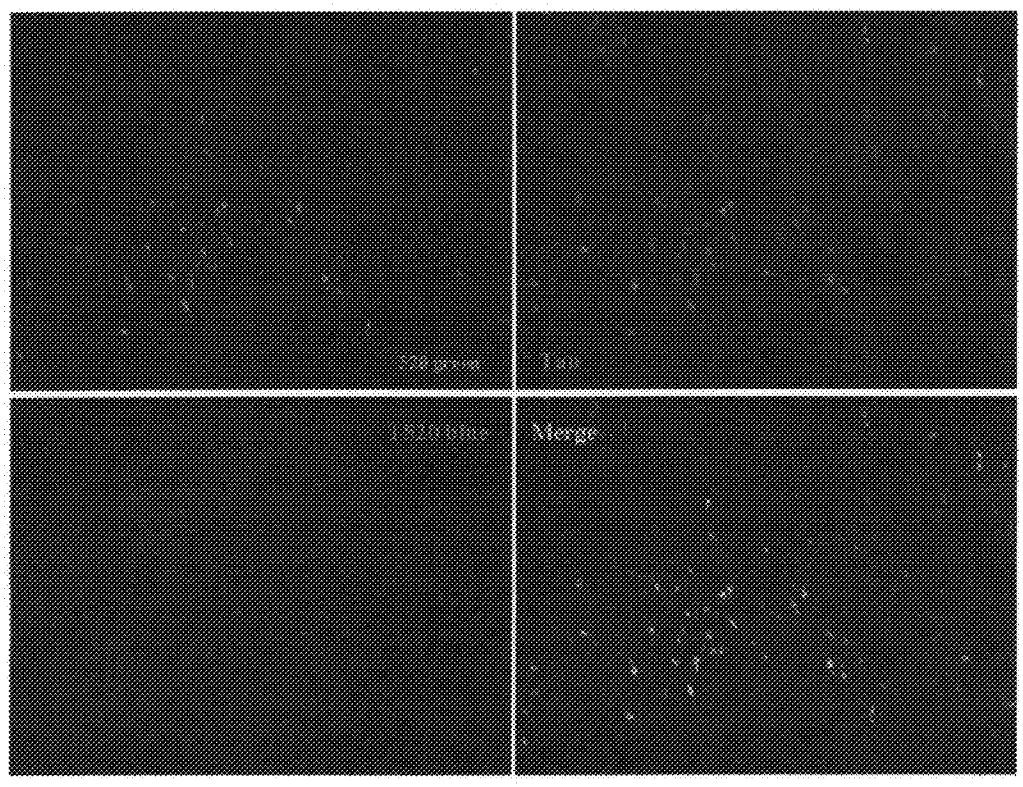
Figure 8a Double labeling of Compound T520 (100uM) and Total-tau IHC Staining on Human Brain Section #0185(40x)

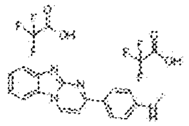
Double labeling of Compound T522 (100uM) and
Total-tau IHC Staining on Human Brain Section #0185 (10x)
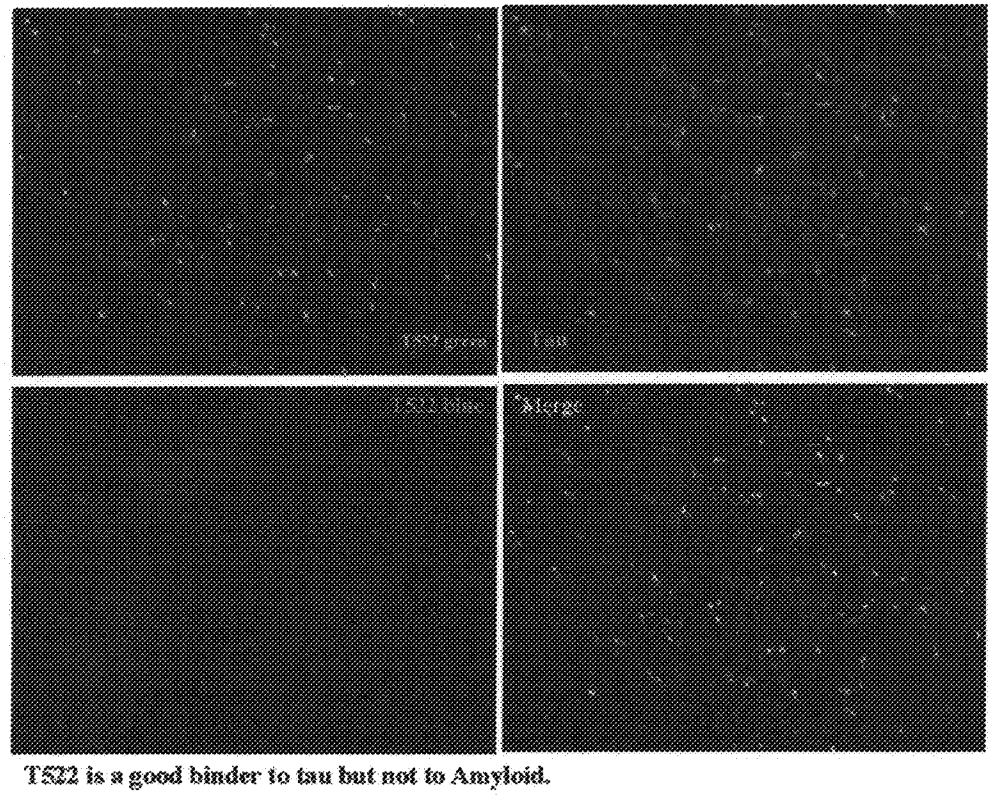
T522 is a good binder to tau but not to Amyloid.
Figure 9a

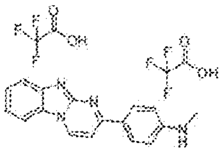
Double labeling of Compound T522 (100uM) and
Total-tau IHC Staining on Human Brain Section #0185 (60x)
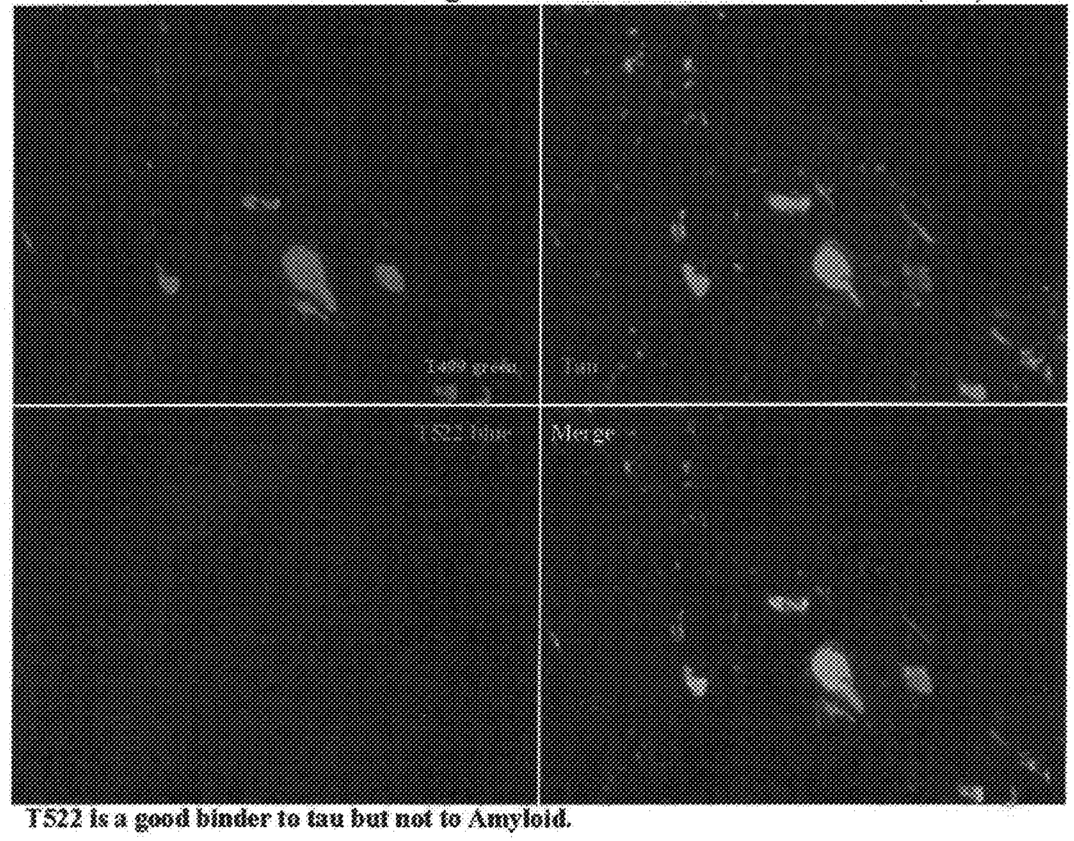
T522 is a good binder to tau but not to Amyloid.
Figure 9b

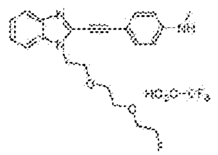
Double labeling of Compound T541 (100uM) and
Total+AD-tau IHC Staining on Human Brain Section #0185(10x)
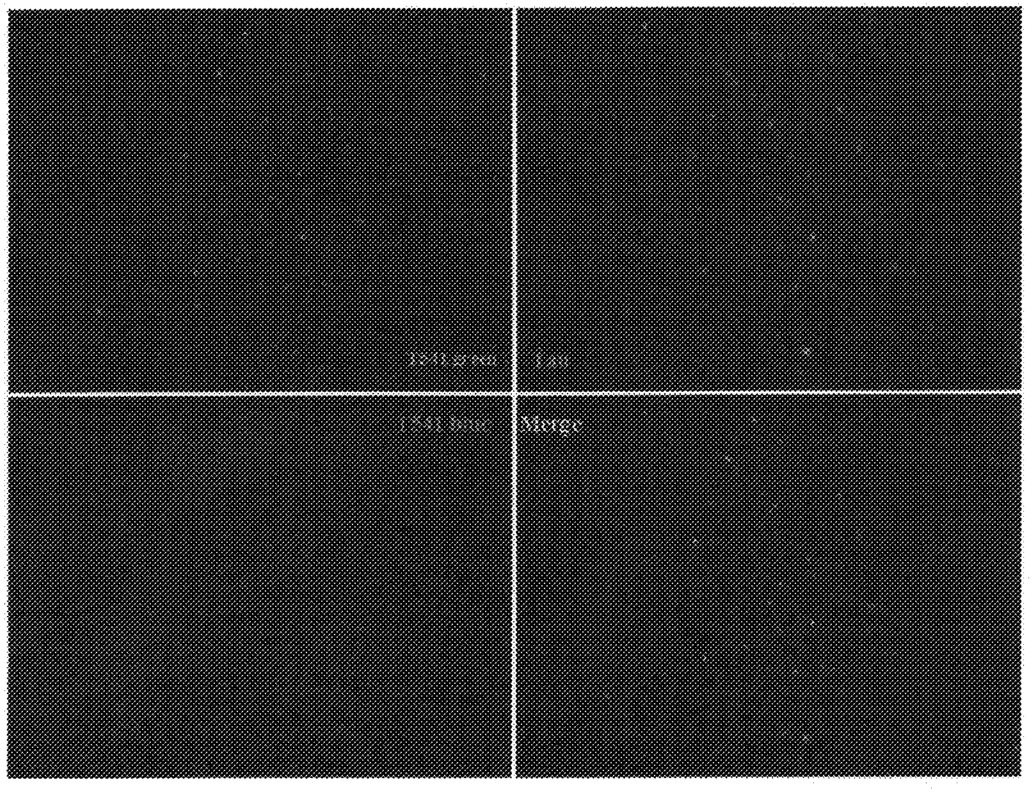
Figure 10a Double labeling of Compound T541 (100uM) and Total+AD-tau IHC Staining on Human Brain Section #0185(60x)

Double labeling of Compound T527 (100uM) and
Total-tau IHC Staining on Human Brain Section #0185(40x)
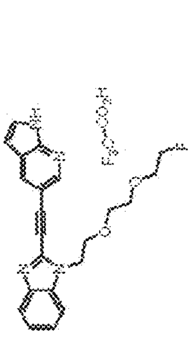
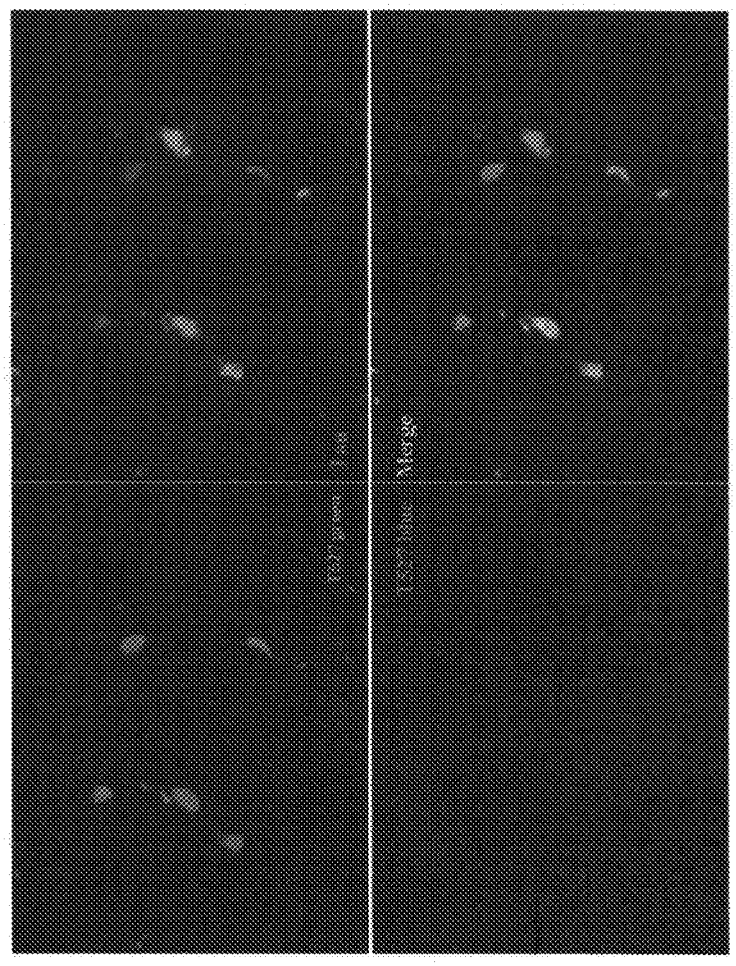
Figure 11

Double labeling of Compound T539 (100uM) and
Total+AD-tau IHC Staining on Human Brain Section #0185(60x)
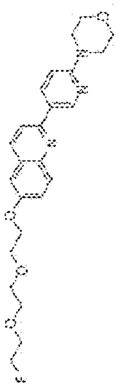
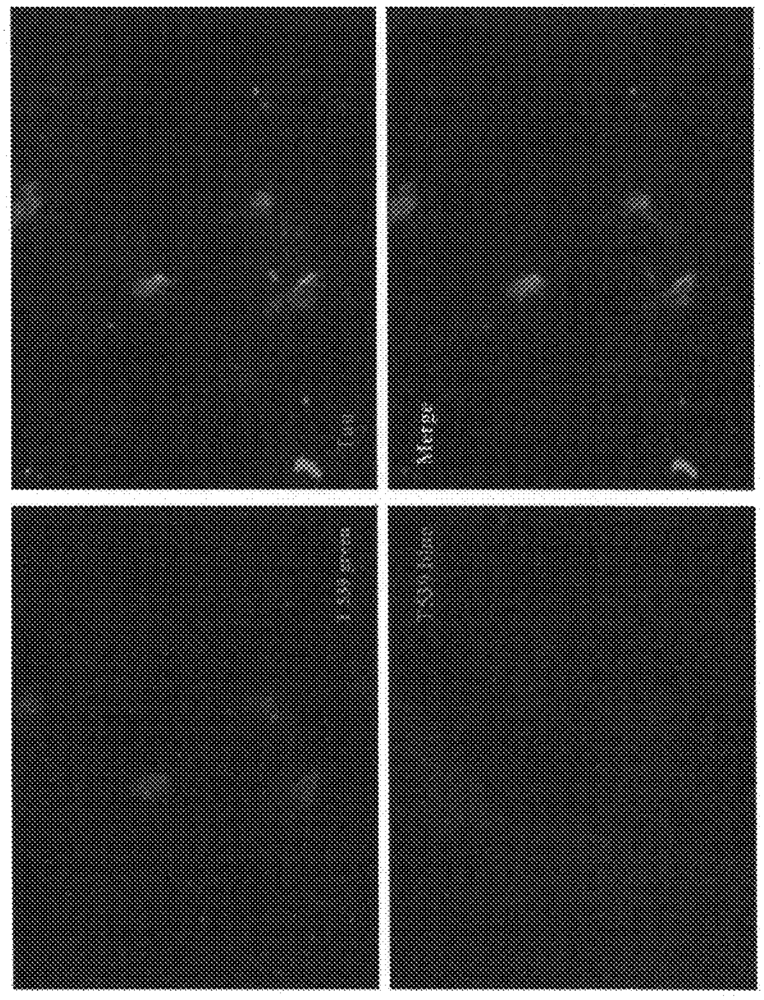
Figure 12

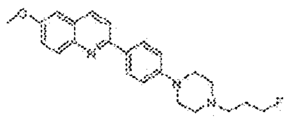
Double labeling of Compound T499 (100uM) and
Total-tau IHC Staining on Human Brain Section #0185 (10x)
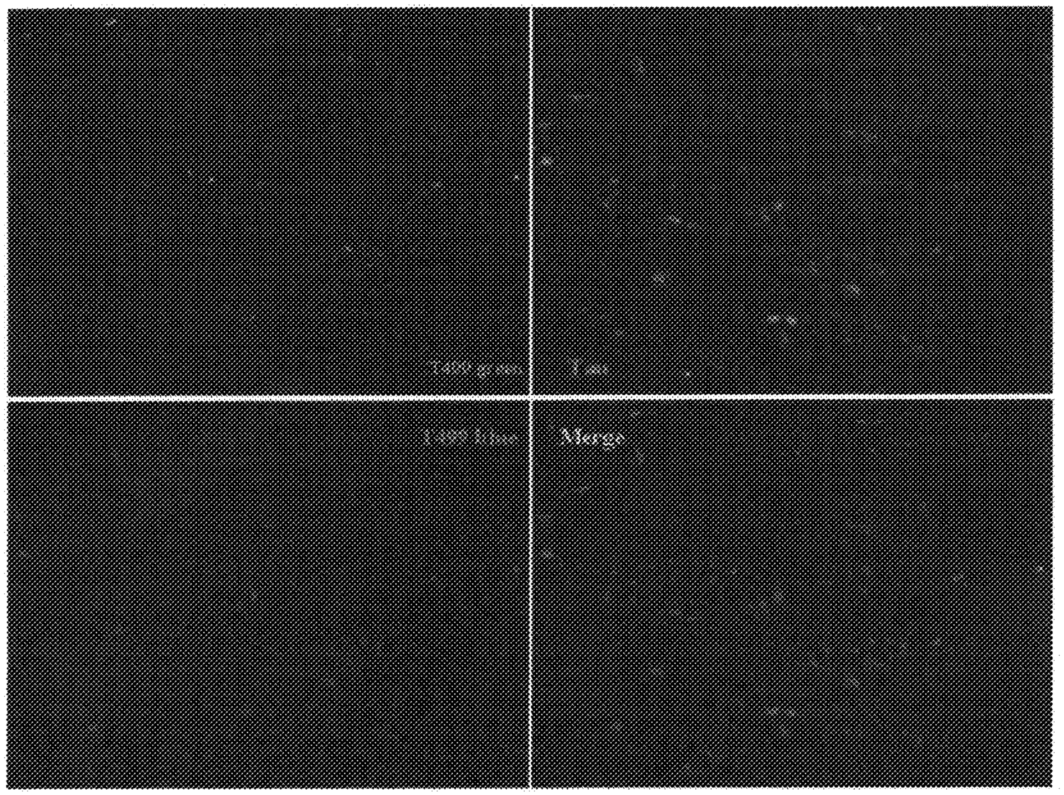
Figure 13a

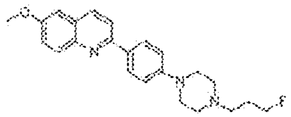
Double labeling of Compound T499 (100uM) and
Total-tau IHC Staining on Human Brain Section #0185 (40x)
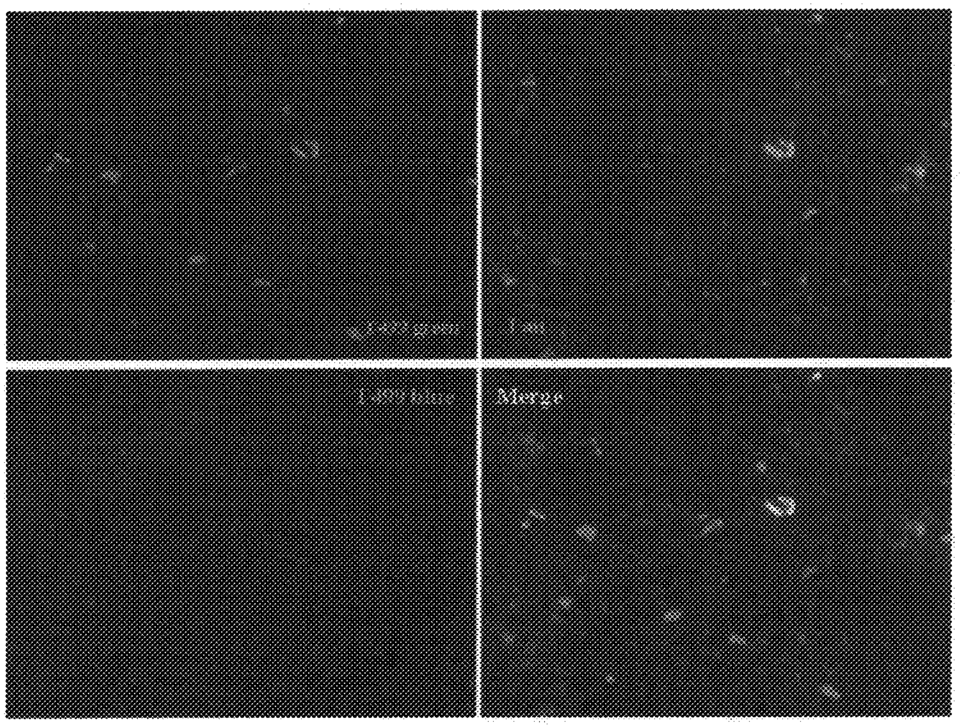
Figure 13b

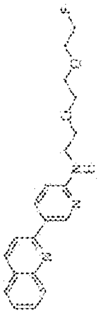
Double labeling of Compound T525 (100uM) and
Total-tau IHC Staining on Human Brain Section #0185(40x)
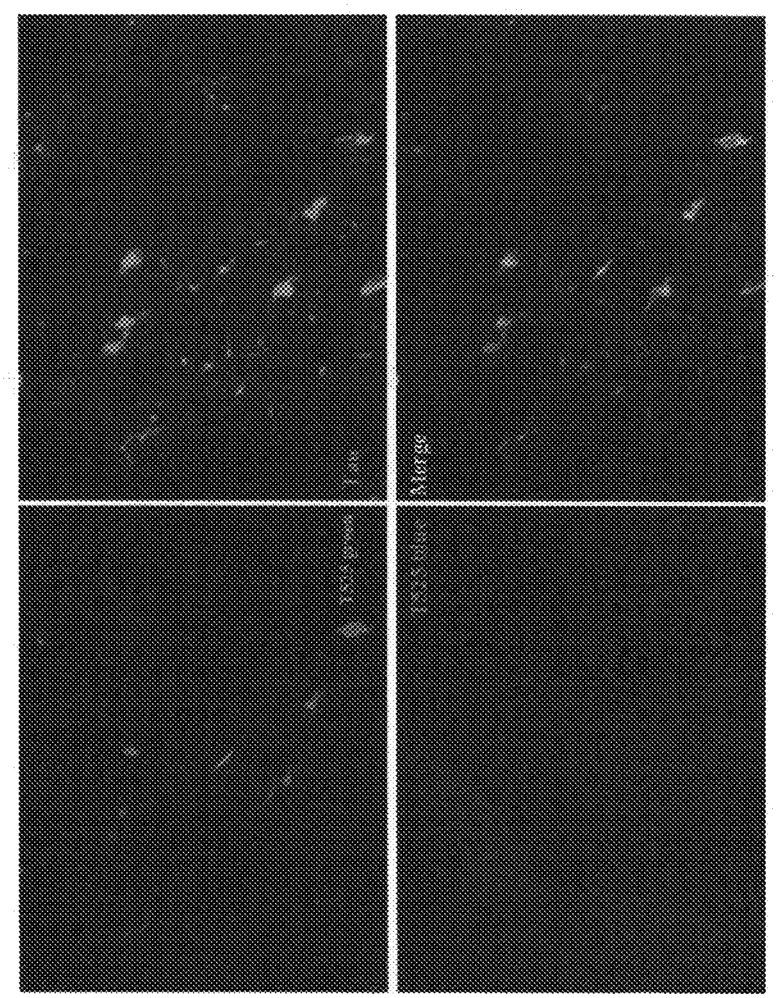
Figure 14

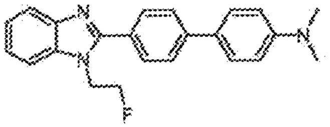
Double labeling of Compound T543 (100uM) and
Total+AD-tau IHC Staining on Human Brain Section #0185(60x)
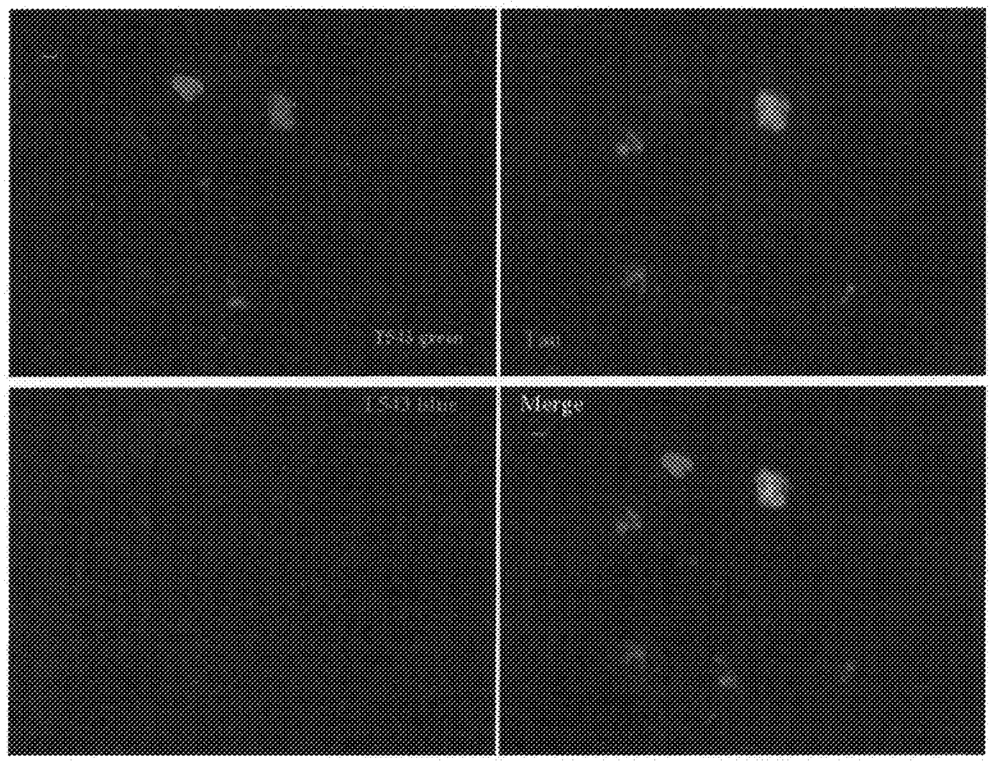
Figure 16

T114 rat H05080921 02-12-10 B/M 3.54 rat H12190810 02-12-10 B/M 2.475

T442 mouse H09060972 12-18-09 B/M 2.2

T549

T525 rat H05080922 02-11-09 B/M 5.93 rat H05080903 02-11-09 B/M 3.24

T510 rat H0508003 02-08-10 B/M 5.86 rat H0508092 02-08-10 B/M 20.66

IMAGING AGENTS FOR DETECTING NEUROLOGICAL DISORDERS

CLAIM TO PRIORITY

The present application is based on and claims a priority benefit of U.S. provisional application No. 61/162,421, filed Mar. 23, 2009, which is incorporated herein by reference in its entirety.

The foregoing application, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates generally to imaging agents for detecting neurological disorders. More specifically, the present invention relates to the discovery of novel diagnostic imaging agents targeting senile plaques (SPs) and/or neurofibrillary tangles (NFTs) for detection, preclinical diagnosis and for tracking progression of Alzheimer's disease (AD).

BACKGROUND OF THE INVENTION

Currently, Alzheimer's disease (AD), a leading cause of dementia, develops in one percent of the population between the ages 65 and 69, and increasing to 40-50% in those 95 years and older. AD patients exhibit telltale clinical symptoms that include cognitive impairment and deficits in memory function. In the current working model, there are three 'stages' that are associated with AD. First, neuronal cells become sick as a result of synaptic/metabolic malfunctioning that leads to neuronal deficiencies. Secondly, in the histological stage, an accumulation of neurofibrillary tangles and beta amyloid plaques begins, leading to the untimely aggregation of insoluble proteins in the brain. Finally, AD ultimately causes neuronal death and shrinkage in brain volume. AD patients typically have a heavy senile plaque (SP) burden found in the cerebral cortex which is verified by postmortem histopathological examination. SPs are extracellular deposits containing β-amyloid peptide cleaved from a longer amyloid precursor protein to produce a 40-43 amino acid peptide. Amyloid aggregates in brain play a key role in a cascade of events leading to AD. Interestingly, despite the development and presence of senile plaques in elderly persons with normal cognitive function, the severity of NFT and senile plaque deposition purportedly correlates with a loss of cognitive function and neuronal circuitry deterioration.

Major neuropathology observations of postmortem examination of AD brains confirm the presence of AD through the detection of extracellular β-amyloid peptides and intracellular neurofibrillary tangles (NFT). NFTs derive from filaments of hyperphosphorylated tau proteins. The presence and severity of NTFs correlate with severity of dementia and cognitive impairment (Dickinson, D. W., *Neurobiol. Aging* 1997, 18 [4 suppl]:S21-S26). The pathological process of AD must begin before the presentation of the clinical symptoms of dementia.

Despite Alzheimer's disease being the fourth leading cause of death in the United States, pharmaceutical intervention has yet to commercialize a curative therapy. Recently, Marwan N. Sabbagh published an overview of the current state of clinical development of AD pharmacotherapy (*The American Journal of Geriatric Pharmacotherapy,* 2009, 7(3), p. 167). Encouraging results from completed Phase II trials of dimebon, huperzine A, intravenous immunoglobulin, and methylthioninium chloride were reported at ICAD 2008. Nineteen compounds are currently in Phase II trials, and 3 compounds (AN1792, lecozotan SR, and SGS742) failed at this stage of development.

In addition to pharmaceutical approaches for curbing the effects of AD, researchers are attempting to detect AD by other means, including establishing technologies for early detection. Currently, there are many strategies that attempt to identify AD-associated pathologies by targeting either the cell sickness or histological stages of the disease. There is an array of AD imaging agents that potentially confirm the well-established manifestation of AD, however, this late stage diagnosis offers little defense against further disease progression past 36 months. Interestingly, the detection of senile plaques and tangles in the brain may not necessarily prove that a patient has developed AD.

As summarized from a recent discussion group on Dec. 5, 2006 (Biochemical Pharmacology Discussion Group, cosponsored by the American Chemical Society's New York section), researchers are now focusing on methods that target AD precursors by blocking either β-amyloid protein (BAP) production or by controlling mutant tau protein formation. Clearly, this focused research effort aims to control the formation of AD precursors that potentially lead to AD and this new strategy might delay full-onset AD more effectively that current therapeutics. In parallel, neurological imaging must mirror the therapeutic trend by identifying AD precursors in a duel effort to compliment both AD therapeutic development and, in addition, identify presymptomatic at-risk AD patients. Recent drug development has been aimed at preventing the accumulation of SPs and NFTs in presymptomatic AD patients. The ability to measure levels of these lesions in the living human brain is thus desirable for presymptomatic diagnosis of AD and also for monitoring the progression of the disease.

Unfortunately, since AD cannot be confirmed in the patients until a histological examination is performed, understanding the link between the uptake of these tracers and the relevant biochemical processes involved could remain unsolved for many years.

Thus, in vivo imaging of NFTs in conjunction with imaging SPs could prove useful for the early and accurate diagnosis of AD. Quantitative evaluation of tau pathology could also be helpful for tracking severity of dementia, because the formation of neuritic pathology correlates well with clinical severity of dementia (Dickson, 1997). NFT deposition in the entorhinal cortex is closely associated with neuronal loss in very early AD patients (Gomez-Isla et al., 1996). If novel treatments that prevent the pathological formation of neurofibrillary pathology could be turned into clinical applications, this imaging technique would be applicable for the evaluation of treatment efficacy.

Currently, neurological imaging of AD has seen the emergence of imaging tracers that appear to confirm the presence of AD based on plaque and fibril mediated tracer uptake and, subsequently, are currently undergoing extensive clinical examination. Many of these tracers contain chemotypes that are derived from fluorescent dyes.

Potential ligands for detecting Aβ aggregates in the living brain must cross the intact blood-brain barrier. Thus brain uptake can be improved by using ligands with relatively smaller molecular size and increased lipophilicity.

Previous neuropathological research suggests that the deposition of NFTs occurs before the presentation of clinical symptoms of AD. Even in the very early stages of AD, patients display considerable numbers of NFTs in the entorhinal cortex and hippocampus, sufficient for the neuropathological diagnosis of AD. Thus, in vivo imaging of NFTs in conjunction with imaging SPs could prove useful for the early and accurate diagnosis of AD, for monitoring the progression of the disease and for evaluation of treatment efficacy.

Optimization of current candidates and discovery of novel compounds that specifically bind tau or Aβ aggregates are of high interest for development of in vivo tau- and Aβ imaging agents for detection of neurological disorders, and inparticular for imaging and detection of AD in patients.

SUMMARY OF THE INVENTION

This invention discloses a series of compounds of formula (I) having enhanced binding properties to SPs and NFTs. The present invention also provides diagnostic pharmaceutical compositions comprising a radiolabeled compound of formula (I) and a pharmaceutically acceptable carrier or diluent. The present invention further relates to a method of imaging and detecting amyloid deposits and/or tau aggregates, the method comprising administering a detectable amount of a labeled compound of formula (I) or its pharmaceutically acceptable salt to a subject in need thereof and detecting the labeled compound associated with amyloid deposits or tau aggregates.

One embodiment of the present invention is directed to a biaryl or bis-aromatic compound of formula (I) or its pharmaceutically acceptable salt.

Another embodiment of the present invention is directed to the compound of formula (I) as described above, wherein at least one of the aryl components is substituted with a side chain having a radiolabel.

Another embodiment of the present invention is directed to the compound of formula (I) as described above, wherein the radiolabel is $^{18}F$.

Another embodiment of the present invention is directed to the compounds of formula (I) as described above, wherein at least one of the aryl components is unsubstituted or substituted phenyl, pyridine, pyrimidine or pyrazine.

Another embodiment of the present invention is directed to the compound of formula (I) as described above, wherein at least one of the aryl components is unsubstituted or substituted fused heteroaryl.

Yet another embodiment of the present invention is directed to the compound of formula (I) as described above, wherein at least one fused heteroaryl is a bicycle.

Yet another embodiment of the present invention is directed to the compound of formula (I) as described above, wherein at least one fused heteroaryl is a tricycle.

Yet another embodiment of the present invention is directed to diagnostic pharmaceutical compositions comprising a radiolabeled compound of formula (I) or its pharmaceutically acceptable salt as described above and, a pharmaceutically acceptable carrier or diluent.

Yet another embodiment of the present invention is directed to a method of imaging and detection of neurological disorders associated with amyloid plaque and/or tau protein aggregation comprising administering a detectable amount of a labeled compound of formula (I) as described above or its pharmaceutically acceptable salt to a subject in need thereof and detecting the labeled compound associated with amyloid deposits and/or tau aggregates.

Yet another embodiment of the present invention is directed to a method of imaging and detection of neurological disorders associated with amyloid plaque aggregation comprising administering a detectable amount of a labeled compound of formula (I) as described above or its pharmaceutically acceptable salt to a subject in need thereof and detecting the labeled compound associated with amyloid deposits.

Yet another embodiment of the present invention is directed to a method of imaging and detection of neurological disorders associated with tau protein aggregation comprising administering a detectable amount of a labeled compound of formula (I) as described above or its pharmaceutically acceptable salt to a subject in need thereof and detecting the labeled compound associated tau aggregates.

Yet another embodiment of the present invention is directed to a method of imaging and detection of Alzheimer's disease associated with amyloid plaque and/or tau protein aggregation comprising administering a detectable amount of a labeled compound of formula (I) as described above or its pharmaceutically acceptable salt to a subject in need thereof and detecting the labeled compound associated with amyloid deposits and/or tau aggregates.

Yet another embodiment of the present invention is directed to a method of imaging and detection of Alzheimer's disease associated with amyloid plaque aggregation comprising administering a detectable amount of a labeled compound of formula (I) as described above or its pharmaceutically acceptable salt to a subject in need thereof and detecting the labeled compound associated with amyloid deposits.

Yet another embodiment of the present invention is directed to a method of imaging and detection of Alzheimer's disease associated with tau protein aggregation comprising administering a detectable amount of a labeled compound of formula (I) as described above or its pharmaceutically acceptable salt to a subject in need thereof and detecting the labeled compound associated with tau aggregates.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments will become apparent from and encompassed by the following Detailed Description when taken in conjunction with the accompanying drawings. The entire disclosures of all patents and references cited throughout this application are incorporated herein by reference in their entirety.

BRIEF DESCRIPTION OF THE DRAWINGS

The application file contains at least one image executed in color. Copies of this patent application publication with color images will be provided by the Office upon request and payment of the necessary fee.

The following detailed description, given by way of example, but not intended to limit the invention solely to the specific embodiments described, may best be understood in conjunction with the accompanying drawings, in which:

FIG. 1*a* shows an example of a brain slice assay used to determine the $IC_{50}$ values of W366 and related compounds.

FIG. 1*b* shows an example of a brain slice assay used to determine the $IC_{50}$ values of W366 and related compounds.

FIG. 2 shows total tau binding of fluorescent compound T482 to AD brain sections confirmed by immunostaining with tau or Aβ antibodies (double labeling of T482 at 100 uM).

FIGS. 6*a*, 6*b*, and 6*c* show binding of fluorescent compound T542 to AD brain sections confirmed by immunostaining with tau or Aβ antibodies.

FIG. 7 binding of fluorescent compound T544 to AD brain sections confirmed by immunostaining with tau or Aβ antibodies.

FIGS. 8*a* and 8*b* show binding of fluorescent compound T520 to AD brain sections confirmed by immunostaining with tau or Aβ antibodies.

FIGS. 9*a* and 9*b* show total binding of fluorescent compound T522 to AD brain sections confirmed by immunostaining with tau or Aβ antibodies.

FIGS. 10*a* and 10*b* show binding of fluorescent compound T541 to AD brain sections confirmed by immunostaining with tau or Aβ antibodies.

FIG. 11 shows binding of fluorescent compound T527 to AD brain sections confirmed by immunostaining with tau or Aβ antibodies.

FIG. 12 shows binding of fluorescent compound T539 to AD brain sections confirmed by immunostaining with tau or Aβ antibodies.

FIGS. 13*a* and 13*b* show binding of fluorescent compound T499 to AD brain sections confirmed by immunostaining with tau or Aβ antibodies.

FIG. 14 shows binding of fluorescent compound T525 to AD brain sections confirmed by immunostaining with tau or Aβ antibodies.

FIG. 16 shows binding of fluorescent compound T543 to AD brain sections confirmed by immunostaining with tau or Aβ antibodies.

DETAILED DESCRIPTION

Figure 3:
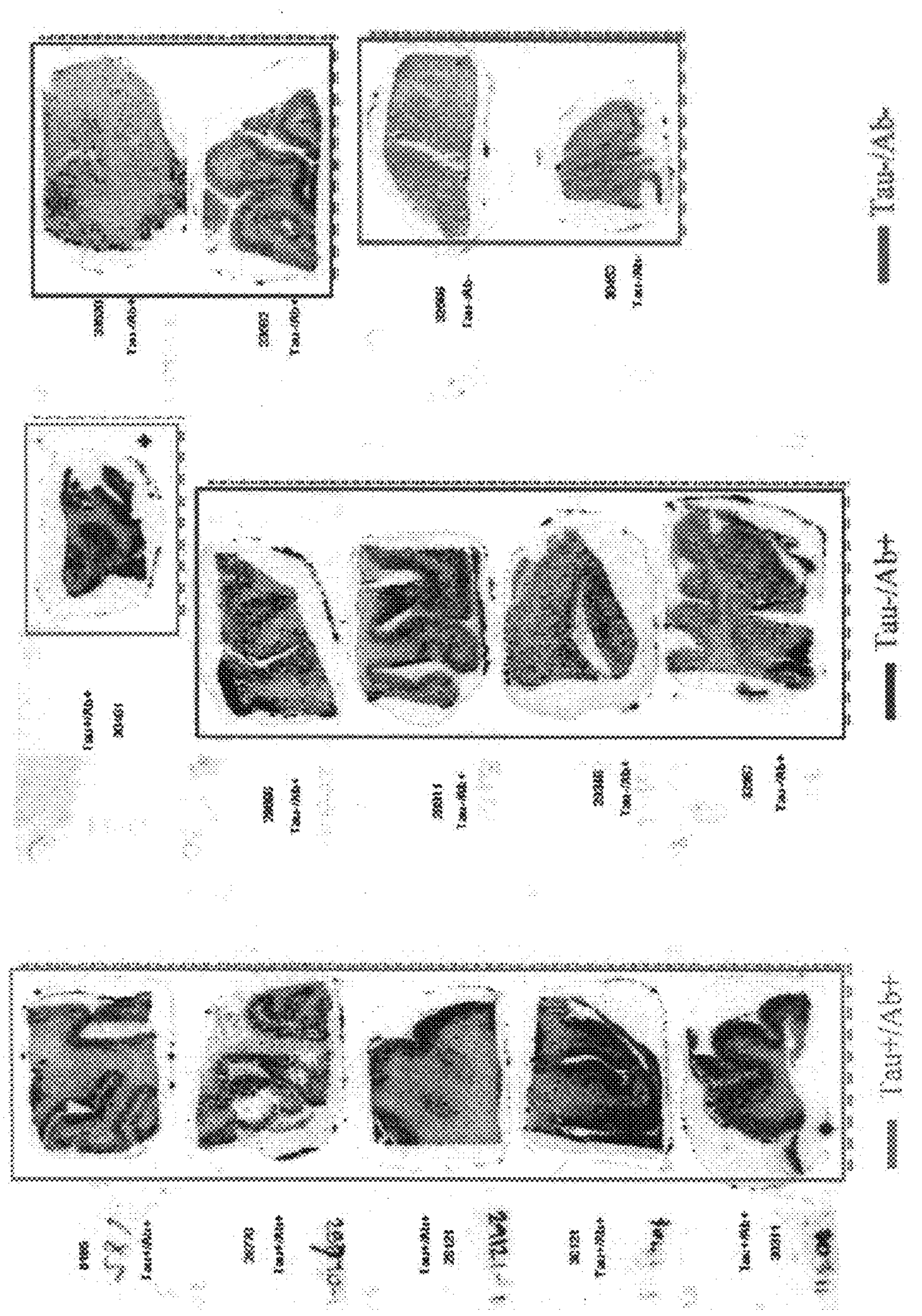
FIG. 3 shows ex vivo autoradiograph images of a preferred compound, T482.

The following description will describe the invention in relation to advantageous embodiments thereof. The invention is in no way limited to these advantageous embodiments as they are purely included to exemplify the invention and the invention is intended to include possible variations and modifications as would be readily apparent to a person skilled in the art without departing from the scope of the invention.

One of the embodiments of the present invention relates to a compound of general formula (I)

(I)

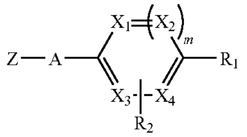

wherein

A is a bond, $(C_1-C_4)$alkyl, $(C_3-C_6)$cycloalkyl, $(C_2-C_4)$alkene, or $(C_1-C_4)$alkyne;

Z is aryl selected from the group consisting of:

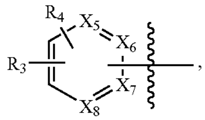
,
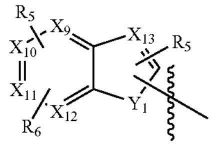
,
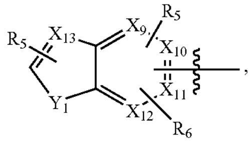
,
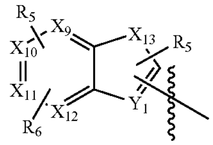
,
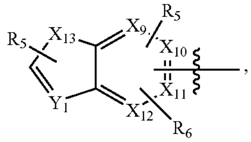
,
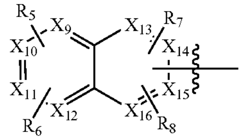
,
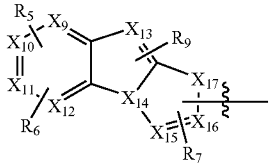
,
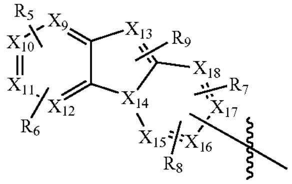
, or
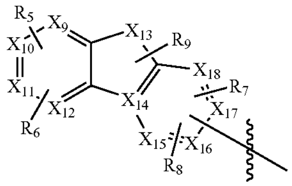
, wherein $X_1$ and $X_{13}$ are each independently C, CH, N, O, or S;

$X_2$-$X_{12}$ and $X_{14}$-$X_{18}$ are each independently C, CH or N;

$Y_1$ is N, O, or S;

$R_1$-$R_2$ are each independently H, halogen, hydroxy, nitro, cyano, amino, alkyl, alkoxy, $-(O-CH_2-CH_2)_n-$, monoalkylamino, dialkylamino, monoarylamino, diarylamino, $NR_{10}$COOalkyl, $NR_{10}$ COOaryl, $NR_{10}$ COalkyl, $NR_{10}$ CO aryl, COOalkyl, COOaryl, COalkyl, COaryl, aryl, saturated heterocyclyl, wherein the last seventeen groups are unsubstituted or substituted by one or more radicals selected from the group consisting of halogen, alkyl, haloalkyl, cyano, hydroxyl, amino, monoalkylamino, dialkylamino, alkoxy, $R_{10}$, a radiolabel or alkyl substituted with a radiolabel; or $R_1$ and $R_2$ together form a five- or six-membered saturated or unsaturated ring which optionally contains an additional heteratom in the ring which is selected from N, O, and S, the ring being unsubstituted or substituted by one or more radicals selected from the group consisting of halogen, alkyl, haloalkyl, cyano, hydroxyl, amino, monoalkylamino, dialkylamino, alkoxy, $R_{10}$, a radiolabel or alkyl substituted with radiolabel;

$R_3$-$R_9$ are each independently H, halogen, hydroxy, nitro, cyano, amino, alkyl, alkoxy, $—(O—CH_2—CH_2)_n—$, monoalkylamino, dialkylamino, monoarylamino, diarylamino, $NR_{10}COOalkyl$, $NR_{10}$ COOaryl, $NR_{10}$ COalkyl, $NR_{10}$ CO aryl, COOalkyl, COOaryl, COalkyl, COaryl, aryl, heterocyclyl, wherein the last seventeen groups are unsubstituted or substituted by one or more radicals selected from the group consisting of halogen, alkyl, haloalkyl, cyano, hydroxyl, amino, monoalkylamino, dialkylamino, alkoxy, $R_{10}$, a radiolabel or alkyl substituted with a radiolabel;

$R_{10}$ is H, alkyl, alkene, aryl unsubstituted or substituted with halogen, hydroxyl, cyano, nitro, amino, $—OSO_2alkyl$, $—OSO_2aryl$, $—OSi(alkyl)_3$, —OTHP or a radiolabel;

n is 1, 2, or 3;

m is 0 or 1, and a pharmaceutically acceptable salt thereof.

Another embodiment of the present invention is directed to the compound of formula (I) as described above wherein Z is

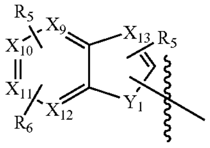

and at least one of $X_9$-$X_{13}$ is nitrogen and m is 1.

Another embodiment of the present invention is directed to the compound of formula (I) as described above, wherein at least one of $R_1$-$R_6$ is $—(O—CH_2—CH_2)_2—$.

Another embodiment of the present invention is directed to the compound of formula (I) as described above, wherein Z is

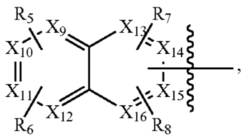

and at least one of $X_9$-$X_{16}$ is nitrogen and m is 1.

Another embodiment of the present invention is directed to the compound of formula (I) as described above, wherein Z is

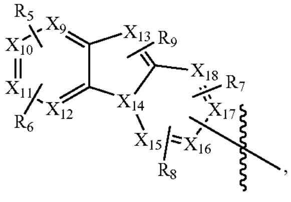

and at least one of $X_9$-$X_{18}$ is nitrogen and m is 1.

Another embodiment of the present invention is directed to the compound of formula (I) as described above, wherein Z is

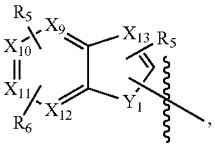

and wherein at least one $X_9$-$X_{12}$ is nitrogen and m is 1.

Another embodiment of the present invention is directed to the compound of formula (I) as described above, wherein Z is

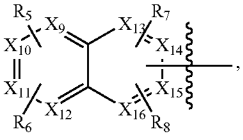

A is acetylene and at least one $X_9$-$X_{16}$ is nitrogen.

Another embodiment of the present invention is directed to the compound of formula (I) as described above, wherein A is a bond and Z is quinoline.

Another embodiment of the present invention is directed to the compound of formula (I) as described above, wherein at least one of $R_1$-$R_9$ is a saturated heterocycle.

Another embodiment of the present invention is directed to the compound of formula (I) as described above, wherein m is 1 and $R_1$ is saturated heterocycle.

Another embodiment of the present invention is directed to the compound of formula (I) as described above, wherein Z is

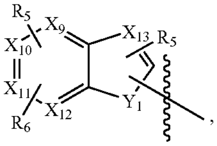,
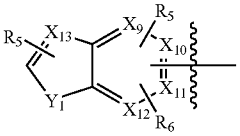,
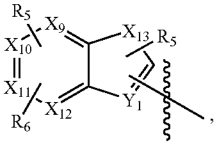,
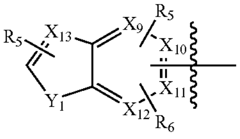,
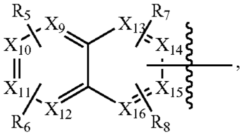,
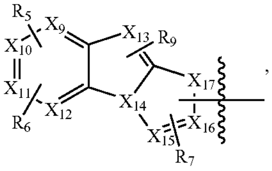,
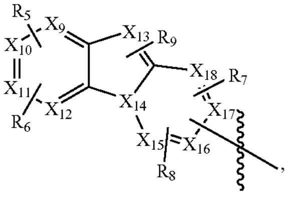, or -continued

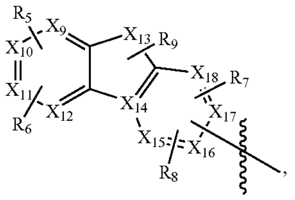

wherein at least two of $X_9$-$X_{16}$ are nitrogens.

Yet another embodiment of the present invention is directed to the compound of formula (I) as described above, wherein A is a bond and Z is

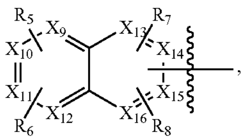

wherein at least three of $X_1$-$X_{16}$ are nitrogens.

Yet another embodiment of the present invention is directed to the compound of formula (I) as described above, wherein A is a bond and Z is

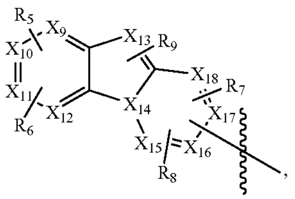

wherein at least two of $X_9$-$X_{18}$ are nitrogens.

Another embodiment of the present invention is directed to the compound of formula (I) as described above, wherein A is $C_2$ alkyne or acetylene and Z is

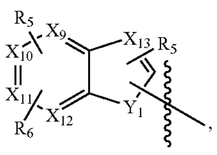

wherein at least two of $X_9$-$X_{13}$ or $Y_1$ are nitrogens.

Another embodiment of the present invention relates to the compound of formula (I) as described above, wherein at least one of $R_1$-$R_2$ comprises a heterocycle.

Another embodiment of the present invention relates to the compound of formula (I) as described above, wherein at least one of $R_1$-$R_2$ comprises a saturated heterocycle.

Another embodiment of the present invention relates to the compound of formula (I) as described above, wherein at least one of $R_1$-$R_9$ comprises —(O—$CH_2$—$CH_2$)$_2$— or —(O—$CH_2$—$CH_2$)$_3$—.

Another embodiment of the present invention relates to the compound of formula (I) as described above, wherein at least one of $R_1$-$R_9$ comprises a radiolabel selected from the group consisting of $^{11}C$, $^{13}N$, $^{15}O$, $^{18}F$, $^{123}I$, $^{124}I$, $^{125}I$, $^{131}I$, $^{76}Br$ and $^{77}Br$.

In another embodiment, the present invention provides the compound of formula (I) as described above, wherein the compound can be presented as formula (II). Formula (II) represents W366 and related compounds containing labeling elements on the left hand portion of the molecule:

(II)

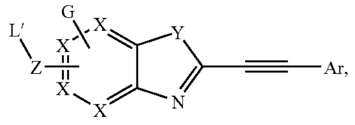

wherein

X is N or C;

Y is S or O;

Z is bond, S, O, alkyl, —$(OCH_2CH_2)_n$—, aryl or heteroaryl;

L* is radioactive label;

Ar is aryl, heteroaryl, optionally substituted with O, S, halogen, alkyl, or —$(OCH_2CH_2)_n$—;

G is H, S, O, halogen, alkyl, —$(OCH_2CH_2)_n$— or aryl; and n is 1, 2, or 3.

In another embodiment, the present invention provides the compound of formula (I) as described above, wherein the compound can be presented as formula (III), which represents W366 and related compounds containing labeling elements on the right hand portion of the molecule:

(III)

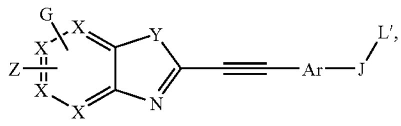

wherein

X is N or C;

Y is S or O;

Z is S, O, alkyl, —$(OCH_2CH_2)_n$—, aryl or heteroaryl optionally substituted with O, S, halogen, alkyl, aryl or —$(OCH_2CH_2)_n$—;

L* is radioactive label;

J is bond, S, O, alkyl, —$(OCH_2CH_2)_n$—, aryl or heteroaryl;

Ar is aryl, heteroaryl, optionally substituted with O, S, halogen, alkyl, or —$(OCH_2CH_2)_n$—;

G is H, S, O, halogen, alkyl, —$(OCH_2CH_2)_n$— or aryl; and n is 1, 2, or 3.

In another embodiment, the present invention provides W366 and related compounds containing labeling elements and substituted pyridyl moieties:

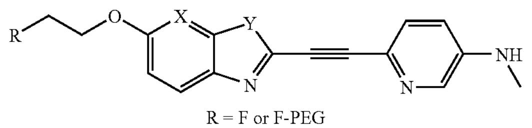

R = F or F-PEG

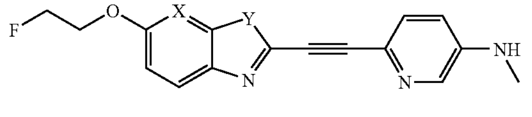

-continued
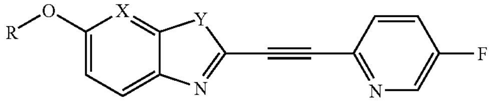
R = alkyl or PEG
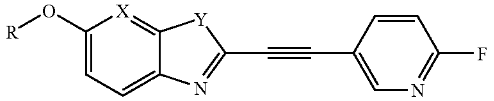
R = alkyl or PEG
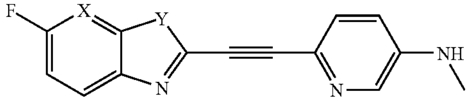
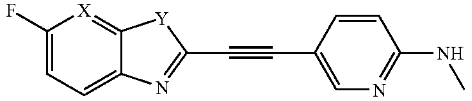
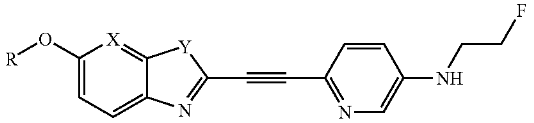
R = alkyl or PEG
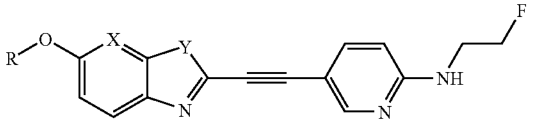
R = alkyl or PEG
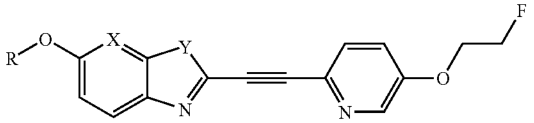
R = alkyl or PEG
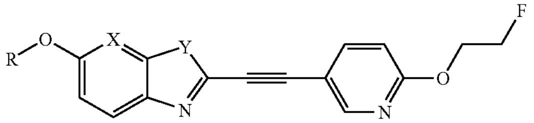
R = alkyl or PEG
X = N, Y = O, S
In another embodiment, the present invention provides the following compounds of formulas (II) and (III) containing labeling element (either $^{11}C$—NHMe or $^{18}F$):
Scheme 1.
Representative examples of Aβ imaging agents of formula (II) and formula (III).
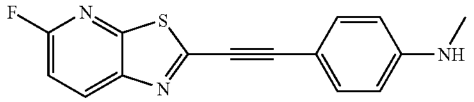
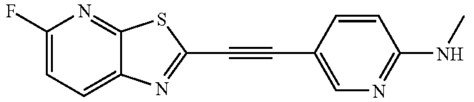
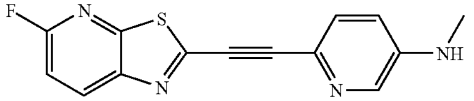
-continued
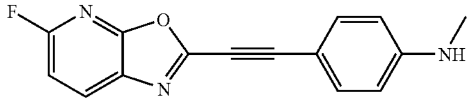
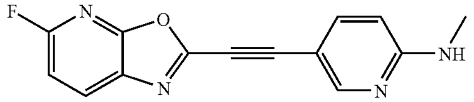
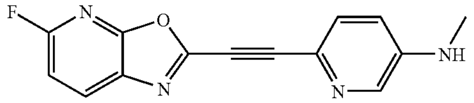
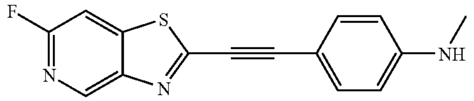
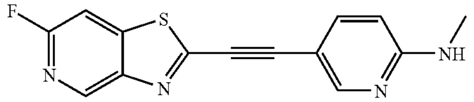
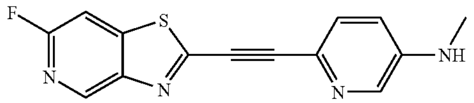
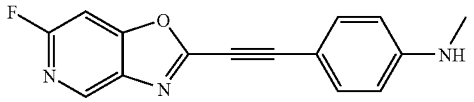
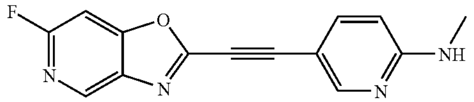
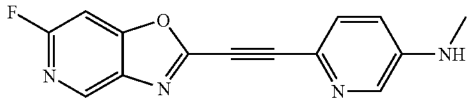
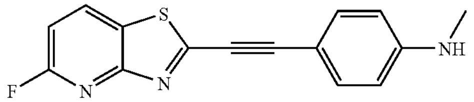
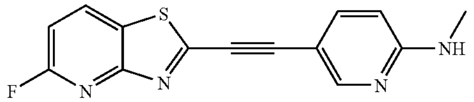
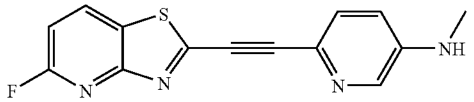
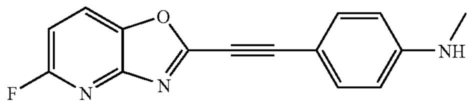
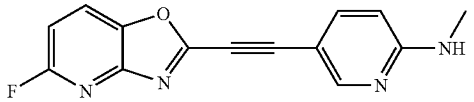
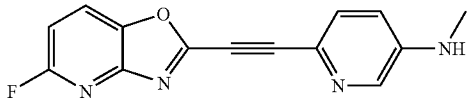
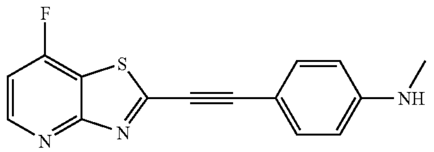

-continued
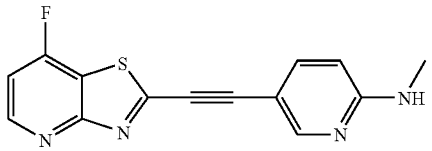
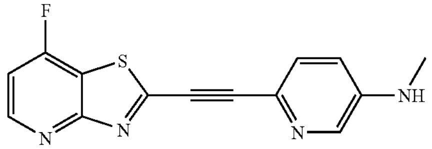
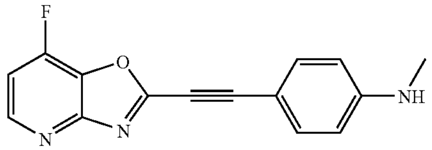
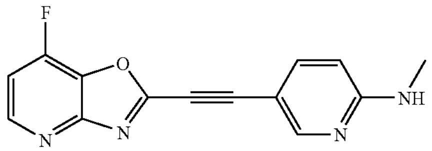
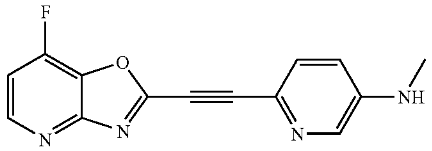
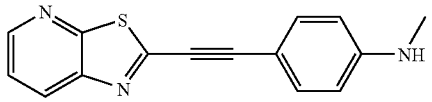
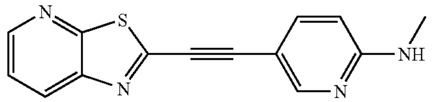
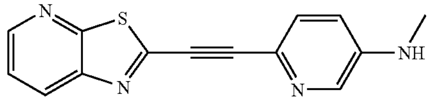
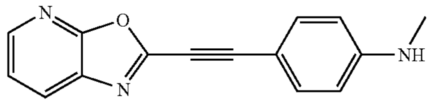
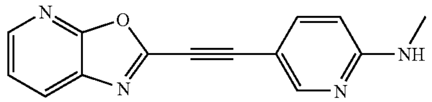
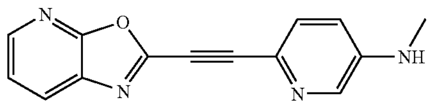
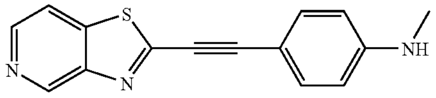
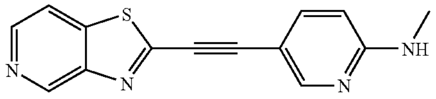
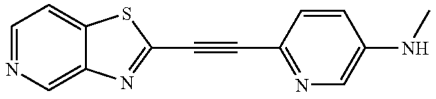
-continued
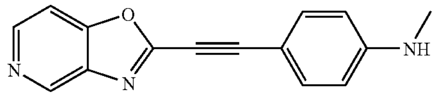
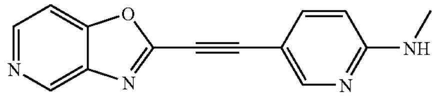
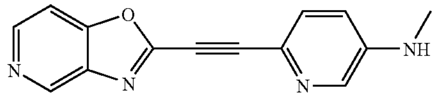
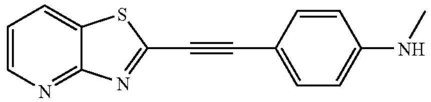
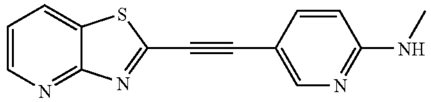
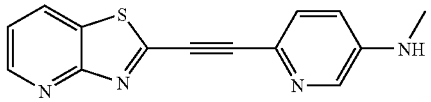
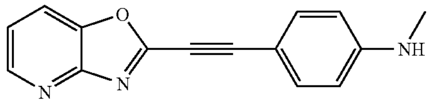
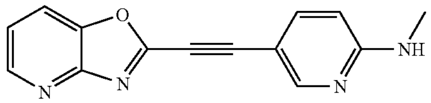
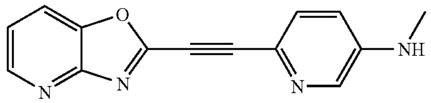
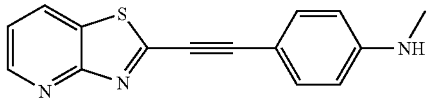
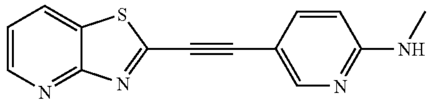
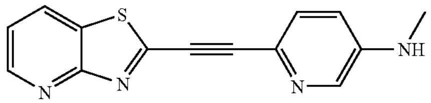
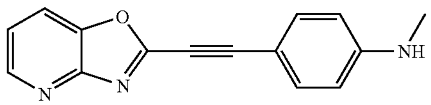
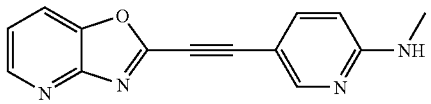
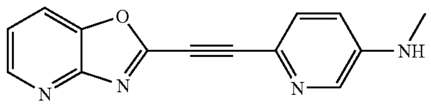
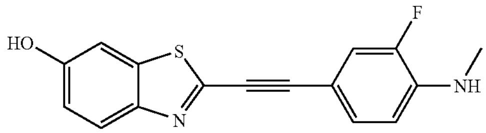

-continued

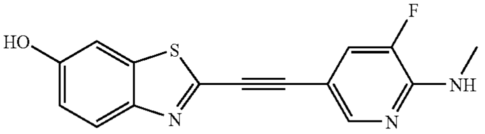

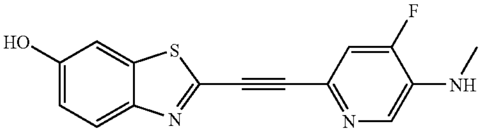

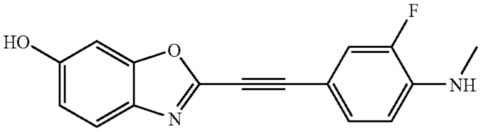

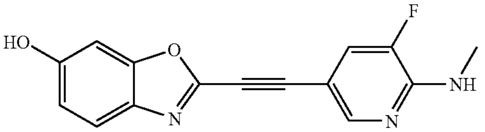

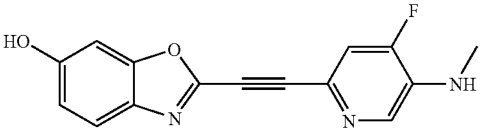

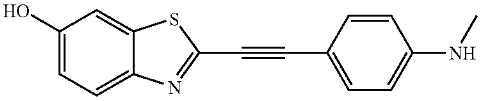

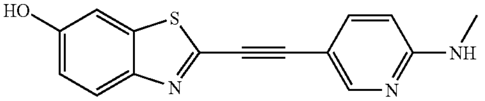

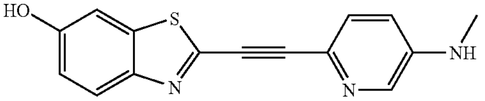

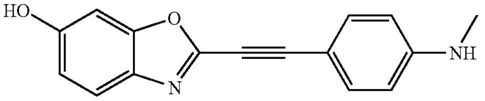

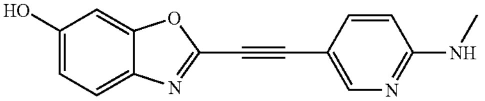

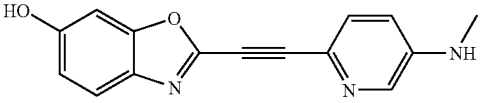

The present invention also includes stereoisomers of compounds of formula (I). Such stereoisomers include, but are not limited to mixtures of enantiomers and diastereomers as well as individual enantiomers and diastereomers.

When any variable occurs more than one time in any constituent of formula (I), its definition in each instance is independent of its definition at any other instance. Also, combinations of substituents and/or variables are permissible only if such combinations result in stable compounds.

The compounds of formula (I) may also be solvated, especially hydrated. Hydration may occur during preparation of the compounds or compositions comprising the compounds of formula (I), or hydration may occur over time due to hydroscopic nature of the compounds.

The compounds of formula (I) can be prepared by the application or adaptation of known methods (i.e. methods heretofore used (methods A-S, as presented in detail in EXPERIMENTAL EXAMPLES section) or described in the chemical literature.

Another embodiment of the present invention relates to a method of imaging amyloid deposits and/or tau aggregates. When the compounds of formula (I) are used as imaging agents, they are labeled with suitable radioactive isotopes, for example radioactive halogens, such as $^{18}F$, radioactive metals and other detectable radioactive atoms such as $^{11}C$.

In another embodiment, the present invention relates to radiolabeled compounds of formulas (II) and (III) as imaging agents. These imaging agents are unique as they contain new binding moieties of tightly tethered through the alkyne linker. These binding motifs may interact simultaneously with orthogonal binding sites providing a more complete overview of the biochemical phenomena associated with AD patients.

Another embodiment of the present invention is directed to compounds containing both benzothiazole and acetylene binding motifs, such as W366 and related compounds, which are designed to interact with the orthogonal binding sites of senile plaques, and potentially NFTs. In this regard, these imaging agents offer the potential to provide a more complete dataset of biochemical information. FIGS. 1*a* and 1*b* show examples of brain slice assay used to determine the $IC_{50}$ values of W366 and related compounds.

Another embodiment of the present invention is directed to compounds of formula (I) as imaging agents for tau aggregates.

It has been shown that solutions of the compounds of the present invention when injected intravenously into normal mice, exhibit excellent brain uptake. These compounds also display high binding affinity to tau fibrils. Autoradiography using the present compounds demonstrated labeling of NFTs in AD brain sections. Fluorescence assay data shows the binding ability of these agents to tau aggregates and Aβ fibrils. In neuropathological staining, compounds of the present invention stained amyloid plaques and/or tau aggregates.

The results presented herein are based on the brain section staining studies and autoradiography of tracers in brain sections of three different types (Tau+/Aβ+, Tau−/Aβ+, and Tau−/Aβ−). These results are shown in FIGS. 2-16 and Tables 1-3.

Another embodiment of the present invention is directed to quinoline compounds of formula (I), having extended side chains containing radiolabel as illustrated in Scheme 2. As shown in Scheme 2 and in Table 1, compounds of this class bind to tau proteins. These compounds incorporate extended side chains, especially containing piperidine or morpholine and/or polyethers such as polyethylene glycols (PEG or $-(OCH_2CH_2)_n-$, wherein n can be 1-10, preferably 1-3). These structural features may play a role in binding affinity of these compounds to tau aggregates. Fluorescence assay data show the binding ability of these agents to tau aggregates.

Figure 15:
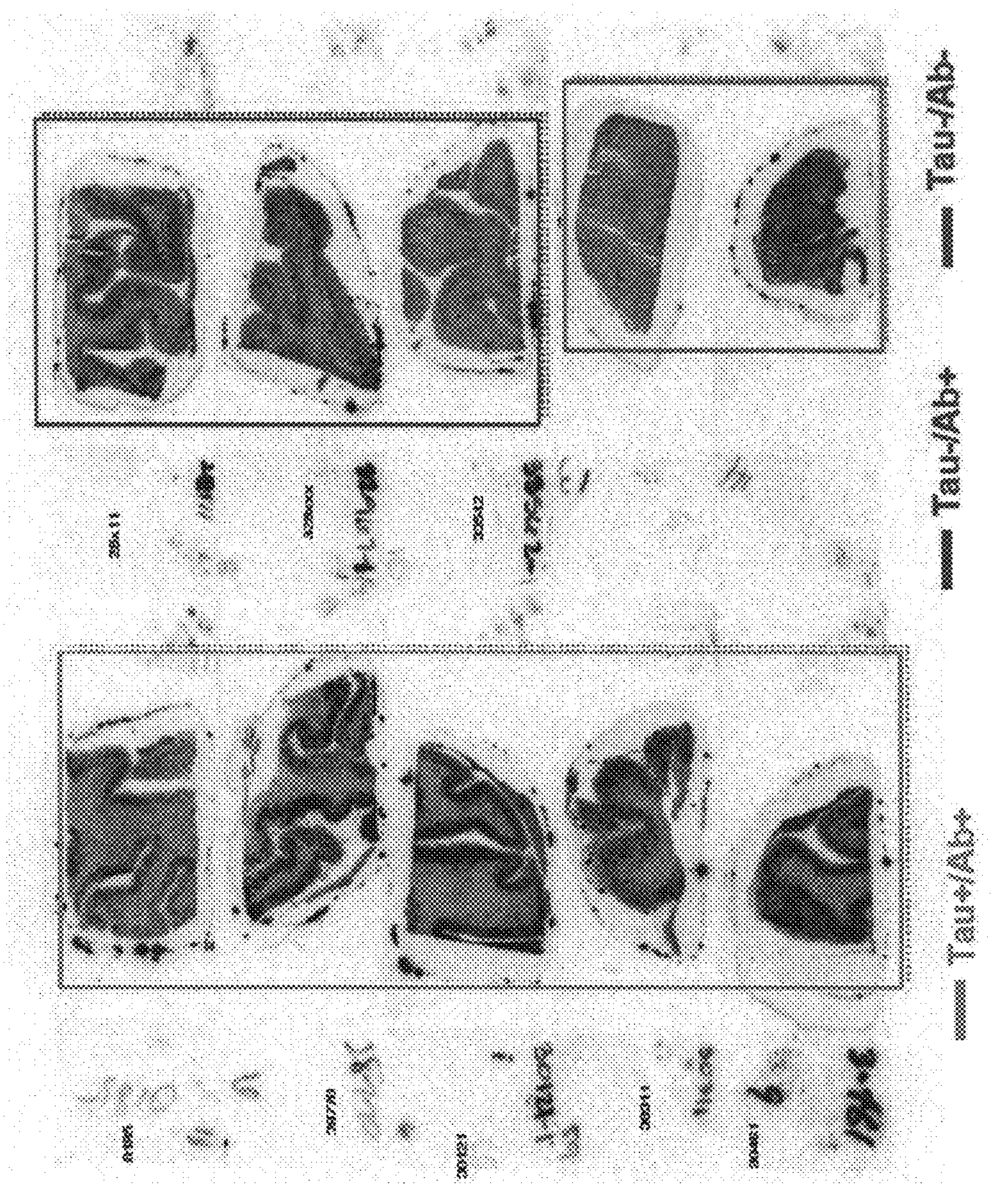
FIG. 15 shows ex vivo autoradiograph images of a preferred compound, T525.
Figure 17:
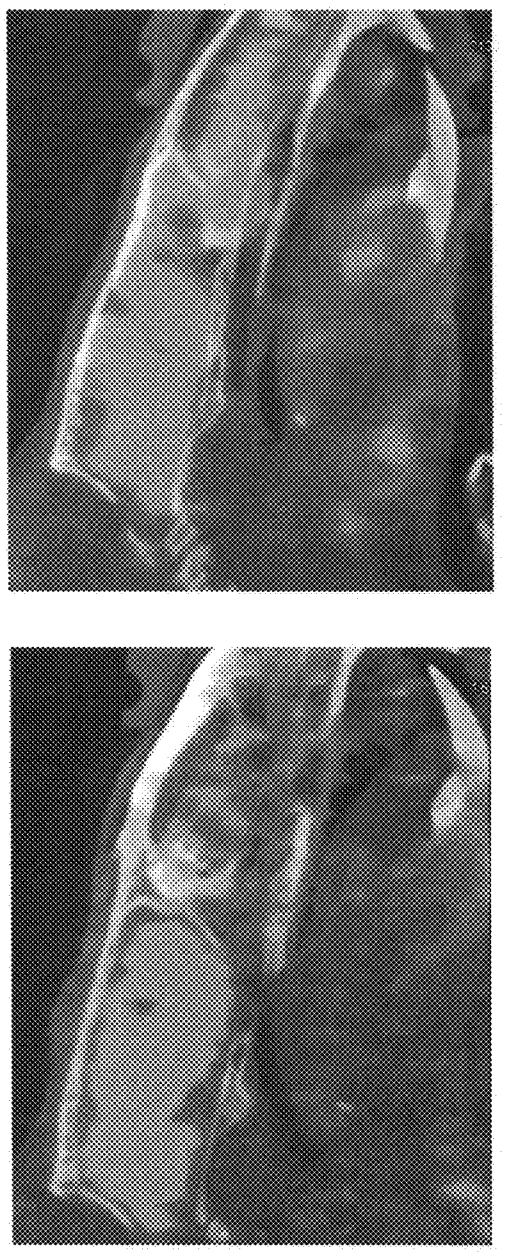
FIG. 17 shows brain images (brain uptake) for tracer T114.
Figure 18:
FIG. 18 shows brain images (brain uptake) for tracer T442.
Figure 19:
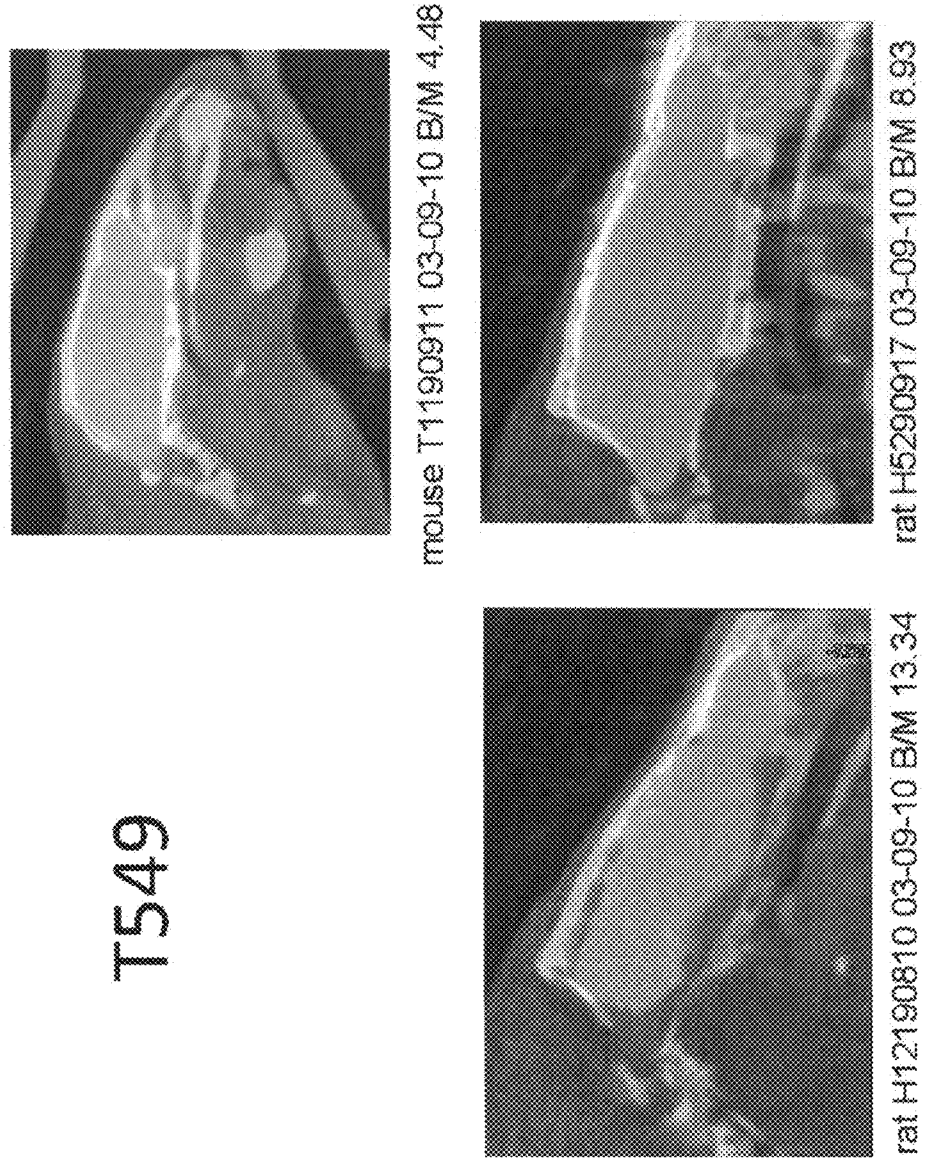
FIG. 19 shows brain images (brain uptake) for tracer T549.
Figure 20:
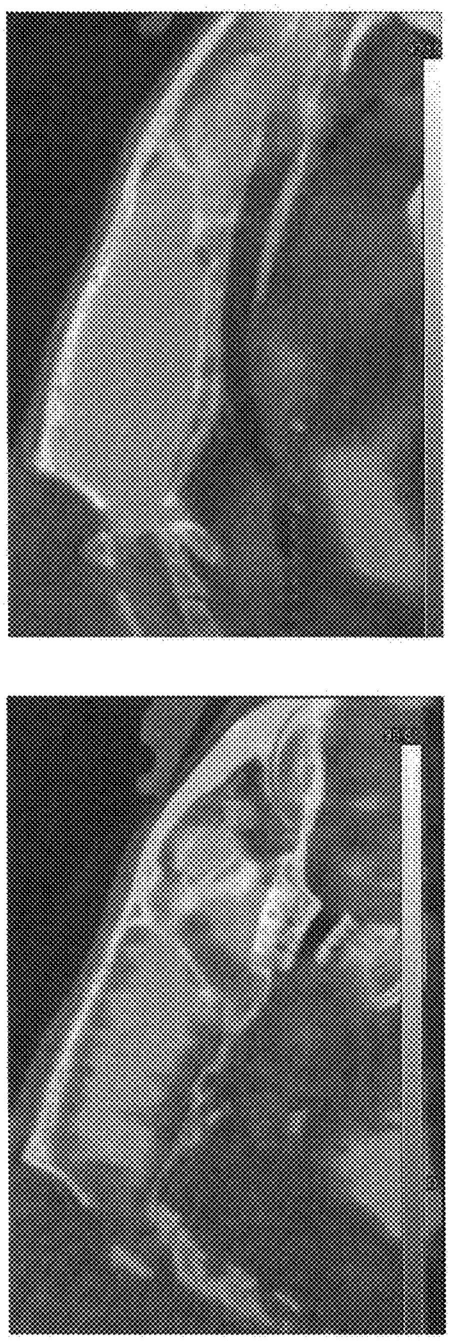
FIG. 20 shows brain images (brain uptake) for tracer T525.
Figure 21:
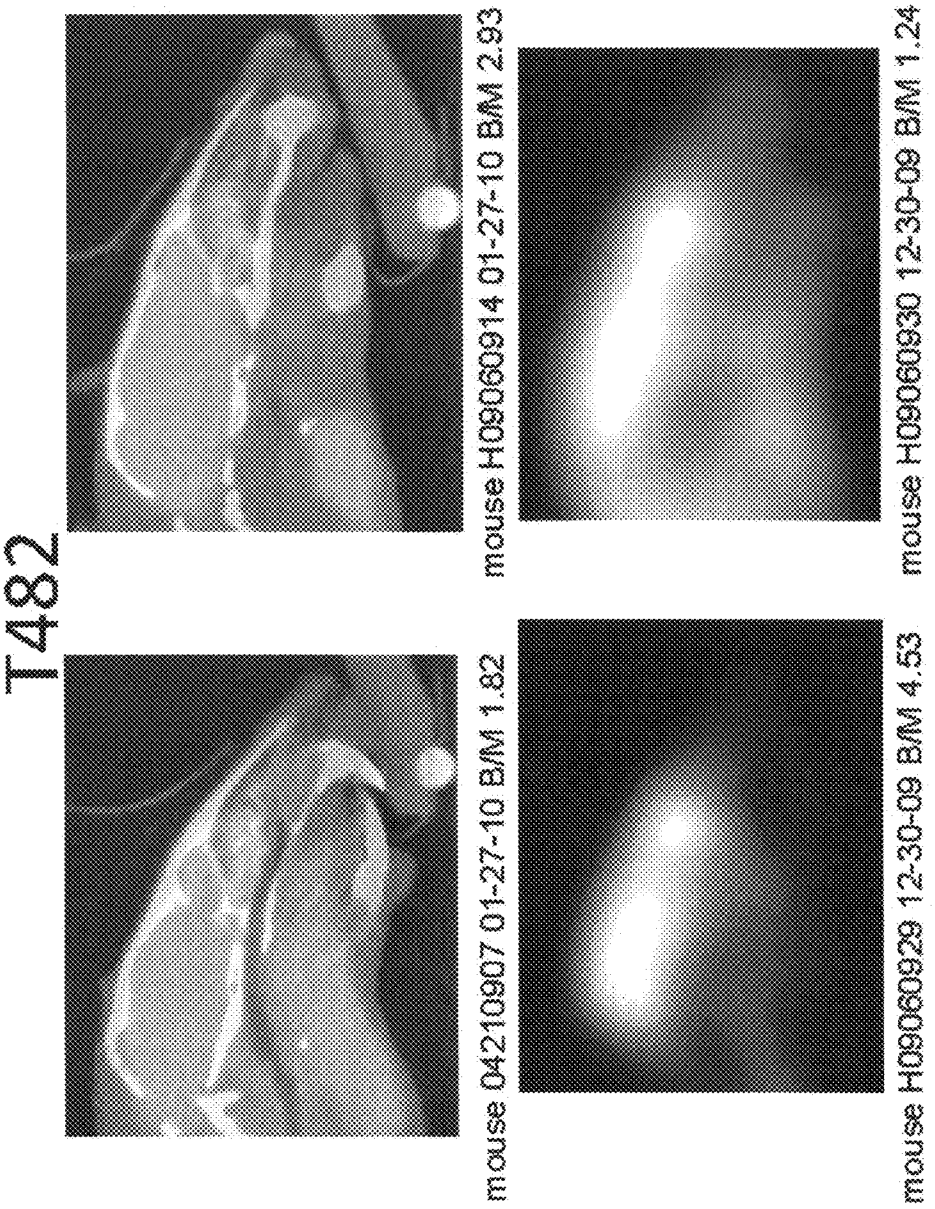
FIG. 21 shows brain images (brain uptake) for tracer T482.
Figure 22:
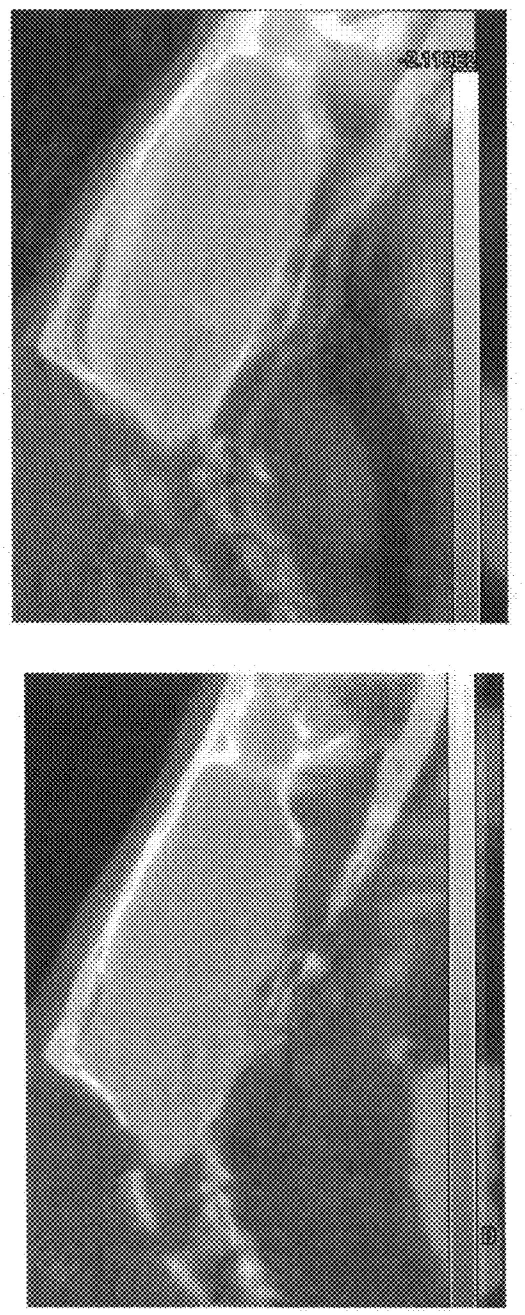
FIG. 22 shows brain images (brain uptake) for tracer T510.

FIGS. 12, 13*a*-13*b*, and 14 show binding of preferred fluorescent compounds T539, T499, and T525 to AD brain sections confirmed by immunostaining with tau or Aβ antibodies. FIG. 15 show ex vivo autoradiograph images of T525, in three different types of brain sections: Aβ+/tau− brains contain Aβ plaques, but no tau aggregates (diagnosis by brain bank as non-AD donor); Aβ+/tau+ brains contain both .Aβ plaques and tau aggregates (diagnosed by brain bank as AD patient), and normal (control) brains. The presence or absence of Aβ and/or tau is confirmed by immunostaining.

Scheme 2.
Qualitative results of Tau/Ab (also used herin as Ab) binding of flourescent compounds in brain section (4+ is the strongest, 1+ is the weakest
T411
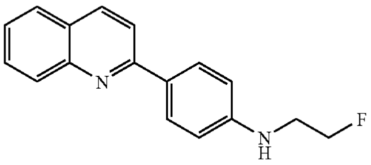
(tau 4+/Ab 4+)
T442
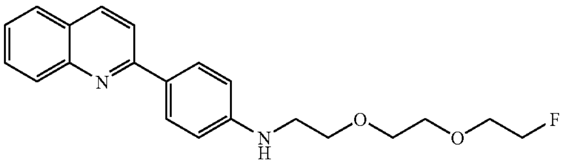
(tau 3+/Ab 2+)
T466
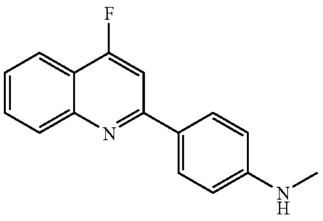
(tau 3+/Ab 3+)
T499
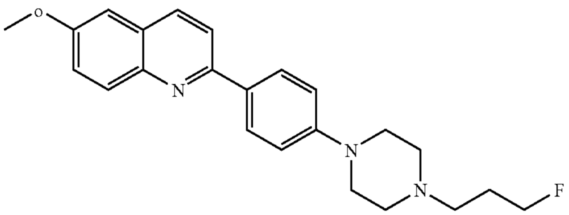
(tau 4+/Ab 1+)
T530
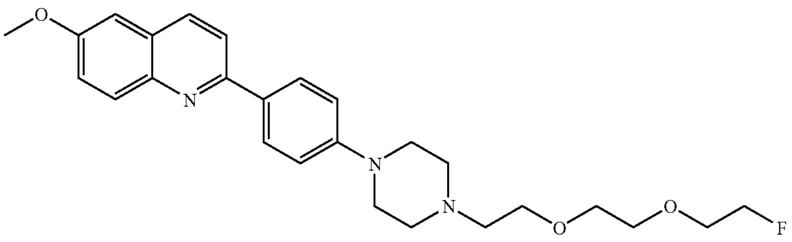
(tau 4+/Ab 2+)
T510
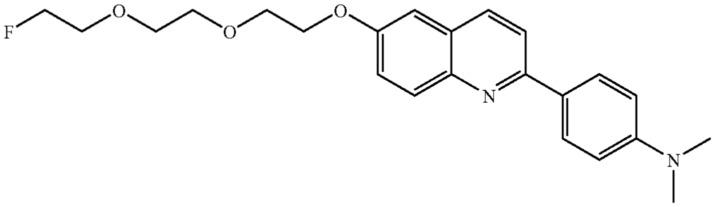
(tau 3+/Ab 2+)
T550
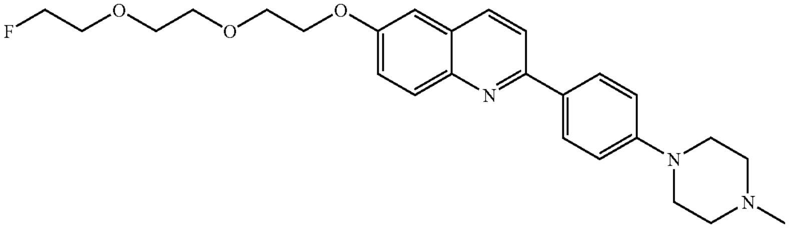
(tau 4+/Ab 1+)

-continued
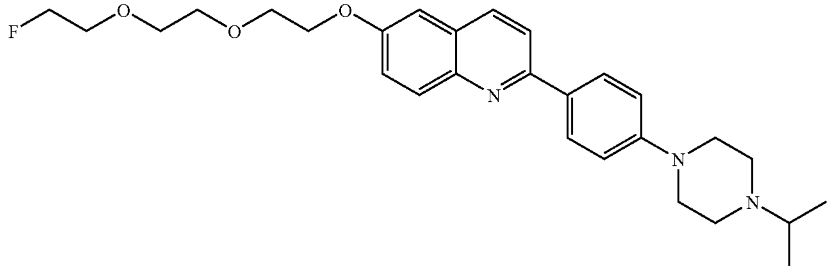
T539
(tau 3+/Ab 1+)
TABLE 1
Representative examples of quinoline compounds of the present invention.
| Comp. ID | Stucture | FW | MW | Brain Section Staining | cLogP |
|---|---|---|---|---|---|
| T046 | 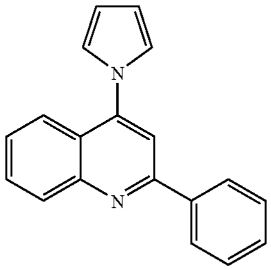 [SMILES: c1ccc(-c2cc(-n3cccc3)c3ccccc3n2)cc1] | 270.3 | | | |
| T047 | 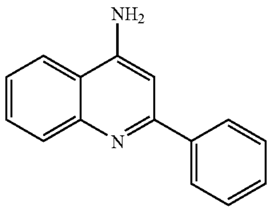 [SMILES: Nc1cc(-c2ccccc2)nc2ccccc12] | 220.3 | 220.1 | | |
| T048 | 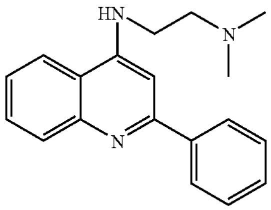 [SMILES: CN(C)CCNc1cc(-c2ccccc2)nc2ccccc12] | 291.4 | 291.2 | binds to Ab (amyloid) (100 uM) | |
| T049 | 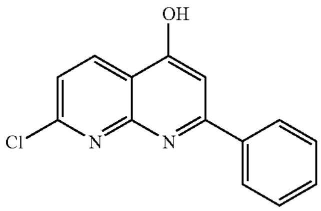 [SMILES: Oc1cc(-c2ccccc2)nc2nc(Cl)ccc12] | 256.7 | 256 | | |
| T050 | 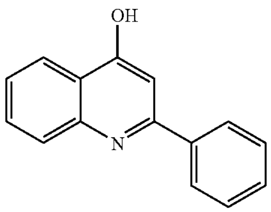 [SMILES: Oc1cc(-c2ccccc2)nc2ccccc12] | 221.3 | 221.1 | | |

TABLE 1-continued
| Comp. ID | Stucture | FW | MW | Brain Section Staining | cLogP |
|---|---|---|---|---|---|
| Representative examples of quinoline compounds of the present invention. | | | | | |
| T051 | 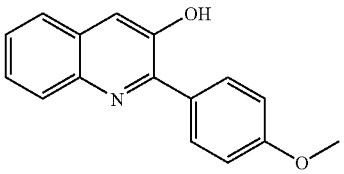 [SMILES: COc1ccc(-c2nc3ccccc3cc2O)cc1] | 251.3 | 251.1 | | |
| T123 | 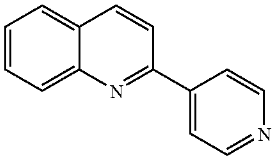 [SMILES: c1ccc2nc(-c3ccncc3)ccc2c1] | 206.2 | 206.1 | No fluorescence is detected at 100 uM | |
| T124 | 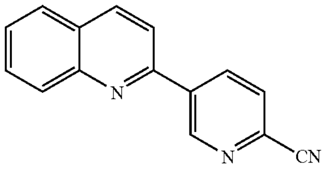 [SMILES: N#Cc1ccc(-c2ccc3ccccc3n2)cn1] | 231.3 | 231.1 | | |
| T125 | 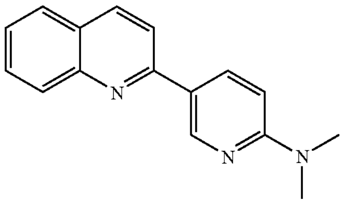 [SMILES: CN(C)c1ccc(-c2ccc3ccccc3n2)cn1] | 249.3 | 249.1 | staining shows strong binding to tau | |
| T126 | 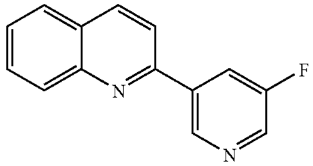 [SMILES: Fc1cncc(-c2ccc3ccccc3n2)c1] | 224.2 | 224.1 | | |
| T127 | 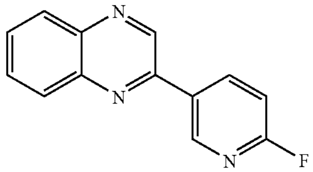 [SMILES: Fc1ccc(-c2cnc3ccccc3n2)cn1] | 225.2 | 225.1 | | |
| T128 | 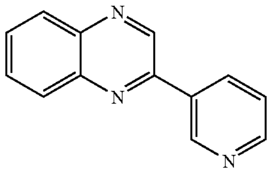 [SMILES: c1cncc(-c2cnc3ccccc3n2)c1] | 207.2 | 207.1 | | |
| T138 | 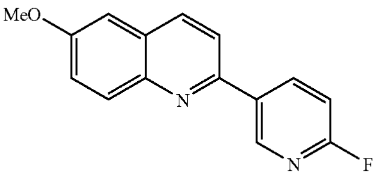 [SMILES: COc1ccc2nc(-c3ccc(F)nc3)ccc2c1] | 254.3 | 254.1 | | |

TABLE 1-continued
| Representative examples of quinoline compounds of the present invention. | | | | | |
|---|---|---|---|---|---|
| Comp. ID | Stucture | FW | MW | Brain Section Staining | cLogP |
| T139 | 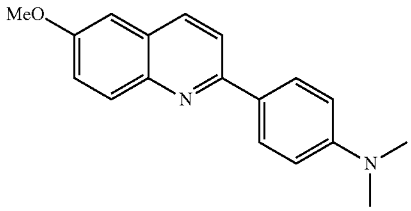 [SMILES: COc1ccc2nc(-c3ccc(N(C)C)cc3)ccc2c1] | 278.4 | 278.1 | binds to amyloid and Tau | |
| T407 | 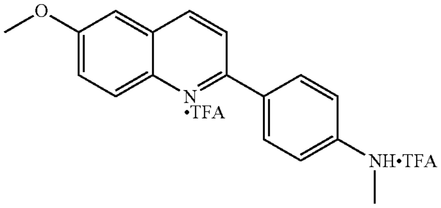 | 458.4 | | | |
| T409 | 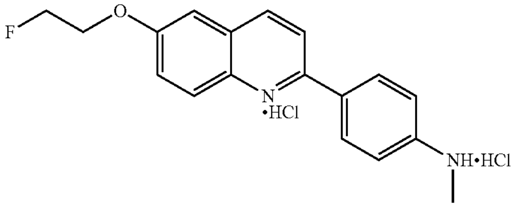 | 369.3 | | binds to amyloid | |
| T411 | 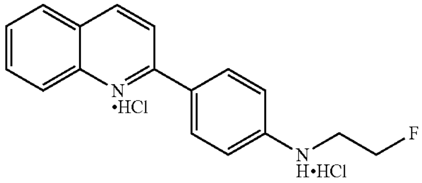 | 339.2 | | binds to tau, weakly binds to Ab. (100 uM) | |
| T412 | 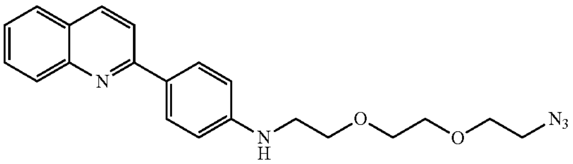 [SMILES: [N-]=[N+]=NCCOCCOCCNc1ccc(-c2ccc3ccccc3n2)cc1] | 377.4 | | binds to tau but not to amyloid | |
| T420 | 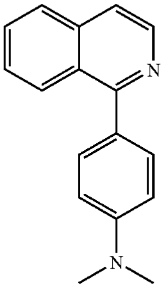 [SMILES: CN(C)c1ccc(-c2nccc3ccccc23)cc1] | 248.3 | | | |

TABLE 1-continued
Representative examples of quinoline compounds of the present invention.
| Comp. ID | Stucture | FW | MW | Brain Section Staining | cLogP |
|---|---|---|---|---|---|
| T427 | 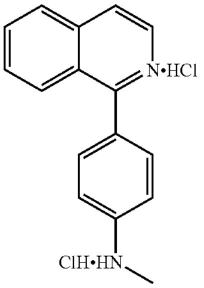 | 307.2 | | | |
| T428 | 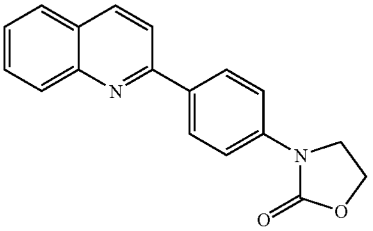 [SMILES: O=C1OCCN1c1ccc(-c2ccc3ccccc3n2)cc1] | 290.3 | | | |
| T429 | 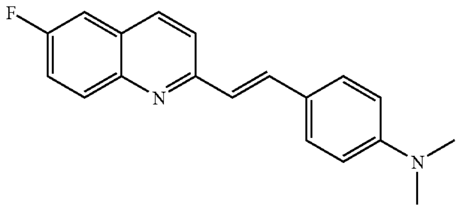 [SMILES: CN(C)c1ccc(/C=C/c2ccc3cc(F)ccc3n2)cc1] | 292.4 | | binds to Ab | |
| T433 | 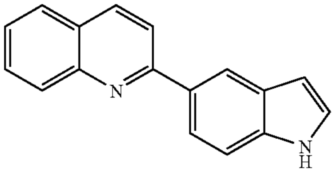 $2CF_3CO_2H$ | 472.3 | | | |
| T434 | 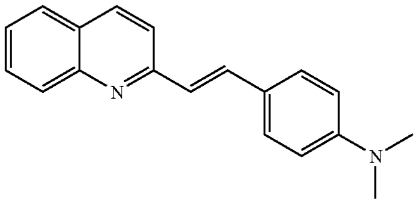 [SMILES: CN(C)c1ccc(/C=C/c2ccc3ccccc3n2)cc1] | 274.4 | | | |
| T442 | 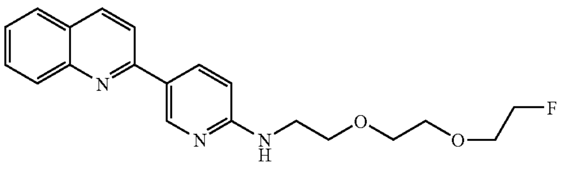 [SMILES: FCCOCCOCCNc1ccc(-c2ccc3ccccc3n2)cn1] | | | binds to Tau and Ab | 3.8 |

TABLE 1-continued
Representative examples of quinoline compounds of the present invention.
| Comp. ID | Stucture | FW | MW | Brain Section Staining | cLogP |
|---|---|---|---|---|---|
| T443 | 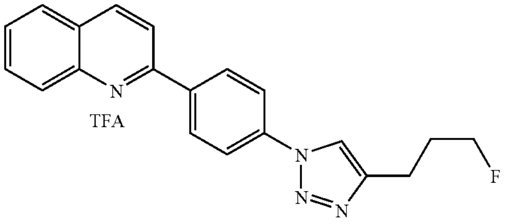 [SMILES: FCCCc1cn(-c2ccc(-c3ccc4ccccc4n3)cc2)nn1] | 429.4 | | | |
| T445 | 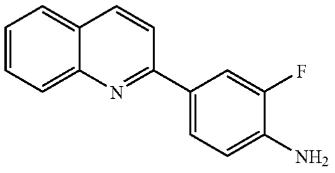 [SMILES: Nc1ccc(-c2ccc3ccccc3n2)cc1F] | 238.3 | | binds to Tau | |
| T446 | 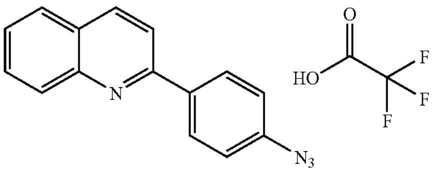 | 360.3 | | | |
| T447 | 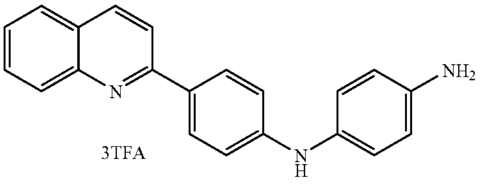 [SMILES: Nc1ccc(Nc2ccc(-c3ccc4ccccc4n3)cc2)cc1] | 311.4 | | | |
| T453 | 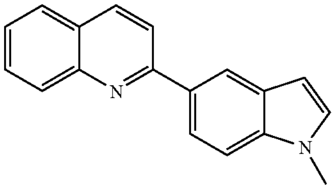 [SMILES: Cn1ccc2cc(-c3ccc4ccccc4n3)ccc21] | 258.3 | | binds to Ab | |
| T454 | 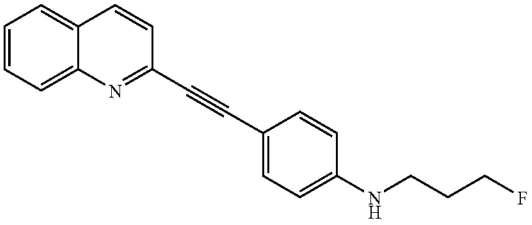 [SMILES: FCCCNc1ccc(C#Cc2ccc3ccccc3n2)cc1] | 304.4 | | binds to Ab | |
| T455 | 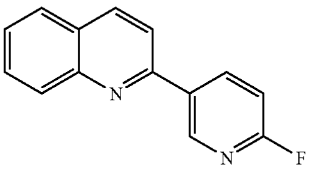 [SMILES: Fc1ccc(-c2ccc3ccccc3n2)cn1] | 224.2 | | No fluorescence | |

TABLE 1-continued
Representative examples of quinoline compounds of the present invention.
| Comp. ID | Stucture | FW | MW | Brain Section Staining | cLogP |
|---|---|---|---|---|---|
| T458 | 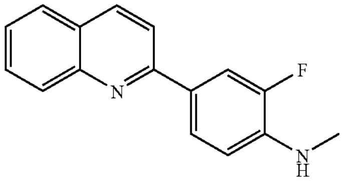 [SMILES: CNc1ccc(-c2ccc3ccccc3n2)cc1F] | 252.3 | | binds to amyloid and tau | 4.1 |
| T461 | 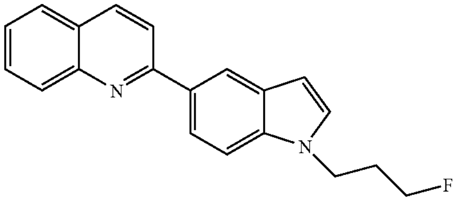 [SMILES: FCCCn1ccc2cc(-c3ccc4ccccc4n3)ccc21] | 304.4 | | | |
| T463 | 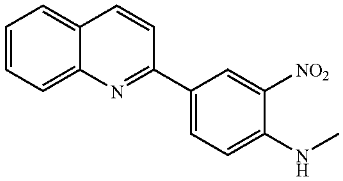 [SMILES: CNc1ccc(-c2ccc3ccccc3n2)cc1[N+](=O)[O-]] | 279.3 | | | |
| T466 | 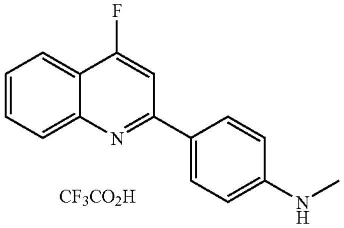 [SMILES: CNc1ccc(-c2cc(F)c3ccccc3n2)cc1 ; "CF3CO2H"] $CF_3CO_2H$ | 366.3 | | binds to tau and amyloid | 4 |
| T467 | 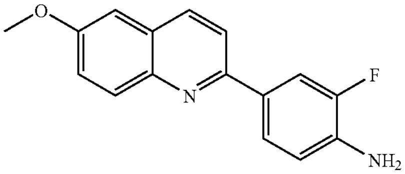 [SMILES: COc1ccc2nc(-c3ccc(N)c(F)c3)ccc2c1] | 268.3 | | binds to tau and amyloid | 3.6 |
| T475 | 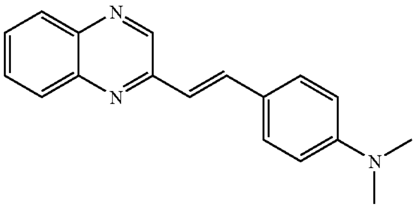 [SMILES: CN(C)c1ccc(/C=C/c2cnc3ccccc3n2)cc1] | 275.4 | | binds to Ab mostly | |
| T476 | 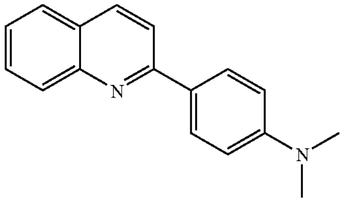 [SMILES: CN(C)c1ccc(-c2ccc3ccccc3n2)cc1] | 248.3 | | | |

TABLE 1-continued
Representative examples of quinoline compounds of the present invention.
| Comp. ID | Stucture | FW | MW | Brain Section Staining | cLogP |
|---|---|---|---|---|---|
| T477 | 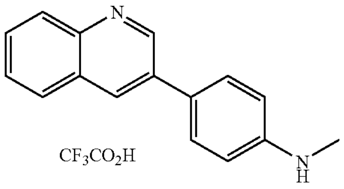 [SMILES: CNc1ccc(-c2cnc3ccccc3c2)cc1 ; "CF3CO2H"] | 348.3 | | binds to Ab mostly | 3.6 |
| T480 | 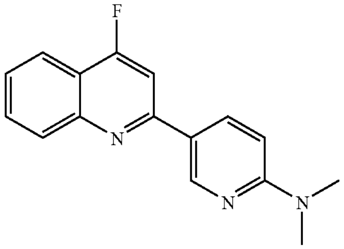 [SMILES: CN(C)c1ccc(-c2cc(F)c3ccccc3n2)cn1] | 267.3 | | | |
| T483 | 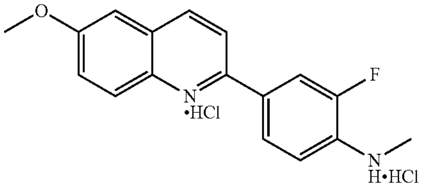 | 355.2 | | Mostly binds to Tau | |
| T484 | 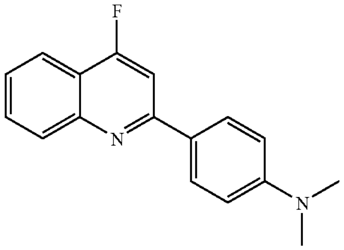 [SMILES: CN(C)c1ccc(-c2cc(F)c3ccccc3n2)cc1] | 266.3 | | binds to Tau and Ab; | 4.6 |
| T485 | 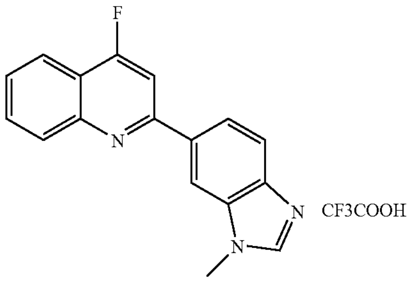 [SMILES: Cn1cnc2ccc(-c3cc(F)c4ccccc4n3)cc21 ; "CF3COOH"] | 391.3 | | weakly binds to Ab | |
| T490 | 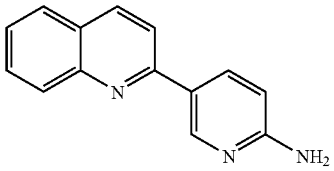 [SMILES: Nc1ccc(-c2ccc3ccccc3n2)cn1] | 221.3 | | | 2.5 |

TABLE 1-continued
Representative examples of quinoline compounds of the present invention.
| Comp. ID | Stucture | FW | MW | Brain Section Staining | cLogP |
|---|---|---|---|---|---|
| T491 | 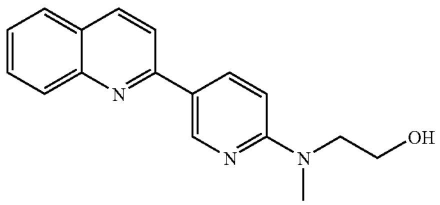 [SMILES: CN(CCO)c1ccc(-c2ccc3ccccc3n2)cn1] | 279.3 | | | |
| T492 | 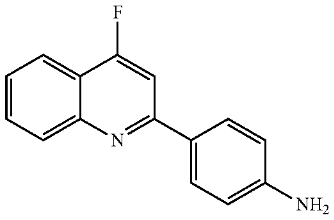 [SMILES: Nc1ccc(-c2cc(F)c3ccccc3n2)cc1] | 238.3 | | | 3.3 |
| T498 | 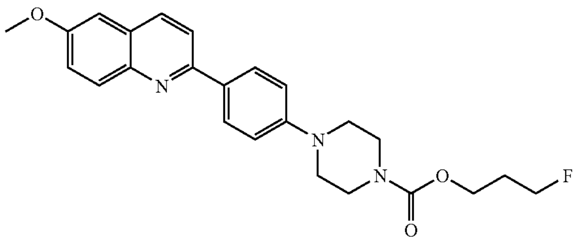 [SMILES: COc1ccc2nc(-c3ccc(N4CCN(C(=O)OCCCF)CC4)cc3)ccc2c1] | 423.5 | | | 5.2 |
| T499 | 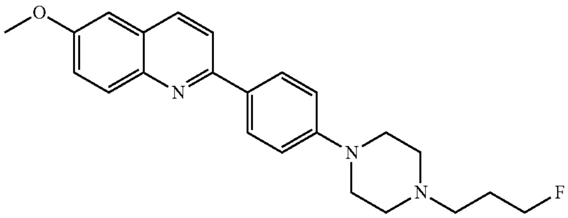 [SMILES: COc1ccc2nc(-c3ccc(N4CCN(CCCF)CC4)cc3)ccc2c1] | 379.5 | | Binds to Tau mostly (+++). Weakly binds to Ab (+) | 4.9 |
| T500 | 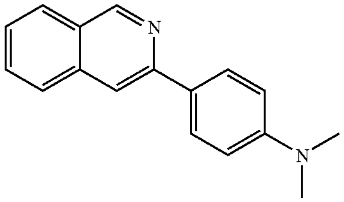 [SMILES: CN(C)c1ccc(-c2cc3ccccc3cn2)cc1] | 248.3 | | | 4.2 |
| T501 | 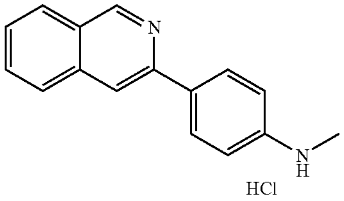 [SMILES: CNc1ccc(-c2cc3ccccc3cn2)cc1 ; Cl] | 270.8 | | No fluorescence | 3.6 |
| T502 | 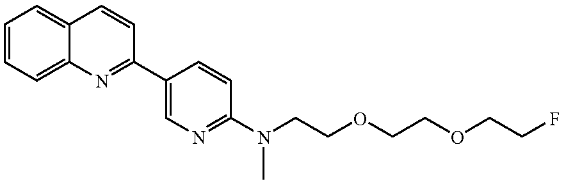 [SMILES: CN(CCOCCOCCF)c1ccc(-c2ccc3ccccc3n2)cn1] | 369.4 | | | 3.5 |

TABLE 1-continued
| Representative examples of quinoline compounds of the present invention. | | | | | |
|---|---|---|---|---|---|
| Comp. ID | Stucture | FW | MW | Brain Section Staining | cLogP |
| T504 | 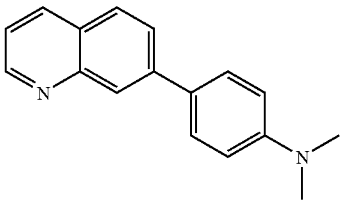 [SMILES: CN(C)c1ccc(-c2ccc3cccnc3c2)cc1] | 248.3 | | binds to Ab strongly (+++) | 4.1 |
| T505 | 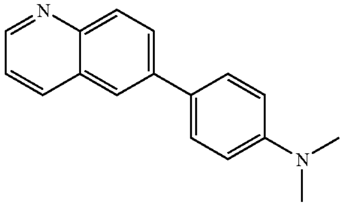 [SMILES: CN(C)c1ccc(-c2ccc3ncccc3c2)cc1] | 248.3 | | binds to Ab weakly (+) | 4.1 |
| T507 | 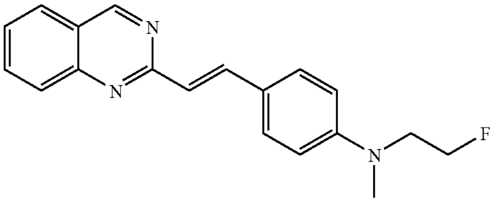 [SMILES: CN(CCF)c1ccc(/C=C/c2ncc3ccccc3n2)cc1] | 307.4 | | Binds to Ab (+++) | 4.1 |
| T510 | 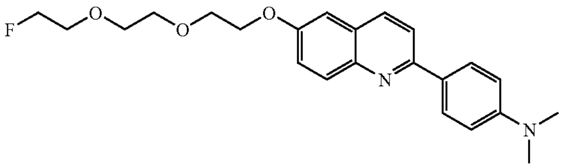 [SMILES: CN(C)c1ccc(-c2ccc3cc(OCCOCCOCCF)ccc3n2)cc1] | 398.5 | | Binds both Tau (+++) and Ab (++) | 4.5 |
| T513 | 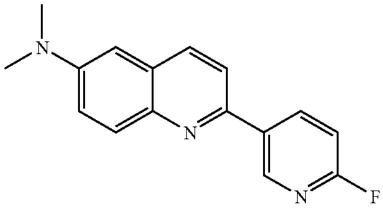 [SMILES: CN(C)c1ccc2nc(-c3ccc(F)nc3)ccc2c1] | 267.3 | | Binds to Tau (+) and Ab (++) | 3.5 |
| T514 | 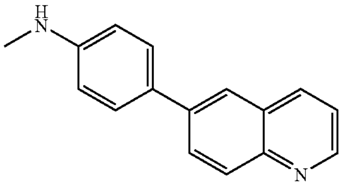 [SMILES: CNc1ccc(-c2ccc3ncccc3c2)cc1] | 234.3 | | | 3.4 |
| T515 | 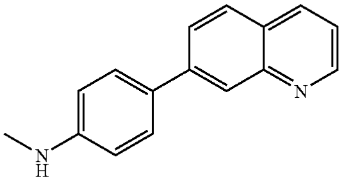 [SMILES: CNc1ccc(-c2ccc3cccnc3c2)cc1] | 234.3 | | weakly to Ab (+) | 3.4 |

TABLE 1-continued
Representative examples of quinoline compounds of the present invention.
| Comp. ID | Stucture | FW | MW | Brain Section Staining | cLogP |
|---|---|---|---|---|---|
| T517 | 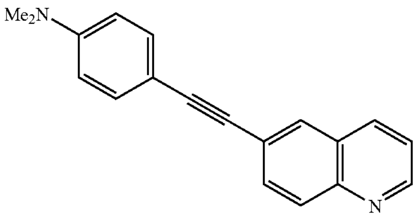 [SMILES: CN(C)c1ccc(C#Cc2ccc3ncccc3c2)cc1] | 272 3 | 272.3 | Binds to Ab (+++) | 4.8 |
| T519 | 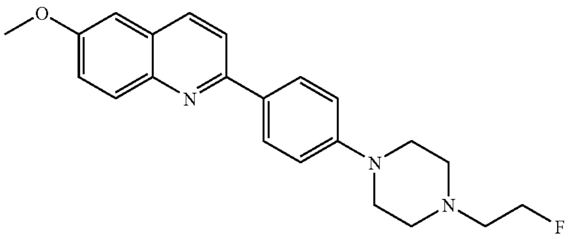 [SMILES: COc1ccc2nc(-c3ccc(N4CCN(CCF)CC4)cc3)ccc2c1] | 365.4 | 365.4 | binds to Tau strongly (+++); weakly to Ab (+). | 4.7 |
| T523 | 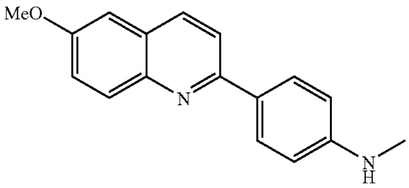 [SMILES: CNc1ccc(-c2ccc3cc(OC)ccc3n2)cc1] | 264.3 | 264.3 | Binds to Tau (++++). | 4.1 |
| T525 | 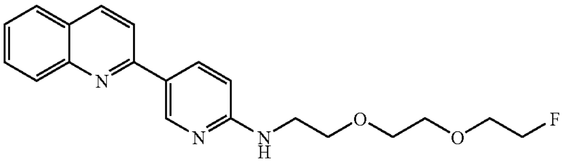 [SMILES: FCCOCCOCCNc1ccc(-c2ccc3ccccc3n2)cn1] | 355.4 | 355.4 | Binds to Tau (++); Binds to Ab (+) | 3.2 |
| T530 | 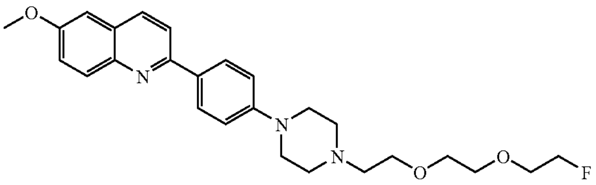 [SMILES: COc1ccc2nc(-c3ccc(N4CCN(CCOCCOCCF)CC4)cc3)ccc2c1] | 453.6 | | Binds to Tau (++++); Binds to Ab (+) | 4.6 |
| T531 | 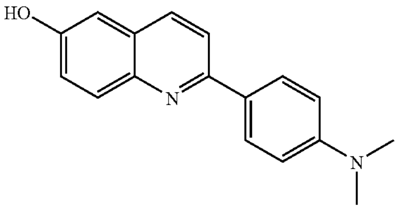 [SMILES: CN(C)c1ccc(-c2ccc3cc(O)ccc3n2)cc1] | 264.4 | 264.4 | Binds to Tau. Binds to Ab (+) | 4.4 |
| T535 | 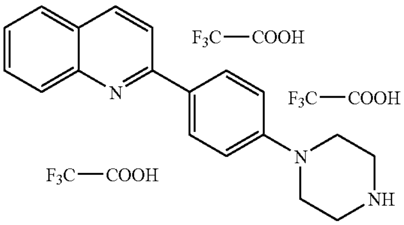 | 631.4 | 289.4 | | 3.7 |

TABLE 1-continued
Representative examples of quinoline compounds of the present invention.
| Comp. ID | Stucture | FW | MW | Brain Section Staining | cLogP |
|---|---|---|---|---|---|
| T536 | 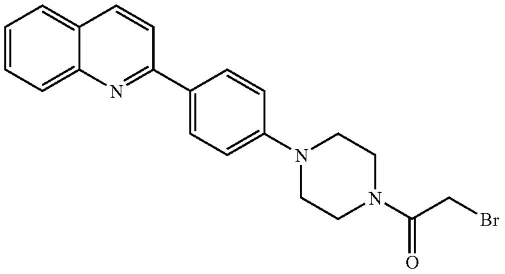 [SMILES: O=C(CBr)N1CCN(c2ccc(-c3ccc4ccccc4n3)cc2)CC1] | 410.3 | 410.3 | | 4 |
| T537 | 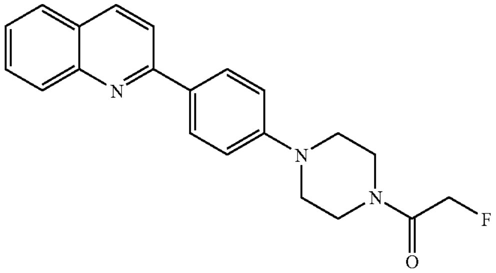 [SMILES: O=C(CF)N1CCN(c2ccc(-c3ccc4ccccc4n3)cc2)CC1] | 349.4 | 349.4 | | 3.4 |
| T539 | 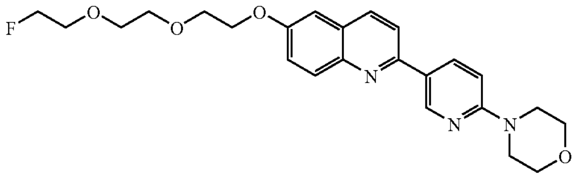 [SMILES: FCCOCCOCCOc1ccc2nc(-c3ccc(N4CCOCC4)nc3)ccc2c1] | 441.5 | 441.5 | | 2.9 |
| T545 | 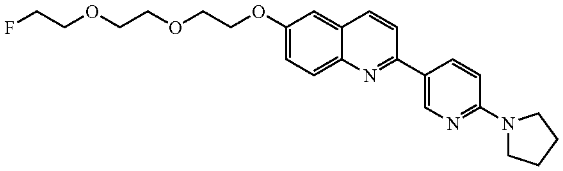 [SMILES: FCCOCCOCCOc1ccc2nc(-c3ccc(N4CCCC4)nc3)ccc2c1] | 425.5 | 425.5 | Binds to Tau (+) and Ab (+) | 3.7 |
| T549 | 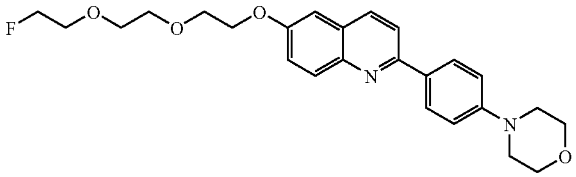 [SMILES: FCCOCCOCCOc1ccc2nc(-c3ccc(N4CCOCC4)cc3)ccc2c1] | 440.5 | 440.5 | Binds to Tau | 3.8 |
| T550 | 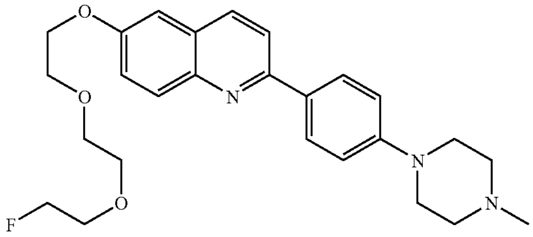 [SMILES: CN1CCN(c2ccc(-c3ccc4cc(OCCOCCOCCF)ccc4n3)cc2)CC1] | 453.6 | 453.6 | Binds to Tau | 4.4 |

TABLE 1-continued

Representative examples of quinoline compounds of the present invention.

| Comp. ID | Stucture | FW | MW | Brain Section Staining | cLogP |
|---|---|---|---|---|---|
| T559 | 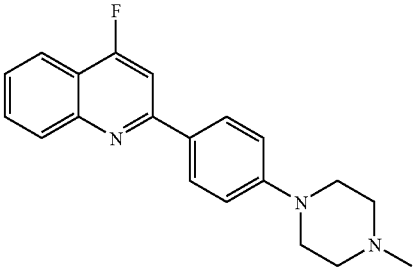 [SMILES: CN1CCN(c2ccc(-c3cc(F)c4ccccc4n3)cc2)CC1] | 321.4 | 321.4 | No fluorescence | 4.5 |
| T565 | 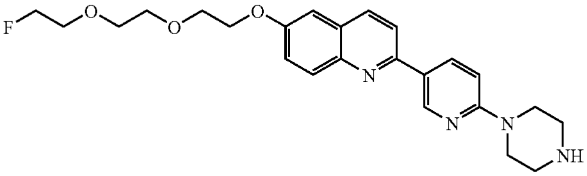 [SMILES: FCCOCCOCCOc1ccc2nc(-c3ccc(N4CCNCC4)nc3)ccc2c1] | 440.5 | 440.5 | | 2.9 |
| T566 | 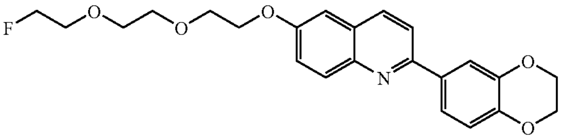 [SMILES: FCCOCCOCCOc1ccc2nc(-c3ccc4c(c3)OCCO4)ccc2c1] | 413.4 | 413.4 | | 4.3 |
| T569 | 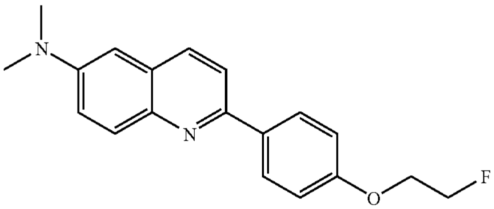 [SMILES: CN(C)c1ccc2nc(-c3ccc(OCCF)cc3)ccc2c1] | 310.4 | 310.4 | | 5 |

Another embodiment of the present invention is directed to acetylene compounds of formula (I) having bicyclic heteroaryl moiety and extended side chains containing radiolabel as illustrated in Scheme 3. As shown in Scheme 3 and in Table 2, compounds of this class have a high binding affinity to tau proteins. These compounds incorporate extended side chains, especially containing polyethers such as PEG in a biaryl alkyne core structure, wherein one of the aryl components is a substituted benzimidazole. Such structural modification leads to an increased selectivity of these compounds.

Scheme 3. Qualitative results of Tau/Aβ binding of fluorescent compounds in brain section (4+ is the strongest, 1+ is the weakest)

T540

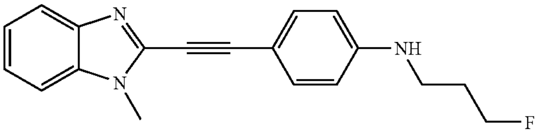

(tau 4+/Ab 1+)

-continued

T465

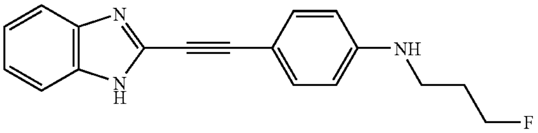

(tau 3+/Ab 2+)

T482

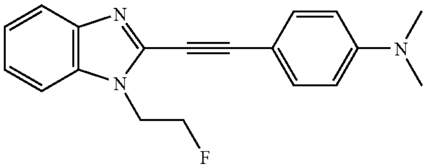

(tau 3+/Ab 1+)

T114

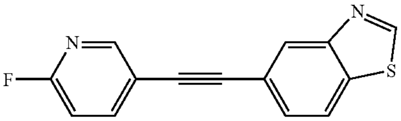

(tau 3+/Ab 3+)

-continued
T527
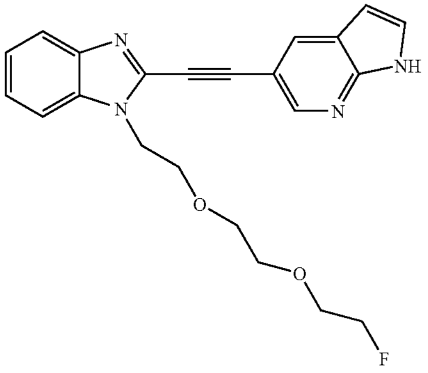
(tau 3+/Ab 1+)
-continued
T541
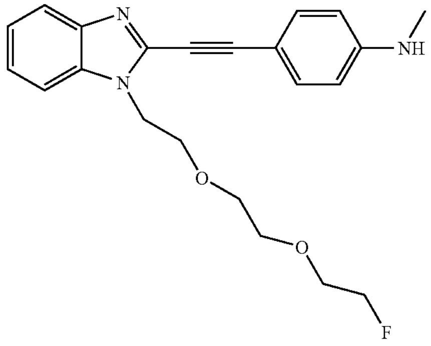
(tau 3+/Ab 1+)
TABLE 2
Representative examples of acetylene compounds of the present invention
| Comp. ID | Stucture | MW | Exact Mass | Brain Section Staining | cLogP |
|---|---|---|---|---|---|
| T110/ W294 | 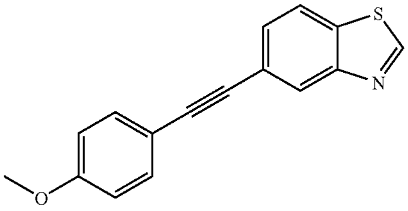 [SMILES: COc1ccc(C#Cc2ccc3scnc3c2)cc1] | 265.33 | | | |
| T114/ W313 | 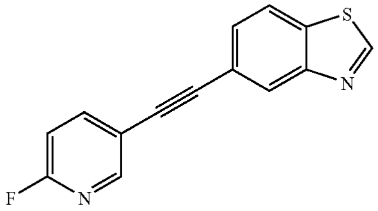 [SMILES: Fc1ccc(C#Cc2ccc3scnc3c2)cn1] | 254.28 | | stains amyloid and tau | |
| T118/ W366 | 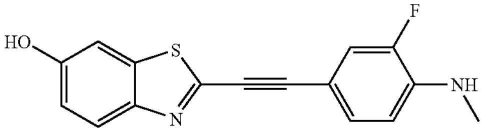 [SMILES: CNc1ccc(C#Cc2nc3ccc(O)cc3s2)cc1F] | 298.33 | | binds to Ab | |
| T444 | 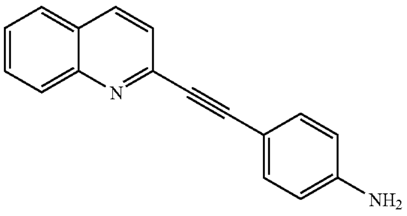 [SMILES: Nc1ccc(C#Cc2ccc3ccccc3n2)cc1] | 244.29 | | | |
| T448 | 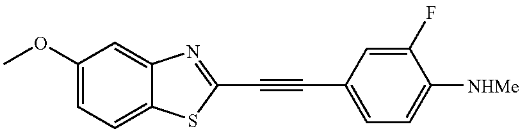 [SMILES: CNc1ccc(C#Cc2nc3cc(OC)ccc3s2)cc1F] | 312.36 | | binds to Ab | |

TABLE 2-continued
Representative examples of acetylene compounds of the present invention
| Comp. ID | Stucture | MW | Exact Mass | Brain Section Staining | cLogP |
|---|---|---|---|---|---|
| T454 | 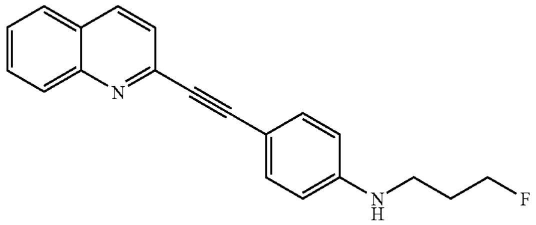 [SMILES: FCCCNc1ccc(C#Cc2ccc3ccccc3n2)cc1] | 304.36 | | binds to Ab | |
| T464 | 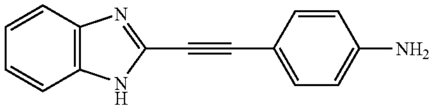 [SMILES: Nc1ccc(C#Cc2nc3ccccc3[nH]2)cc1] | 233.27 | | | |
| T465 | 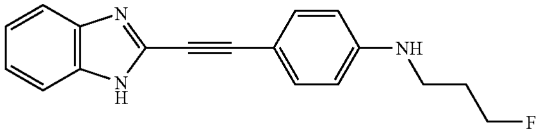 [SMILES: FCCCNc1ccc(C#Cc2nc3ccccc3[nH]2)cc1] | 293.34 | | binds to tau and Ab | 4.2 |
| T481 | 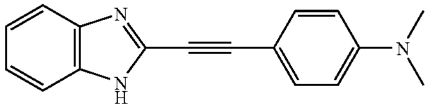 | 261.32 | | | |
| T482 | 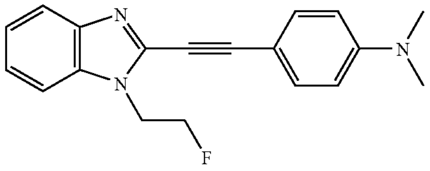 | 307.36 | | Mostly binds to Tau | 4.6 |
| T496 | 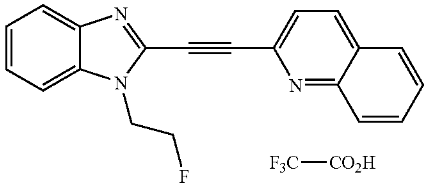 $F_3C—CO_2H$ | 429.37 | | Weakly binds to Ab | 4.3 |
| T508 | 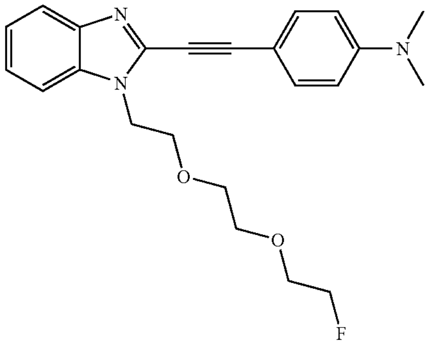 [SMILES: CN(C)c1ccc(C#Cc2nc3ccccc3n2CCOCCOCCF)cc1] | 395.47 | | | 4.2 |
| T516 | 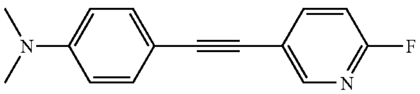 [SMILES: CN(C)c1ccc(C#Cc2ccc(F)nc2)cc1] | 240.28 | | Weakly binds to Tau (+) and Ab (++) | 3.6 |

TABLE 2-continued
| Representative examples of acetylene compounds of the present invention | | | | | |
|---|---|---|---|---|---|
| Comp. ID | Stucture | MW | Exact Mass | Brain Section Staining | cLogP |
| T517 | 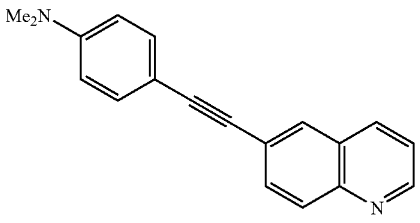 [SMILES: CN(C)c1ccc(C#Cc2ccc3ncccc3c2)cc1] | 272.34 | 272.34 | Binds to Ab(+++) | 4.8 |
| T526 | 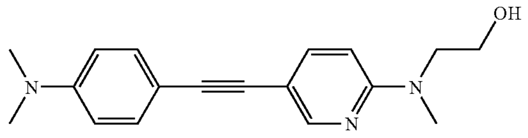 [SMILES: CN(C)c1ccc(C#Cc2ccc(N(C)CCO)nc2)cc1] | 295.38 | 295.38 | Binds to Tau (++); Binds to Ab (+) | 3.4 |
| T527 | 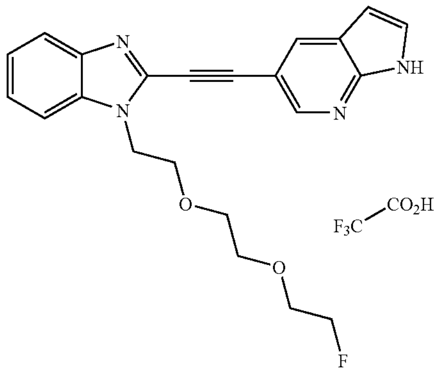 [SMILES: FCCOCCOCCn1c(C#Cc2cnc3[nH]ccc3c2)nc2ccccc21 ; O=C(O)C(F)(F)F] | 506.45 | | Binds to Tau (+++); Binds to Ab (+) | 3.1 |
| T528 | 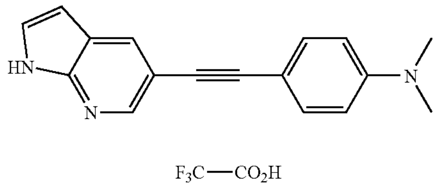 [SMILES: CN(C)c1ccc(C#Cc2cnc3[nH]ccc3c2)cc1 ; O=C(O)C(F)(F)F] | 375.34 | 261.32 | Binds to Tau (++++); Binds to Ab(+) | 3.9 |
| T534 | 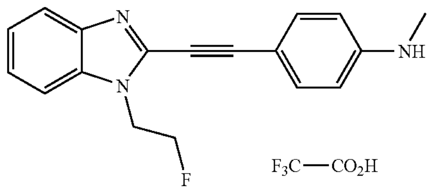 [SMILES: CNc1ccc(C#Cc2nc3ccccc3n2CCF)cc1 ; O=C(O)C(F)(F)F] | 407.36 | 293.34 | | 4 |
| T540 | 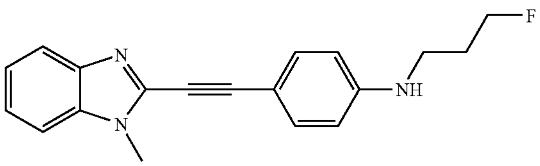 [SMILES: Cn1c(C#Cc2ccc(NCCCF)cc2)nc2ccccc21] | 307.36 | 307.36 | Binds to Tau (++++). Binds to Ab (+) | 4.2 |

TABLE 2-continued
| Representative examples of acetylene compounds of the present invention | | | | | |
|---|---|---|---|---|---|
| Comp. ID | Stucture | MW | Exact Mass | Brain Section Staining | cLogP |
| T541 | 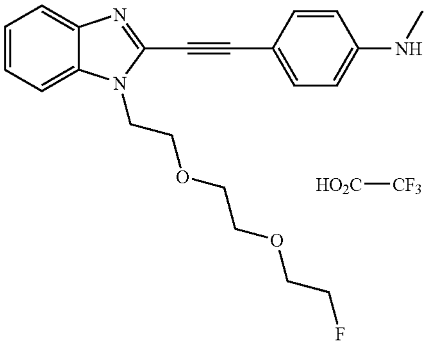 [SMILES: CNc1ccc(C#Cc2nc3ccccc3n2CCOCCOCCF)cc1 ; O=C(O)C(F)(F)F] | 495.47 | 381.44 | Binds to Tau (+++). Binds to Ab (+) | 3.6 |
| T546 | 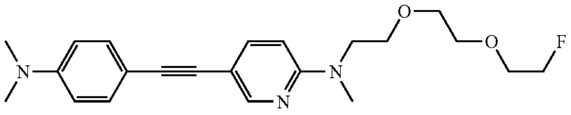 [SMILES: CN(C)c1ccc(C#Cc2ccc(N(C)CCOCCOCCF)nc2)cc1] | 385.48 | 385.48 | | 4.1 |
| T547 | 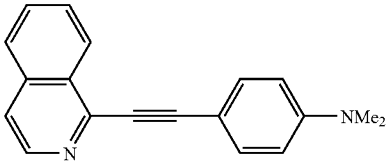 [SMILES: CN(C)c1ccc(C#Cc2nccc3ccccc23)cc1] | 272.34 | 272.34 | | 4.6 |
| T551 | 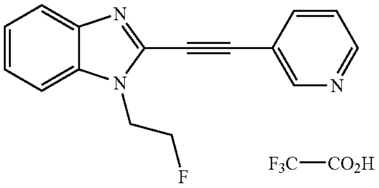 [SMILES: FCCn1c(C#Cc2cccnc2)nc2ccccc21 ; O=C(O)C(F)(F)F] | 379.31 | 265.28 | | 3 |
| T552 | 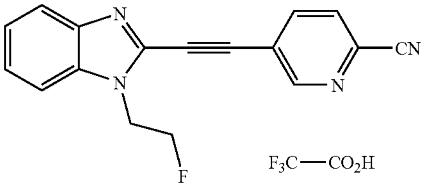 [SMILES: N#Cc1ccc(C#Cc2nc3ccccc3n2CCF)cn1 ; O=C(O)C(F)(F)F] | 404.32 | 266.27 | | 2 |
| T553 | 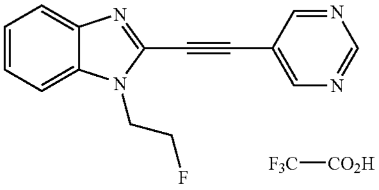 [SMILES: FCCn1c(C#Cc2cncnc2)nc2ccccc21 ; O=C(O)C(F)(F)F] | 380.3 | 266.27 | | 2.8 |
| T554 | 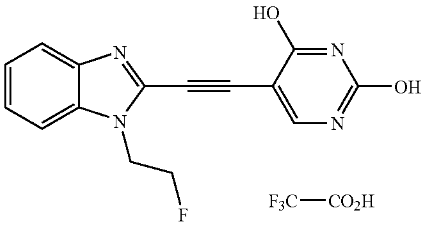 [SMILES: Oc1ncc(C#Cc2nc3ccccc3n2CCF)c(O)n1 ; O=C(O)C(F)(F)F] | 412.3 | 298.27 | Blue. Tau +++. Ab + | 3.2 |

TABLE 2-continued

Representative examples of acetylene compounds of the present invention

| Comp. ID | Stucture | MW | Exact Mass | Brain Section Staining | cLogP |
|---|---|---|---|---|---|
| T564 | 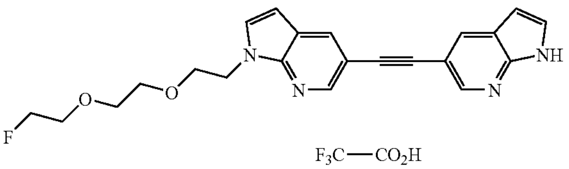 [SMILES: FCCOCCOCCn1ccc2cc(C#Cc3cnc4[nH]ccc4c3)cnc21 ; O=C(O)C(F)(F)F] $F_3C$—$CO_2H$ | 506.45 | 392.43 | | 2.9 |
| T568 | 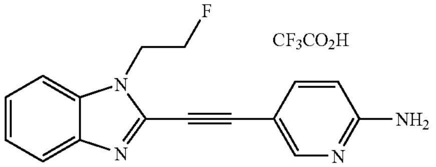 [SMILES: Nc1ccc(C#Cc2nc3ccccc3n2CCF)cn1 ; "CF3CO2H"] $CF_3CO_2H$ | 394.32 | 280.3 | | 2.6 |

Figure 4A:
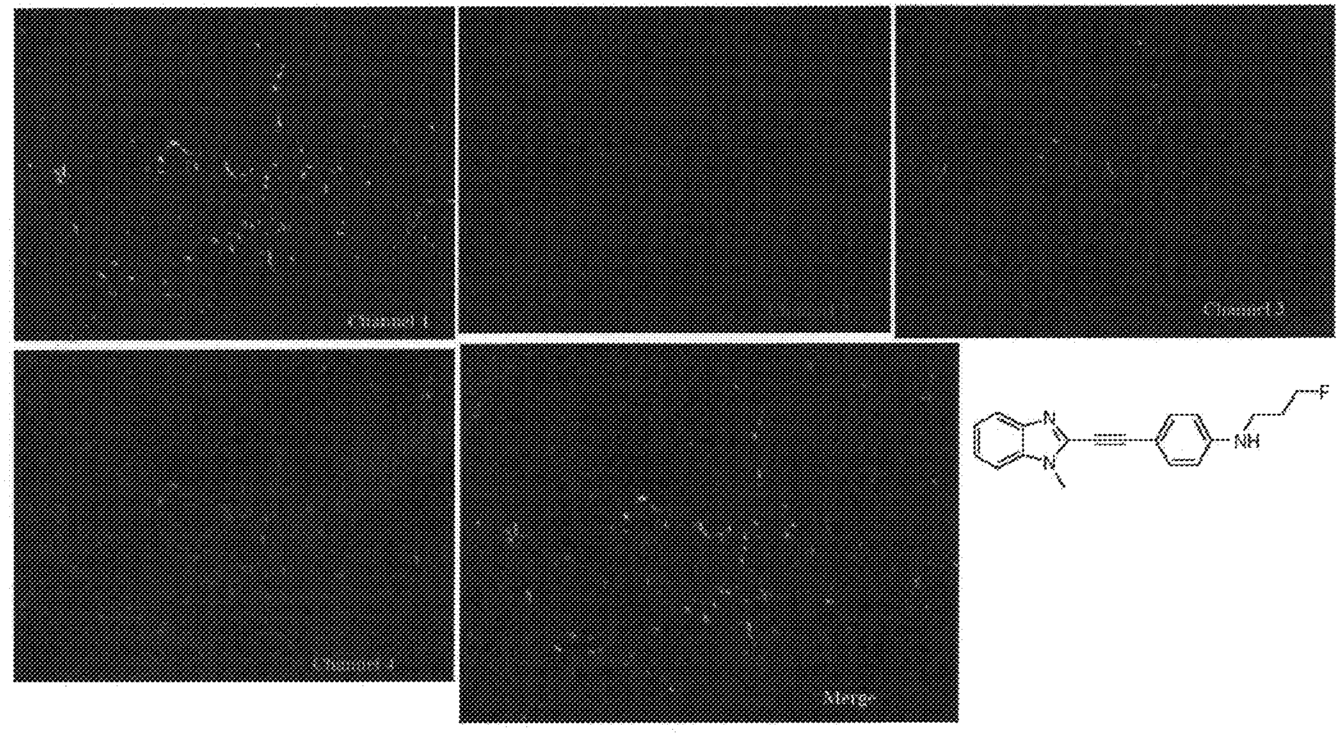
FIGS. 4*a* and 4*b* binding of fluorescent compound T540 to AD brain sections, which contain Aβ plaques and tau aggregates as confirmed by immunostaining with Aβ or tau antibodies (double labeling of T540 at 100 uM).
Figure 4B:
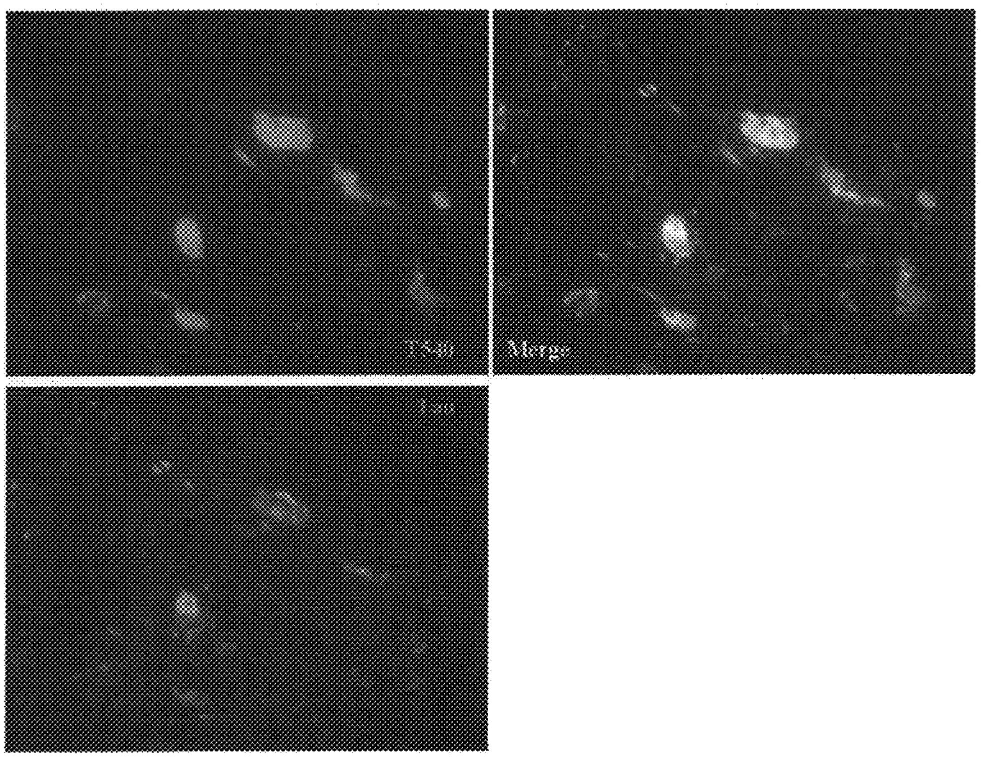
Figure 5:
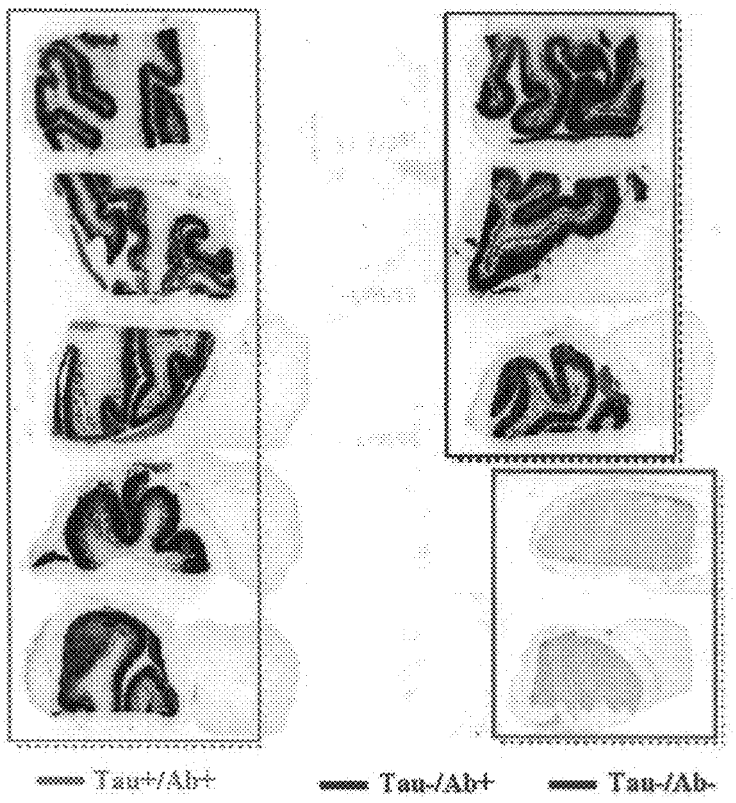
FIG. 5 shows ex vivo autoradiograph images of a preferred compound, T540, in three different types of brain sections: Aβ+/tau− brains contain Aβ plaques, but no tau aggregates (diagnosis by brain bank as non-AD donor); Aβ+/tau+ brains contain both Aβ plaques and tau aggregates (diagnosed by brain bank as AD patient), and normal (control) brains. The presence or absence of Aβ and/or tau was confirmed by immunostaining.
Figure 6B:
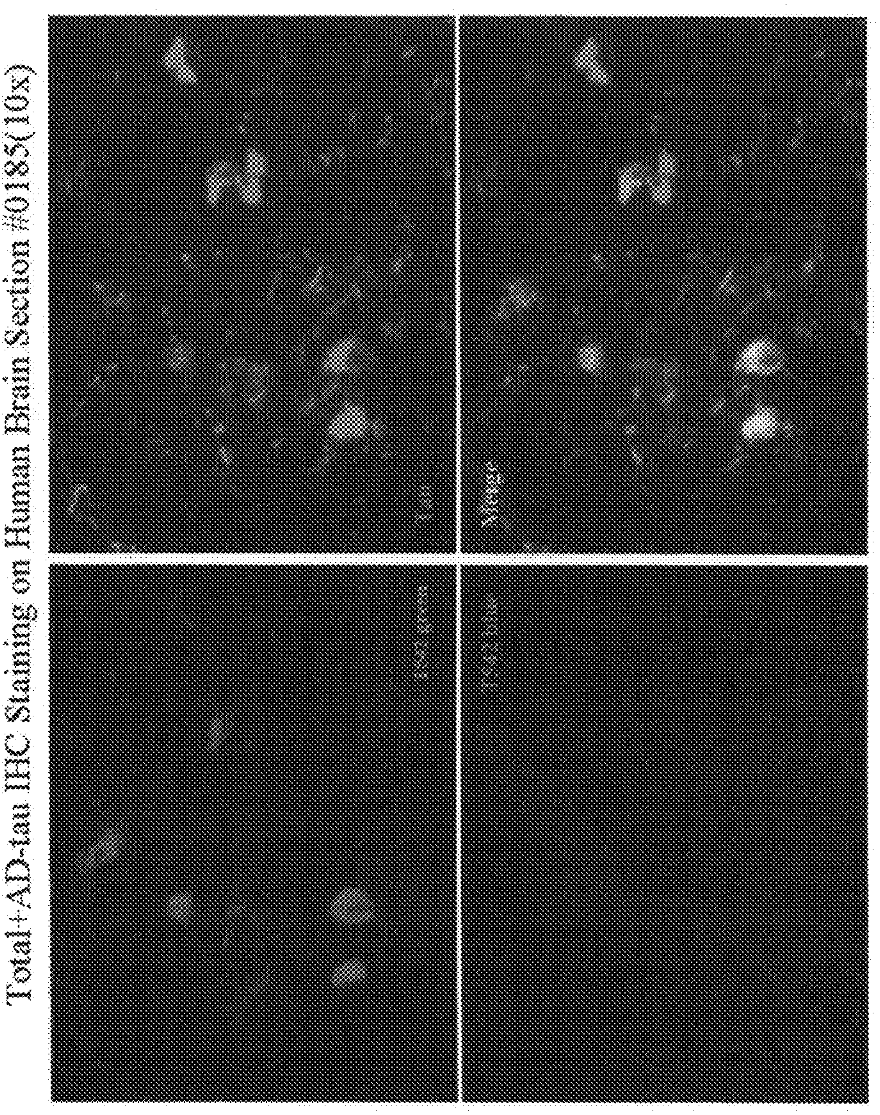
Figure 6C:
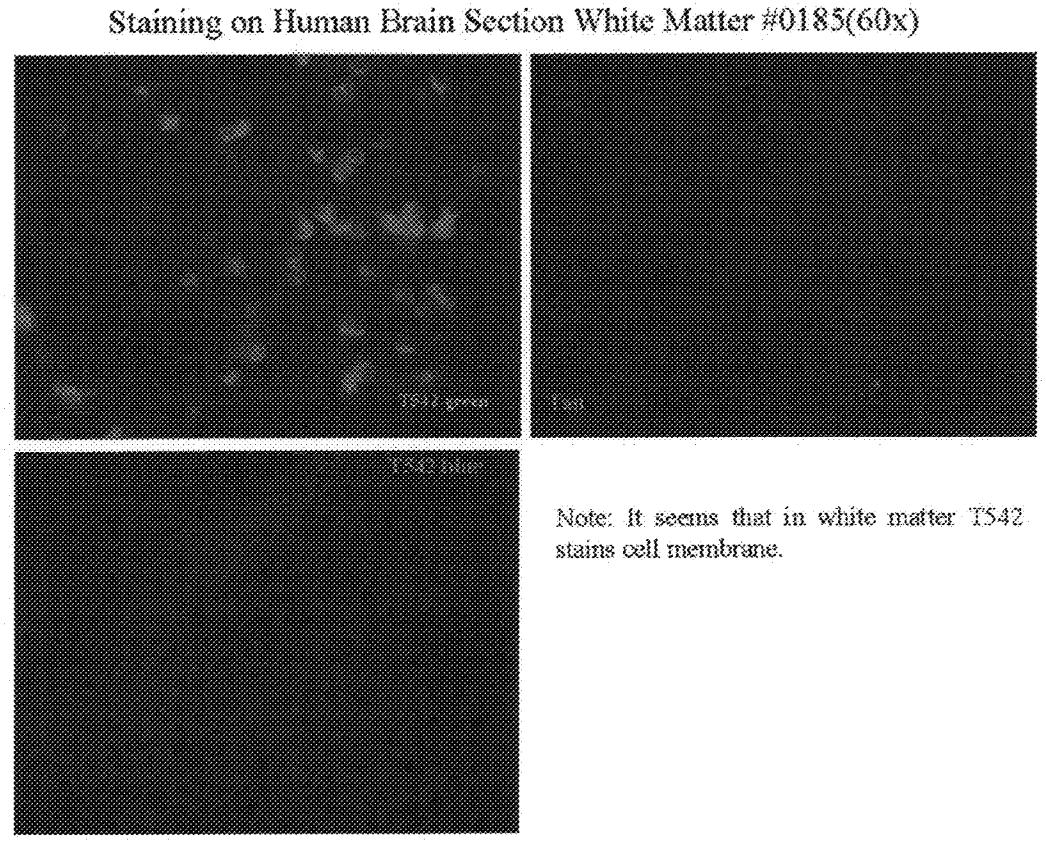
Figure 8B:
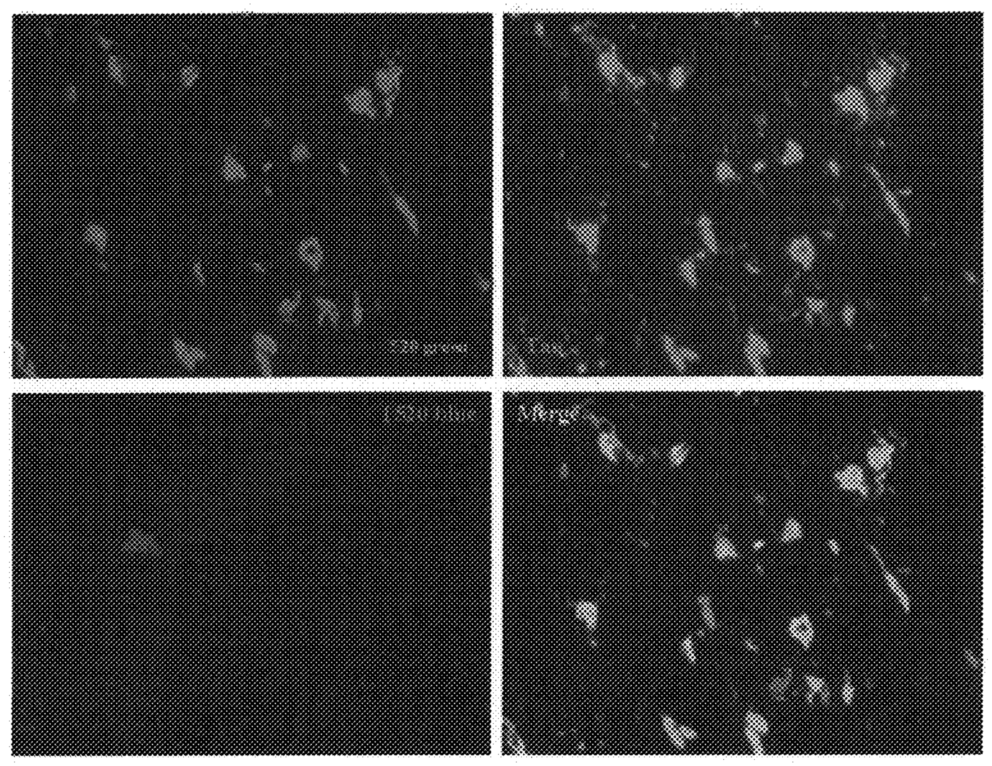
Figure 10B:
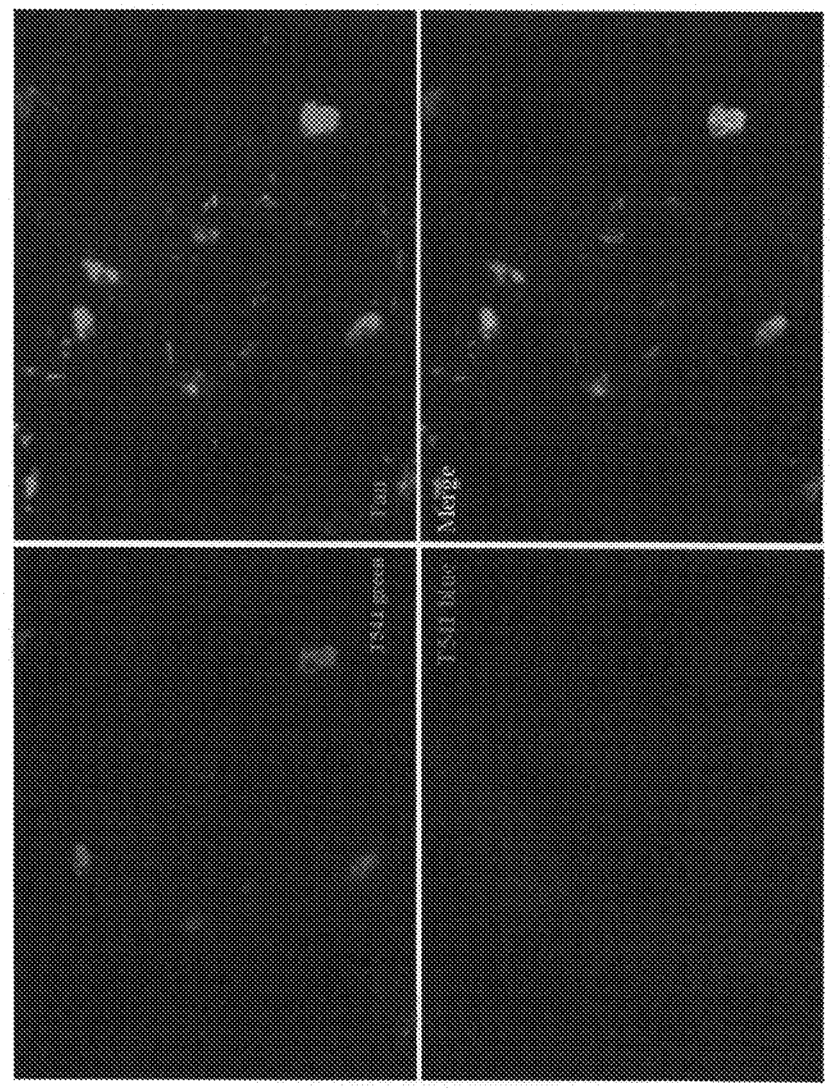

FIGS. 2 and 4*a*-4*b* show binding of fluorescent compounds T482 and T540 to AD brain sections confirmed by immunostaining with tau or Aβ antibodies. FIGS. 3 and 5 show ex vivo autoradiograph images of the preferred compounds T482 and T540, in three different types of brain sections: Aβ+/tau− brains contain Aβ plaques, but no tau aggregates (diagnosis by brain bank as non-AD donor); Aβ+/tau+ brains contain both .Aβ plaques and tau aggregates (diagnosed by brain bank as AD patient), and normal (control) brains. The presence or absence of Aβ and/or tau is confirmed by immunostaining.

Another embodiment of the present invention is directed to compounds of formula (I) comprising a tricyclic aryl moiety. For example, benzimidazole pyrimidines shown in Scheme 4, exhibit high binding affinity to tau proteins. FIGS. 6*a*-6*c*, 7, 8*a*-8*b*, 9*a*-9*b*, 10*a*-10*b*, and 11 show binding of fluorescent compounds T542, T544, T520, T522, T541, and T527 to AD brain sections confirmed by immunostaining with tau or Aβ antibodies.

Scheme 4. Qualitative results of Tau/Aβ binding of fluorescent compounds in brain section (4+ is the strongest, 1+ is the weakest)

T522

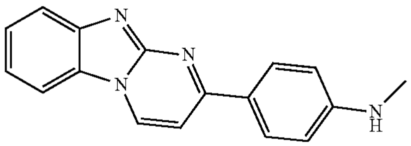

Tau 4+, Ab 1+

T542

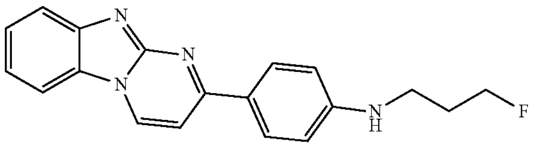

Tau 4+, Ab 3+

-continued

T557

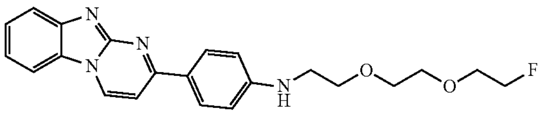

Tau 4+, Ab 2+

T520

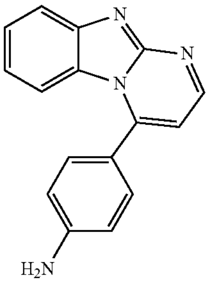

Tau 4+, Ab 1+

T544

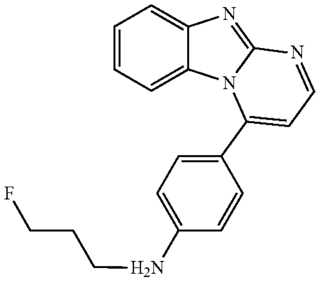

Tau 3+, Ab 1+

TABLE 3
Representative examples of benzimidazole and tricyclic benzimidazole compounds of the present invention.
| Compound ID | Structure | MW | Brain Section Staining |
|---|---|---|---|
| T506 | 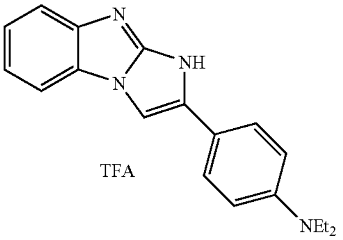 | 401.4 | |
| T511 | 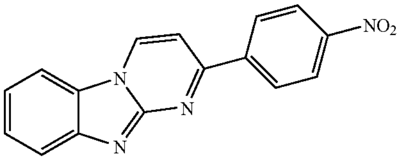 [SMILES: O=[N+]([O-])c1ccc(-c2ccn3c(n2)nc2ccccc23)cc1] | 290.28 | |
| T512 | 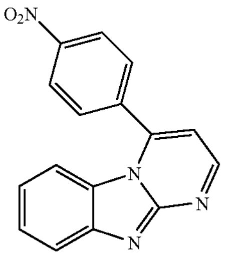 [SMILES: O=[N+]([O-])c1ccc(-c2ccnc3nc4ccccc4n23)cc1] | 290.28 | |
| T518 | 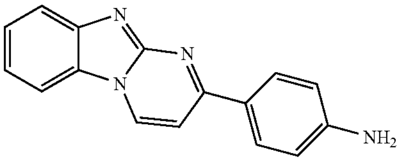 [SMILES: Nc1ccc(-c2ccn3c(n2)nc2ccccc23)cc1] | 260.29 | Aβ/1+<br>Tau/4+ |
| T520 | 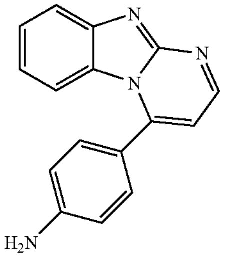 [SMILES: Nc1ccc(-c2ccnc3nc4ccccc4n23)cc1] | 260.29 | Aβ/1+<br>Tau/4+ |
| T521 | 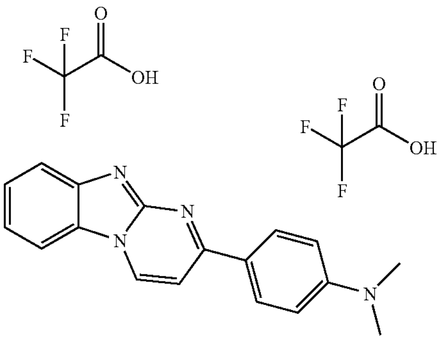 | 516.39 | Aβ/1+<br>Tau/4+ |

TABLE 3-continued
| Representative examples of benzimidazole and tricyclic benzimidazole compounds of the present invention. | | | |
|---|---|---|---|
| Compound ID | Structure | MW | Brain Section Staining |
| T522 | 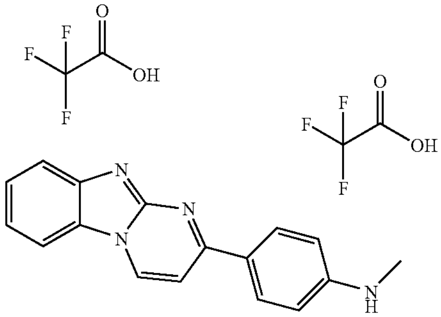 | 502.37 | Aβ/1+ Tau/4+ |
| T542 | 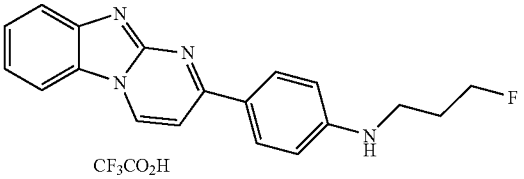 $CF_3CO_2H$ $CF_3CO_2H$ | 548.41 | Aβ/3+ Tau/4+ |
| T544 | 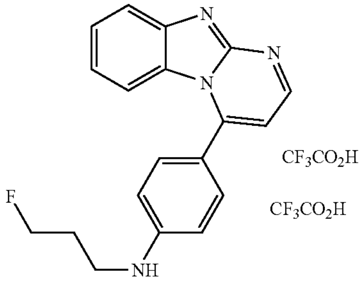 $CF_3CO_2H$ $CF_3CO_2H$ | 548.41 | Aβ/1+ Tau/3+ |
| T557 | $CF_3CO_2H$ 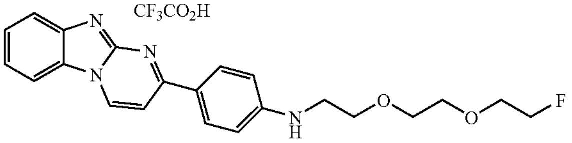 $CF_3CO_2H$ | 622.49 | Aβ/2+ Tau/4+ |
| T452 | 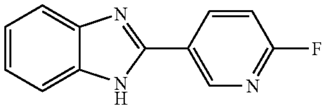 [SMILES: Fc1ccc(-c2nc3ccccc3[nH]2)cn1] | 213.21 | |
| T460 | 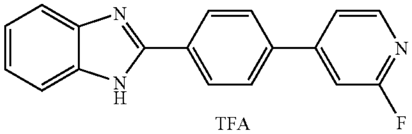 [SMILES: Fc1cc(-c2ccc(-c3nc4ccccc4[nH]3)cc2)ccn1] TFA | 386.3 | |
| T469 | 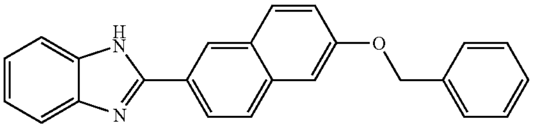 [SMILES: c1ccc(COc2ccc3cc(-c4nc5ccccc5[nH]4)ccc3c2)cc1] | 350.41 | |

TABLE 3-continued
Representative examples of benzimidazole and tricyclic benzimidazole compounds of the present invention.
| Compound ID | Structure | MW | Brain Section Staining |
|---|---|---|---|
| T470 | 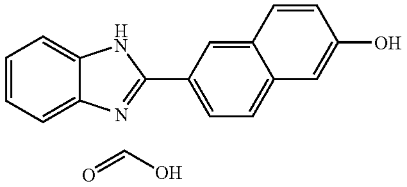 | 306.32 | |
| T473 | 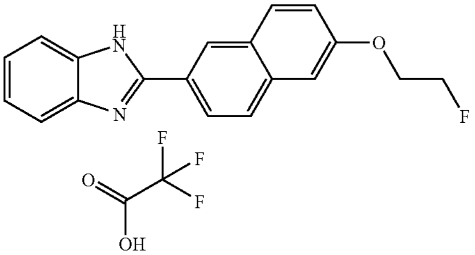 | 420.36 | |
| T474 | 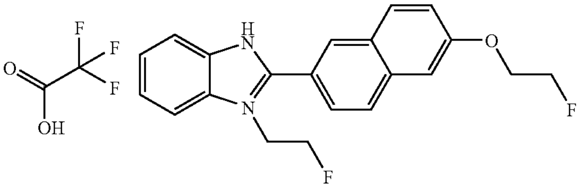 | 466.4 | |
| T487 | 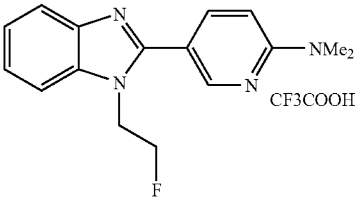 CF3COOH | 398.35 | |
| T488 | 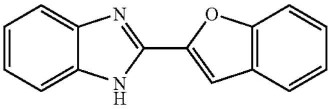 [SMILES: c1ccc2oc(-c3nc4ccccc4[nH]3)cc2c1] | 234.3 | |
| T489 | 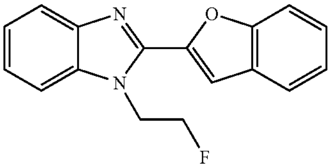 | 280.3 | |
| T493 | 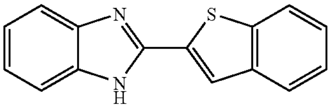 $CF_3COOH$ | 364.3 | |
| T494 | 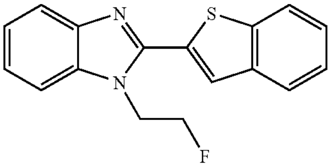 [SMILES: FCCn1c(-c2cc3ccccc3s2)nc2ccccc21] | 296.4 | |

TABLE 3-continued
Representative examples of benzimidazole and tricyclic benzimidazole compounds of the present invention.
| Compound ID | Structure | MW | Brain Section Staining |
|---|---|---|---|
| T495 | 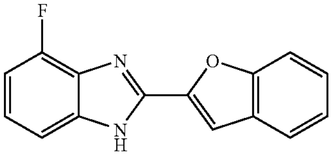 $CF_3COOH$ | 366.3 | |
| T497 | 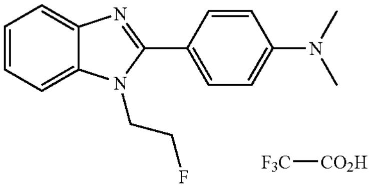 [SMILES: CN(C)c1ccc(-c2nc3ccccc3n2CCF)cc1 ; O=C(O)C(F)(F)F] $F_3C—CO_2H$ | 397.37 | |
| T524 | 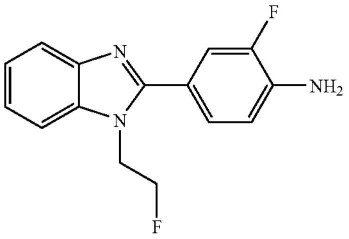 [SMILES: Nc1ccc(-c2nc3ccccc3n2CCF)cc1F] | 273.28 | Tau +++; Ab ++ |
| T538 | 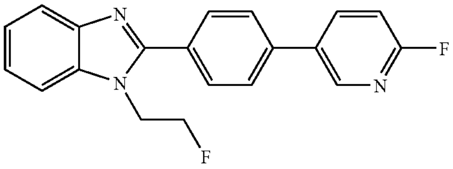 | 335.4 | |
| T543 | 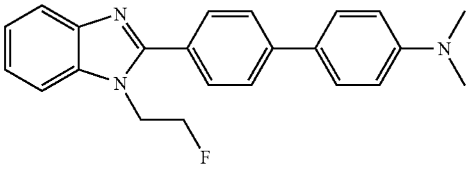 | 473.5 | Tau ++; Ab no binding |
| T548 | 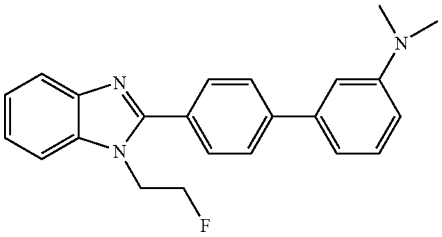 [SMILES: CN(C)c1cccc(-c2ccc(-c3nc4ccccc4n3CCF)cc2)c1] | 359.2 | |
| T556 | 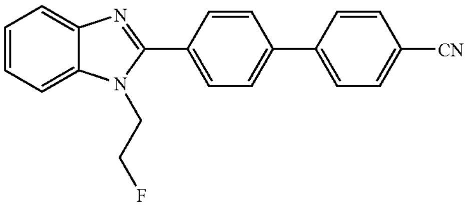 [SMILES: N#Cc1ccc(-c2ccc(-c3nc4ccccc4n3CCF)cc2)cc1] | 341.4 | |

In another embodiment, the present invention relates to compounds and compositions which comprise the formulae as disclosed herein, wherein the compound is an amyloid and/or tau protein binding compound. An amyloid and/or tau protein binding compound of the invention may be administered to a patient in amounts suitable for in vivo imaging of amyloid deposits and/or NTFs, and distinguish between neurological tissue with amyloid deposits and/or NTfs and normal neurological tissue.

Aβ compounds are typically evaluated in a competitive binding assay using synthetic Aβ1-42 fibrils ($IC_{50}$s). The situation is more complicated for tau, because there are 6 isoforms of tau potentially present in AD brains as products of alternate splicing of a single tau gene. Most reports in the literature rely therefore on only one recombinant isoform, Tau-441. To add more complexity, the various tau isoforms are hyperphosphorylated in vivo, something that is difficult to mimic in vitro. Furthermore, structural information on these tau fibrils is lacking, making an interpretation of binding of compounds difficult.

Native forms of tau (various isoforms, hyperphosphorylated) and amyloid aggregates are present in brain sections and therefore preferred for compound testing. Using the self-fluorescence of a test compound can give an indication of whether the compound binds to tau tangles/PHFs and/or amyloid plaques. This is further confirmed by immunostaining with Aβ and tau antibodies and overlaying the images. The drawback is that the fluorescent signals cannot be used for quantitation as some compounds might exhibit a strong fluorescent signal than others and the coexistence of Aβ plaques and tau tangles in AD brains. However, it is possible to "rate" the signal strength qualitatively and distinguish compounds that show binding to these aggregates.

Furthermore, the selectivity can be evaluated in brains containing only Aβ plaques/no tau aggregates, Aβ plaques/ and tau aggregates, and control brains. Unfortunately, there are no AD brains with only tau and no Aβ present. By testing radiolabeled tracers in these brain sections, one can more quantitative evaluate the relative binding strength (signal strength) and selectivity of various test compounds as they all contain the same radioactive tracer. For examples, if a test tracer binds only to tau, and not amyloid, it should show no signal in the Aβ plaques only brain sections. If a compound binds only to amyloid, it should show uptake in both types of brains. The difficulty of identifying and further quantifying selective compounds lies in the relative abundance of amyloid vs. tau, which is difficult to measure.

In one of the embodiments of the present invention, the self-fluorescence of the compound of formula (I) is used to determine whether the compound binds to tau/amyloid in the brain sections and to give it a qualitative rating. The next step is to proceed to the autoradiography using different brain types for further evaluation and quantitation.

Amyloid and/or tau protein probes of the invention may be used to detect and quantitate amyloid deposits and/or NTFs in diseases including, but not limited to Mediterranean fever, MuckleWells syndrome, idiopathetic myeloma, amyloid polyneuropathy, amyloid cardiomyopathy, systemic senile myloidosis, amyloid polyneuropathy, hereditary cerebral hemorrhage with amyloidosis, Down's syndrome, Scrapie, Creutzfeldt-Jacob disease, Kuru, Gerstamnn-Straussler-Scheinker syndrome, medullary carcinoma of the thyroid, Isolated atrial amyloid, $\beta_2$-microglobulin amyloid in dialysis patients, inclusionbody myositis, $\beta_2$-amyloiddeposits in muscle wasting disease, chronic traumatic encephalopathy (CTE), and Islets of Langerhans diabetes Type II insulinoma.

The compounds and probes of the invention preferably exhibit low toxicity at dosages effective to image (including diagnostic, detection, quantification and evaluation) amyloid and/or related afflictions.

In one of the embodiment, the present invention is directed to a pharmaceutical diagnostic formulation comprising a radiolabeled compound of formula (I) or a pharmaceutically acceptable salt thereof in a suitable vehicle or diluent for imaging and detection of neurological disorders.

In another embodiment, the present invention is directed to a pharmaceutical diagnostic formulation for detection of amyloid peptides.

In another embodiment, the present invention is directed to a pharmaceutical diagnostic formulation for detection of tau proteins of neurofibrillary tangles.

In another embodiment, the present invention is directed to a pharmaceutical diagnostic formulation for detection of the neurological disorder.

In another embodiment, the present invention is directed to a pharmaceutical diagnostic formulation for detection of Alzheimer's disease.

In another embodiment of the present invention, the radioactive diagnostic agent composition may contain any additive such as pH controlling agents (e.g., acids, bases, buffers), stabilizers (e.g., ascorbic acid) or isotonizing agents (e.g., sodium chloride).

In yet another embodiment, the invention further relates to a method for imaging and detection of senile plaques and/or neurofibrillary tangles in a brain tissue, the method comprising treating the tissue with a compound of formula (I).

In yet another embodiment, the invention further relates to a method for ex vivo or in vitro detection of amyloid deposit in a brain tissue, the method comprising treating the tissue with a compound of formula (I) for detection of the amyloid deposit.

In yet another embodiment, the invention further relates to a method for in vivo detection of amyloid deposits in a patient, the method comprising administering an effective amount of the compound of formula (I) to the patient, and detecting the binding level of the compound to the amyloid deposit to the patient.

In yet another embodiment, the invention further relates to a method for ex vivo or in vitro detection of tau proteins in a brain tissue, the method comprising treating the tissue with a compound of formula (I) for detecting of the neurofibrillary tangles.

In yet another embodiment, the invention further relates to a method for in vivo detection of neurofibrillary tangles in a patient, the method comprising administering an effective amount of the compound of formula (I) to the patient, and detecting the binding level of the compound to tau proteins.

In yet another embodiment, the invention further relates to a method of detecting a SPs and NTFs characteristic for a neurological disorder.

In yet another embodiment, the invention further relates to a method of detecting Alzheimer's disease (AD).

In yet another embodiment, the invention further relates to a method of imaging and detection of neurological disorder performed by using gamma imaging, magnetic resonance imaging, magnetic resonance spectroscopy or fluorescence spectroscopy.

In yet another embodiment, the invention further relates to a method of imaging and detection of SPs and NTFs, wherein the detection is by PET or SPECT.

According to a particular embodiment of the present invention, the compounds and methods of the present invention are used for imaging, especially medical imaging.

Diagnostic techniques in nuclear medicine use radioactive tracers which emit gamma rays from within the body. These tracers are generally short-lived isotopes linked to chemical compounds which permit specific physiological processes to be scrutinised. They can be given by injection, inhalation or orally. The first type is where single photons are detected by a gamma camera which can view organs from many different angles. The camera builds up an image from the points from which radiation is emitted; this image is enhanced by a computer and viewed by a physician on a monitor for indications of abnormal conditions.

Positron Emission Tomography (PET) is a precise and sophisticated technique using isotopes produced in a cyclotron.

A positron-emitting radionuclide is introduced, usually by injection, and accumulates in the target tissue. As it decays it emits a positron, which promptly combines with a nearby electron resulting in the simultaneous emission of two identifiable gamma rays in opposite directions. These are detected by a PET camera and give very precise indication of their origin. PET's most important clinical role is in oncology, with fluorine-18 as the tracer, since it has proven to be the most accurate non-invasive method of detecting and evaluating most cancers. It is also well used in cardiac and brain imaging.

A number of medical diagnostic procedures, including PET and SPECT utilize radiolabeled compounds, are well known in the art. PET and SPECT are very sensitive techniques and require small quantities of radiolabeled compounds, called tracers. The labeled compounds are transported, accumulated and converted in vivo in exactly the same way as the corresponding non-radioactively compound. Tracers, or probes, can be radiolabeled with a radionuclide useful for PET imaging, such as $^{11}C$, $^{13}N$, $^{15}O$, $^{18}F$, $^{64}Cu$ and $^{124}I$, or with a radionuclide useful for SPECT imaging, such as $^{99}Tc$, $^{77}Br$, $^{61}Cu$, $^{153}Gd$, $^{123}I$, $^{125}I$, $^{131}I$ and $^{32}P$.

PET creates images based on the distribution of molecular imaging tracers carrying positron-emitting isotopes in the tissue of the patient. The PET method has the potential to detect malfunction on a cellular level in the investigated tissues or organs. PET has been used in clinical oncology, such as for the imaging of tumors and metastases, and has been used for diagnosis of certain brain diseases, as well as mapping brain and heart function. Similarly, SPECT can be used to complement any gamma imaging study, where a true 3D representation can be helpful, for example, imaging tumor, infection (leukocyte), thyroid or bones.

According to another embodiment, the present invention is also directed at a method of imaging amyloid deposits and NTFs. When the compounds of this invention are used as imaging agents, they are labeled with suitable radioactive isotopes or radiolabel or radioactive label, for example, radioactive halogens, such as $^{18}F$ or, radioactive metals and other detectable radioactive atoms such as $^{11}C$.

Regarding radiohalogens, $^{125}I$ isotopes are useful for laboratory testing but they will generally not useful for diagnostic purposes because of the relatively long half-life (60 days) and low gamma-emission (30-65 Key) of $^{125}I$. The isotope $^{123}I$ has a half-life of thirteen hours and gamma energy of 159 Key, and it is therefore expected that labeling of ligands to be used for diagnostic purposes would be with this isotope or with $^{18}F$ (half-life of 2 hours). Other isotopes which may be used include $^{131}I$, $^{77}Br$, and $^{76}Br$.

In another embodiment, compounds of the present invention also contain a radioactive isotope of carbon as the radiolabel. This refers to a compound that comprises one or more radioactive carbon atoms, preferably $^{11}C$, with a specific activity above that of the background level for that atom. It is well known that naturally occurring elements are present in the form of varying isotopes, some of which are radioactive. The radioactivity of the naturally occurring elements is a result of the natural distribution or abundance of these isotopes, and is commonly referred to as a background level. The carbon labeled compounds of the present invention have a specific activity that is higher than the natural abundance, and therefore above the background level. The carbon labeled compositions of the present invention can be used for tracing, imaging, radiotherapy, and the like.

Those skilled in the art are familiar with the various ways to detect labeled compounds for imaging purposes. For example, positron emission tomography (PET) or single photon emission computed tomography (SPECT) can be used to detect radiolabeled compounds. The label that is introduced into the compound can depend on the detection method desired. Those skilled in the art are familiar with PET detection of a positron-emitting atom, such as $^{18}F$. The present invention is also directed to specific compounds described herein where the $^{18}F$ atom is replaced with a non-radiolabeled fluorine atom. Those skilled in the art are familiar with SPECT detection of a photon-emitting atom, such as $^{123}I$ or $^{99m}Tc$.

The radioactive diagnostic agent should have sufficient radioactivity and radioactivity concentration which can assure reliable diagnosis. The desired level of radioactivity can be attained by the methods provided herein for preparing compounds of Formula I. The imaging of amyloid deposits and NTFs can also be carried out quantitatively so that the amount of amyloid deposits and NTFs can be determined.

One of the key prerequisites for an in vivo imaging agent of the brain is the ability to cross the intact blood-brain barrier after a bolus i.v. injection. In the first step of the present method of imaging, a labeled compound of Formula I is introduced into a tissue or a patient in a detectable quantity. The compound is typically part of a pharmaceutical composition and is administered to the tissue or the patient by methods well known to those skilled in the art. For example, the compound can be administered either orally, rectally, parenterally (intravenous, by intramuscularly or subcutaneously), intracistemally, intravaginally, intraperitoneally, intravesically, locally (powders, ointments or drops), or as a buccal or nasal spray.

In other embodiments of the invention, the labeled compound is introduced into a patient in a detectable quantity and after sufficient time has passed for the compound to become associated with amyloid deposits and/or tau proteins, the labeled compound is detected noninvasively. In another embodiment of the invention, a labeled compound of Formula I is introduced into a patient, sufficient time is allowed for the compound to become associated with amyloid deposits, and then a sample of tissue from the patient is removed and the labeled compound in the tissue is detected apart from the patient. In another embodiment of the invention, a tissue sample is removed from a patient and a labeled compound of Formula I is introduced into the tissue sample. After a sufficient amount of time for the compound to become bound to amyloid deposits and/or tau proteins, the compound is detected.

A detectable quantity is a quantity of labeled compound necessary to be detected by the detection method chosen. The amount of a labeled compound to be introduced into a patient in order to provide for detection can readily be determined by those skilled in the art. For example, increasing amounts of the labeled compound can be given to a patient until the compound is detected by the detection method of choice. A label is introduced into the compounds to provide for detection of the compounds.

The amount of time necessary can easily be determined by introducing a detectable amount of a labeled compound of Formula I into a patient and then detecting the labeled compound at various times after administration.

The administration of the labeled compound to a patient can be by a general or local administration route. For example, the labeled compound may be administered to the patient such that it is delivered throughout the body. Alternatively, the labeled compound can be administered to a specific organ or tissue of interest. For example, it is desirable to locate and quantitate amyloid deposits in the brain in order to diagnose or track the progress of Alzheimer's disease in a patient.

The term "pharmaceutically acceptable salt" as used herein refers to those carboxylate salts or acid addition salts of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic and organic acid addition salts of compounds of the present invention. Also included are those salts derived from non-toxic organic acids such as aliphatic mono and dicarboxylic acids, for example acetic acid, phenyl-substituted alkanoic acids, hydroxy alkanoic and alkanedioic acids, aromatic acids, and aliphatic and aromatic sulfonic acids. These salts can be prepared in situ during the final isolation and purification of the compounds or by separately reacting the purified compound in its free base form with a suitable organic or inorganic acid and isolating the salt thus formed. Further representative salts include, but are not limited to hydrobromide, hydrochloride, sulfate, bisulfate, nitrate, acetate, trifluoroacetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, propionate, pivalate, cyclamate, isethionate, and the like. These may include cations based on the alkali and alkaline earth metals, such as sodium, lithium, potassium, calcium, magnesium, and the like, as well as, nontoxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, Berge S. M., et al., *Pharmaceutical Salts, J. Pharm. Sci.* 66:1-19 (1977), which is incorporated herein by reference).

The term "alkyl" as employed herein by itself or as part of another group refers to both straight and branched chain radicals of up to 6 carbons, preferably up to 4 carbons.

The term "alkene" as employed herein by itself or as part of another group refers to both straight and branched chain radicals of up to 6 carbons, preferably up to 4 carbons, which have a double bond between any two carbon atoms.

The term "alkyne" as employed herein by itself or as part of another group refers to both straight and branched chain radicals of up to 6 carbons, preferably up to 4 carbons, which have a triple bond between any two carbon atoms. Alkynes are traditionally known as acetylenes, although the name acetylene refers specifically to $C_2H_2$.

The term "alkoxy" is used herein to mean a straight or branched chain alkyl radical, as defined above, unless the chain length is limited thereto, bonded to an oxygen atom, including, but not limited to, methoxy, ethoxy, n-propoxy, isopropoxy, and the like. Preferably the alkoxy chain is 1 to 4 carbon atoms in length, more preferably 1 or 2 carbon atoms in length.

The term "halo" or "halogen" employed herein by itself or as part of another group refers to chlorine, bromine, fluorine or iodine, unless defined otherwise in specific uses in the text and/or claims.

The term "radiohalogen" employed herein by itself or as part of another group refers to $^{18}F$, $^{123}I$, $^{125}I$, $^{131}I$, $^{76}Br$ and $^{77}Br$.

The term "haloalkyl" as employed herein refers to any of the above alkyl groups substituted by one or more chlorine, bromine, fluorine or iodine with fluorine being preferred. Most preferably, the alkyl is substituted with a single halo, such as fluorine, at the distal end of the alkyl.

The term "radiohaloalkyl" refers to a haloalkyl group as defined above that contains a halogen radioisotope. One example of this type of group is $^{18}F$—$(C_{1-4})$alkyl-.

The term "hydroxyalkyl" as employed herein by itself or as part of another group refers to linear or branched alkyl groups containing an —OH substituent.

The term "aryl" as employed herein by itself or as part of another group refers to monocyclic, bicyclic, tricyclic or polycyclic aromatic groups containing from 5 to 14 atoms in the ring portion. Aryl compounds of the present invention include, but are not limited to non-substituted or further substituted phenyl, naphthyl, tetrahydronaphthyl and the like. The aryl group can also contain at least one heteroatom, such as N, S or O, to form a "heteroaryl." Examples of heteroaryls include, but are not limited to non-substituted or further substituted thienyl, benzo[b]thienyl, benzothiazolyl, furyl, pyranyl, isobenzofuranyl, benzofuranyl, benzoxazolyl, 2H-pyrrolyl, pyrrolyl, imidazolyl, benzopyrazolyl, benzoimidazolyl, benzoimidazole pyrimidines, imidazoimidazole pyridine, benzofuropyridine, benzofuropyrimidine, pyrazolyl, pyridyl, pyrazinyl, pyrimidinyl, pyridazinyl, indolizinyl, isoindolyl, 3H-indolyl, indolyl, indazolyl, 4H-quinolizinyl, isoquinolyl, quinolyl, quinazolinyl, isothiazolyl, phenothiazinyl, isoxazolyl, furazanyl, phenoxazinyl groups and the like.

The term "aryloxy" as employed herein refers to an "aryl" group bonded to an oxygen atom, and include benzyloxy and phenoxy, which can be further substituted and the like.

The term "tissue" means a part of a patient's body. It is an ensemble of cells, not necessarily identical, but from the same origin, that together carry out a specific function. Examples of tissues include, but are not limited to the brain, heart, liver, blood vessels, and arteries.

The term "patient" or "subject" means humans and other animals.

Those skilled in the art are also familiar with determining the amount of time sufficient for a compound to become associated with amyloid deposits for imaging purposes.

The term "associated" means a chemical interaction between the labeled compound and the amyloid deposit. Examples of associations include covalent bonds, ionic bonds, hydrophilic-hydrophilic interactions, hydrophobichydrophobic interactions, and complexes.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXPERIMENTAL EXAMPLES

Note: equivalents refer to molar equivalents. Actual volumes are calculated by multiplying the molar equivalents by liters. Thus, 1 mmol times 5 vol equals 5 mmol.

1. General Experimental Procedures for the Preparation of Disclosed Compounds

Method A General Procedure for Suzuki Coupling Reactions:

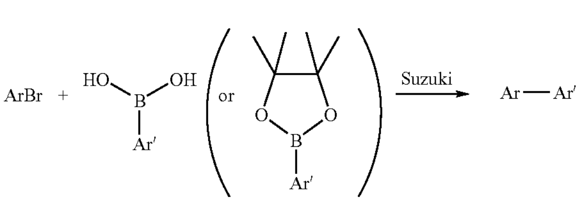

A mixture of aryl/heterocyclic halide (1.0 equiv.), boronic acid or boronate ester (1.1-1.5 equiv.), $K_2CO_3$ (3.0 equiv.) and $Pd[PPh_3]_4$ (0.01-0.05 equiv) in DMF (30 mL) was irradiated in a Biotage Emrys Initiator microwave reactor (250 W) at 100° C. for 30 min. After cooling to room temperature, the solvent was removed in vacuo. The residue was purified on flash column chromatography over silica gel using EtOAc: Hexanes or EtOAc:DCM or MeOH:DCM as the eluent to afford the desired biaryl products.

Method B General Procedure for Sonogashira Coupling Reaction:

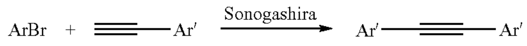

A mixture of halide (1.0 equiv.), acetylene (1.1-1.5 equiv.), CuI (0.05 equiv.), $Pd[PPh_3]_4$ or $PdCl_2(PPh_3)_2$ (0.01-0.05 equiv.) and DIPEA (3.0 equiv.) in ACN (30 mL) was irradiated in a Biotage Emrys Initiator microwave reactor (250 W) at 100° C. for 30 min. After cooling to room temperature, the solvent was removed in vacuo. The residue was purified on flash column chromatography over silica gel using EtOAc: Hexanes or EtOAc:DCM or MeOH:DCM as the eluent to afford the disubstituted acetylene derivatives.

Method C General Procedure for Phenolic Alkylation:

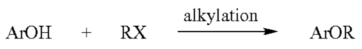

A mixture of phenol derivatives (1.0 equiv.), alkylating agent (1.1 equiv.), and $Cs_2CO_3$ (3.0 equiv.) in DMF (10 mL) was heated at 60° C. under Ar for 1-3 hrs. After the reaction was completed, the solvents were removed in vacuo. The residue was purified on flash column chromatography over silica gel using EtOAc:Hexanes or EtOAc:DCM or MeOH: DCM as the eluent to afford the alkylated products.

Method D General Procedure for N-Alkylation Using NaH as the Base:

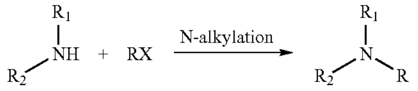

To a solution of amine (1.0 equiv.) in DMF (10 mL) was added NaH (1.5-6 equiv.), followed by alkylating agent (1.1-2 equiv.). The reaction mixture was allowed to stir at room temperature for 1-15 hrs and monitored by LCMS. The reaction mixture was then poured into water (50 mL) and extracted with EtOAc (4×20 mL). The combined organic layers were washed with $H_2O$ (3×20 mL), brine (50 mL), dried ($Na_2SO_4$) and concentrated in vacuo. The residue was purified on a flash column chromatography over silica gel using EtOAc:Hexanes or EtOAc:DCM or MeOH:DCM as the eluent to afford the N-alkylated products.

Method E General Procedure for N-Alkylation Using $Cs_2CO_3$ as the Base:

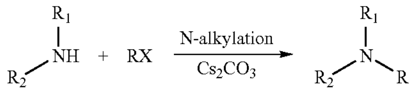

To a solution of amine (1.0 equiv.) in DMF (10 mL) was added alkylating agent (1.1-2 equiv.) and $Cs_2CO_3$ (2-3 equiv.). The reaction mixture was allowed to stir at 60° C. for 1-15 hrs. After the reaction was completed, the solvents were removed in vacuo. Water (30 mL) was added was added to the residue. If the desired products are precipitated as a solid, they are filtered, washed with water and dried to give the pure products. If the desired products are not precipitated out, the mixtures are extracted with EtOAc (4×40 mL). The combined organic layers were washed with $H_2O$ (3×40 mL), brine (50 mL), dried ($Na_2SO_4$) and concentrated in vacuo. The residue was purified on a flash column chromatography over silica gel using EtOAc:Hexanes or EtOAc:DCM or MeOH:DCM as the eluent to afford the N-alkylated products.

Method F General Procedure of Tosylation of Alcohol:

$$ROH+Ts_2O \rightarrow ROTs$$

To a cooled solution of alcohol (1.0 equiv.) in DCM (20 mL) was added $Ts_2O$ (1.5 equiv.) and $Et_3N$ (3.0 equiv.). The reaction mixture was stirred at 0° C. and then gradually warmed to room temperature, and stirred at room temperature for 1-5 hrs. After the reaction was completed, DCM was removed in vacuo. The residue was purified on flash column chromatography over silica gel using EtOAc:Hexanes as the eluent to afford the final tosylates.

Method G General Procedure for Demethylation of Aryl Methyl Ether:

ArOMe→ArOH

To a cooled solution of aryl methyl ether (1.0 equiv.) in DCM (10 mL) was added $BBr_3$ (5.0 equiv.) slowly. The resulting mixture was stirred at 0° C. and then warmed gradually to room temperature, and stirred at room temperature for 15 hrs. After the reaction was completed, the reaction was quenched with $NaHCO_3$ solution (50 mL) and extracted with DCM (4×10 mL). The combined organic layers were washed with $H_2O$ (3×10 mL), dried ($Na_2SO_4$) and concentrated in vacuo to afford the expected phenols.

Method H General Procedure for Click Reaction Between Azides and Acetylenes Using CuI and DIPEA:

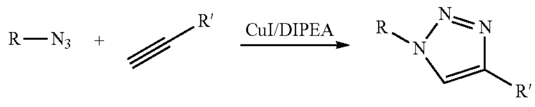

To a solution of azide derivatives (1.0 equiv.) in THF (29 mL) was added acetylene derivatives (1.0 equiv.), CuI (0.2 equiv.), DIPEA (0.4 equiv.). The reaction mixture was allowed to stir at room temperature under Ar until deemed completion of reaction by LCMS. The reaction mixture was then concentrated in vacuo. The residue was purified on a flash column chromatography over silica gel using EtOAc:Hexanes as the eluent to afford the final triazoles.

Method I General Procedure for Silyl Deprotection Using $K_2CO_3$:

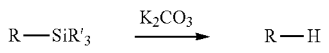

To a solution of silyl protected compounds (1.0 equiv.) in MeOH (20 mL) was added $K_2CO_3$ (1.2 equiv.). The reaction mixture was allowed to stir at room temperature for 1 h. After the reaction was completed, the solvent was removed in vacuo. The residue was purified on a flash column chromatography over silica gel using EtOAc:Hexanes as the eluent to give the deprotected products.

Method J General Procedure for Silyl Deprotection with TBAF:

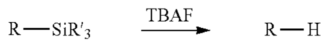

To a solution of silyl protected compound (1.0 equiv.) in THF (20 mL) was added a solution of TBAF in THF (1.0M, 1.0 equiv.). The reaction mixture was allowed to stir at room temperature for 10 min. After the reaction was completed, the solvents were removed in vacuo. The residue was purified on a flash column chromatography over silica gel using EtOAc:Hexanes as the eluent to afford the deprotected products.

Method K General Procedure for the Deprotection of Boc, THP and Ketal Derivatives:

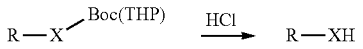

To a solution of protected derivatives (1.0 equiv.) in 1,4-dioxane (20 mL) was added a solution of HCl in 1,4-dioxane (4.0M, 3.8 mL). The reaction mixture was allowed to stir at room temperature and monitored by LCMS. After the reaction was completed, the solvents were removed in vacuo to afford the desired deprotected products.

Method L General Procedure for the Conversion of Nitropyridyl to Fluoropyridyl Compounds:

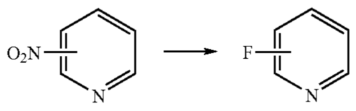

To a solution of nitropyridyl derivatives (1.0 equiv.) in DMSO (10 mL) was added KF (5 equiv.). The reaction mixture was allowed to stir at 140° C. for 1.5 hrs. After the reaction was completed, the reaction was quenched with water (10 mL) and extracted with DCM (4×10 mL). The combined organic layers were washed with $H_2O$ (3×10 mL), dried ($Na_2SO_4$) and concentrated in vacuo. The residue was purified on a flash column chromatography over silica gel using EtOAc:Hexanes or EtOAc:DCM or MeOH:DCM as the eluent to afford the F-pyridyl compounds.

Method M General Procedure for the Conversion of Fluoroopyridyl to Aminopyridyl Compounds:

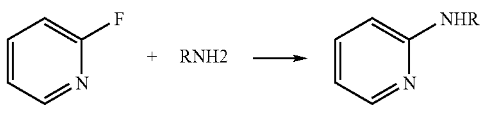

A suspension of fluoropyridyl derivatives (1.0 equiv.) and amine derivatives (excess) was irradiated in a Biotage Emrys Initiator microwave reactor (250 W) at 120° C. for 10 min. After the reaction was completed, the reaction was quenched with water (10 mL) and extracted with DCM (4×10 mL). The combined organic layers were washed with $H_2O$ (3×10 mL), dried ($Na_2SO_4$) and concentrated in vacuo. The residue was purified on a flash column chromatography over silica gel using EtOAC:DCM as the eluent to afford the aminopyridyl compounds.

Method N General Procedure for Click Reaction Between Azides and Acetylenes Using $CuSO_4.H_2O$ and Sodium Ascorbate:

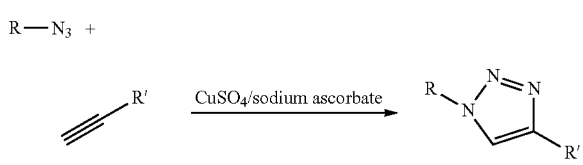

To a solution of azide derivatives (1.0 equiv.) in a mixture of tert-BuOH:$H_2O$ (1:1, 100 mL) was added acetylene (0.9-1.2 equiv.), $CuSO_4.5H_2O$ (0.2 equiv.), and sodium L-ascorbate (0.4 equiv.). The resulting reaction mixture was allowed to stir at room temperature under Ar until deemed complete by LCMS. After the reaction was completed, the solvents were removed in vacuo. The residue was mixed with water (100 mL), cooled to 0° C., and filtered. The solid collected was washed with ether (5×10 mL) and dried in vacuo to afford the final triazoles.

Method O General Procedure for Fluorination:

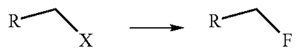

X = OTs or Br

To a solution of precursor (alkyl tosylates/bromides, 1.0 equiv.) in acetonitrile (1.0 mL) was added a solution $Bu_4NF$ in THF (4M, 1.0 equiv.). The reaction mixture was allowed to stir at 90° C. for 30 min and cooled. The reaction mixture was diluted with water/acetonitrile (1 mL), filtered through 0.45 μm filter prior to purification by HPLC using ACN:Water both containing 0.05% TFA to afford the fluorinated product.

Method P General Procedure for Boc and Ketal Deprotections Using TFA:

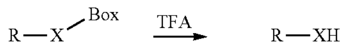

To a solution of protected compound (1.0 equiv.) in DCM (100 mL) was added TFA (10 mL). The resulting reaction mixture was stirred at room temperature for 15 hrs, and then poured into water (200 mL). The mixture was extracted with DCM (2×100 mL). The combined organic layers were washed with sat. $NaHCO_3$ solution (50 mL), brine (50 mL), dried ($Na_2SO_4$) and concentrated in vacuo. The residue was purified on a flash column chromatography over silica gel using EtOAc:Hexanes as the eluent to afford the deprotected products.

Method Q General Procedure for One-Pot Reductive Amination of Anilines from Alcohols.

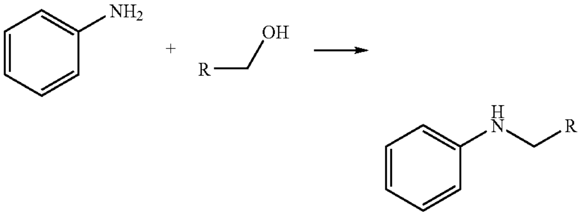

To a solution of alcohols (0.2 mmol) in DCE (1 mL) was added Dess-martin reagent (0.2 mmol). The mixture was stirred at room temperature for 15 minutes and filtered off solid with syringe filter. The filtrate was added to a solution of substituted anilines (0.1 mmol) and $NaBH(OAc)_3$ (0.3 mmol) in DCE (1 mL). The mixture was stirred 5 to 10 min at room temperature and quickly quenched with 1 N NaOH solution (1 mL). The DCE layer was separated and concentrated in vacuo. The residue was purified by flash chromatography (silica gel, 0-20% EtOAc/DCM) to give the desired mono alkylated anilines.

Method R General Procedure for Reductive Dimethylation of Anilines with Paraformaldehyde.

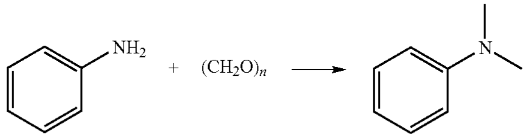

To a suspension of paraformaldehyde (1.0 mmol) in THF (5 mL) was added concentrated sulfuric acid (98%, 0.1 mL, 1.9 mmol). The mixture was stirred at room temperature while a suspension of anilines (0.1 mmol) and $NaBH_4$ (1.0 mmol) in THF (5 mL) was added to above paraformaldehyde suspension. The mixture was stirred at room temperature for 30 minutes and quenched by adding 1 N NaOH solution (1 mL). The mixture was concentrated and the residue was partitioned between DCM and water. The DCM layer was separated and concentrated in vacuo. The residue was purified by flash chromatography (silica gel, 0-10% EtOAc/DCM) to give the desired N,N-dimethyl anilines.

Method S General Procedure for the Preparation of Benzimidazole Derivatives:

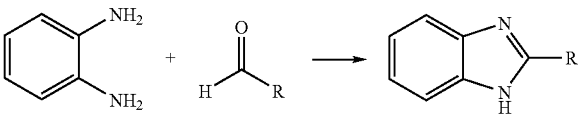

A solution of 2-aminoaniline (1.0 equiv.), benzoaldehyde/aldehyde derivatives (1.0 equiv.) and 1,4-benzoquinone (1.0 equiv.) in EtOH (10 mL) was heated at 95° C. for 4-6 hrs, and then cooled and concentrated in vacuo. The residue was purified on flash column chromatography (silica gel, 0-5% EtOAc/DCM) to give the desired products.

2. The Preparation of Claimed Compounds According to the General Procedures Described Above

Preparation of W366

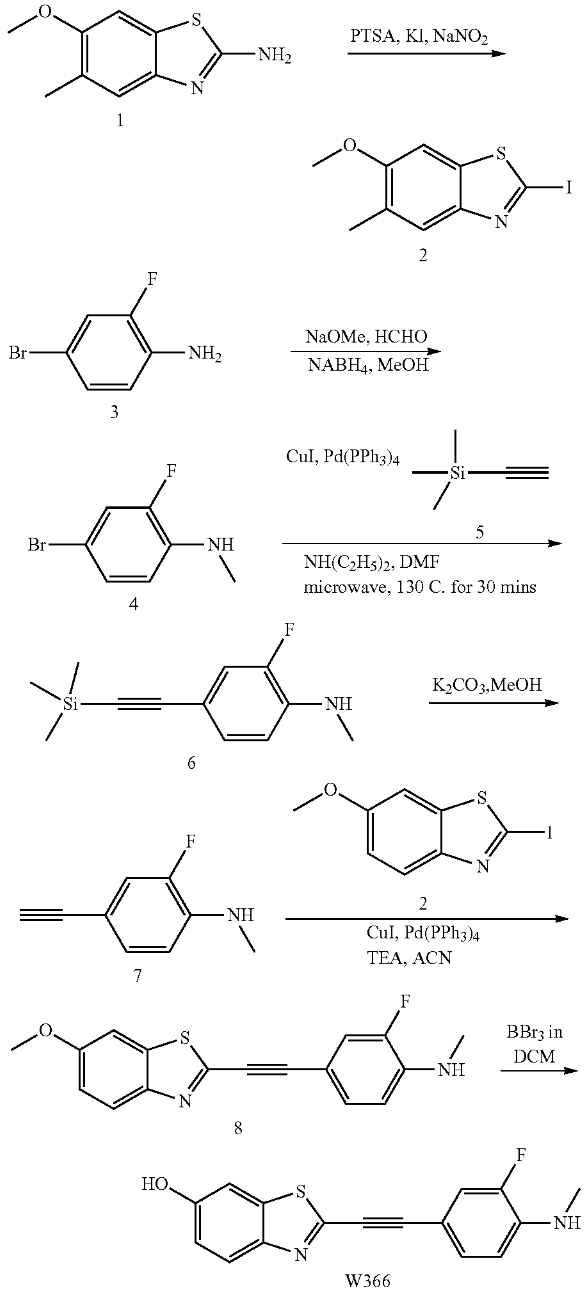

Preparation of 2-iodo-6-methoxybenzo[d]thiazole (2)

To a 100 mL round bottomed flask equipped with a magnetic stir bar, ACN (33.0 mL) and PTSA (6.3 g, 33.33 mmol), 1 (2.0 g, 11.11 mmol) was added at 0° C. and stirred for 15 min. To this, a solution of $NaNO_2$ (1.5 g, 22.22 mmol) and KI (4.6 g, 27.78 mmol) in $H_2$0 (7 mL) was added and stirred for 4 hr at RT. To the reaction mixture was added $H_2$0 (175 mL) and was then made basic with sat. $NaHCO_3$ (pH=9) and $Na_2S_2O_3$ (2M, 23 mL). The resulting reaction mixture was extracted with EtOAc (3×50 mL). The combined organic extracts were washed with water (50 mL), brine (50 mL), dried over $MgSO_4$ and concentrated in vacuo. The residue was purified over silica gel using EtOAc:Hexanes (0.5:9.5) as the eluent to afford 2 (1.62 g, 50%) as a white crystalline solid. $^1$H NMR (400 MHz, $CDCl_3$), δ: 3.85 (s, 3H), 7.00 7.04 (m, 1H), 7.24-7.27 (m, 1H), 7.89 (d, J=9.19 Hz, 1H); MS (ESI) 291.9 (M+H$^+$).

Preparation of 4-bromo-2-fluoro-N-methylaniline (4)

To a 100 mL round bottomed flask equipped with a magnetic stir bar was added at RT MeOH (26.0 mL), 3 (0.5 g, 2.63 mmol), NaOMe (0.71 g, 13.16 mmol) and paraformaldehyde (0.394 g, 13.16 mmol). The reaction was refluxed for 2 hr. The reaction mixture was then cooled to 0° C. and $NaHB_4$ (0.5 g, 13.16 mmol) was added in portions. After the addition, the reaction mixture was again refluxed for 1 hr. After the reaction is complete, MeOH was removed, water (50 mL) added and extracted with EtOAc (3×30 mL). The combined organic extracts were washed with water (30 mL), brine (30 mL), dried over $MgSO_4$ and concentrated in vacuo. The residue was purified over silica gel using EtOAc:Hexanes (0.5:9.5) as the eluent to afford 4 (0.5 g, 93%) as a brown oil. $^1$H NMR (400 MHz, $CDCl_3$), δ: 2.86 (s, 3H), 6.64 6.68 (m, 1H), 7.11-7.15 (m, 2H); MS (ESI): 203.9 (M+H$^+$).

Preparation of 2-fluoro-N-methyl-4-((trimethylsilyl)ethynyl)aniline (6)

A 5 mL microwave tube was charged with 4 (0.5 g, 2.45 mmol), 5 (0.7 mL, 4.9 mmol), [$Pd(PPh_3)_4$] (0.3 g, 0.245 mmol), CuI (0.07 g, 0.37 mmol) and $NH(C_2H_5)_2$ (0.8 mL, 7.35 mmol) in DMF (2.5 mL). The suspension was irradiated in a Biotage Emrys Optimizer microwave reactor (250 W) at 100° C. for 15 min. After cooling to room temperature water (50 mL) was added and then extracted with EtOAc (3×30 mL). The combined organic extracts were washed with water (30 mL), brine (30 mL), dried over $MgSO_4$ and the crude mixture was used for the next step. MS (ESI): 222.1 (M+H$^+$).

Preparation of 4-ethynyl-2-fluoro-N-methylaniline (7)

To a 25 mL round bottom flask equipped with a magnetic stir bar, 6 (crude 0.4 g), MeOH (9 mL) and $K_2CO_3$ (0.5 g, 3.62 mmol) were added. The reaction was stirred at RT for 30 min. To the reaction mixture, silica gel added (approximately 10 g) and concentrated in vacuo. The residue was purified over silica gel using EtOAc:Hexanes (1:3) as the eluent to afford 7 (0.26 g, 96%) as brown oil. MS (ESI): 150.1 (M+H$^+$).

Preparation of 2-fluoro-4-{(6-methoxybenzo[d]thiazol-2-yl)ethynyl)-N-methylaniline (8)

A 5 mL microwave tube was charged with 2 (0.2 g, 0.68 mmol), 7 (0.1 g, 0.68 mmol) [$Pd(PPh_3)_4$] (0.08 g, 0.034 mmol), CuI (0.02 g, 0.05 mmol) and TEA (0.28 mL, 2.04 mmol) in ACN (2.0 mL). The suspension was irradiated in a Biotage Emrys Optimizer microwave reactor (250 W) at 100° C. for 5 min. After cooling to room temperature the solvent was evaporated in vacuo. The residue was purified over silica gel using Hexanes:Dichloromethane (DCM) (0-100%) as the eluent to afford the coupling product 8 (0.084 g, 39%) as yellow solid. NMR (400 MHz, $CDCl_3$), δ: 2.92 (s, 3H), 3.87 (s, 3H), 6.64 (t, J=8.4 Hz, 1H), 7.11 (dd, J=12.0, 4.0 Hz, 1H), 7.22 (dd, J=10.4, 2 Hz, 1H), 7.27 (d, J=2.4, 1H), 7.33-7.35, (m, 1H), 7.96 (d, J=12 Hz, 1H); MS (ESI): 313.0 ($M+H^+$).

Preparation of 2-((3-fluoro-4-(methylamino)phenyl) ethynyl)benzo[d]thiazol-6-ol (W366)

To a 25 mL round bottomed flask equipped with a magnetic stir bar containing DCM (5.2 mL) was placed 8 (0.08 g, 0.26 mmol). The reaction mixture was cooled to 0° C. and $BBr_3$ (0.75 mL of 1M in DCM) was added drop wise. The reaction was stirred at RT for 8 hr. The reaction was then neutralized with sat. $NaHCO_3$ and extracted into DCM (2×10 mL). The combined organic extracts were washed with water (10 mL), brine (10 mL), dried over $MgSO_4$ and concentrated in vacuo. The residue was purified over silica gel using EtOAc:Hexanes (1:3) as the eluent to afford W366 (0.02 g, 26%) as a brown solid. $^1H$ NMR (400 MHz, DMSO-$d_6$), δ: 2.5 (d, J=10.4 Hz, 3H), 6.06-6.08 (m, 1H), 6.42 (t, J=8.8 Hz, 1H), 6.74 (dd, J=8.8, 2.4 Hz, 1H), 7.05-7.14 (m, 2H), 7.54 (d, J=8.8, 1H), 9.76 (br s, 1H); MS (ESI): 299.0 ($M+H^+$).

Preparation of W378 Standard

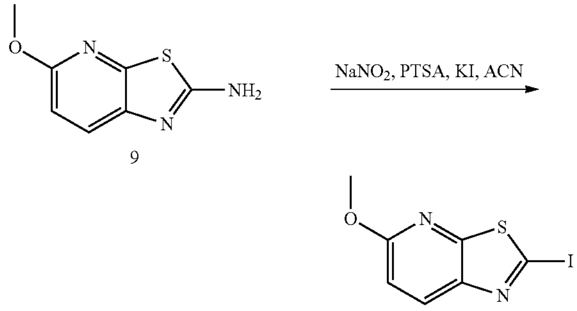

9

10

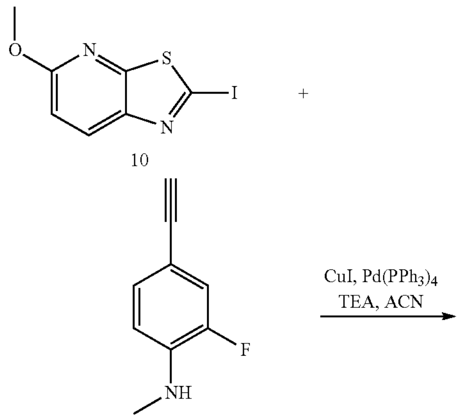

10

7

-continued

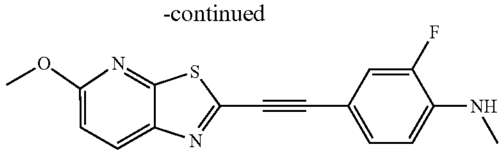

W378

Preparation of 2-iodo-5-methoxythiazolo[5,4-b]pyridine (10)

To a 25 mL round bottomed flask equipped with a magnetic stir bar, ACN (4.0 mL), PTSA (0.79 g, 4.14 mmol) and 9 (0.25 g, 1.38 mmol) were added at 0° C. and stirred for 15 min. To this, a solution of $NaNO_2$ (0.19 g, 2.76 mmol) and KI (0.57 g, 3.45 mmol) in $H_2O$ (0.9 mL) was added and stirred for 4 hr at RT. The reaction mixture was then added to $H_2O$ (15 mL), made basic with sat. $NaHCO_3$ (pH=9) and $Na_2S_2O_3$ (2M, 3 mL) was added. The resulting reaction mixture was extracted with EtOAc (3×20 mL). The combined organic extracts were washed with water (20 mL), brine (20 mL), dried over $MgSO_4$ and concentrated in vacuo. The residue was purified over silica gel using EtOAc:Hexanes (1:4) as the eluent to afford 10 (0.12 g, 30%) as a white crystalline solid. $^1H$ NMR (400 MHz, $CDCl_3$), δ: 3.97 (s, 3H), 6.77 (d, J=8.8 Hz, 1H), 8.08 (d, J=8.8 Hz, 1H); MS (ESI): 292.9 ($M+H^+$).

Preparation of 2-fluoro-4-((5-methoxythiazolo[5,4-b]pyridin-2-yl)ethynyl)-N-methylaniline (W378)

A 5 mL microwave tube was charged with 10 (0.12 g, 0041 mmol), 7 (0.06 g, 0041 mmol) [$Pd(PPh_3)_4$] (0.05 g, 0.004 mmol), CuI (0.012 g, 0.06 mmol) and TEA (0.2 mL, 1.23 mmol) in ACN (2.0 mL). The suspension was irradiated in a Biotage Emrys Optimizer microwave reactor (250 W) at 100° C. for 5 min. After cooling to room temperature the solvent was evaporated in vacuo. The residue was purified over silica gel using Hexanes:DCM (0-100%) as the eluent to afford the coupling product W378 (0.04 g, 31%) as yellow solid. MS (ESI): 314.0 ($M+H^+$).

Preparation of W366 Labeling Precursor

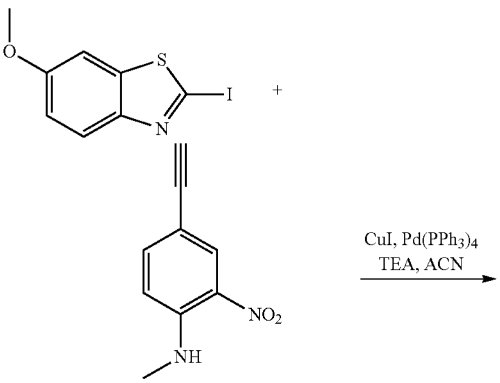

4-ethynyl-N-methyl-2-nitroaniline

-continued

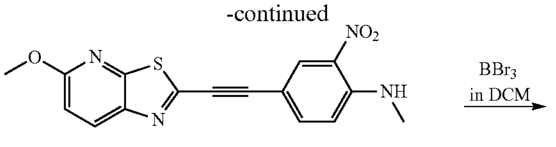

4-((6-methoxybenzo[d]thiazol-2-yl)ethynyl)-N-methyl-2-nitroaniline

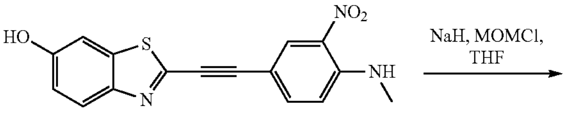

2-((4-methylamino)-3-nitrophenyl)-ethynyl)benzo[d]thiazol-6-ol

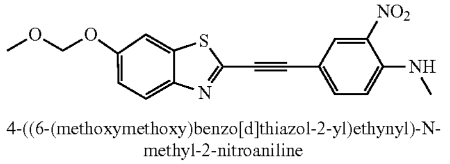

4-((6-(methoxymethoxy)benzo[d]thiazol-2-yl)ethynyl)-N-methyl-2-nitroaniline

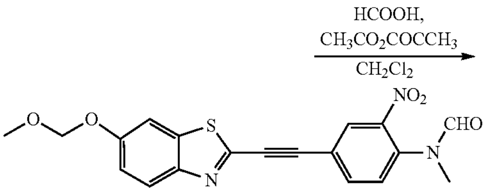

N-(4-((6-(ethoxymethoxy)benzo[d]thiazol-2-yl)ethynyl)-2-nitrophenyl)-N-methylformamide W366 labeling precursor

Preparation of 4-((6-methoxybenzo[d]thiazol-2-yl)ethynyl)-N-methyl-2-nitroaniline A 5 mL microwave tube is charged with 2 (1 equiv), 4-ethynyl-N-methyl-2-nitroaniline (1 equiv) [$Pd(PPh_3)_4$] (0.05 equiv), CuI (0.05 equiv) and TEA (5 equiv) in ACN (5 vol). The suspension is irradiated in a Biotage Emrys Optimizer microwave reactor (250 W) at 100° C. for 5 min. After cooling to room temperature, the solvent is evaporated in vacuo. The residue is purified over silica gel using Hexanes:DCM (0-100%) as the eluent to afford the coupling product.

Preparation of 2-((4-(methylamino)-3-nitrophenyl)ethynyl)benzo[d]thiazol-6-ol To a round bottomed flask equipped with a magnetic stir bar containing DCM (5 vol) is placed 4-((6-methoxybenzo[d]thiazol-2-yl)ethynyl)-N-methyl-2-nitroaniline (1 equiv). The reaction mixture is cooled to 0° C., $BBr_3$ (5 equiv of 1M in DCM) is added dropwise and the reaction is stirred at RT for 8 hours. The reaction is neutralized with sat. $NaHCO_3$, extracted into DCM (2×5 vol). The combined organic extracts are washed with water (5 vol), brine (5 vol), dried over $MgSO_4$ and concentrated in vacuo. The residue is purified over silica gel using EtOAc:Hexanes (1:3) as an eluent to afford the desired product.

Preparation of 4-((6-(ethoxymethoxy)benzo[d]thiazol-2-yl)ethynyl)-N-methyl-2-nitroaniline To a round bottom flask under Ar containing 2-((4-(methylamino)-3-nitrophenyl)ethynyl)benzo[d]thiazol-6-ol (1 equiv) is added THF (5 vol). To this solution is added NaH (1.3 equiv). The solution is stirred at RT for 30 min. To this solution is added MOM-Cl (1.5 equiv). The reaction is stirred overnight at RT. The reaction is poured onto water (10 vol) and extracted into DCM (10 vol). The organic layer is washed with water (10 vol), dried ($MgSO_4$), filtered and concentrated to dryness. The material is purified using EtOAc:Hexanes as the eluent over silica gel to afford the final product.

Preparation of N-(4-((6-(ethoxymethoxy)benzo[d]thiazol-2-yl)ethynyl)-2-nitrophenyl)-N-methylformamide (W366 Labeling Precursor)

To a round bottom flask containing 4-((6-(ethoxymethoxy)benzo[d]thiazol-2-yl)ethynyl)N-methyl-2-nitroaniline (1 equiv) is added formic acid (5 equiv), acetic anhydride (5 equiv) and DCM (5 vol). The reaction is warmed to 60° C. for 7 days. The rxn is then concentrated in vacuo and the material is purified using EtOAc:Hexanes as the eluent over silica gel to afford the final product.

Preparation of 2-(Pyridin-4-yl)quinoline (T123)

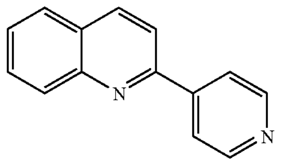 [SMILES: c1ccc2nc(-c3ccncc3)ccc2c1]

2-(Pyridin-4-yl)quinoline T123 was prepared using general procedure A from 2-chloroquinoline (82 mg, 0.5 mmol) and pyridin-4-ylboronic acid (61.5 mg, 0.5 mmol). The product was obtained as an off white solid (100 mg, 97%). $^1H$ NMR (400 MHz, $CDCl_3$): δ 8.75 (dd, J=5.0, 1.6 Hz, 2H), 8.26 (d, J=8.8 Hz, 1H), 8.16 (d. J=8.4 Hz, 1H), 8.04 (m, 2H), 7.87 (d, J=8.4 Hz, 1H), 7.83 (d, J=8.0 Hz, 1H), 7.74 (m, 1H), 7.55 (m, J=1H); MS (ESI): 207 (M+H$^+$).

Preparation of 5-(Quinolin-2-yl)picolinonitrile (T124)

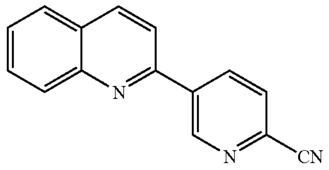 [SMILES: N#Cc1ccc(-c2ccc3ccccc3n2)cn1]

5-(Quinolin-2-yl)picolinonitrile T124 was prepared using general procedure A from 2-chloroquinoline (82 mg, 0.5 mmol) and 5-(4,4,5,5-tetramethyl-1,3,2-dioxaborolan-2-yl)picolinonitrile (115 mg, 0.5 mmol). The product was obtained as yellow solid (3 mg, 3%). NMR (400 MHz, $CDCl_3$): δ 9.48 (dd, J=2.4, 0.8 Hz, 1H), 8.69 (dd, J=8.0, 2.0 Hz, 1H), 8.33 (d, J=8.8 Hz, 1H), 8.19 (d, J=8.4 Hz, 1H), 7.93 (d, J=8.4 Hz, 1H), 7.90 (dd, J=8.4, 1.2 Hz, 1H), 7.87 (dd, J=8.4, 0.8 Hz, 1H), 7.81 (m, 1H), 7.63 (m, 1H); MS (ESI):232 (M+H$^+$).

Preparation of N,N-Dimethyl-5-(quinolin-2-yl)pyridin-2-amine (T125)

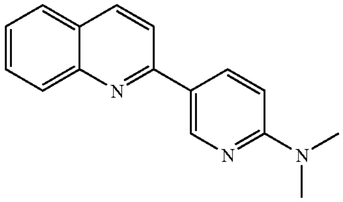 [SMILES: CN(C)c1ccc(-c2ccc3ccccc3n2)cn1]

N,N-Dimethyl-5-(quinolin-2-yl)pyridin-2-amine T125 was prepared using general procedure A from 2-chloroquinoline (82 mg, 0.5 mmol) and (6-(dimethylamino)-pyridin-3-yl)boronic acid (83 mg, 0.5 mmol). The product was obtained as yellow solid (90 mg, 72%). $^1$H NMR (400 MHz, $CDCl_3$): δ 8.93 (dd, J=2.4, 1H), 8.40 (dd, J=8.8, 2.4 Hz, 1H), 8.15 (d, J=8.4 Hz, 1H), 8.09 (d, J=8.6 Hz, 1H), 7.78 (d, J=7.2 Hz, 1H), 7.70 (m, 1H), 7.47 (m, 1H), 6.65 (dd, J=8.8, 0.8 Hz, 1H), 3.18 (s, 6H); MS (ESI): 250 (M+H$^+$).

Preparation of 2-(4-Fluoropyridin-3-yl)quinoline (T126)

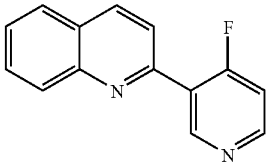 [SMILES: Fc1ccncc1-c1ccc2ccccc2n1]

2-(4-Fluoropyridin-3-yl)quinoline T126 was prepared using general procedure A from 2-chloroquinoline (82 mg, 0.5 mmol) and (5-fluoropyridin-3-yl)boronic acid (70 mg, 0.5 mmol). The product was obtained as white solid (80 mg, 71%). $^1$H NMR (400 MHz, $CDCl_3$): δ 8.93 (m, 1H), 8.63 (m, 1H), 8.24 (d, J=8.8 Hz, 1H), 8.13 (dd, J=8.8, 0.8 Hz, 1H), 7.82 (m, 2H), 7.74 (m, 1H), 7.06 (m, 1H); MS (ESI): 225 (M+H$^+$).

Preparation of 2-(6-Fluoropyridin-3-yl)quinoxaline (T127)

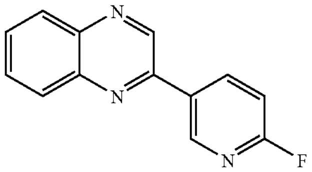 [SMILES: Fc1ccc(-c2cnc3ccccc3n2)cn1]

2-(6-Fluoropyridin-3-yl)quinoxaline T127 was prepared using general procedure A from 2-(6-fluoropyridin-3-yl)quinoxaline (82 mg, 0.5 mmol) and 2-fluoro-5-(4,4,5,5-tetramethyl-1,3,2-dioxaborolan-2-yl)pyridine (111 mg, 0.5 mmol). The product was obtained as white solid (93 mg, 82%). $^1$H NMR (400 MHz, $CDCl_3$): δ 9.32 (s, 1H), 9.00 (m, 1H), 8.66 (m, 1H), 8.15 (m, 2H), 7.82 (m, 2H), 7.15 (m, 1H); MS (ESI): 226 (M+H$^+$).

Preparation of 2-(Pyridin-3-yl)quinoxaline (T128)

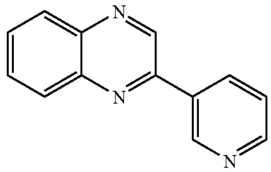 [SMILES: c1cncc(-c2cnc3ccccc3n2)c1]

2-(Pyridin-3-yl)quinoxaline T128 was prepared using general procedure A from 2-chloroquinoline (82 mg, 0.5 mmol) and (5-fluoropyridin-3-yl)boronic acid (70 mg, 0.5 mmol). The product was obtained as white solid (80 mg, 71%). $^1$H NMR (400 MHz, $CDCl_3$): δ 9.40 (d, J=2.0 Hz, 1H), 9.33 (s, 1H), 8.75 (dd, J=4.8 Hz, 1 Hz, 8.51 (m, 1H), 8.15 (m, 2H), 7.79 (m, 2H), 7.49 (m, 1H); MS (ESI): 208 (M+H$^+$).

Preparation of

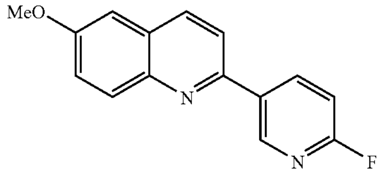 [SMILES: COc1ccc2nc(-c3ccc(F)nc3)ccc2c1]

2-(6-Fluoropyridin-3-yl)-6-methoxyquinoline T138 was prepared using general procedure A from 2-chloro-6-methoxyquinoline (65 mg, 0.33 mmol) and 2-fluoro-5-(4,4,5,5-tetramethyl-1,3,2-dioxaborolan-2-yl)pyridine (75 mg, 0.33 mmol). The product was obtained as yellow solid (30 mg, 35%). $^1$H NMR (400 MHz, $CDCl_3$): δ 8.91 (m, 1H), 8.63 (m, 1H), 8.16 (d, J=8.4 Hz, 1H), 8.05 (d, J=9.2 Hz, 1H), 7.80 (d, J=8.8 Hz, 1H), 7.41 (dd, J=9.2, 2.8 Hz, 1H), 7.11 (d, J=2.8 Hz, 1H), 7.08 (m, 1H); 3.96 (s, 3H); MS (ESI): 255 (M+H$^+$).

Preparation of

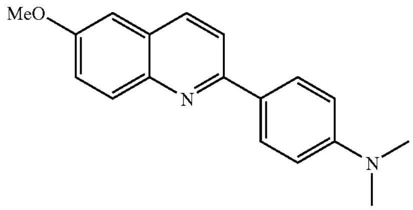 [SMILES: COc1ccc2nc(-c3ccc(N(C)C)cc3)ccc2c1]

4-(6-Methoxyquinolin-2-yl)-N,N-dimethylaniline T139 was prepared using general procedure A from 2-chloro-6-methoxyquinoline (65 mg, 0.33 mmol) and (4-(dimethylamino)phenyl)boronic acid (55 mg, 0.33 mmol). The product was obtained as yellow solid (30 mg, 33%). $^1$H NMR (400 MHz, $CDCl_3$): δ 8.06 (d, J=8.8 Hz, 2H), 8.02 (dd, J=8.4, 6.4

Hz, 2H), 7.78 (d, J=8.8 Hz, 1H), 7.33 (dd, J=9.2, 2.8 Hz, 1H), 7.06 (d, J=2.8 Hz, 1H), 6.83 (m, 2H), 3.93 (s, 3H), 3.03 (s, 6H); MS (ESI): 279 (M+H$^+$).

Preparation of

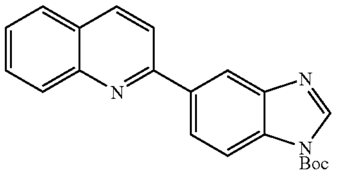 [SMILES: CC(C)(C)OC(=O)n1cnc2cc(-c3ccc4ccccc4n3)ccc21]

tert-Butyl 5-(quinolin-2-yl)-1H-benzo[d]imidazole-1-carboxylate T432 was prepared using general procedure A from 2-chloroquinoxaline (24 mg, 0.145 mmol) and tert-butyl 5-(4,4,5,5-tetramethyl-1,3,2-dioxaborolan-2-yl)-1H-indole-1-carboxylate (50 mg, 0.145 mmol). The product was obtained as white wax (30 mg, 60%). $^1$H NMR (400 MHz, $CDCl_3$): δ 8.55 (dd, J=1.6, 0.8 Hz, 1H), 8.41 (dd, J=8.8, 2.0 Hz, 1H), 8.32 (d, J=8.8 Hz, 1H), 8.29 (s, 1H), 8.26 (d, J=8.4 Hz, 1H), 8.18 (d, J=8.4 Hz, 1H), 7.95 (d, J=8.8 Hz, 1H), 7.75 (m, 1H), 7.55 (m, 1H), 1.76 (s, 9H); MS (ESI): 346 (M+H$^+$).

Preparation of

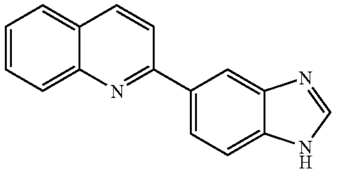 [SMILES: c1ccc2nc(-c3ccc4[nH]cnc4c3)ccc2c1]

2-(1H-Indol-5-yl)quinoline T433 was prepared using general procedure P. The reaction was performed on a 10 mg scale of T432. T433 was isolated as a yellow solid (5 mg, 35%). $^1$H NMR (400 MHz, $CDCl_3$): δ 8.83 (t, 1H), 8.70-8.51 (m, 4H), 8.24-8.22 (m, 1H), 8.14-8.08 (m, 3H), 8.00 (d, J=8.8 Hz, 0.5H), 7.88 (m, 1H), 7.68 (d, J=8.4 Hz, 0.5H); MS (ESI): 246 (M+H$^+$).

Preparation of

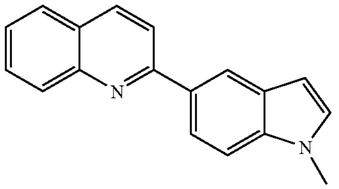 [SMILES: Cn1ccc2cc(-c3ccc4ccccc4n3)ccc21]

2-(1-Methyl-1H-indol-5-yl)quinoline T453 was prepared using general procedure A from 2-chloroquinoline (32 mg, 0.2 mmol) and 1-methyl-5-(4,4,5,5-tetramethyl-1,3,2-dioxaborolan-2-yl)-1H-indole (51 mg, 0.2 mmol). The product was obtained as off-white solid (22 mg, 42%). $^1$H NMR (400 MHz, $CDCl_3$): δ 8.43 (dd, J=2.0, 0.8 Hz, 1H), 8.17 (d, J=8.8 Hz, 2H), 8.12 (dd, J=8.8, 2.0 Hz, 1H), 7.95 (d, J=8.8 Hz, 1H), 7.80 (dd, J=8.4, 1.6 Hz, 1H), 7.70 (m, 1H), 7.48 (m, 1H), 7.44 (d, J=8.8 Hz, 1H), 7.09 (d, J=3.2 Hz, 1H), 6.60 (dd, J=3.2, 0.8 Hz, 1H), 3.82 (s, 3H); MS (ESI): 259 (M+H$^+$).

Preparation of 2-(1-(3-fluoropropyl)-1H-indol-5-yl) quinoline (T461)

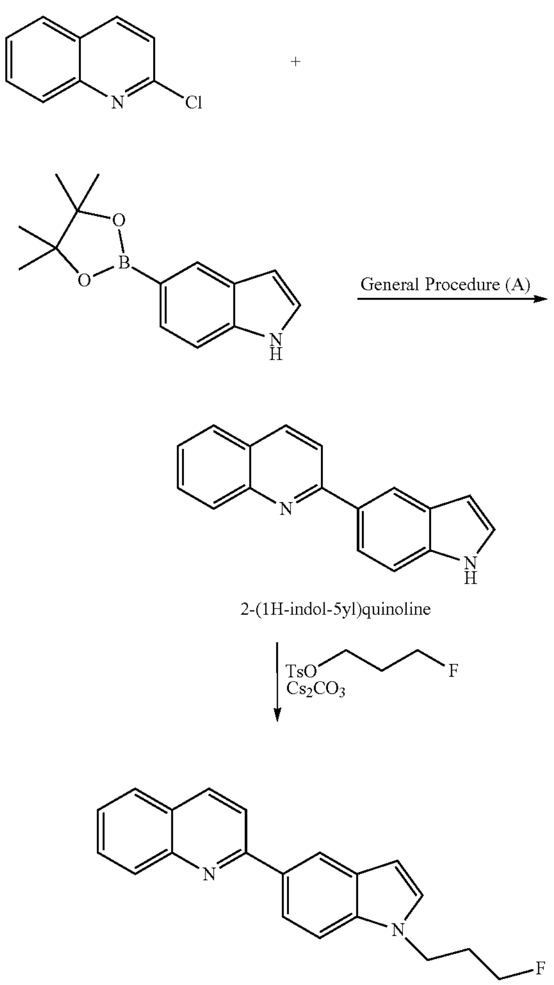

2-(1H-indol-5yl)quinoline 2-(1-(3-fluoropropyl)-1H-indol-5yl)quinoline 2-(1H-indol-5-yl)quinoline was prepared using general procedure A from 2-chloroquinoline (32 mg, 0.2 mmol) and 1-methyl-5-(4,4,5,5-tetramethyl-1,3,2-dioxaborolan-2-yl)-1H-indole (51 mg, 0.2 mmol). The product was obtained as off-white solid (22 mg, 42%). MS (ESI): 245 (M+H$^+$).

2-(1-(3-fluoropropyl)-1H-indol-5-yl)quinoline T461 was prepared using general procedure E. The reaction was performed on a 24 mg scale of 2-(1H-indol-5-yl)quinoline. T461 was isolated as a yellow wax (0.8 mg, 2.6%). $^1$H NMR (400 MHz, $CDCl_3$): δ 8.70 (d, J=8.4 Hz, 1H), 8.67 (d, J=8.8 Hz, 1H), 8.44 (d, J=1.2 Hz, 1H), 8.10 (d, J=9.2 Hz, 1H), 8.03-7.98 (m, 3H), 7.78 (t, J=7.2 Hz, 1H), 7.56 (d, J=8.8 Hz, 1H), 7.24 (d, J=3.2 Hz, 1H), 6.71 (d, J=3.2 Hz, 1H), 4.47 (t, J=5.2 Hz, 1H), 4.36 (m, 3H), 2.29-2.16 (m, 2H); MS (ESI): 305 (M+H$^+$).

Preparation of 4-(4-fluoroquinolin-2-yl)-N-methylaniline (T466)

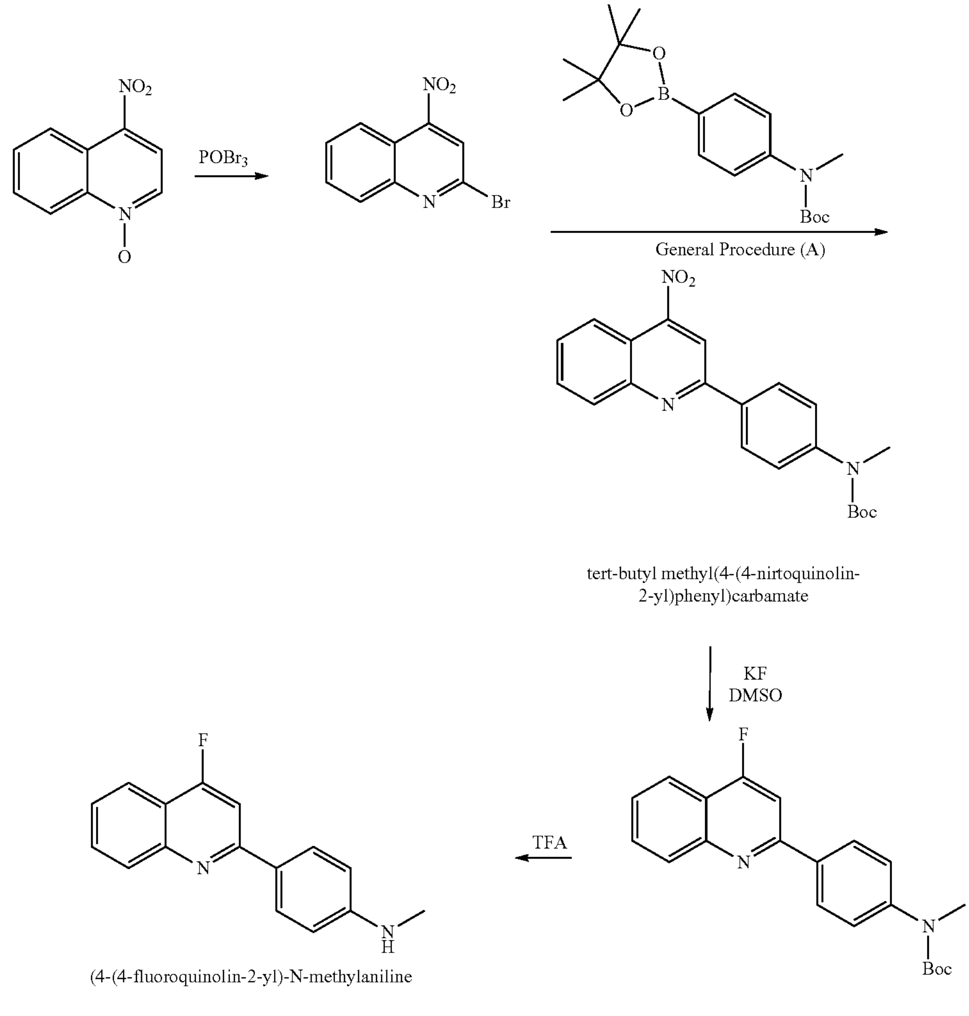

tert-butyl methyl(4-(4-nirtoquinolin-2-yl)phenyl)carbamate tert-butyl(4-(4-fluoroquinolin-2-yl)phenyl)(methyl)carbamate (4-(4-fluoroquinolin-2-yl)-N-methylaniline tert-Butyl methyl(4-(4-nitroquinolin-2-yl)phenyl)carbamate

4-Nitroquinoline 1-oxide (940 mg, 4.9 mmol) in chloroform (12 mL) was cooled to 0° C. To this solution, $POBr_3$ (1.77 g, 6.2 mmol) was added in small portions. The mixture was stirred at 0° C. for 2 h and diluted with DCM (50 mL), and poured on ice (50 g). To this suspension, 1 M NaOH was added to adjust pH to about 9. Layers were separated and the organic layer was washed with water (2×50 mL) and dried over MgSO4 and concentrated. The crude product was purified by silica chromatography to afford 2-bromo-4-nitroquinoline as a yellow solid (620 mg, 50%). $^1H$ NMR (400 MHz, $CDCl_3$): δ 7.63-7.94 (m, 2H), 8.06 (s, 1H), 8.17 (t, J=7.16, 6.84 Hz, 1H), 8.38 (d, J=8.76 Hz, 1H).

2-Bromo-4-nitroquinoline (50 mg, 0.2 mmol) and tert-butyl methyl(4-(4,4,5,5-tetramethyl-1,3,2-dioxaborolan-2-yl)phenyl)carbamate (66 mg, 0.2 mmol) were reacted using General Procedure (A) to afford tert-butyl methyl(4-(4-nitroquinolin-2-yl)phenyl)carbamate as a yellow oil (52 mg, 68%). $^1H$ NMR (400 MHz, $CDCl_3$): δ 8.43-8.40 (m, 2H), 8.28 (m, 1H), 8.19 (m, 2H), 7.87 (m, 1H), 7.73 (m, 1H), 7.46 (m, 2H), 3.35 (s, 3H), 1.59 (s, 3H), 1.50 (s, 9H); MS (ESI): 380 ($M+H^+$).

4-(4-fluoroquinolin-2-yl)-N-methylaniline T466 tert-Butyl methyl(4-(4-fluoroquinolin-2-yl)phenyl)carbamate was prepared using general procedure M from tert-butyl methyl(4-(4-nitroquinolin-2-yl)phenyl)carbamate (10 mg, 0.026 mmol) and KF (60 mg, 1 mmol). tert-butyl (4-(4-fluoroquinolin-2-yl)phenyl)(methyl)carbamate was isolated as a clear oil (4.5 mg, 49%). $^1H$ NMR (400 MHz, $CDCl_3$): δ 8.16 (m, 1H), 8.12-8.07 (m, 3H), 7.78 (m, 1H), 7.59-7.54 (m, 2H), 7.41 (m, 1H), 3.32 (s, 3H), 1.48 (s, 9H); MS (ESI): 353 ($M+H^+$).

tert-Butyl (4-(4-fluoroquinolin-2-yl)phenyl)(methyl)carbamate (4.5 mg, 0.013 mmol) was treated with TFA by using general procedure P. The crude product was purified by HPLC to afford T466 as an orange-colored solid (1.8 mg, 55%). $^1$H NMR (400 MHz, $CDCl_3$): δ 8.57 (d, J=8.4 Hz, 1H), 8.02-7.97 (m, 3H), 7.75 (t, J=7.6 Hz, 1H), 7.56 (d, J=10.0 Hz, 1H), 6.72 (d, J=8.4 Hz, 2H), 2.95 (s, 3H); MS (ESI): 253 (M+H$^+$).

Preparation of N-Methyl-4-(quinolin-3-yl)aniline (T477)

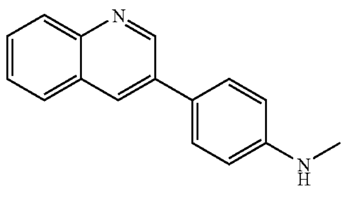 [SMILES: CNc1ccc(-c2cnc3ccccc3c2)cc1]

3-Bromoquinoline (42 mg, 0.2 mmol) and tert-butyl methyl(4-(4,4,5,5-tetramethyl-1,3,2-dioxaborolan-2-yl)phenyl)carbamate (66 mg, 0.2 mmol) were reacted using General Procedure (A) to afford tert-butyl methyl(4-(quinolin-3-yl) phenyl)carbamate a clear wax (44 mg, 66%). $^1$H NMR (400 MHz, $CDCl_3$): δ 9.18 (d, J=2.4 Hz, 1H), 8.31 (d, J=2.0 Hz, 1H), 8.15 (m, 1H), 7.89 (m, 1H), 7.73 (m, 1H), 7.68 (m, 2H), 7.59 (m, 1H), 7.42 (m, 2H), 3.3 (s, 3H), 1.50 (s, 9H); MS (ESI): 335 (M+H$^+$).

tert-Butyl methyl(4-(quinolin-3-yl)phenyl)carbamate (44 mg, 0.13 mmol) was then treated with TFA by using the general procedure P. The crude product was purified by HPLC to afford T477 as an orange-colored wax (13 mg, 29%). $^1$H NMR (400 MHz, $CDCl_3$): δ 9.46 (d, J=2.0 Hz, 1H), 8.79 (d, J=1.6 Hz, 1H), 8.47 (d, J=8.4 Hz, 1H), 8.08 (d, J=8.4 Hz, 1H), 7.95 (m, 1H), 7.83 (m, 1H), 7.62 (m, 2H), 6.82 (m, 2H), 2.94 (s, 3H); MS (ESI): 235 (M+H$^+$).

Preparation of

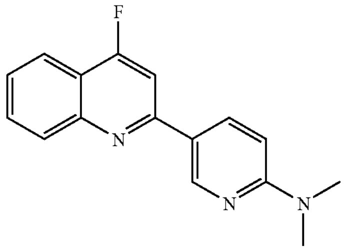

5-(4-Fluoroquinolin-2-yl)-N,N-dimethylpyridin-2-amine T480 was prepared using general procedure M from N,N-dimethyl-5-(4-nitroquinolin-2-yl)pyridin-2-amine (4 mg, 0.014 mmol) and KF (16 mg, 0.28 mmol). The crude product was purified by silica chromatography to afford 5-(4-fluoroquinolin-2-yl)-N,N-dimethylpyridin-2-amine as a light-brown solid (1.4 mg, 37%). $^1$H NMR (400 MHz, $CDCl_3$): δ 8.89 (d, J=2.8 Hz, 1H), 8.36 (dd, J=11.6 Hz, 1H), 8.09 (m, 1H), 8.04 (m, 1H), 7.73 (m, 1H), 7.51 (m, 1H), 7.47 (d, J=11.6 Hz, 1H), 6.64 (d, J=9.2 Hz, 1H), 3.19 (s, 6H); MS (ESI): 268 (M+H$^+$).

Preparation of

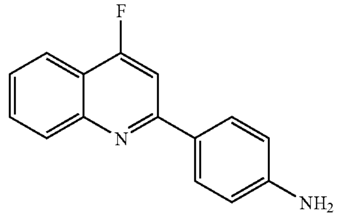 [SMILES: Nc1ccc(-c2cc(F)c3ccccc3n2)cc1]

4-(4-Fluoroquinolin-2-yl)aniline T492 was prepared by using general procedure M from 4-(4-Nitroquinolin-2-yl) aniline (6 mg, 0.02 mmol) and KF (26 mg, 0.45 mmol), The crude product was purified by silica chromatography to afford 4-(4-fluoroquinolin-2-yl)aniline as a yellow solid (2 mg, 42%). $^1$H NMR (400 MHz, $CDCl_3$): δ 8.11 (m, 1H), 8.03 (m, 1H), 8.00 (m, 2H), 7.72 (m, 1H), 7.51 (m, 1H), 7.48 (d, J=11.6 Hz, 1H), 6.80 (m, 2H), 3.93 (br s, 2H); MS (ESI): 239 (M+H$^+$).

Preparation of

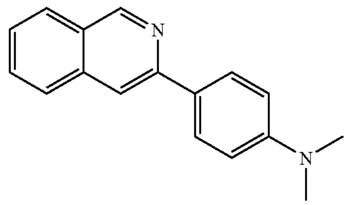 [SMILES: CN(C)c1ccc(-c2cc3ccccc3cn2)cc1]

4-(Isoquinolin-3-yl)-N,N-dimethylaniline T500 was by prepared using general procedure A from 3-chloroisoquinoline (41 mg, 0.25 mmol) and (4-(dimethylamino)phenyl)boronic acid (41 mg, 0.25 mmol). The product T500 was obtained as a white solid (11 mg, 17%). NMR (400 MHz, $CDCl_3$): δ 9.27 (s, 1H), 8.05 (m, 2H), 7.94 (s, 1H), 7.93 (d, J=6.8 Hz, 1H), 7.81 (d, J=8.4 Hz, 1H), 7.63 (m, 1H), 7.49 (m, 1H), 6.84 (m, 2H), 3.03 (s, 6H); MS (ESI): 249 (M+H$^+$).

Preparation of

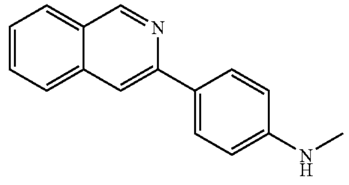 [SMILES: CNc1ccc(-c2cc3ccccc3cn2)cc1]

3-Chloroisoquinoline (33 mg, 0.2 mmol) and tert-butyl methyl(4-(4,4,5,5-tetramethyl-1,3,2-dioxaborolan-2-yl)phenyl)carbamate (66 mg, 0.2 mmol) were reacted using general procedure A to afford tert-butyl (4-(isoquinolin-3-yl)phenyl) (methyl)carbamate as a clear oil (12 mg, 18%). $^1$H NMR (400 MHz, $CDCl_3$): δ 9.33 (s, 1H), 8.09 (m, 2H), 8.05 (s, 1H), 7.99 (m, 1H), 7.87 (m, 1H), 7.69 (m, 1H), 7.58 (m, 1H), 7.38 (m, 2H), 3.32 (s, 3H), 1.48 (s, 9H); MS (ESI): 335 (M+H$^+$).

4-(Isoquinolin-3-yl)-N-methylaniline T501 was prepared using general procedure K. The reaction was performed on a 12 mg scale of tert-Butyl (4-(isoquinolin-3-yl)phenyl)(methyl). T501 was isolated as a off-white solid (7 mg, 72%). $^1$H NMR (400 MHz, $CDCl_3$): δ 9.71 (s, 1H), 8.68 (s, 1H), 8.47 (d, J=8.4 Hz, 1H), 8.29 9d, J=8.0 Hz, 1H), 8.19 (m, 1H), 8.01-7.95 (m, 3H), 7.34 9d, J=8.8 Hz, 2H), 3.02 (s, 3H); MS (ESI): 235 (M+H$^+$).

Preparation of

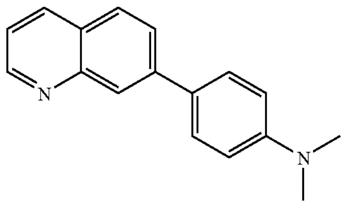 [SMILES: CN(C)c1ccc(-c2ccc3cccnc3c2)cc1]

N,N-Dimethyl-4-(quinolin-7-yl)aniline T504 was prepared using general procedure A from 7-bromoquinoline (52 mg, 0.25 mmol) and (4-(dimethylamino)phenyl)boronic acid (41 mg, 0.25 mmol). The product T504 was obtained as a yellow solid (52 mg, 83%). $^1$H NMR (400 MHz, $CDCl_3$): δ 8.89 (dd, J=4.4, 1.6 Hz, 1H), 8.28 (m, 1H), 8.12 (dq, J=8.4, 0.8 Hz, 1H), 7.81 (d, J=1.2 Hz, 2H), 7.68 (m, 2H), 7.33 (dd, J=8.4, 4.4 Hz, 1H), 6.84 (m, 2H), 3.00 (s, 3H); MS (ESI): 249 (M+H$^+$).

Preparation of

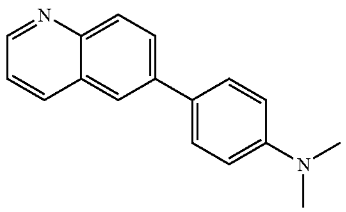 [SMILES: CN(C)c1ccc(-c2ccc3ncccc3c2)cc1]

N,N-Dimethyl-4-(quinolin-6-yl)aniline T505 was prepared using general procedure A from 6-bromoquinoline (52 mg, 0.25 mmol) and (4-(dimethylamino)phenyl)boronic acid (41 mg, 0.25 mmol). The product T505 was obtained as a yellow solid (42 mg, 67%). $^1$H NMR (400 MHz, $CDCl_3$): δ 8.85 (dd, J=4.4, 1.6 Hz, 1H), 8.15 (m, 2H), 7.97 (dd, J=8.4, 1.6 Hz, 1H), 7.92 (d, J=2.0 Hz, 1H), 7.63 (m, 2H), 7.38 (dd, J=8.4, 4.4 Hz, 1H), 6.84 (m, 2H), 3.01 (s, 6H); MS (ESI): 249 (M+H$^+$).

Preparation of

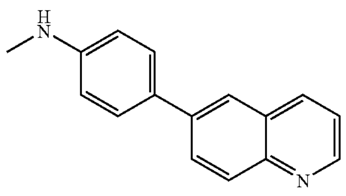 [SMILES: CNc1ccc(-c2ccc3ncccc3c2)cc1]

N-Methyl-4-(quinolin-6-yl)aniline T514 was prepared using general procedure A from 6-bromoquinoline (41 mg, 0.2 mmol) and N-methyl-4-(4,4,5,5-tetramethyl-1,3,2-dioxaborolan-2-yl)aniline (46 mg, 0.2 mmol). The product T514 was obtained as a black solid (20 mg, 43%). $^1$H NMR (400 MHz, $CDCl_3$): δ 8.86 (dd, J=4.4, 1.6 Hz, 1H), 8.18 9m, 1H), 8.13 (d, J=9.2 Hz, 1H), 7.96 (dd, J=8.8, 2.4 Hz, 1H), 7.92 (d, J=2.0 Hz, 1H), 7.59 (m, 2H), 7.40 (dd, J=8.4, 4.4 Hz, 1H), 6.74 (m, 2H), 2.91 (s, 3H); MS (ESI): 235 (M+H$^+$).

Preparation of

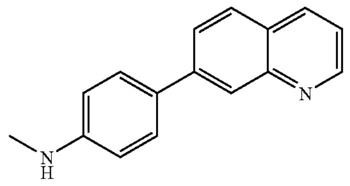 [SMILES: CNc1ccc(-c2ccc3cccnc3c2)cc1]

N-Methyl-4-(quinolin-7-yl)aniline T515 was prepared using general procedure A from 7-bromoquinoline (41 mg, 0.2 mmol) and N-methyl-4-(4,4,5,5-tetramethyl-1,3,2-dioxaborolan-2-yl)aniline (46 mg, 0.2 mmol). T515 was obtained as a yellow wax (18 mg, 38%). $^1$H NMR (400 MHz, $CDCl_3$): δ 8.90 (dd, J=4.0, 1.2 Hz, 1H), 8.26 (m, 1H), 8.13 (m, 1H), 7.82-7.81 (m, 2H), 7.64 (m, 2H), 7.34 (dd, J=8.4, 4.4 Hz, 1H), 6.73 (m, 2H), 2.90 (s, 3H); MS (ESI): 235 (M+H$^+$).

Preparation of

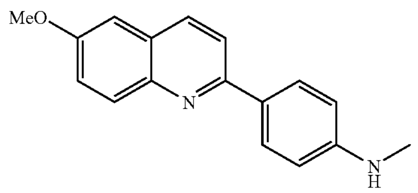 [SMILES: CNc1ccc(-c2ccc3cc(OC)ccc3n2)cc1]

4-(6-Methoxyquinolin-2-yl)-N-methylaniline T523 was prepared using general procedure A from 2-chloro-6-methoxyquinoline (39 mg, 0.2 mmol) and N-methyl-4-(4,4,5,5-tetramethyl-1,3,2-dioxaborolan-2-yl)aniline (46 mg, 0.2 mmol). T523 was obtained as a brown solid (27 mg, 51%). $^1$H NMR (400 MHz, $CDCl_3$): δ 8.03-7.99 (m, 4H), 7.75 (d, J=8.4 Hz, 1H), 7.33 (dd, J=9.2, 2.8 Hz, 1H), 7.04 (d, J=2.8 Hz, 1H), 6.71 (m, 2H), 3.92 (s, 3H), 2.89 (s, 3H); MS (ESI): 235 (M+H$^+$).

Preparation of

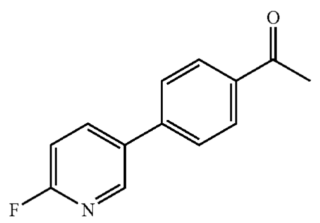 [SMILES: CC(=O)c1ccc(-c2ccc(F)nc2)cc1]

1-(4-(6-Fluoropyridin-3-yl)phenyl)ethanone T405 was prepared using general procedure A from 1-(4-bromophenyl)

ethanone (117 mg, 0.5 mmol) and 2-fluoro-5-(4,4,5,5-tetramethyl-1,3,2-dioxaborolan-2-yl)pyridine (100 mg, 0.5 mmol). T405 was obtained as a yellow solid (64 mg, 59%). $^1$H NMR (400 MHz, $CDCl_3$): δ 8.47 (m, 1H), 8.06 9m, 2H), 8.04-7.99 (m, 1H), 7.65 (m, 2H), 7.05 (ddd, J=8.4, 3.2, 0.8 Hz, 1H), 2.65 (s, 3H); MS (ESI): 216 ($M+H^+$).

Preparation of 5-((1-(2-Fluoroethyl)-1H-benzo[d]imidazol-2-yl)ethynyl)pyridin-2-amine (T568)

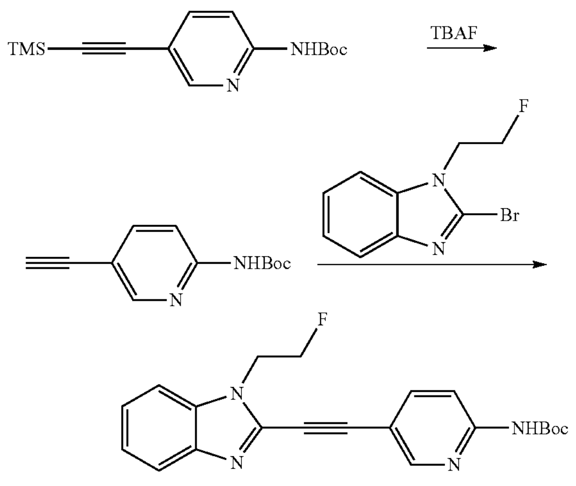

tert-butyl(5-((1-(2-fluoroethyl)-1H-benzo[d]imidazol-2-yl)ethynyl)pyridin-2-yl)carbamate

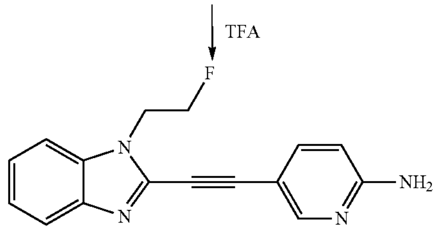

5-((1-(2-fluoroethyl)-1H-benzo[d]imidazol-2-yl)ethynyl)pyridin-2-amine tert-Butyl (5-ethynylpyridin-2-yl)carbamate was prepared from tert-butyl (5-((trimethylsilyl)ethynyl)pyridin-2-yl)carbamate (200 mg, 0.69 mmol) using general procedure J. The product was obtained as a white solid (98 mg, 65%). $^1$H NMR (300 MHz, $CDCl_3$): δ 8.44 (dd, J=2.0, 0.8 Hz, 1H), 7.69 (dd, J=8.4, 2.4 Hz, 1H), 7.33 (dd, J=8.4, 0.8 Hz, 1H), 6.09 (s, 1H), 3.17 (s, 1H), 1.26 (s, 9H).

tert-Butyl (5-ethynylpyridin-2-yl)carbamate (22 mg, 0.1 mmol) and 2-bromo-1-(2-fluoroethyl)-1H-benzo[d]imidazole (24.3 mg, 0.1 mmol) was reacted using general procedure B to afford tert-butyl (5-((1-(2-fluoroethyl)-1H-benzo[d]imidazol-2-yl)ethynyl)pyridin-2-yl)carbamate (12 mg, 31%). $^1$H NMR (300 MHz, $CDCl_3$): 8.51 (d, J=1.6 Hz, 1H), 8.47 (m, 1H), 7.88 (dd, J=8.8, 2.4 Hz, 7.40-7.34 (m, 3H), 7.31 (d, J=12.8 Hz, 6.22 (s, 1H), 4.80 (t, J=4.8 Hz, 1H), 4.68 (t, J=4.8 Hz, 1H), 4.53 (m, 1H), 4.47 (m, 1H), 1.55 (s, 9H).

5-((1-(2-Fluoroethyl)-1H-benzo[d]imidazol-2-yl)ethynyl)pyridin-2-amine was prepared using general procedure P from tert-butyl (5-((1-((2-fluoroethyl)-1H-benzo[d]imidazol-2-yl)ethynyl)pyridin-2-yl)carbamate (10 mg, 0.026 mmol). The product T568 was obtained as a yellow solid (0.5 mg, 5%). $^1$H NMR (300 MHz, MeOH-d4): δ 8.32 (br s, 1H), 8.01 (dd, J=9.2, 1.6 Hz, 1H), 7.71-7.66 (m, 2H), 7.45 (t, J=7.2 Hz, 1H), 7.412 (m, 1H), 6.98 (d, J=9.2 Hz, 1H), 4.89-4.76 (m, 4H); MS (ESI): 281 ($M+H^+$).

Preparation of

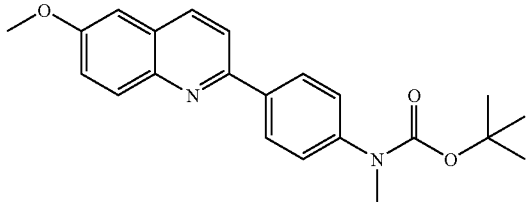 [SMILES: COc1ccc2nc(-c3ccc(N(C)C(=O)OC(C)(C)C)cc3)ccc2c1]

tert-Butyl-4-(6-methoxyquinolin-2-yl)phenyl)(N-methyl) carbamate T406 was prepared using general procedure A. Reaction was performed on a 0.1 g scale. T406 was isolated as off white solid (0.118 g, 62%). $^1$H NMR (400 MHz, $CDCl_3$): δ 8.10-8.07 (m, 4H), 7.80 (d, J=8.4 Hz, 1H), 7.36 (dt, J=8.4, 2.0 Hz, 3H), 7.07 (d, J=2.8 Hz, 1H), 3.93 (s, 3H), 3.30 (s, 3H), 1.46 (s, 9H), 2.56 (br s, 2H); MS (ESI): 365.2 ($M+H^+$).

Preparation of

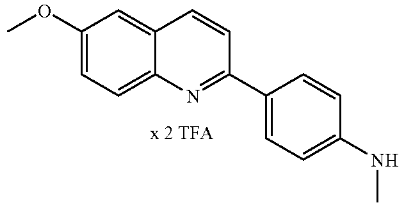

4-(6-Methoxyquinolin-2-yl)-N-methylaniline bis TFA salt T407 was prepared using general procedure P. Reaction was performed on a 0.045 g scale. The crude mixture was purified by HPLC (Acetnitrile: $H_2O$: 0.05% TFA) system. T407 was isolated as an orange solid (0.018 g, 33%). $^1$H NMR (400 MHz, $CD_3OD$): δ 8.72 (d, J=9.2 Hz, 1H), 8.17 (d, J=9.2 Hz, 1H), 8.10 (d, J=9.2 Hz, 1H), 7.95 (dt, J=9.2, 2.8 Hz, 2H), 7.64 (dd, J=9.2, 2.8 Hz, 1H), 7.56 (d, J=2.8 Hz, 1H), 6.81 (dt, J=9.2, 2.8 Hz, 2H), 3.98 (s, 3H), 2.89 (s, 3H); MS (ESI): 265.1 ($M+H^+$).

Preparation of

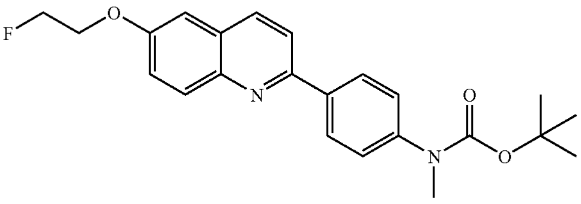 [SMILES: CN(C(=O)OC(C)(C)C)c1ccc(-c2ccc3cc(OCCF)ccc3n2)cc1]

tert-Butyl 4-(6-fluoroethoxy)quinolin-2-yl)-N-methylaniline carbamate T408 was prepared using general procedure A and general procedure C sequentially. Reaction was performed on a 0.042 g scale. T408 was isolated as an off white solid (0.070 g, 76%, in two steps). $^1$H NMR (400 MHz, $CDCl_3$): δ 8.10-8.08 (m, 4H), 7.80 (d, J=8.8 Hz, 1H), 7.40 (dd, J=9.2, 2.8 Hz, 1H), 7.37 (br d, J=8.8 Hz, 2H), 7.08 (d, J=2.4 Hz, 1H), 4.88 (t, J=4.0 Hz, 1H), 4.76 (t, J=4.0 Hz, 1H), 4.37 (t, J=4.4 Hz, 1H), 4.30 (t, J=4.4 Hz, 1H), 3.30 (s, 3H), 1.46 (s, 9H); MS (ESI): 397.2 ($M+H^+$).

Preparation of

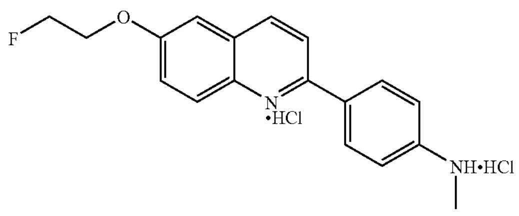

4-(6-Fluoroethoxy)quinolin-2-yl)-N-methylaniline dihydrochloride T409 was prepared using general procedure K. Reaction was performed on a 0.045 g scale. T409 was isolated as an orange solid (0.035 g, 83%). $^1$H NMR (400 MHz, $CD_3OD$): δ 8.74 (d, J=8.4 Hz, 1H), 8.18 (dd, J=15.2, 9.2 Hz, 2H), 7.98 (d, J=7.2 Hz, 2H), 7.71 (br d, J=9.2 Hz, 1H), 7.61 (br s, 1H), 6.88 (dt, J=9.2, 2.8 Hz, 2H), 4.84 (t, J=4.0 Hz, 1H), 4.74 (t, J=4.0 Hz, 1H), 4.46 and 4.39 (t, J=4.0 Hz, 1H), 2.91 (s, 3H); MS (ESI): 297.1 ($M+H^+$).

Preparation of

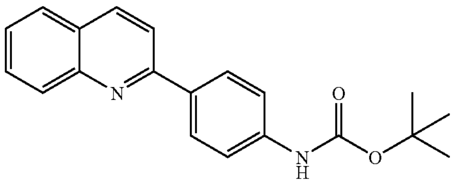 [SMILES: CC(C)(C)OC(=O)Nc1ccc(-c2ccc3ccccc3n2)cc1]

tert-Butyl (4-(quinolin-2-yl) phenyl)carbamate T410 was prepared using general procedure A. Reaction was performed on a 0.164 g scale. T410 was isolated as an off white solid (0.203 g, 64%). $^1$H NMR (400 MHz, $CDCl_3$): δ 8.16 (t, J=8.0 Hz, 2H), 8.12 (dt, J=8.8, 2.4 Hz, 2H), 7.83 (d, J=8.4 Hz, 1H), 7.79 (dd, J=8.0, 1.2 Hz, 1H), 7.69 (ddd, J=8.4, 7.2, 1.6 Hz, 1H), 7.55-7.47 (m, 3H), 6.63 (br s, 1H), 1.53 (s, 9H); MS (ESI): 321.1 ($M+H^+$).

Preparation of

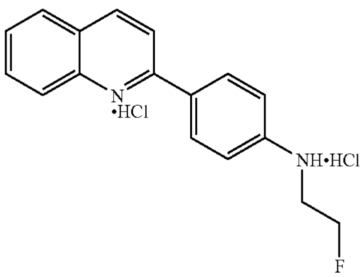

N-(2-Fluoroethyl)-4-(quinolin-2-yl)aniline dihydrochloride T411 was prepared using general procedure A and general procedure D sequentially. Reaction was performed on a 0.036 g scale. T411 was isolated as an orange solid (0.018 g, 48%, in two steps). $^1$H NMR (400 MHz, $CD_3OD$): δ 9.11 (br s, 1H), 8.72 (d, J=8.8 Hz, 1H), 8.38 (dt, J=9.2, 2.8 Hz, 1H), 8.10 (d, J=8.8 Hz, 2H), 8.007 (td, J=8.8, 1.6 Hz, 1H), 7.78 (td, J=8.8, 1.6 Hz, 1H), 6.83 (dt, J=9.2, 2.8 Hz, 2H), 4.68 (t, J=4.8 Hz, 1H), 4.56 (t, J=4.8 Hz, 1H), 3.57 (q, J=4.8 Hz, 1H), 3.51 (q, J=4.8 Hz, 1H); MS (ESI): 267.1 ($M+H^+$).

Preparation of

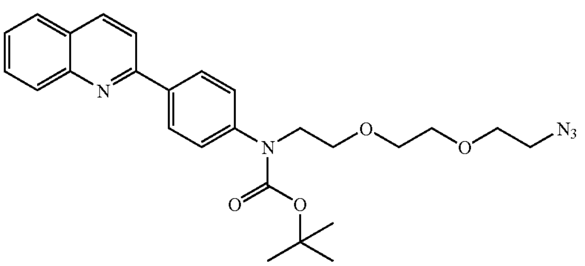 [SMILES: CC(C)(C)OC(=O)N(CCOCCOCCN=[N+]=[N-])c1ccc(-c2ccc3ccccc3n2)cc1]

tert-butyl-(2-(2-(2-azidoethoxy)ethoxy)ethyl)(4-(quinolin-2-yl)phenyl-carbamate (AS-5306-190 Boc) was prepared using general procedure D. Reaction was performed on 0.020 g scale. AS-5332-190 Boc was isolated as an off semi solid (0.020, 70%). $^1$H NMR (400 MHz, $CDCl_3$): δ 8.21 (br d, J=8.8 Hz, 2H), 8.11 (dt, J=8.8, 2.0 Hz, 2H), 7.85 (d, J=8.4 Hz, 1H), 7.81 (dd, J=9.2, 1.6 Hz, 1H), 7.71 (ddd, J=8.4, 7.2, 1.2 Hz, 1H), 7.51 (ddd, J=8.4, 7.2, 1.2 Hz, 1H), 7.40 (br d, J=8.4 Hz, 2H), 3.86 (t, J=6.0 Hz, 2H), 3.65 (t, J=6.0 Hz, 2H), 3.62-3.59 (m, 6H), 3.34 (t, J=5.2 Hz, 2H), 1.44 (s, 9H); MS (ESI): 478.1 ($M+H^+$).

Preparation of

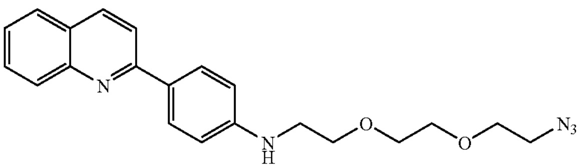 [SMILES: [N-]=[N+]=NCCOCCOCCNc1ccc(-c2ccc3ccccc3n2)cc1]

N-(2-(2-(2-azidoethoxy)ethoxy)ethyl)(4-(quinolin-2-yl) aniline T412 was prepared using general procedure K. Reaction was performed on a 0.020 g scale. The crude product was neutralized with $NaHCO_3$ and purified. T412 was isolated as yellow oil (0.010 g, 63%). $^1$H NMR (400 MHz, $CDCl_3$): δ 8.26-8.14 (m, 4H), 7.88-7.72 (m, 3H), 7.57-7.48 (m, 1H), 7.45 (d, J=8.0 Hz, 1H), 6.75 (d, J=8.8 Hz, 2H), 3.74 (t, J=4.8 Hz, 2H), 3.70-3.60 (m, 6H), 3.39 (t, J=5.2 Hz, 4H); MS (ESI): 378.1 ($M+H^+$).

Preparation of

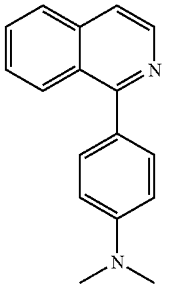 [SMILES: CN(C)c1ccc(-c2nccc3ccccc23)cc1]

4-(Isoquinolin-1-yl)-N,N-dimethylaniline T420 was prepared using general procedure A. Reaction was performed on a 0.105 g scale. T420 was isolated as off white solid (0.115 g, 72%). $^1$H NMR (400 MHz, $CDCl_3$): δ 8.55 (d, J=5.6 Hz, 1H), 8.25 (d, J=8.8 Hz, 1H), 7.85 (d, J=7.6 Hz, 1H), 7.69 (t, J=7.6 Hz, 1H), 7.66 (dt, J=8.8, 2.0 Hz, 2H), 7.53 (d, J=6.0 Hz, 1H), 7.54 (t, J=7.6 Hz, 1H), 6.86 (dt, J=8.8, 2.0 Hz, 2H), 3.05 (s, 6H); MS (ESI): 249.1 (M+H).

Preparation of

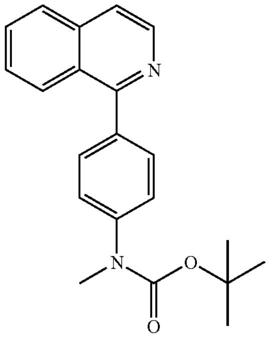 [SMILES: CN(C(=O)OC(C)(C)C)c1ccc(-c2nccc3ccccc23)cc1]

tert-Butyl (4-(isoquinolin-1-yl)phenyl)-N-methyl)carbamate T426 was prepared using general procedure A. Reaction was performed on a 0.082 g scale. T426 was isolated as a colorless oil (0.0.78 g, 46%). $^1$H NMR (400 MHz, $CDCl_3$): δ 8.56 (dd, J=6.8, 0.8 Hz, 1H), 8.10 (d, J=8.4 Hz, 1H), 7.84 (d, J=8.4 Hz, 1H), 7.67-7.64 (m, 3H), 7.60 (d, J=5.6 Hz, 1H), 7.50 (td, J=8.4, 1.6 Hz, 1H), 7.39 (br d, J=8.8 Hz, 2H), 3.31 (s, 3H), 1.47 (s, 9H); MS (ESI): 335.1 (M+H$^+$).

Preparation of

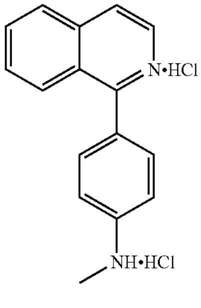

4-(Isoquinolin-1-yl)phenyl)-N-methylaniline dihydrochloride T427 was prepared using general procedure K. Reaction was performed on a 0.048 g scale. T427 was isolated as yellow solid (0.038 g, 72%). $^1$H NMR (400 MHz, $CD_3CN$): δ 8.42 (d, J=7.6 Hz, 1H), 8.35 (d, J=6.4 Hz, 1H), 8.24 (d, J=8.0 Hz, 1H), 8.18 (d, J=7.2 Hz, 1H), 8.14 (ddd, J=8.4, 7.2, 1.2 Hz, 1H), 7.94 (ddd, J=8.4, 7.2, 1.2 Hz, 1H), 7.72 (dt, J=8.8, 2.0 Hz, 2H), 7.08 (d, J=8.8 Hz, 2H), 2.93 (s, 3H); MS (ESI): 235.1 (M+H$^+$).

Preparation of

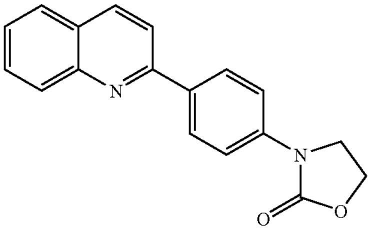 [SMILES: O=C1OCCN1c1ccc(-c2ccc3ccccc3n2)cc1]

3(4-(Quinolin-2-yl)phenyl)oxazolidin-2-one T428 was isolated as a by-product during N-alkylation of T-410 using NaH as the base (0.010 g, 33%); $^1$H NMR (400 MHz, $CDCl_3$): δ 8.20 (dt, J=9.2, 2.4 Hz, 2H), 8.15 (d, J=8.4 Hz, 2H), 7.86 (d, J=8.4 Hz, 1H), 7.81 (dd, J=9.2, 1.2 Hz, 1H), 7.71 (ddd, J=8.4, 7.2, 1.2 Hz, 1H), 7.70 (dt, J=9.2, 2.4 Hz, 2H), 7.51 (ddd, J=8.4, 7.2, 1.2 Hz, 1H), 4.52 (t, J=8.0 Hz, 2H), 4.14 (t, J=8.0 Hz, 2H); MS (ESI): 291.1 (M+H$^+$).

Preparation of

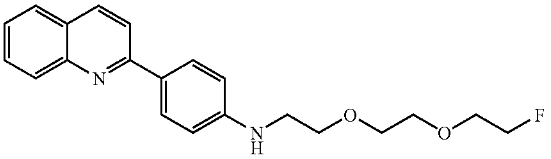 [SMILES: FCCOCCOCCNc1ccc(-c2ccc3ccccc3n2)cc1]

N-(2-(2-(2-Fluoroethoxy)ethoxy)ethyl-4-(quinolin-2-yl)aniline T442 was prepared using general procedure D. Reaction performed on a 0.031 g scale. T442 was isolated as a yellow oil (0.015 g, 42%). $^1$H NMR (400 MHz, $CDCl_3$): δ 8.12 (d, J=8.0 Hz, 2H), 8.05 (dd, J=8.0 Hz, 2H), 7.79 (d, J=8.0 Hz, 1H), 7.76 (d, J=8.0 Hz, 1H), 7.66 (dt, J=8.4, 1.6 Hz, 1H), 7.45 (dt, J=8.4, 1.6 Hz, 1H), 6.75-6.72 (m, 3H), 4.64 (m, 1H), 4.52 (m, 1H), 4.38 (br s, 1H), 3.80-3.67 (m, 8H), 3.38 (m, 2H), MS (ESI): 355.2 (M+H$^+$).

Preparation of

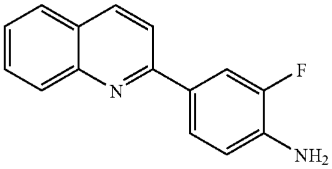 [SMILES: Nc1ccc(-c2ccc3ccccc3n2)cc1F]

2-Fluoro-4-(quinolin-2-yl) aniline T445 was prepared using general procedure A. Reaction was performed on a 0.090 g scale. T445 was isolated as white solid (0.120 g, 91%). $^1$H NMR (400 MHz, $CDCl_3$): δ 8.17 (d, J=8.8 Hz, 2H), 7.92 (dd, J=12.8, 2.0 Hz, 1H), 7.82-7.62 (m, 3H), 7.70 (t, J=8.0 Hz, 1H), 7.49 (t, J=8.0 Hz, 1H), 6.88 (t. J=8.0 Hz, 1H), 3.95 (br s, 2H); MS (ESI): 239.1 ($M+H^+$).

Preparation of

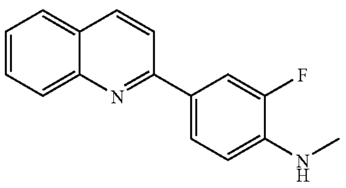 [SMILES: CNc1ccc(-c2ccc3ccccc3n2)cc1F]

A mixture of T445 (0.024 g, 0.95 mmol) and paraformaldehyde (0.06 g, 2.0 eq) in DCE-AcOH (10:1, 5 ml) was stirred at room temperature for 2 hrs, and then Sodium triacetoxyborohydride (0.061 g, 3.0 eq) was added. The resulting mixture was stirred overnight. After the reaction was complete, the solvents were removed in vacuo and product was purified on a Combiflash purification system (silica gel, 0-10% EtOAc:DCM). T458 was isolated as off white semi solid (0.005 g, 20%). $^1$H NMR (400 MHz, $CDCl_3$): δ 8.14 (dt, J=8.4, 5.6 Hz, 2H), 7.93 (dd, J=13.6, 2.0 Hz, 1H), 7.87 (d, J=8.0 Hz, 1H), 7.78 (d, J=8.4 Hz, 1H), 7.77 (ddd, J=8.4, 6.8, 1.2 Hz, 1H), 7.68 (ddd, J=8.4, 6.8, 1.2 Hz, 1H), 6.77 (t, J=8.8 Hz, 1H), 2.95 (s, 3H); MS (ESI): 253.1 [$M+H^+$].

Preparation of

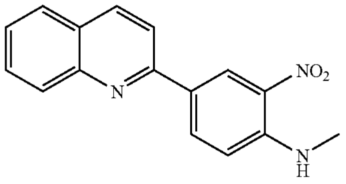 [SMILES: CNc1ccc(-c2ccc3ccccc3n2)cc1[N+](=O)[O-]]

N-Methyl-2-nitro-4-(quinolin-2-yl)aniline T463 was prepared using general procedure A. Reaction was performed on a 0.045 g scale. T463 was isolated as yellow solid (0.068 g, 88%). $^1$H NMR (400 MHz, $CDCl_3$): δ 8.97 (d, J=2.4 Hz, 1H), 8.49 (dd, J=9.2, 2.0 Hz, 1H), 8.25 (br s, 1H), 8.19 (d, J=8.4 Hz, 1H), 8.12 (d, J=8.0 Hz, 1H), 7.86 (d, J=8.8 Hz, 2H), 7.80 (dd, J=9.6, 1.2 Hz, 1H), 7.71 (ddd, J=8.8, 6.8, 1.6 Hz, 1H), 7.50 (ddd, J=8.8, 6.8, 1.6 Hz, 1H), 7.00 (d, J=9.2 Hz, 1H), 3.10 (d, J=5.2 Hz, 3H); MS (ESI): 280.1 ($M+H^+$).

Preparation of

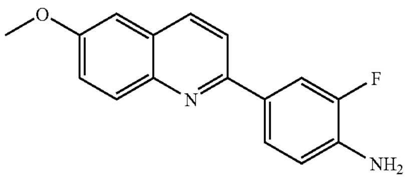 [SMILES: COc1ccc2nc(-c3ccc(N)c(F)c3)ccc2c1]

2-Fluoro-4-(6-methoxyquinolin-2-yl)aniline T467 was prepared using general procedure A. Reaction was performed on a 0.1 g scale. T467 was isolated as off white solid (0.112 g, 81%). $^1$H NMR (400 MHz, $CDCl_3$): δ 8.08 (br d, J=8.8 Hz, 2H), 7.87 (dd, J=12.4, 2.0 Hz, 1H), 7.77 (br d, J=7.6 Hz, 1H), 7.73 (d, J=8.8 Hz, 1H), 7.36 (dd, J=9.2, 2.8 Hz, 1H), 7.06 (d, J=2.4 Hz, 1H), 6.87 (t, J=8.4 Hz, 1H), 3.32 (s, 3H); MS (ESI): 269.0 ($M+H^+$).

Preparation of

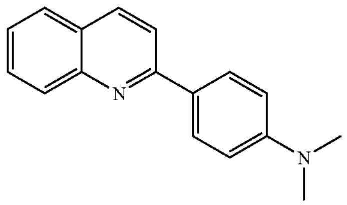 [SMILES: CN(C)c1ccc(-c2ccc3ccccc3n2)cc1]

N—N-Dimethyl-4-(quinolin-2-yl)aniline T476 was prepared using general procedure A. Reaction was performed on a 0.092 g scale. T-467 was isolated as yellow solid (0.120 g, 86%). $^1$H NMR (400 MHz, $CDCl_3$): δ 8.11 (br t, J=7.6 Hz, 4H), 7.81 (d, J=8.8 Hz, 1H), 7.75 (dd, J=9.6, 1.6 Hz, 1H), 7.66 (ddd, J=9.2, 6.8, 1.6 Hz, 1H), 7.44 (ddd, J=9.2, 6.8, 1.6 Hz, 1H), 6.82 (dt, J=9.2, 2.8 Hz, 1H), 3.94 (s, 6H); MS (ESI): 249.1 ($M+H^+$).

Preparation of

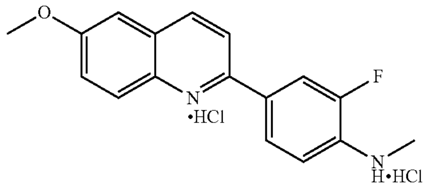

2-Fluoro-4-(6-methoxyquinolin-2-yl)-N-methylaniline dihydrochloride T483 was prepared using general procedure D and general procedure K sequentially. Reaction was performed on a 0.030 g scale. T483 was isolated as an orange color solid (0.025 g, 86% in two steps). $^1$H NMR (400 MHz, $CDCl_3$): δ 9.07 (d, J=9.2 Hz, 1H), 8.65 (d, J=8.8 Hz, 1H), 8.21 (dd, J=13.6, 2.4 Hz, 1H), 8.09 (dd, J=8.4, 2.4 Hz, 1H), 8.05 (d, J=9.2 Hz, 1H), 7.64 (dd, J=9.6, 2.8 Hz, 1H), 7.49 (d, J=2.8 Hz, 1H), 6.85 (t, J=8.8 Hz, 1H), 3.98 (s, 3H), 2.91 (s, 3H); MS (ESI): 283.1 ($M+H^+$).

Preparation of

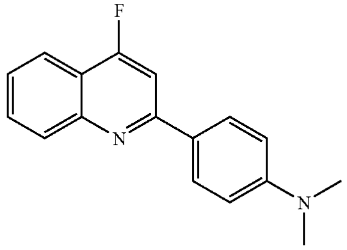 [SMILES: CN(C)c1ccc(-c2cc(F)c3ccccc3n2)cc1]

4-(4-Fluoroquinolin-2-yl)-N—N-dimethylaniline T484 was prepared using general procedure L. Reaction was performed on a 0.030 g scale. T484 was isolated as a light yellow color solid (0.012 g, 44%), $^1$H NMR (400 MHz, $CDCl_3$): δ 8.11 (d, J=8.4 Hz, 1H), 8.04 (dt, J=9.2, 2.8 Hz, 2H), 8.01 (dd, J=8.8, 0.8 Hz, 1H), 7.70 (td, J=8.4, 1.2 Hz, 1H), 7.50-7.46 (m, 2H), 6.80 (dt, J=9.2, 2.8 Hz, 2H), 3.04 (s, 6H); MS (ESI): 267.1 (M+H$^+$).

Preparation of

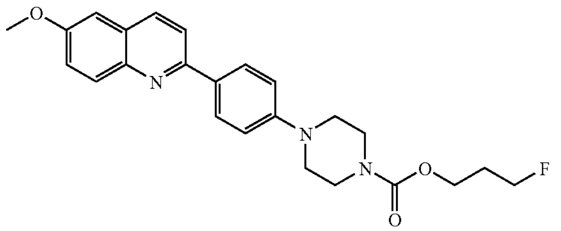 [SMILES: COc1ccc2nc(-c3ccc(N4CCN(C(=O)OCCCF)CC4)cc3)ccc2c1]

3-Fluoropropyl 4-(4-(6-methoxyquinolin-2-yl)phenyl) piperazine-1-carboxylate T498 was prepared using general procedure E. Reaction performed on a 0.032 g scale. T498 was isolated as off white solid (0.030 g, 70%). $^1$H NMR (400 MHz, $CDCl_3$): δ 8.07 (br t, J=8.0 Hz, 4H), 7.78 (d, J=8.8 Hz, 1H), 7.35 (dd, J=9.2, 2.8 Hz, 1H), 7.06 (d, J=2.8 Hz, 1H), 7.02 (dt, J=9.2, 2.8 Hz, 2H), 4.61 (t, J=6.0 Hz, 1H), 4.49 (t, J=6.0 Hz, 1H), 4.26 (t, J=6.0 Hz, 2H), 3.93 (s, 3H), 3.65 (t, J=4.8 Hz, 4H), 2.57 (t, J=4.8 Hz, 4H), 2.09 (quintet, J=6.0 Hz, 1H), 2.02 (quintet, J=6.0 Hz, 1H); MS (ESI): 224.1 (M+H$^+$).

Preparation of

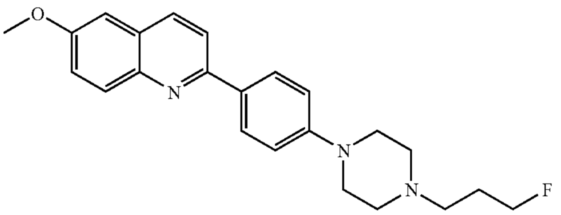 [SMILES: COc1ccc2nc(-c3ccc(N4CCN(CCCF)CC4)cc3)ccc2c1]

2-(4-(4-(3-Fluoropropyl)piperazin-1-yl)phenyl)-6-methoxyquinoline T499 was prepared using general procedure E. Reaction performed on a 0.032 g scale. T499 was isolated as off white solid (0.005 g, 13%). $^1$H NMR (400 MHz, $CDCl_3$): δ 8.05 (dt, J=9.2, 2.8 Hz, 2H), 8.03 and 8.00 (d, J=7.6 and 9.2 Hz, 2H), 7.77 (d, J=8.8 Hz, 1H), 7.54 (dd, J=9.2, 3.2 Hz, 1H), 7.05 (d, J=2.8 Hz, 1H), 7.02 (dt, J=9.2, 2.8 Hz, 2H), 4.60 (t, J=6.0 Hz, 1H), 4.48 (t, J=6.0 Hz, 1H), 3.92 (s, 3H), 3.34 (br s, 4H), 2.68 (br s, 4H), 2.56 (br s, 2H), 1.97 (br d, J=24.8 Hz, 2H); MS (ESI): 380.2 (M+H$^+$).

Preparation of

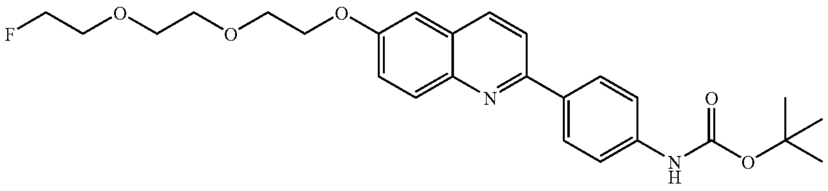 [SMILES: CC(C)(C)OC(=O)Nc1ccc(-c2ccc3cc(OCCOCCOCCF)ccc3n2)cc1]

tert-Butyl-(4-(6-(2-(2-(2-fluoroethoxy)ethoxy)ethoxy) quinoline-2-yl)-phenyl)-carbamate T509 was prepared using general procedure C and general procedure A sequentially. Reaction was performed on a 0.045 g scale T509 was isolated as off white solid (0.010 g, 8.4% in two steps). $^1$H NMR (400 MHz, $CDCl_3$): δ 8.05 (dt, J=8.0, 2.0 Hz, 2H), 8.04 (t, J=10.4 Hz, 2H), 7.78 (d, J=8.8 Hz, 1H), 7.49 (d, J=8.4 Hz, 1H), 7.38 (dd, J=9.2, 2.8 Hz, 1H), 7.07 (d, J=2.8 Hz, 1H), 6.59 (s, 1H), 4.61 (td, J=4.4, 0.4 Hz, 1H), 4.49 (td, J=4.4, 0.4 Hz, 1H), 4.26 (t, J=4.8 Hz, 2H), 3.93 (t, J=4.8 Hz, 2H), 3.80-3.76 (m, 3H), 3.74-3.70 (m, 3H), 1.53 (s, 9H); MS (ESI): 471.2 (M+H$^+$).

Preparation of

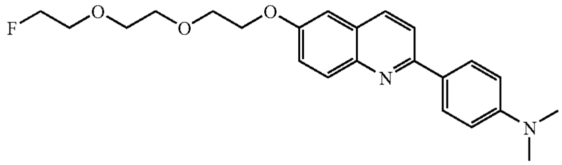 [SMILES: CN(C)c1ccc(-c2ccc3cc(OCCOCCOCCF)ccc3n2)cc1]

4-(6-(2-(2-(Fluoroethoxy)ethoxy)ethoxy)quinoline-2-yl)-N—N-dimethylaniline T510 was prepared using general procedure C and general procedure A sequentially. Reaction was performed on a 0.037 g scale. T510 was isolated as a light yellow color solid (0.006 g, 7.2% in two steps). $^1$H NMR (400 MHz, $CDCl_3$): δ 8.05 (d, J=8.0 Hz, 2H), 8.0 (d, J=8.0 Hz, 2H), 7.76 (d, J=8.8 Hz, 1H), 7.34 (dd, J=9.2, 2.8 Hz, 1H), 7.05 (d, J=2.4 Hz, 1H), 6.81 (m, 1H), 4.61 (m, 1H), 4.49 (m, 1H), 4.25 (t, J=4.4 Hz, 2H), 3.93 (t, J=4.4 Hz, 2H), 3.80-3.70 (m, 5H), 3.02 (s, 6H); MS (ESI): 399.2 (M+H$^+$).

Preparation of

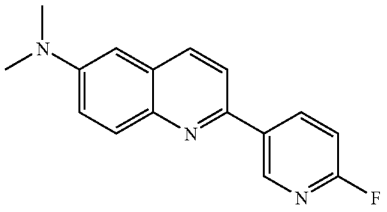 [SMILES: CN(C)c1ccc2nc(-c3ccc(F)nc3)ccc2c1]

2-(6-Fluoropyridin-3-yl)-N—N-dimethylquinolin-6-amine T513 was prepared using general procedure A. Reaction was performed on a 0.0.036 g scale. T513 was isolated as a yellow color solid (0.015 g, 54%). $^1$H NMR (400 MHz, $CDCl_3$): δ 8.86 (m, 1H), 8.57 (td, J=10.0, 2.4 Hz, 1H), 8.02 (d, J=8.8 Hz, 1H), 7.97 (d, J=9.6 Hz, 1H), 7.69 (d, J=8.8 Hz, 1H), 7.38 (dd, J=9.2, 2.8 Hz, 1H), 7.02 (dd, J=8.4, 0.8 Hz, 1H), 6.80 (d, J=2.8 Hz, 1H), 3.09 (s, 6H); MS (ESI): 268.1 [M+H$^+$].

Preparation of

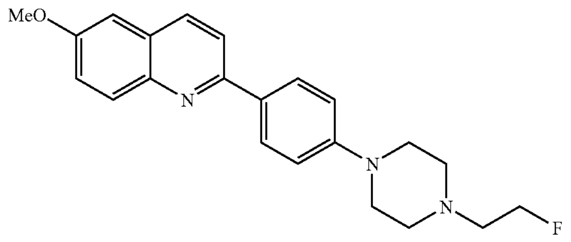 [SMILES: COc1ccc2nc(-c3ccc(N4CCN(CCF)CC4)cc3)ccc2c1]

2-(4-(4-(2-Fluoroethyl)piperizin-1-yl)-6-methoxyquinoline T519 was prepared using general procedure E. Reaction performed on a 0.050 g scale. T519 was isolated as a off white solid (0.010 g, 17.5%). $^1$H NMR (400 MHz, $CDCl_3$): δ 8.01 (dt, J=6.8, 2.0 Hz, 2H), 7.95 (d, J=10.4 Hz, 2H), 7.71 (d, J=8.4 Hz, 1H), 7.27 (dd, J=9.2, 2.4 Hz, 1H), 6.99 (d, J=2.4 Hz, 1H), 6.96 (dt, J=6.8, 2.0 Hz, 2H), 4.62 (t, J=4.0 Hz, 1H), 4.50 (t, J=4.0 Hz, 1H), 3.86 (s, 3H), 3.27 (t, J=5.2 Hz, 4H), 2.75 (t, J=5.2 Hz, 1H), 2.69-2.66 (m, 5H); MS (ESI): 366.1 (M+H$^+$).

Preparation of

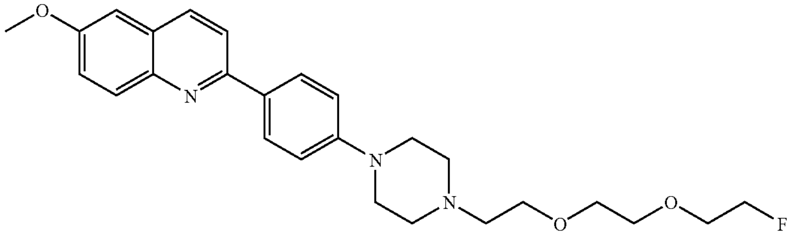 [SMILES: COc1ccc2nc(-c3ccc(N4CCN(CCOCCOCCF)CC4)cc3)ccc2c1]

2-(4-(4-(2-(2-Fluoroethoxy)ethyl)piperazin-1-yl)phenyl)-6-methoxyquinoline T530 was prepared using general procedure D. Reaction performed on a 0.032 g scale. T530 was isolated as off white semi solid (0.004 g, 9%). $^1$H NMR (400 MHz, CDCl3): δ 8.04 (dt, J=8.0, 1.2 Hz, 2H), 8.01 (dd, J=10.4, 7.6 Hz, 2H), 7.77 (d, J=8.0 Hz, 1H), 7.32 (dd, J=9.2, 2.8 Hz, 1H), 7.05 (d, J=2.8 Hz, 1H), 7.01 (dt, J=8.0, 1.2 Hz, 2H), 4.62 (t, J=4.4 Hz, 1H), 4.50 (t, J=4.4 Hz, 1H), 3.92 (s, 3H), 3.78 (t, J=4.4 Hz, 1H), 3.72-3.64 (m, 4H), 3.19 (t, J=4.8 Hz, 2H), 2.70 (m, 3H); MS (ESI): 454.1 (M+H$^+$).

Preparation of

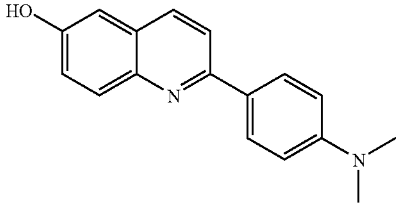 [SMILES: CN(C)c1ccc(-c2ccc3cc(O)ccc3n2)cc1]

2-(4-Dimethylamino)phenyl)quinoline-6-ol T531 was prepared using general procedure A. Reaction was performed on a 0.0.236 g scale. T531 was isolated as a yellow solid (0.218 g, 53%). $^1$H NMR (400 MHz, $CD_3CN$): δ 8.08 (td, J=8.4, 2.0 Hz, 3H), 7.86 (dd, J=8.8, 5.2 Hz, 1H), 7.28 (ddd, J=8.8, 5.6, 2.8 Hz, 1H), 7.14 (d, J=2.8 Hz, 1H), 6.86 (dt, J=8.8, 2.0 Hz, 2H), 3.03 (s, 6H); MS (ESI): 365.1 (M+H$^+$).

Preparation of

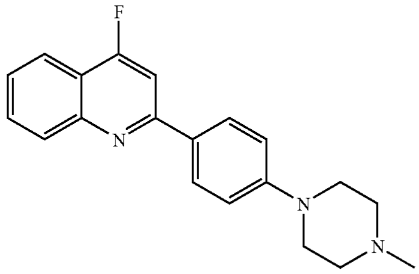 [SMILES: CN1CCN(c2ccc(-c3cc(F)c4ccccc4n3)cc2)CC1]

4-Fluoro-2-(4-(4-methylpiperazin-1yl)phenylquinoline T559 was prepared using general procedure L. Reaction was performed on a 0.005 g scale. T559 was isolated as light yellow solid (0.004 g, 89%). $^1$H NMR (400 MHz, $CDCl_3$): δ 8.06-7.96 (m, 4H), 7.66 (td, J=8.4, 1.6 Hz, 1H), 7.44 (td, J=8.4, 1.6 Hz, 1H), 7.43 (d, J=11.2 Hz, 1H), 6.96 (dt, J=9.2, 2.4 Hz, 2H), 3.28 (t, J=4.8 Hz, 4H), 2.54 (t, J=4.8 Hz, 4H), 2.31 (s, 3H); MS (ESI): 322.1 (M+H$^+$).

Preparation of

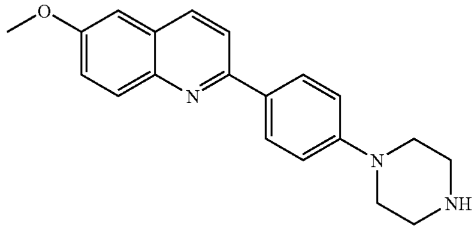 [SMILES: COc1ccc2nc(-c3ccc(N4CCNCC4)cc3)ccc2c1]

6-Methoxy-2-(4-(piperizine-1-yl) phenyl) quinoline AS-5332-52 was prepared using general procedure A. Reaction was performed on a 0.194 g scale. AS-5332-52 was isolated as a off white solid (0.269 g, 84%). $^1$H NMR (400 MHz, $CDCl_3$): δ 8.01 (dt, J=8.0, 4.0 Hz, 2H), 7.98 (d, J=9.2 Hz, 1H), 7.95 (d, J=9.2 Hz, 1H), 7.72 (d, J=8.8 Hz, 1H), 7.27 (dd, J=8.0, 4.0 Hz, 1H), 7.01-6.96 (m, 3H), 3.87 (s, 2H), 3.24 (td, J=5.2, 2.8 Hz, 4H), 3.06 (td, J=5.2, 2.8 Hz, 4H); MS (ESI): 320.1 (M+H$^+$).

Preparation of

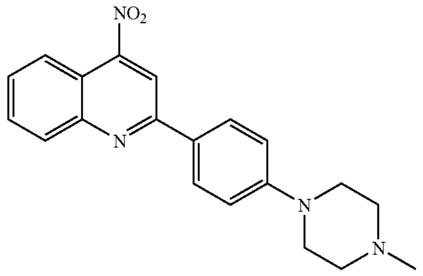 [SMILES: CN1CCN(c2ccc(-c3cc([N+](=O)[O-])c4ccccc4n3)cc2)CC1]

2-(4-(4-Methylpiperazin-1-yl)phenyl)-4-nitroquinoline AS-5332-80 was prepared using general procedure A. Reaction was performed on a 0.06 g scale. AS-5332-80 was isolated as red color solid (0.062 g, 75%). $^1$H NMR (400 MHz, $CDCl_3$): δ 8.35 (dd, J=9.2, 0.4 Hz, 2H), 8.25 (dd, J=9.2, 0.4 Hz, 1H), 8.13 (dt, J=9.2, 2.0 Hz, 2H). 7.80 (td, J=8.0, 1.2 Hz, 1H), 7.64 (td, J=8.0, 1.2 Hz, 1H), 7.03 (dt, J=8.8, 2.0 Hz, 2H), 3.36 (t, J=6.4 Hz, 4H), 2.59 (t, J=6.4 Hz, 4H), 2.36 (s, 3H); MS (ESI): 349 (M+H$^+$).

Preparation of

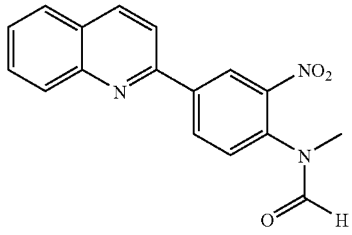 [SMILES: CN(C=O)c1ccc(-c2ccc3ccccc3n2)cc1[N+](=O)[O-]]

N-methyl-N-(2-nitro-4-(quinolin-2-yl)phenyl)formamide AS-5332-30. A mixture of acetic anhydride (0.600 g, 22 equiv.) and $HCO_2H$ (0.252 g, 22 equiv.) was heated at 60° C. for 15 min. To this mixture was added a solution of T463 (0.078 g) in DCM (5 mL). The resulting mixture was heated at 80° C. for 2 days. The volatiles were removed in vacuo. The crude product was purified on a Combiflash purification system (silica gel, 0-20% EtOAc:DCM). AS-5332-30 was isolated as yellow solid (0.054 g, 70%). $^1$H-NMR (400 MHz, $CDCl_3$) δ: 8.84 and 8.82 (d, J=2.0 Hz, 1H each), 8.52-8.49 (m, 1H), 8.29 and 8.27 (d, J=8.8 Hz, 1H each), 8.26 (s, 1H), 8.18 and 8.15 (d, J=8.8 Hz, 1H each), 7.89 (d, J=8.4 Hz, 1H), 7.88-7.84 (m, 2H), 7.79-7.75 (m, 1H), 7.61-7.57 (m, 1H), 7.47 (d, J=8.4 Hz, 1H), 3.7 and 3.28 (s, 3H each); MS (ESI): 308.1 (M+H$^+$).

Preparation of

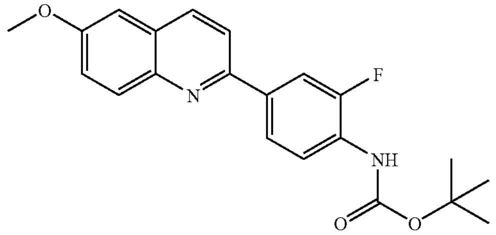 [SMILES: COc1ccc2nc(-c3ccc(NC(=O)OC(C)(C)C)c(F)c3)ccc2c1]

tert-Butyl 2-fluoro-4-(6-methoxyquinolin-2-yl)phenyl) carbamate AS-5332-32): To a solution of T467 (0.050 g, 0.186 mmol) in THF (3.0 mL) was added Boc anhydride (0.82 g, 0.373 mmol). The resulting reaction mixture was heated at 100° C. overnight. The volatiles were removed in vacuo and residue was purified on a Combiflash purification system silica gel, 0-20% EtOAc:DCM). AS-5332-32 was isolated as off white solid (0.040 g, 58%). $^1$H-NMR (400 MHz, $CDCl_3$): δ 8.22 (br, 1H), 8.09 (d, J=8.4 Hz, 1H), 8.12 (d, J=9.2 Hz, 1H), 7.98 (dd, J=8.8, 2.0 Hz, 1H), 7.83 (d, J=8.8 Hz, 1H), 7.77 (d, J=8.8 Hz, 1H), 7.35 (dd, J=9.2 Hz, 2.8 Hz, 1H), 7.06 (d, J=2.8 Hz, 1H), 6.83 (br, 1H), 3.93 (s, 3H), 1.54 (s, 9H); MS (ESI): 369.2 (M+H$^+$).

Preparation of

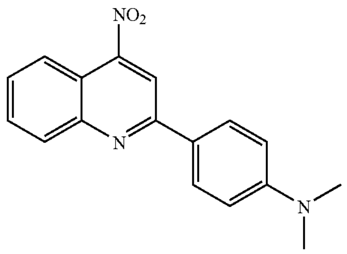 [SMILES: CN(C)c1ccc(-c2cc([N+](=O)[O-])c3ccccc3n2)cc1]

N—N-Dimethyl-4-(4-nitroquinolin-2-yl)aniline AS-5332-36 was prepared using general procedure A. Reaction was performed on a 0.126 g scale. AS-5332-36 was isolated as yellow solid (0.103 g, 70%). $^1$H NMR (400 MHz, $CDCl_3$): δ 8.34-8.32 (m, 2H), 8.20 (d, J=8.8 Hz, 1H), 8.13 (dt, J=9.2, 2.8 Hz, 2H), 7.78 (ddd, J=8.4, 7.2, 1.2 Hz, 1H), 7.62 (ddd, J=8.4, 7.6, 1.2 Hz, 1H), 6.82 (br d, J=9.2 Hz, 2H), 3.07 (s, 6H); MS (ESI): 294.1 (M+H$^+$).

Preparation of

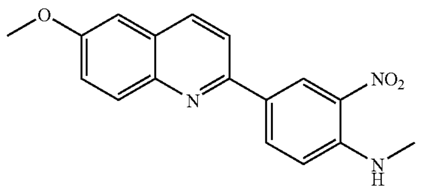

4-(6-Methoxyquinolin-2-yl)-N-methyl-2-nitroaniline AS-5332-42 was prepared using general procedure A. Reaction was performed on a 0.050 g scale. AS-5332-42 was isolated as yellow solid (0.080 g, 100%). $^1$H NMR (400 MHz, $CDCl_3$): δ 8.92 (d, J=2.0 Hz 1H), 8.50 (br, 1H), 8.23 (br, 1H), 8.12 (d, J=8.4 Hz, 1H), 7.83 (d, J=8.8 Hz, 1H), 7.37 (dd, J=9.2 Hz, 2.8 Hz, 1H), 7.08 (d, J=2.8 Hz, 1H), 7.00 (d, J=8.8 Hz 1H), 3.94 (s, 3H), 3.11 (d, J=4.8 Hz, 3H); MS (ESI): 310.1 (M+H$^+$).

Preparation of

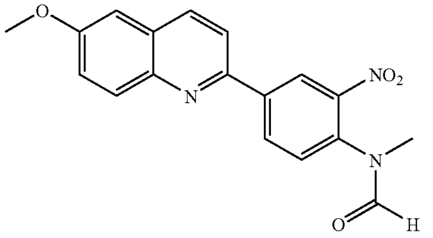 [SMILES: COc1ccc2nc(-c3ccc(N(C)C=O)c([N+](=O)[O-])c3)ccc2c1]

N-(4-(6-Methoxyquinolin-2-yl)-2-nitrophenyl)-N-methylformamide AS-5332-43: A mixture of acetic anhydride (0.305 g, 22 eq) and $HCO_2H$ (0.137 g, 22 eq) was heated at 60° C. for 15 min. To this mixture was added a solution of AS-5332-42 (0.042 g) in DCM (5 mL). The resulting mixture was heated at 80° C. for 3 days. The volatiles were removed in vacuo. The residue was purified on a Combiflash purification system (silica gel, 0-20% EtOAc:DCM) to give AS-5332-43 as a yellow solid (0.034 g, 74%). $^1$H-NMR (400 MHz, $CDCl_3$) δ: 8.80 and 8.76 (d, J=2.0 Hz, 1H), 8.47-8.46 (m, 1H), 8.25 and 8.24 (s, 1H each), 8.17 (t, J=8.4 Hz, 1H), 8.05 (d, J=9.2 Hz, 1H), 7.85 and 7.83 (d, J=5.2 Hz, 1H each), 7.45 (d, J=8.4 Hz, 1H), 7.44-7.40 (m, 1H), 7.11 and 7.10 (d, J=0.8 Hz, 1H each), 3.96 and 3.95 (s, 3H each), 3.46 and 3.27 (s, 3H each); MS (ESI): 338.1 ($M+H^+$).

Preparation of

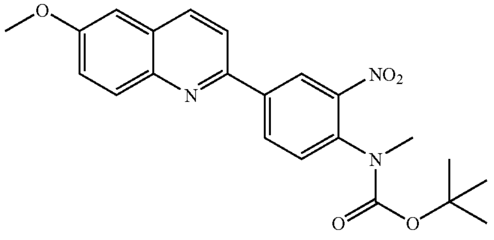 [SMILES: COc1ccc2nc(-c3ccc(N(C)C(=O)OC(C)(C)C)c([N+](=O)[O-])c3)ccc2c1]

tert-Butyl 4-(6-methoxyquinolin-2-yl)-2-nitrophenyl(methyl)carbamate AS-5332-46: To a solution AS-5332-42 (0.030 g, 0.186 mmol) in THF (3.0 mL) was added Boc anhydride (0.063 g, 0.0.291 mmol) and DMAP (0.012 g, 0.097 mmol). The resulting reaction mixture was heated at 100° C. for 30 min. The volatiles were removed in vacuo and residue was purified on a Combiflash purification system (silica gel, 0-7% EtOAc:DCM) to afford AS-5332-43 as a off white solid (0.040 g, 100%). $^1$H-NMR (400 MHz, $CDCl_3$) δ: 8.69 (d, J=2.0 Hz, 1H), 8.40 (d, J=8.0 Hz, 1H), 8.16 (d, J=8.8 Hz, 1H), 8.07 (d, J=9.2 Hz, 1H), 7.85 (d, J=8.8 Hz, 1H), 7.44 (d, J=8.0 Hz, 1H), 7.41 (dd, J=9.2, 2.8 1H), 7.10 (d, J=2.8 Hz, 1H), 3.95 (s, 3H), 3.34 (s, 3H), 1.32 (s, 9H); MS (ESI): 410.1 ($M+H^+$).

Preparation of

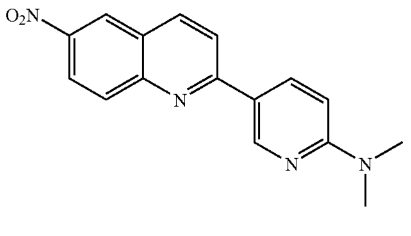 [SMILES: CN(C)c1ccc(-c2ccc3cc([N+](=O)[O-])ccc3n2)cn1]

N,N-dimethyl-5-(6-nitroquinolin-2-yl)pyridin-2-amine AS-5332-49 was prepared using general procedure A. for Suzuki coupling (method A) was followed. Reaction was performed on a 0.104 g scale. AS-5332-49 was isolated as a orange red color solid (0.1 g, 68%). $^1$H-NMR (400 MHz, $CDCl_3$) δ: 8.99 (d, J=2.4 Hz, 1H), 8.72 (d, J=2.4 Hz, 1H), 8.44-8.41 (m, 2H), 8.27 (d, J=8.8 Hz, 1H), 8.14 (d, J=8.8 Hz, 1H), 7.93 (d, J=8.8 Hz, 1H), 6.66 (d, J=8.8 Hz, 1H), 3.21 (s, 6H); MS (ESI): 295.1 ($M+H^+$).

Preparation of

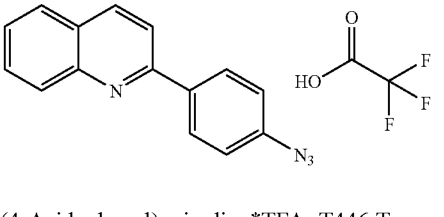

2-(4-Azidophenyl)quinoline*TFA: T446 To a solution of 4-(quinolin-2-yl)aniline dihydrochloride (29.0 mg, 0.1 mmol) in 1 N HCl (1 mL) was added $NaNO_2$ solution (7.0 mg in 0.3 mL water, 0.1 mmol) at 0° C. The mixture was stirred at 0° C. for 2 hrs before $NaN_3$ (7.8 mg in 1.0 mL water, 0.12 mmol) was added at 0° C. The mixture was stirred at 0° C. for 1 hour and concentrated. The residue was purified by HPLC (acetonitrile/water) to give T446 as a light yellow solid (23.0 mg, 64%). $^1$H NMR (400 MHz, $CD_3OD$): δ 8.31 (d, J=8.8 Hz, 1H), 8.10 (m, 2H), 8.00 (m, 1H), 7.90 (d, J=8.8 Hz, 1H), 7.85 (dd, J=8.2, 1.4 Hz, 1H), 7.69 (m, 1H), 7.50 (m, 1H), 7.16 (m, 2H); MS (ESI): 247 ($M+H^+$).

Preparation of

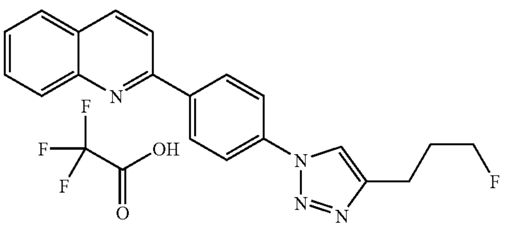

2-(4-(4-(3-Fluoropropyl)-1H-1,2,3-triazol-1-yl)phenyl) quinoline*TFA: T443 was prepared using general procedure N. Reaction was performed on a 4.0 mg scale of T446. T443 was isolated as a brown solid (2.7 mg, 39%). $^1$H NMR (400 MHz, $CD_3OD$): δ 8.72 (d, J=8.8 Hz, 1H), 8.50 (s, 1H), 8.34-8.38 (m, 2H), 8.19-8.24 (m, 2H), 8.09-8.14 (m, 3H), 7.94 (m, 1H), 7.74 (m, 1H), 4.59 (t, J=6.0 Hz, 1H), 4.47 (t, J=6.0 Hz, 1H), 2.94 (t, J=7.6 Hz, 1H), 2.14 (m, 2H); MS (ESI): 333 ($M+H^+$).

Preparation of

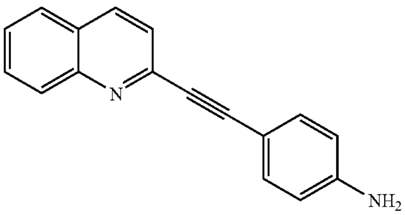 [SMILES: Nc1ccc(C#Cc2ccc3ccccc3n2)cc1]

4-(Quinolin-2-ylethynyl)aniline: T444 was prepared using general procedure B. Reaction was performed on a 16.0 mg scale of 2-chloroquinoline. T444 was isolated as a light yellow solid (6.0 mg, 25%). $^1$H NMR (400 HMz, $CDCl_3$): δ 8.11 (d, J=8.4 Hz, 2H), 7.79 (dd, J=8.0, 1.4 Hz, 1H), 7.72 (m, 1H), 7.57 (d, J=8.4 Hz, 1H), 7.53 (m, 1H), 7.48 (m, 2H), 6.66 (m, 2H), 3.91 (br s, 2H); MS (ESI): 245 (M+H$^+$).

Preparation of

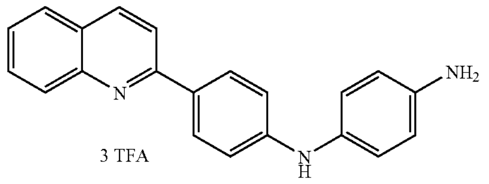 [SMILES: Nc1ccc(Nc2ccc(-c3ccc4ccccc4n3)cc2)cc1]

3 TFA

N-(4-(Quinolin-2-yl)phenyl)benzene-1,4-diamine*3TFA: T447 To a solution of 4-(quinolin-2-yl)aniline dihydrochloride (7.6 mg, 0.026 mmol) in DCM (1.0 mL) was added 4-(tert-butoxycarbonylamino)phenylboronic acid (12.4 mg, 0.052 mmol), $Cu(OAc)_2$ (4.8 mg, 0.026 mmol) and triethylamine (0.036 mL, 0.26 mmol). The mixture was stirred at room temperature for 3 hrs. LCMS showed that the desired product was formed. To the mixture was added 4 N HCl in dioxane (1.0 mL) and stirred for another hour. The mixture was concentrated in vacuo and purified by HPLC (acetonitrile/water) to give T447 as a brown solid (4.3 mg, 25%). $^1$H NMR (400 MHz, $CD_3OD$): δ 8.77 (d, J=8.8 Hz, 1H), 8.16 (m, 2H), 8.10 (d, J=8.4 Hz, 1H), 8.01 (m, 2H), 7.96 (m, 1H), 7.73 (m, 1H), 7.21-729 (m, 6H); MS (ESI): 312 (M+H$^+$).

Preparation of

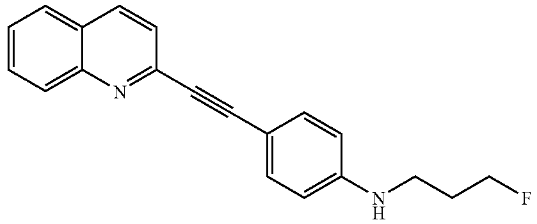 [SMILES: FCCCNc1ccc(C#Cc2ccc3ccccc3n2)cc1]

N-(3-Fluoropropyl)-4-(quinolin-2-ylethynyl)aniline: T454 was prepared using general procedure Q. Reaction was performed on a 4.0 mg scale of T444. T454 was isolated as a light yellow solid (2.3 mg, 46%). $^1$H NMR (400 MHz, $CDCl_3$): δ 8.11 (d, J=8.4 Hz, 2H), 7.79 (dd, J=8.0, 1.4 Hz, 1H), 7.26-7.58 (m, 4H), 6.59 (m, 2H), 4.66 (t, J=5.6 Hz, 1), 4.54 (t, J=5.6 Hz, 1H), 4.05 (m, 1H), 3.36 (m, 2H), 2.05 (m, 2H); MS (ESI): 305 (M+H$^+$).

Preparation of

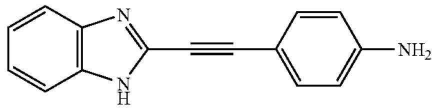 [SMILES: Nc1ccc(C#Cc2nc3ccccc3[nH]2)cc1]

4-((1H-Benzo[d]imidazol-2-yl)ethynyl)aniline: T464 was prepared using general procedure B. Reaction was performed on a 60.0 mg scale of 2-bromo-1H-benzo[d]imidazole. T464 was isolated as a light yellow solid (35.9 mg, 51%). $^1$H NMR (400 MHz, $CD_3OD$): δ 7.50 (br s, 2H), 7.31 (m, 2H), 7.24 (m, 2H), 6.64 (m, 2H); MS (ESI): 234 (M+H$^+$).

Preparation of

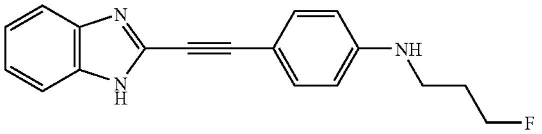 [SMILES: FCCCNc1ccc(C#Cc2nc3ccccc3[nH]2)cc1]

4-((1H-Benzo[d]imidazol-2-yl)ethynyl)-N-(3-fluoropropyl)aniline: T465 was prepared using general procedure Q. Reaction was performed on a 33.3 mg scale of T464. T465 w isolated as a white solid (8.9 mg, 21%). $^1$H NMR (400 MHz, $CD_3OD$): δ 7.50 (m, 2H), 7.35 (m, 2H), 7.26 (m, 2H), 6.61 (m, 2H), 4.58 (t, J=5.6 Hz, 1H), 4.46 (t, J=5.6 Hz, 1H), 3.27 (m, 2H), 1.95 (m, 2H); MS (ESI): 294 (M+H$^+$).

Preparation of

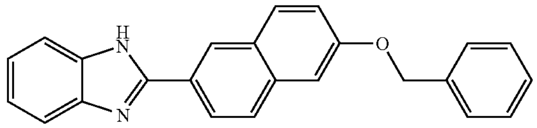

2-(6-(Benzyloxy)naphthalen-2-yl)-1H-benzo[d]imidazole: T469 was prepared using general procedure A. Reaction was performed on a 100 mg scale of 2-bromo-1H-benzo[d]imidazole. T469 was isolated as a white solid (75.0 mg, 42%). $^1$H NMR (400 MHz, DMSO-$d_6$): δ 12.95 (s, 1H), 8.63 (d, J=1.2 Hz, 1H), 8.22 (dd, J=8.4, 2.0 Hz, 1H), 7.93 (t, J=9.2 Hz, 2H), 7.64 (m, 1H), 7.50 (m, 4H), 7.40 (m, 2H), 7.34 (m, 1H), 7.29 (m, 1H), 7.17 (m, 2H), 5.24 (s, 2H); MS (ESI): 351 (M+H$^+$).

Preparation of

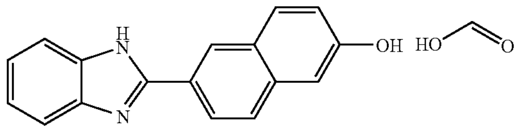

6-(1H-Benzo[d]imidazol-2-yl)naphthalen-2-ol*formate: T470 To a solution of 2-(6-(benzyloxy)naphthalen-2-yl)-1H-benzo[d]imidazole (73 mg, 0.21 mmol) in THF (2 mL) was added MeOH (2 mL), Pd—C (10%, 30 mg), and formic acid (0.30 mL). The mixture was flushed with argon and sealed in a microwave vial. The mixture was heated at 100° C. for 5 minutes in a microwave synthesizer. The mixture was filtered off Pd—C and the filtrate was concentrated to give T470 as a white solid (60 mg, 94%). $^1$H NMR (400 MHz, $CD_3OD$): δ 8.46 (t, J=1.0 Hz, 1H), 8.12 (s, 1H), 8.05 (dd, J=8.8, 2.0 Hz, 1H), 7.85 (d, J=9.6 Hz, 1H), 7.79 (d, J=8.8 Hz, 1H), 7.62 (m, 2H), 7.29 (m, 2H), 7.16 (m, 2H); MS (ESI): 261 (M+H$^+$).

Preparation of

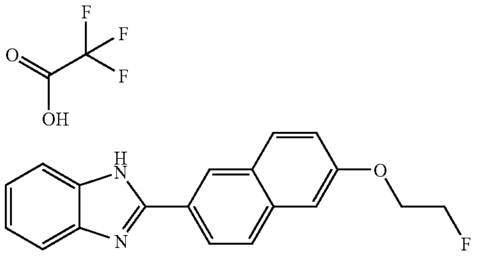

2-(6-(2-Fluoroethoxy)naphthalen-2-yl)-1H-benzo[d]imidazole*TFA: T473 was prepared using general procedure. Reaction was performed on a 16 mg scale of T470. T473 was isolated as a light yellow solid (1.9 mg, 8.6%). $^1$H NMR (400 MHz, $CD_3OD$): δ 8.63 (d, J=1.6 Hz, 1H), 8.01-8.11 (m, 3H), 7.82 (m, 2H), 7.62 (m, 2H), 7.45 (m, 1H), 7.38 (dd, J=9.0, 2.6 Hz, 1H), 4.87 (t, J=4.0 Hz, 1H), 4.75 (t, J=4.0 Hz, 1H), 4.44 (t, J=4.0 Hz, 1H), 4.37 (t, J=4.0 Hz, 1H); MS (ESI): 307 (M+H$^+$).

Preparation of

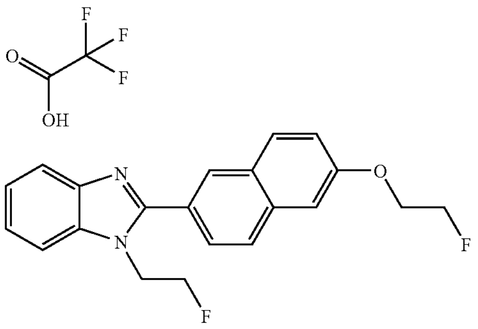

2-(6-(2-Fluoroethoxy)naphthalen-2-yl)-1-(2-fluoroethyl)-1H-benzo[d]imidazole*TFA: T474 was prepared using general procedure C. Reaction was performed on a 16 mg scale T470. T474 was isolated as a light yellow solid (9.4 mg, 39%). $^1$H NMR (400 MHz, $CD_3OD$): δ 8.41 (d, J=1.6 Hz, 1H), 8.12 (d, J=8.4 Hz, 1H), 8.02 (m, 2H), 7.82-7.89 (m, 2H), 7.71 (m, 2H), 7.47 (d, J=2.4 Hz, 1H), 7.38 (dd, J=9.0, 2.6 Hz, 1H), 4.95-5.00 (m, 2H), 4.86-4.92 (m, 3H), 4.75 (m, 1H), 4.44 (m, 1H), 4.37 (m, 1H); MS (ESI): 353 (M+H$^+$).

Preparation of

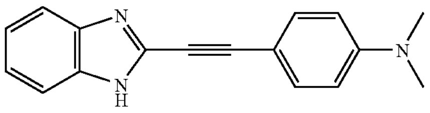 [SMILES: CN(C)c1ccc(C#Cc2nc3ccccc3[nH]2)cc1]

4-((1H-Benzo[4:1]imidazol-2-yl)ethynyl)-N,N-dimethylaniline: T481 was prepared using general procedure R. Reaction was performed on a 26.0 mg scale of T464. T481 was isolated as a light yellow solid (11.2 mg, 39%). NMR (400 MHz, $CD_3OD$): δ 7.51 (m, 2H), 7.44 (m, 2H), 7.25 (m, 2H), 6.73 (m, 2H), 3.00 (s, 6H); MS (ESI): 262 (M+H$^+$).

Preparation of

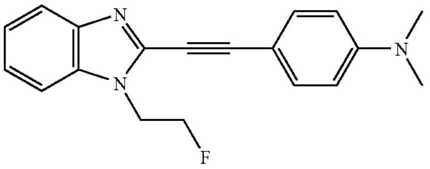 [SMILES: CN(C)c1ccc(C#Cc2nc3ccccc3n2CCF)cc1]

4-((1-(2-Fluoroethyl)-1H-benzo[d]imidazol-2-yl)ethynyl)-N,N-dimethylaniline: T482 was prepared using general procedure E. Reaction was performed on a 10.1 mg scale of T481. T482 was isolated as a light yellow solid (9.6 mg, 81%). $^1$H NMR (400 MHz, $CDCl_3$): δ 7.76 (m, 1H), 7.48 (m, 2H), 7.37 (m, 1H), 7.28 (m, 2H), 4.87 (t, J=5.2 Hz, 1H), 4.76 (t, J=5.2 Hz, 1H), 4.66 (t, J=5.2 Hz, 1H), 4.60 (t, J=5.2 Hz, 1H), 3.02 (s, 6H); MS (ESI): 308 (M+H$^+$).

Preparation of

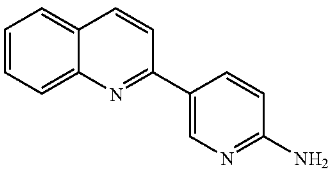

5-(Quinolin-2-yl)pyridin-2-amine: T490 was prepared using general procedure A. Reaction was performed on a 106 mg scale of 2-chloroquinoline. T490 was isolated as a white solid (135 mg, 94%). $^1$H NMR (400 MHz, $CDCl_3$): δ 8.85 (d, J=2.4 Hz, 1H), 8.37 (dd, J=8.4, 2.4 Hz, 1H), 8.18 (d, J=8.8 Hz, 1H), 8.11 (d, J=8.8 Hz, 1H), 7.79 (m, 2H), 7.71 (m, 1H), 7.50 (m, 1H), 6.65 (dd, J=8.4, 0.8 Hz, 1H), 4.66 (br s, 2H); MS (ESI): 222 (M+H$^+$).

Preparation of

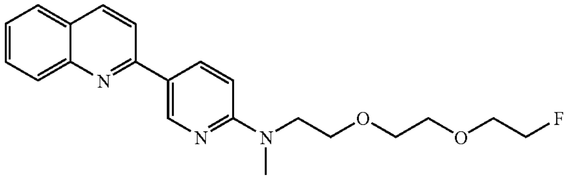 [SMILES: CN(CCOCCOCCF)c1ccc(-c2ccc3ccccc3n2)cn1]

N-(2-(2-(2-Fluoroethoxy)ethoxy)ethyl)-N-methyl-5-(quinolin-2-yl)pyridin-2-amine: T502 was prepared using general procedure S. Reaction was performed on a 7.4 mg scale of T502-precursor. T502 as light yellow oil (3.8 mg, 73%). $^1$H NMR (400 MHz, $CDCl_3$): δ 8.92 (dd, J=2.4, 0.8 Hz, 1H), 8.38 (dd, J=8.8, 2.4 Hz, 1H), 8.15 (d, J=8.4 Hz, 1H), 8.09 (dd, J=8.4, 1.2 Hz, 1H), 7.79 (m, 2H), 7.69 (m, 1H), 7.47 (m, 1H), 6.67 (dd, J=8.8, 0.8 Hz, 1H), 4.61 (t, J=4.2 Hz, 1H), 4.49

(t, J=4.2 Hz, 1H), 3.86 (t, J=5.8 Hz, 2H), 3.65-3.78 (m, 8H), 3.19 (s, 3H); MS (ESI): 370 (M+H$^+$).

Preparation of

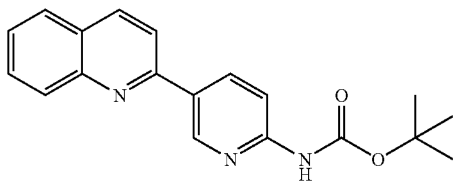 [SMILES: CC(C)(C)OC(=O)Nc1ccc(-c2ccc3ccccc3n2)cn1]

tert-Butyl 5-(quinolin-2-yl)pyridin-2-yl-carbamate T503: To a solution of 5-(quinolin-2-yl)pyridin-2-amine (130 mg, 0.59 mmol) in DCM (5 mL) was added $Boc_2O$ (154 mg, 0.71 mmol), DIEA (76 mg, 0.59 mmol) an DMAP (14 mg, 0.11 mmol). The mixture was stirred at room temperature for 24 hrs. LCMS showed that mono-Boc, di-Boc product, and starting material were present. The solvent was removed and the residue was dissolved in a mixture of ethyl acetate and DCM. As DCM evaporated, and needle crystals were formed. The crystals were collected by filtration, washed with ethyl acetate, and dried to give T503 white needles (67 mg, 35%). $^1$H NMR (400 MHz, DMSO-$d_6$): δ 10.03 (s, 1H), 9.11 (dd, J=2.4, 0.8 Hz, 1H), 8.60 (dd, J=8.8, 2.4 Hz, 1H), 8.43 (d, J=8.8 Hz, 1H), 8.15 (d, J=8.8 Hz, 1H), 8.04 (dd, J=8.2, 1.0 Hz, 1H), 7.96 (m, 2H), 7.76 (m, 1H), 7.57 (m, 1H), 1.47 (s, 9H); MS (ESI): 322 (M+H$^+$).

Preparation of

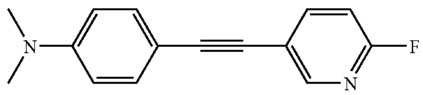

4-((6-Fluoropyridin-3-yl)ethynyl)-N,N-dimethylaniline: T516 was prepared using general procedure B. Reaction was performed on a 90 mg scale of 5-bromo-2-fluoropyridine. T516 was isolated as a light yellow solid (50 mg, 41%). $^1$H NMR (400 MHz, $CDCl_3$): δ 8.34 (m, 1H), 7.85 (m, 1H), 7.39 (m, 2H), 6.90 (m, 1H), 6.66 (m, 2H), 3.00 (s, 6H); MS (ESI): 241 (M+H$^+$).

Preparation of

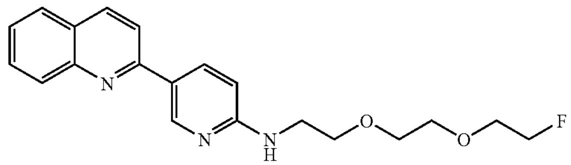 [SMILES: FCCOCCOCCNc1ccc(-c2ccc3ccccc3n2)cn1]

N-(2-(2-(2-Fluoroethoxy)ethoxy)ethyl)-5-(quinolin-2-yl)pyridin-2-amine: T525 was prepared using general procedure D. Reaction was performed on a 22.0 mg scale of T490. T525 was isolated as light yellow oil (3.3 mg, 9.3%). $^1$H NMR (400 MHz, $CDCl_3$): δ 8.86 (d, J=2.4 Hz, 1H), 8.35 (dd, J=8.8, 2.4 Hz, 1H), 8.15 (d, J=8.8 Hz, 1H), 8.09 (d, J=8.4 Hz, 1H), 7.79 (d, J=8.4 Hz, 2H), 7.69 (m, 1H), 7.48 (m, 1H), 6.57 (dd, J=8.8, 0.8 Hz, 1H), 5.15 (m, 1H), 4.65 (t, J=4.0 Hz, 1H), 4.53 (t, J=4.0 Hz, 1H), 3.81 (t, J=4.0 Hz, 1H), 3.68-3.77 (m, 7H), 6.63 (dd, J=10.6, 5.0 Hz, 2H); MS (ESI): 356 (M+H$^+$).

Preparation of

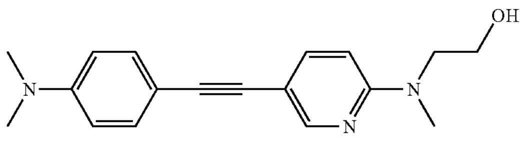 [SMILES: CN(C)c1ccc(C#Cc2ccc(N(C)CCO)nc2)cc1]

2-((5-((4-(Dimethylamino)phenyl)ethynyl)pyridin-2-yl)(methyl)amino)ethanol: T526 was prepared using general procedure M from 2-fluoropyridine derivatives and 2-(methylamino)ethanol. Reaction was performed on a 45 mg scale of T516. T526 was isolated as a light yellow solid (40 mg, 72%). $^1$H NMR (400 MHz, $CDCl_3$): δ 8.22 (dd, J=2.4, 0.8 Hz, 1H), 7.57 (dd, J=8.8, 2.4 Hz, 1H), 7.37 (m, 2H), 6.65 (m, 2H), 6.90 (d, J=8.8, 0.8 Hz, 1H), 4.58 (br s, 1H), 3.85 (t, J=4.8 Hz, 2H), 3.74 (t, J=4.8 Hz, 2H), 3.09 (s, 3H), 2.98 (s, 6H); MS (ESI): 296 (M+H$^+$).

Preparation of

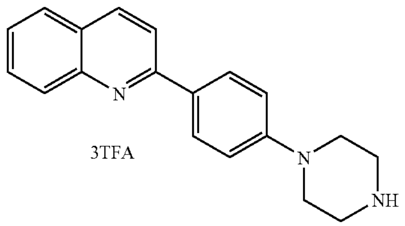 [SMILES: c1ccc2nc(-c3ccc(N4CCNCC4)cc3)ccc2c1]

3TFA 2-(4-(piperazin-1-yl)phenyl)quinoline*3TFA: T535 was prepared using general procedure A. Reaction was performed on a 17.0 mg scale of 2-chloroquinoline. T535 was isolated as a light yellow solid (10.0 mg, 42%). NMR (400 MHz, $CD_3OD$): δ 8.74 (d, J=8.8 Hz, 1H), 8.11-8.21 (m, 5H), 7.96 (t, J=7.2 Hz, 1H), 7.75 (t, J=7.2 Hz, 1H), 7.26 (m, 2H), 3.66 (br t, J=5.4 Hz, 4H), 3.40 (br t, J=5.4 Hz, 4H); MS (ESI): 290 (M+H$^+$).

Preparation of

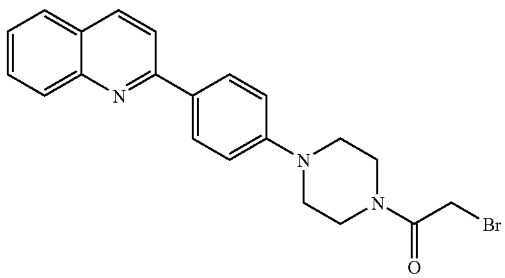 [SMILES: O=C(CBr)N1CCN(c2ccc(-c3ccc4ccccc4n3)cc2)CC1]

2-Bromo-1-(4-(4-(quinolin-2-yl)phenyl)piperazin-1-yl)ethanone T536: To a solution of 2-(4-(piperazin-1-yl)phenyl)quinoline*3TFA (8.6 mg, 0.014 mmol) in DCM (2 mL) was added TEA (9.0 mg, 0.089 mmol), followed by 2-bromoacetyl bromide (12.0 mg, 0.059 mmol). The mixture was stirred at room temperature for 1 hour and quenched by adding $NaHCO_3$ solution. The DCM layer was separated and concentrated. The residue was purified by flash chromatography (silica gel, 0-30% ethyl acetate/DCM) to give T536 as a white solid (3.7 mg, 66%). $^1$H NMR (400 MHz, $CDCl_3$): δ 8.11-8.18 (m, 4H), 7.84 (d, J=8.8 Hz, 1H), 7.80 (dd, J=8.0, 1.6 Hz, 1H), 7.72 (m, 1H), 7.49 (m, 1H), 7.05 (m, 2H), 3.91 (s, 2H), 3.83 (br t, J=5.2 Hz, 2H), 3.72 (br t, J=5.2 Hz, 2H), 3.39 (br t, J=5.2 Hz, 2H), 3.32 (br t, J=5.2 Hz, 2H); MS (ESI): 410 (M+H$^+$).

Preparation of

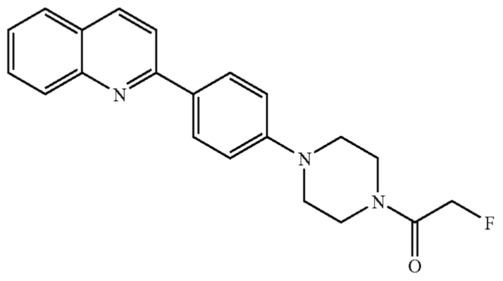 [SMILES: O=C(CF)N1CCN(c2ccc(-c3ccc4ccccc4n3)cc2)CC1]

2-Fluoro-1-(4-(4-(quinolin-2-yl)phenyl)piperazin-1-yl) ethanone: T537 was prepared using general procedure O. Reaction was performed on a 2.8 mg scale of T536. T537 was isolated as a white solid (1.9 mg, 80%). $^1$H NMR (400 MHz, $CDCl_3$): δ 8.11-8.18 (m, 4H), 7.84 (d, J=8.8 Hz, 1H), 7.80 (d, J=8.4 Hz, 1H), 7.70 (m, 1H), 7.49 (m, 1H), 7.05 (m, 2H), 5.11 (s, 1H), 4.99 (s, 1H), 3.84 (br s, 2H), 3.67 (br s, 2H), 3.33 (br t, J=5.0 Hz, 2H); MS (ESI): 350 (M+H$^+$).

Preparation of

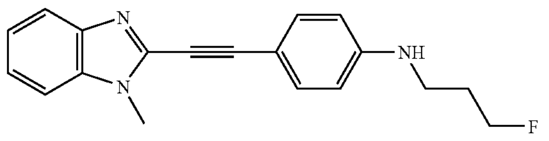

N-(3-Fluoropropyl)-4-((1-methyl-1H-benzo[d]imidazol-2-yl)ethynyl)aniline: T540 was prepared using general procedure E. Reaction was performed on a 6.7 mg scale of T465. T540 was isolated as a white solid (5.9 mg, 84%). $^1$H NMR (400 MHz, $CDCl_3$): δ 7.74 (m, 1H), 7.46 (m, 2H), 7.27-7.32 (m, 3H), 6.59 (m, 2H), 4.66 (t, J=5.6 Hz, 1H), 4.54 (t, J=5.6 Hz, 1H), 4.15 (br s, 1H), 3.91 (s, 3H), 3.36 (m, 2H), 2.02 (m, 2H); MS (ESI): 308 (M+H$^+$).

Preparation of

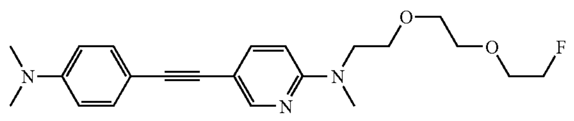

5-((4-(Dimethylamino)phenyl)ethynyl)-N-(2-(2-(2-fluoroethoxy)ethoxy)ethyl)-N-methylpyridin-2-amine: T546 was prepared using general procedure O. Reaction was performed on a 30.2 mg scale of T546-precursor. T546 was isolated as a light yellow gum (11.6 mg, 53%). $^1$H NMR (400 Hz, $CDCl_3$): δ 8.27 (d, J=2.4 Hz, 1H), 7.52 (dd, J=8.8, 2.4 Hz, 1H), 7.36 (m, 2H), 6.64 (br d, J=8.8 Hz, 2H), 6.47 (d, J=8.8 Hz, 1H), 4.59 (t, J=4.2 Hz, 1H), 4.47 (t, J=4.2 Hz, 1H), 3.60-3.79 (m, 10H), 3.11 (s, 3H), 2.97 (br s, 6H); MS (ESI): 386 (M+H$^+$).

Preparation of

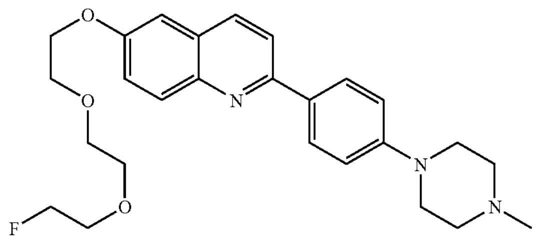 [SMILES: CN1CCN(c2ccc(-c3ccc4cc(OCCOCCOCCF)ccc4n3)cc2)CC1]

6-(2-(2-(2-Fluoroethoxy)ethoxy)ethoxy)-2-(4-(4-methylpiperazin-1-yl)phenyl)quinoline: T550 was prepared using general procedure A. Reaction was performed on a 38.6 mg scale of 2-chloro-6-(2-(2-(2-fluoroethoxy)ethoxy)ethoxy) quinoline. T550 was isolated as a white crystal (7.2 mg, 13%). $^1$H NMR (400 MHz, $CDCl_3$): δ 7.99-8.08 (m, 4H), 7.77 (d, J=9.2 Hz, 1H), 7.37 (dd, J=9.2, 2.8 Hz, 1H), 7.07 (d, J=2.8 Hz, 1H), 7.02 (m, 2H), 4.62 (t, J=4.4 Hz, 1H), 4.50 (t, J=4.4 Hz, 1H), 4.26 (t, J=5.0 Hz, 2H), 3.94 (t, J=5.0 Hz, 2H), 3.70-3.81 (m, 6H), 3.43 (br s, 4H), 2.78 (br s, 4H), 2.50 (br s, 3H); MS (ESI): 454 (M+H$^+$).

Preparation of

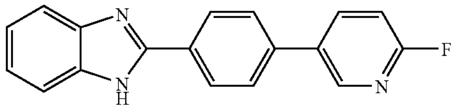

2-(4-(6-Fluoropyridin-3-yl)phenyl)-1H-benzo[d]imidazole: T468 was prepared using general procedure S. Reaction was performed on a 0.029 g scale of 2-aminoaniline. The desired product T468 was isolated as a yellow solid (0.043 g, 55%). $^1$H NMR (400 MHz, MeOH-$d_4$): δ 8.61 (d, J=2.8 Hz, 1H), 8.33 (dd, J=8.4, 2.8 Hz, 1H), 8.24 (d, J=8.8 Hz, 2H), 8.03 (d J=8.8 Hz, 2H), 7.82 (dd, J=8.8, 2.4 Hz, 2H), 7.61 (dd, J=8.8, 2.4 Hz, 2H), 7.22 (dd, J=8.8, 2.8 Hz, 1H); MS (ESI): 290 (M+H$^+$).

Preparation of

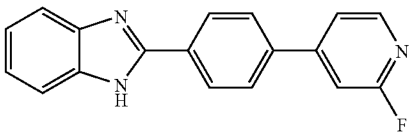 [SMILES: Fc1cc(-c2ccc(-c3nc4ccccc4[nH]3)cc2)ccn1]

2-(4-(2-Fluoropyridin-4-yl)phenyl)-1H-benzo[d]imidazole: T460 was prepared using general procedure S. Reaction was performed on a 0.027 g scale of 2-aminoaniline. The desired product T460 as a yellow solid (0.010 g, 14%). $^1$H NMR (400 MHz, MeOH-$d_4$): δ 8.25 (d, J=5.2 Hz, 1H), 8.19 (d, J=8.8 Hz, 2H), 8.04 (d, J=8.8 Hz, 2H), 8.03 (d, J=8.8 Hz, 2H), 7.72 (q, J=3.2 Hz, 2H), 7.64 (dt, J=5.2, 1.6 Hz, 1H), 7.49 (q, J=3.2 Hz, 2H), 7.42 (s, 1H); MS (ESI): 290 (M+H$^+$).

Preparation of

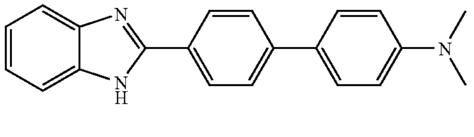

4'-(1H-Benzo[d]imidazol-2-yl)-N,N-dimethyl-[1,1'-biphenyl]-4-amine: EW5338-028 was prepared using general procedure S. Reaction was performed on a 0.052 g scale of 2-aminoaniline. EW5338-028 was isolated as a yellow solid (0.076 g, 50%). NMR (400 MHz, MeOH-$d_4$): δ 8.08 (d, J=8.8 Hz, 2H), 7.72 (d, J=8.8 Hz, 2H), 7.51-7.62 (m, 4H), 7.23 (dd, J=8.8, 2.8 Hz, 2H), 6.84 (d, J=8.8 Hz, 2H), 2.97 (s, 6H); MS (ESI): 314 (M+H$^+$).

Preparation of

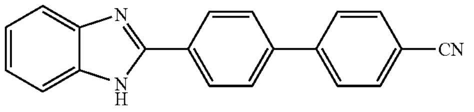 [SMILES: N#Cc1ccc(-c2ccc(-c3nc4ccccc4[nH]3)cc2)cc1]

4'-(1H-Benzo[d]imidazol-2-yl)-[1,1'-biphenyl]-4-carbonitrile: EW5338-043 was prepared using general procedure S. Reaction was performed on a 0.052 g scale of 2-aminoaniline. EW5338-043 was isolated as a yellow solid (0.076 g, 50%). NMR (DMSO-$d_6$): δ 8.66 (s, 2H), 8.28 (d, J=8.4 Hz, 2H), 7.92-8.02 (m, 6H), 7.16-7.22 (m, 2H); MS (ESI): 296 (M+H$^+$).

Preparation of

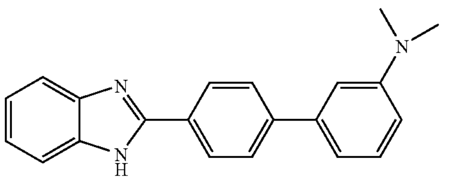 [SMILES: CN(C)c1cccc(-c2ccc(-c3nc4ccccc4[nH]3)cc2)c1]

4'-(1H-Benzo[d]imidazol-2-yl)-N,N-dimethyl-[1,1'-biphenyl]-3-amine: EW5338-036 was prepared using general procedure S. Reaction was performed on a 0.052 g scale of 2-aminoaniline. EW5338-036 was isolated as a yellow solid (0.076 g, 50%). $^1$H NMR (400 MHz, MeOH-$d_4$): δ 8.08 (d, J=8.8 Hz, 2H), 7.56-7.62 (m, 3H), 7.20-7.51 (m, 4H), 6.99 (s, 1H), 6.84-6.91 (m, 2H), 3.02 (s, 6H); MS (ESI): 314 (M+H$^+$).

Preparation of

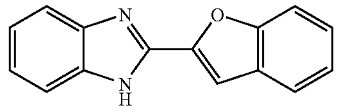 [SMILES: c1ccc2oc(-c3nc4ccccc4[nH]3)cc2c1]

2-(Benzofuran-2-yl)-1H-benzo[d]imidazole: T488 was prepared using general procedure S. Reaction was performed on a 0.34 g scale of 2-aminoaniline. T488 was isolated as a yellow solid (0.1 g, 14%). $^1$H NMR (400 MHz, MeOH-$d_4$): δ 7.54-7.74 (m, 5H), 7.36-7.44 (m, 1H), 7.26-7.34 (m, 3H); MS (ESI): 235 (M+H$^+$).

Preparation of

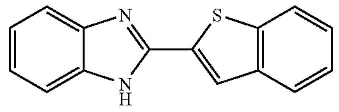 [SMILES: c1ccc2sc(-c3nc4ccccc4[nH]3)cc2c1]

2-(Benzo[b]thiophen-2-yl)-1H-benzo[d]imidazole: T493 was prepared using general procedure S. Reaction was performed on a 0.4 g scale of 2-aminoaniline. T493 was isolated as a yellow solid (0.7 g, 76%). $^1$H NMR (400 MHz, MeOH-$d_4$): δ 8.25 (d, J=0.8 Hz, 1H), 7.98-8.06 (m, 2H), 7.73 (dd, J=8.8, 2.4 Hz, 2H), 7.48-7.56 (m, 4H); MS (ESI): 251 (M+H$^+$).

Preparation of

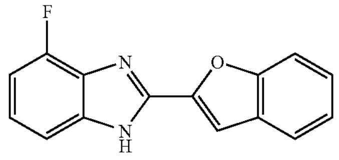 [SMILES: Fc1cccc2[nH]c(-c3cc4ccccc4o3)nc12]

2-(Benzofuran-2-yl)-4-fluoro-1H-benzo[d]imidazole: T495 was prepared using general procedure S. Reaction was performed on a 0.34 g scale of 2-aminoaniline. T495 was isolated 0 as a solid (0.3 g, 50%). $^1$H NMR (400 MHz, MeOH-$d_4$): δ 7.72-7.78 (m, 1H), 7.71 (d, J=1.2 Hz, 1H), 7.62-7.68 (m, 1H), 7.43-7.49 (m, 2H), 7.30-7.38 (m, 2H), 7.09 (dd, J=8.0, 0.8 Hz, 1H); MS (ESI): 253 (M+H$^+$).

Preparation of

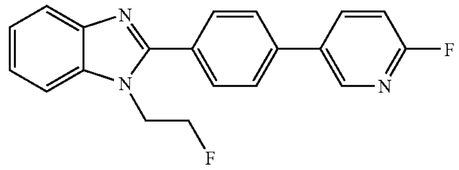 [SMILES: FCCn1c(-c2ccc(-c3ccc(F)nc3)cc2)nc2ccccc21]

1-(2-Fluoroethyl)-2-(4-(6-fluoropyridin-3-yl)phenyl)-1H-benzo[d]imidazole: T538 was prepared using general procedure E. Reaction was performed on a 0.01 g scale of T468. T538 was isolated as a white solid (0.012 g, 100%). $^1$H NMR (400 MHz, $CDCl_3$): δ 8.49 (dt, J=2.4, 0.8 Hz, 1H), 8.30 (dd, J=8.4, 2.4 Hz, 1H), 7.93-7.97 (m, 1H), 7.90 (d, J=8.8 Hz, 2H), 7.72 (d, J=8.8 Hz, 2H), 7.38-7.51 (m, 3H), 7.05 (dd, J=8.8, 0.4 Hz, 1H), 4.84 (dt, J=46.4, 5.2 Hz, 2H), 4.61 (dt, J=24, 4.8 Hz, 2H); MS (ESI): 336 (M+H$^+$).

Preparation of

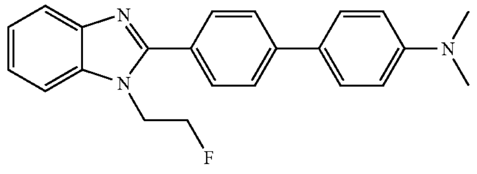

4'-(1-(2-Fluoroethyl)-1H-benzo[d]imidazol-2-yl)-N,N-dimethyl-[1,1'-biphenyl]-4-amine: T543 was prepared using general procedure E. Reaction was performed on a 0.030 g scale of EW5338-028. T543 was isolated as a yellow solid (0.007 g, 20%). $^1$H NMR (400 MHz, MeOH-$d_4$): δ 7.83-8.20 (m, 6H), 7.67-7.73 (m, 4H), 6.97 (d, J=8.8 Hz, 2H), 4.96 (dt, J=46.4, 5.2 Hz, 2H), 4.61 (dt, J=24, 4.8 Hz, 2H), 3.05 (s, 6H); MS (ESI): 360 (M+H$^+$).

Preparation of

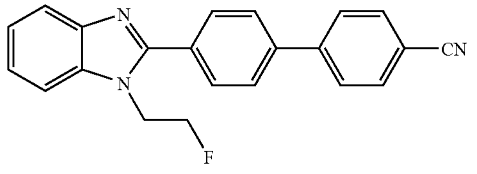 [SMILES: N#Cc1ccc(-c2ccc(-c3nc4ccccc4n3CCF)cc2)cc1]

4'-(1-(2-Fluoroethyl)-1H-benzo[d]imidazol-2-yl)-[1,1'-biphenyl]-4-carbonitrile: T556 was prepared using general procedure E. Reaction was performed on a 0.036 g scale of EW5338-043. T556 was isolated as a yellow solid (0.009 g, 22%). $^1$H-NMR (400 MHz, $CDCl_3$): δ 7.89 (d, J=8.0 Hz, 3H), 7.72-7.79 (m, 6H), 7.42-7.48 (m, 1H), 7.34-7.41 (m, 2H), 4.83 (dt, J=46, 4.8 Hz, 2H), 4.59 (dt, J=24, 5.2 Hz, 2H); MS (ESI): 342 (M+H$^+$).

Preparation of

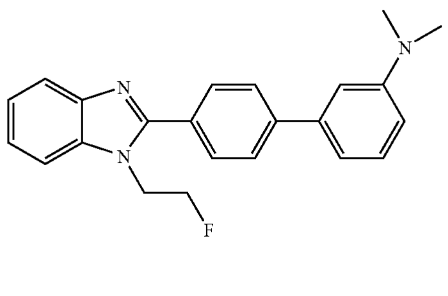 [SMILES: CN(C)c1cccc(-c2ccc(-c3nc4ccccc4n3CCF)cc2)c1]

4'-(1-(2-Fluoroethyl)-1H-benzo[d]imidazol-2-yl)-N,N-dimethyl-[1,1'-biphenyl]-3-amine: T548 was prepared using general procedure E. Reaction was performed on a 0.036 g scale of EW5338-036. T548 was isolated as a yellow solid (0.014 g, 33%). $^1$H NMR (400 MHz, $CDCl_3$): δ 7.85-7.89 (m, 1H), 7.79 (d, J=8.4 Hz, 2H), 7.75 (d, J=8.4 Hz, 2H), 7.42-7.47 (m, 1H), 7.31-7.37 (m, 3H), 6.95-7.02 (m, 2H), 6.78 (dd, J=8.4, 0.8 Hz, 1H), 3.02 (s, 6H); MS (ESI): 360 (M+H$^+$).

Preparation of

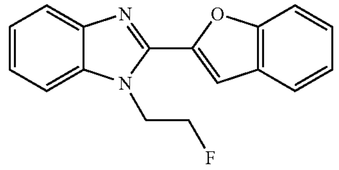 [SMILES: FCCn1c(-c2cc3ccccc3o2)nc2ccccc21]

2-(Benzofuran-2-yl)-1-(2-fluoroethyl)-1H-benzo[d]imidazole: T489 was prepared using general procedure E. Reaction was performed on a 0.052 g scale of T488. T489 was isolated as a yellow solid (0.076 g, 50%). $^1$H NMR (400 MHz, $CDCl_3$): δ 7.81-7.88 (m, 1H), 7.69-7.74 (m, 1H), 7.55-7.63 (m, 2H), 7.45-7.51 (m, 1H), 7.30-7.44 (m, 4H), 4.92-5.03 (m, 2H), 4.85-4.95 (m, 2H); MS (ESI): 281 (M+H$^+$).

Preparation of

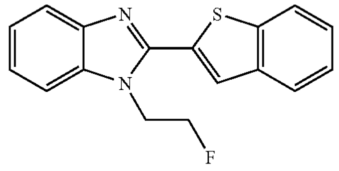

2-(Benzo[b]thiophen-2-yl)-1-(2-fluoroethyl)-1H-benzo[d]imidazole: T494 was prepared using general procedure E. Reaction was performed on a 0.052 g scale of T493. T494 was isolated as a yellow solid (0.076 g, 50%). $^1$H NMR (400 MHz, $CDCl_3$): δ 7.85-7.92 (m, 3H), 7.77 (s, 1H), 7.81-7.95 (m, 3H), 7.60-7.75 (m, 2H), 4.91 (dt, J=46.4, 4.8 Hz, 2H), 4.75 (dt, J=24, 4.8 Hz, 2H); MS (ESI): 297 (M+H$^+$).

Preparation of

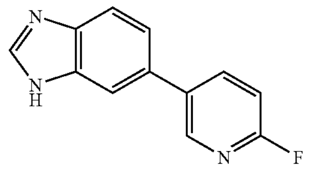 [SMILES: Fc1ccc(-c2ccc3nc[nH]c3c2)cn1]

6-(6-Fluoropyridin-3-yl)-1H-benzo[d]imidazole: T532 was prepared using general procedure A. Reaction was performed on a 0.08 g scale of 6-bromobenzoimidazole. T532 was isolated as a yellow solid (0.025 g, 29%). $^1$H NMR (400 MHz, MeOH-$d_4$): δ 9.16 (s, 1H), 8.15 (d, J=2.8 Hz, 1H), 8.26 (dd, J=10, 2.4 Hz, 1H), 8.0-8.04 (m, 1H), 7.90 (d, J=8.8 Hz, 1H), 7.83 (dd, J=8.4, 1.6 Hz, 1H), 7.19 (dd, J=8.4, 1.6 Hz, 1H); MS (ESI): 214 (M+H$^+$).

Preparation of

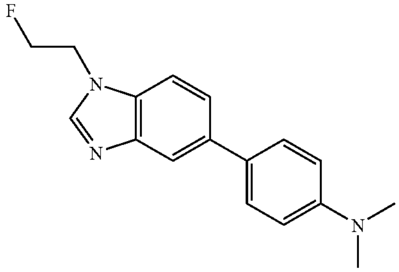 [SMILES: CN(C)c1ccc(-c2ccc3c(c2)ncn3CCF)cc1]

4-(1-(2-Fluoroethyl)-1H-benzo[d]imidazol-5-yl)-N,N-dimethylaniline: T533 was prepared using general procedure A. Reaction was performed on a 0.08 g scale of 6-bromo-N-2-fluoroethylbenzoimidazole. T533 was isolated as a yellow solid (0.025 g, 29%). $^1$H NMR (400 MHz, $D_2O$): δ 9.23 (s, 1H), 8.05 (d, J=1.2 Hz, 1H), 7.81-7.89 (m, 4H), 7.64 (d, J=8.8 Hz, 2H), 4.90 (dt, J=27.2, 5.2 Hz, 2H), 4.78-4.83 (m, 2H), 3.25 (s, 6H); MS (ESI): 284 (M+H$^+$).

Preparation of

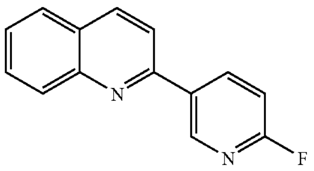 [SMILES: Fc1ccc(-c2ccc3ccccc3n2)cn1]

2-(6-Fluoropyridin-3-yl)quinoline: T455 was prepared using general procedure A. Reaction was performed on a 0.1 g scale. T455 was isolated as a white solid (0.14 g, 100%). $^1$H NMR (400 MHz, $CDCl_3$): δ 8.94 (d, J=2.4 Hz, 1H), 8.66 (ddd, J=10.4, 7.6, 2.4 Hz, 1H), 8.27 (d, J=8.0 Hz, 1H), 8.14 (dd, J=8.4, 1.2 Hz, 1H), 7.75 (ddd, J=8.4, 6.8, 1.6 Hz, 1H), 7.85 (d, J=8.8 Hz, 2H), 7.56 (ddd, J=8.0, 6.3, 1.2 Hz, 1H), 7.09 (ddd, J=8.8, 3.2, 0.2 Hz, 1H); MS (ESI): 225.0 (M+H$^+$).

Preparation of

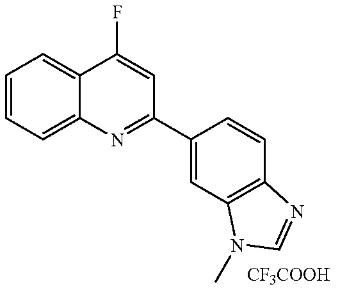 [SMILES: Cn1cnc2ccc(-c3cc(F)c4ccccc4n3)cc21 ; "CF3COOH"]

4-Fluoro-2-(1-methyl-1H-benzo[d]imidazol-6-yl)quinoline 2,2,2-trifluoroacetate: T485 was prepared using general procedure L. Reaction was performed on a 0.017 g scale. Product was purified by HPLC using ACN (0.05% TFA)/H2O (0.05% TFA). T485 was isolated as a white solid (0.09 g, 58%). $^1$H NMR (400 MHz, $CD_3OD$): δ 9.24 (s, 1H), 8.65-8.64 (m, 1H), 8.44 (dd, J=8.8, 2.4 Hz, 1H), 8.13-8.07 (m, 2H), 7.95 (d, J=11.6 Hz, 1H), 7.90-7.88 (m, 1H), 7.81 (ddd, J=8.4, 6.8, 1.6 Hz, 1H), 7.62 (ddd, J=8.0, 6.8, 0.8 Hz, 1H), 4.14 (s, 3H); MS (ESI): 278.1 (M+H$^+$).

Preparation of

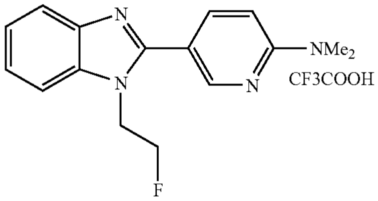

5-(1-(2-Fluoroethyl)-1H-benzo[d]imidazol-2-yl)-N,N-dimethylpyridin-2-amine 2,2,2-trifluoroacetate: T487 was prepared using general procedure A. Reaction was performed on a 0.02 g scale. Product was purified by HPLC using ACN (0.05% TFA)/$H_2O$ (0.05% TFA). T487 was isolated as a white solid (0.018 g, 77%). $^1$H NMR (400 MHz, $CD_3OD$): δ 8.55 (d, J=2.4 Hz, 1H), 7.98 (ddd, J=9.2, 2.4, 0.4 Hz, 1H), 7.93-7.91 (m, 1H), 7.81-7.78 (m, 1H), 7.63 (ddd, J=5.6, 2.4, 1.2 Hz, 1H), 6.93 (dd, J=9.2, 0.8 Hz, 1H), 5.00 (t, J=4.4 Hz, 1H), 4.89 (m, 1H), 4.83 (s, 6H), 4.84 (m, 1H), 4.79 (t, J=4.4 Hz, 1H); MS (ESI): 285.1 (M+H$^+$).

Preparation of

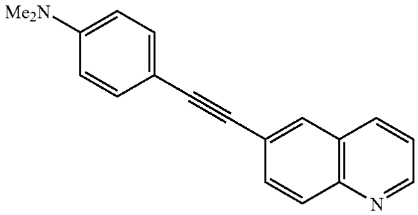 [SMILES: CN(C)c1ccc(C#Cc2ccc3ncccc3c2)cc1]

N,N-Dimethyl-4-(quinolin-6-ylethynyl)aniline: T517 was prepared using general procedure B. Reaction was performed on a 0.1 g scale. T517 was isolated as a yellow solid (0.1 g, 76%). NMR (400 MHz, $CDCl_3$): δ 8.87 (dd, J=4.4, 2.0 Hz, 1H), 8.09 (d, J=8.0 Hz, 1H), 8.03 (d, J=8.8 Hz, 1H), 7.95 (d, J=1.6 Hz, 1H), 7.78 (dd, J=8.8, 2.0 Hz, 1H), 7.44 (d, J=8.8 Hz, 2H), 7.39 (dd, J=8.4, 4.4 Hz, 1H), 6.67 (d, J=9.2 Hz, 2H), 3.00 (s, 6H); MS (ESI): 273.1 (M+H$^+$).

Preparation of

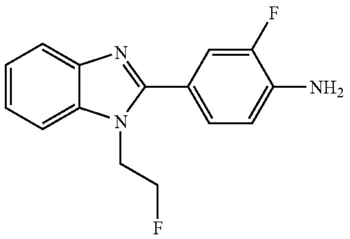 [SMILES: Nc1ccc(-c2nc3ccccc3n2CCF)cc1F]

2-Fluoro-4-(1-(2-fluoroethyl)-1H-benzo[d]imidazol-2-yl)aniline: T524 was prepared using general procedure A. Reaction was performed on a 0.1 g scale. T524 was isolated as a white solid (0.09 g, 76%). $^1$H NMR (400 MHz, $CDCl_3$): δ 7.81-7.78 (m, 1H), 7.43-7.37 (m, 2H), 7.33-7.29 (m, 3H), 6.87 (dd, J=8.8, 8.4 Hz, 1H), 4.84 (t, J=4.8 Hz, 1H), 4.72 (t, J=5.2 Hz, 1H), 4.54 (t, J=4.8 Hz, 1H), 4.48 (t, J=5.2 Hz, 1H); MS (ESI): 274.1 (M+H$^+$).

Preparation of

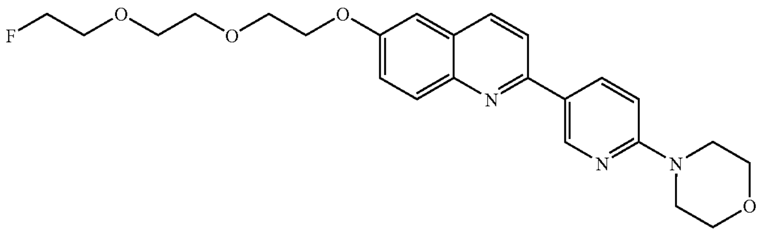 [SMILES: FCCOCCOCCOc1ccc2nc(-c3ccc(N4CCOCC4)nc3)ccc2c1]

4-(5-(6-(2-(2-(2-Fluoroethoxy)ethoxy)ethoxy)quinolin-2-yl)pyridin-2-yl)morpholine: T539 was prepared using general procedure A. Reaction was performed on a 0.037 g scale. T539 was isolated as white solid (0.04 g, 77%). $^1$H NMR (400 MHz, DMSO-$d_6$): δ 8.99 (d, J=2.0 Hz, 1H), 8.41 (dd, J=8.8, 2.8 Hz, 1H), 8.25 (d, J=8.8 Hz, 1H), 8.03 (d, J=8.8 Hz, 1H), 7.91 (d, J=8.8 Hz, 1H), 7.41-7.37 (m, 2H), 6.98 (d, J=9.6 Hz, 1H), 4.58 (t, J=4.0 Hz, 1H), 4.46 (t, J=4.0 Hz, 1H), 4.25 (t, J=4.4 Hz, 2H), 3.84 (t, J=4.8 Hz, 2H), 3.74-3.69 (m, 6H), 3.66-3.56 (m, 4H), 3.58-3.56 (m, 4H); MS (ESI): 442.1 (M+H$^+$).

Preparation of

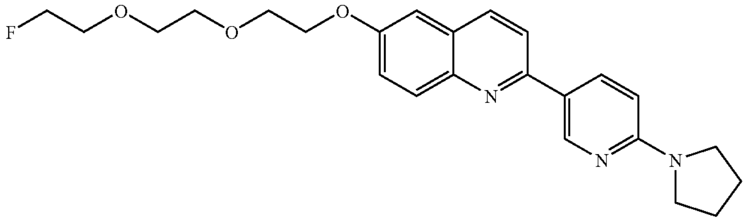 [SMILES: FCCOCCOCCOc1ccc2nc(-c3ccc(N4CCCC4)nc3)ccc2c1]

6-(2-(2-(2-Fluoroethoxy)ethoxy)ethoxy)-2-(6-(pyrrolidin-1-yl)pyridin-3-yl)quinoline: T545 was prepared using general procedure A. Reaction was performed on a 0.039 g scale. T545 was isolated as white solid (0.035 g, 66%). $^1$H NMR (400 MHz, $CDCl_3$): δ 8.86 (d, J=2.4 Hz, 1H), 8.34 (dd, J=8.8, 2.4 Hz, 1H), 8.01 (d, J=8.4 Hz, 1H), 7.97 (d, J=9.2 Hz, 1H), 7.73 (d, J=8.8 Hz, 1H), 7.36 (dd, J=9.2, 2.8 Hz, 1H), 7.06 (d, J=2.04 Hz, 1H), 6.49 (d, J=8.8 Hz, 1H), 4.62 (t, J=4.0 Hz, 1H), 4.50 (t, J=4.0 Hz, 1H), 4.26 (t, J=4.8 Hz, 2H), 3.94 (t, J=4.0 Hz, 2H), 3.80-3.71 (m, 6H), 3.55-3.52 (m, 4H), 2.05-2.02 (m, 4H); MS (ESI): 426.1 (M+H$^+$).

Preparation of

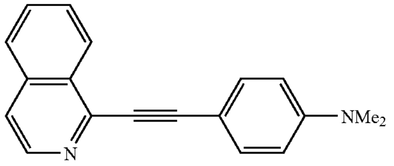 [SMILES: CN(C)c1ccc(C#Cc2nccc3ccccc23)cc1]

4-(Isoquinolin-1-ylethynyl)-N,N-dimethylaniline: T547 was prepared using general procedure B. Reaction was performed on a 0.064 g scale. T547 was isolated as yellow solid (0.1 g, 76%). $^1$H NMR (400 MHz, $CDCl_3$): δ 8.52 (d, J=7.2 Hz, 1H), 8.49 (d, J=6.0 Hz, 1H), 7.82 (d, J=8.0 Hz, 1H), 7.73-7.65 (m, 2H), 7.622-7.56 (m, 3H), 6.70 (d, J=9.2 Hz, 2H), 3.03 (s, 6H); MS (ESI): 273.1 (M+H$^+$).

Preparation of

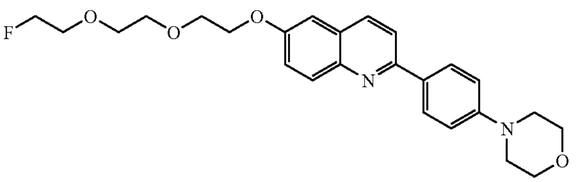 [SMILES: FCCOCCOCCOc1ccc2nc(-c3ccc(N4CCOCC4)cc3)ccc2c1]

4-(4-(6-(2-(2-(2-Fluoroethoxy)ethoxy)ethoxy)quinolin-2-yl)phenyl)morpholine: T549 was prepared using general procedure A. Reaction was performed on a 0.033 g scale. T549 was isolated as white solid (0.035 g, 76%). $^1$H NMR (400 MHz, $CDCl_3$): δ 8.02 (d, J=8.8 Hz, 2H), 7.96 (dd, J=9.6, 8.8 Hz, 2H), 7.72 (d, J=8.4 Hz, 1H), 7.31 (dd, J=9.2, 3.2 Hz, 1H), 7.01 (d, J=2.4 Hz, 1H), 6.96 (d, J=9.2 Hz, 2H), 4.56 (t, J=4.0 Hz, 1H), 4.44 (t, J=4.4 Hz, 1H), 4.20 (t, J=4.8 Hz, 2H), 3.88 (t, J=4.8 Hz, 2H), 3.83 (t, J=4.8 Hz, 4H), 3.75-3.65 (m, 6H), 3.19 (t, J=4.8 Hz, 4H); MS (ESI): 441.1 (M+H$^+$).

Preparation of

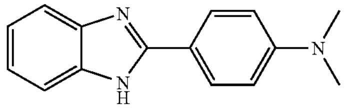 [SMILES: CN(C)c1ccc(-c2nc3ccccc3[nH]2)cc1]

T450: A mixture of 1,2-phenylenediamine (80 mg, 0.740 mmol) and 4-dimethylamino-benzoyl chloride (80 mg, 0.436 mmol) in DMF (1.0 mL) was heated at 200° C. for 15 mins in a microwave. The crude product was purified by prepHPLC and neutralized with NaHCO3 to afford T450 (20 mg, 19.35%). $^1$H NMR (400 MHz, DMSO-$d_6$) δ 8.03-8.01 (d, 2H), 7.72-7.69 (m, 2H), 7.47-7.45 (m, 2H), 6.95-6.93 (m, 2H), 3.06 (s, 6H); MS (ESI): 238.1 (M+H$^+$).

Preparation of

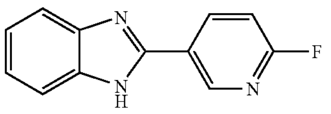 [SMILES: Fc1ccc(-c2nc3ccccc3[nH]2)cn1]

T452 A mixture of 2-bromobenzimidazole (0.05 g, 0.254 mmol), 2-fluoropyridine-5-boronic acid (0.036 g, 0.254 mmol), Potassium carbonate (0.190 ml, 0.381 mmol), and $PdCl_2(dppf)_2DCM$ (10.36 mg, 0.013 mmol) in DMF (1.0 mL) was heated at 150° C. for 15 min. The crude product was purified by prepHPLC to afford T452 (6 mg, 11.09%). $^1$H NMR (400 MHz, $CD_3CN$) δ 9.01 (s, 1H), 8.70-8.65 (m, 1H), 7.81-7.79 (m, 2H), 7.45-7.43 (m, 2H), 7.29-7.26 (m, 1H); MS (ESI): 214.0 (M+H$^+$).

Preparation of

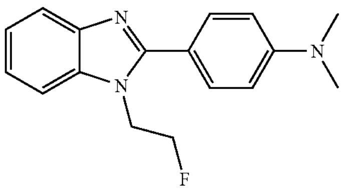 [SMILES: CN(C)c1ccc(-c2nc3ccccc3n2CCF)cc1]

T497 was prepared using general procedure D. The reaction was performed on a 20 mg scale of T450. T497 TFA salt was isolated (6 mg, 25.1%). $^1$H NMR (400 MHz, $CD_3CN$) δ 7.96-7.93 (m, 1H), 7.77-7.75 (m, 1H), 7.70-7.67 (m, 2H), 7.56-7.53 (m, 2H), 6.94-6.90 (m, 2H), 4.94-4.92 (m, 1H), 4.83-4.80 (m, 2H), 4.76-4.74 (m, 1H), 3.04 (s, 6H); MS (ESI): 284.10 (M+H$^+$).

Preparation of

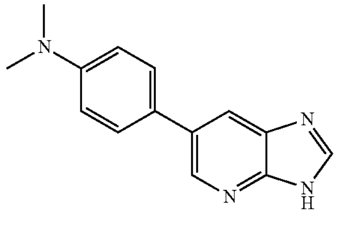 [SMILES: CN(C)c1ccc(-c2cnc3[nH]cnc3c2)cc1]

T555: To a solution of 5-bromo-7-azaindole (0.1 g, 0.508 mmol), 4-Dimethylaminophenyl boronic acid (0.084 g, 0.508 mmol), Copper(I) iodide (9.67 mg, 0.051 mmol), and Potassium carbonate (0.508 ml, 1.015 mmol) in DMF (2.0 mL) was added a solution of [1,1'-bis(diphenylphosphino)ferrocene] dichloropalladium(II) (0.021 g, 0.025 mmol) in DCM (2.0 mL). The resulting mixture was heated at 120° C. in a microwave for 30 min. and then cooled to room temperature. The crude product was purified by prep HPLC to afford T555 TFA salt (0.010 g, 5.61%). $^1$H NMR (400 MHz, DMSO-$d_6$) δ 11.80 (s, 1H), 8.48-8.47 (m, 1H), 8.22-8.21 (m, 1H), 7.61-7.58 (m, 2H), 7.51-7.50 (m, 1H), 6.98-6.96 (m, 2H), 6.51-6.50 (m, 1H), 2.97 (s, 6H); MS (ESI): 238.7 (M+H$^+$).

Preparation of

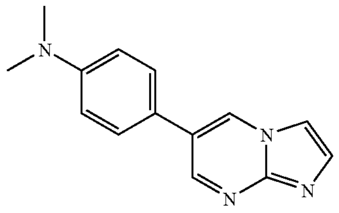 [SMILES: CN(C)c1ccc(-c2cnc3nccn3c2)cc1]

T558: To a solution of 6-bromoimidazo[1,2-a]pyrimidine (0.08 g, 0.404 mmol), 4-dimethylaminophenylboronic acid (0.087 g, 0.525 mmol), Copper(I) iodide (7.69 mg, 0.040 mmol) and Potassium carbonate (0.404 ml, 0.808 mmol) in DMF (2.0 mL) was added a solution of [1,1'-bis(diphenylphosphino)ferrocene]dichloropalladium(II) (0.016 g, 0.020 mmol) in DCM (2.0 mL). The resulting mixture was microwaved at 120° C. for 30 min., cooled and filtered. The filtrate was concentrated in vacuo. The residue was purified on prep HPLC to afford T558 TFA salt (0.008 g, 0.023 mmol, 5.62% yield). $^1$H NMR (400 MHz, DMSO-$d_6$) δ 9.44 (m, 1H), 9.26 (m, 1H), 8.14-8.11 (m, 2H), 7.69-7.66 (m, 2H), 6.90-6.88 (m, 2H), 2.99 (s, 3H); MS (ESI): 239.1 (M+H$^+$).

Preparation of

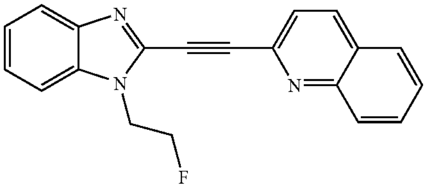 [SMILES: FCCn1c(C#Cc2ccc3ccccc3n2)nc2ccccc21]

T496 was prepared using general procedure B. Reaction was performed on a 50 mg scale. Filtered and purified on prep HPLC to afford T496 TFA salt (0.02 g, 30.8%). $^1$H NMR (400 MHz, DMSO-$d_6$) δ 8.52-8.50 (m, 1H), 8.07-8.04 (m, 2H), 7.90-7.82 (m, 2H), 7.74-7.69 (m, 3H), 7.40-7.37 (m, 1H), 7.34-7.32 (m, 1H), 4.92-4.90 (m, 1H), 4.87-4.86 (m, 1H), 4.80 (m, 2H); MS (ESI): 316.1 (M+H$^+$).

Preparation of

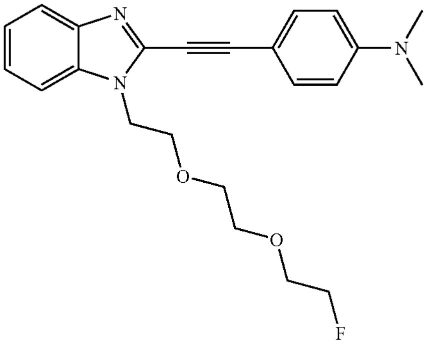 [SMILES: CN(C)c1ccc(C#Cc2nc3ccccc3n2CCOCCOCCF)cc1]

T508 was prepared using general procedure D from T481 and 2-(2-(2-fluoroethoxy)-ethoxy)ethyl 4-methylbenzene-sulfonate. The reaction was performed on a 60 mg scale of T481. The crude product was purified by prep HPLC to afford T508 (5 mg, 5.51%). $^{1}$H NMR (400 MHz, $CD_3CN$) δ 7.83-7.77 (m, 2H), 7.59-7.52 (m, 4H), 6.79-6.77 (m, 2H), 4.66-4.63 (m, 2H), 4.43-4.41 (m, 1H), 4.31-4.29 (m, 1H), 3.96-3.94 (m, 2H), 3.57-3.52 (m, 3H), 3.48-3.44 (m, 3H), 3.05 (s, 6H); MS (ESI): 396.20 ($M+H^+$).

Preparation of

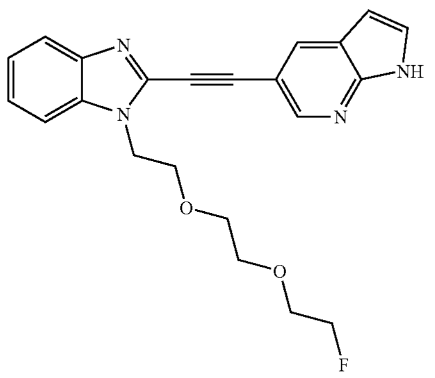

T527 was prepared using general procedure B from 2-bromo-1-(2-(2-(2-fluoroethoxy)ethoxy)ethyl)-1H-benzo[d]imidazole and 5-ethynyl-7-azaindole. The reaction was performed on a 105 mgs scale of 2-bromo-1-(2-(2-(2-fluoroethoxy)ethoxy)ethyl)-1H-benzo[d]imidazole. The crude product was purified by Prep HPLC to afford T527 TFA salt (0.01 g, 6.24%). $^{1}$H NMR (400 MHz, $CD_3CN$) δ 10.14 (s, 1H), 8.59-8.58 (m, 1H), 8.32 (m, 1H), 7.82-7.80 (m, 1H), 7.73-7.71 (m, 1H), 7.52-7.45 (m, 3H), 6.61-6.59 (m, 1H), 4.69-4.67 (m, 2H), 4.42-4.40 (m, 1H), 4.30-4.28 (m, 1H), 3.98-3.95 (m, 2H), 3.58-3.52 (m, 3H), 3.49-3.44 (m, 3H); MS (ESI): 393.10 ($M+H^+$).

Preparation of

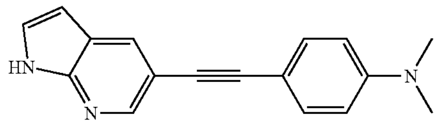

T528 was prepared using general procedure B. Reaction was performed on a 63 mgs scale. The crude product was purified by prep HPLC to afford T528 TFA salt (0.005 g, 4.21%). $^{1}$H NMR (400 MHz, $CD_3CN$) δ 8.28 (m, 1H), 7.98 (m, 1H), 7.33-7.28 (m, 3H), 6.66-6.64 (m, 2H), 6.42-6.41 (m, 1H), 2.88 (s, 6H); MS (ESI): 261.1 ($M+H^+$).

Preparation of

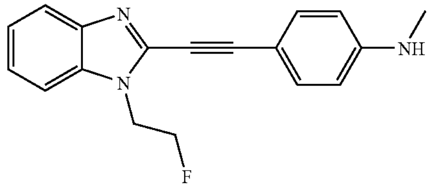 [SMILES: CNc1ccc(C#Cc2nc3ccccc3n2CCF)cc1]

T534 was prepared using general procedure B from 2-bromo-1-(2-fluoroethyl)-1H-benzo[d]imidazole and tert-butyl methyl-4-(ethynyl)phenylcarbamate. Reaction was performed on a 53 mgs scale of 2-bromo-1-(2-fluoroethyl)-1H-benzo[d]imidazole. The crude product was purified by ISCO column to afford tert-butyl 4-((1-(2-fluoroethyl)-1H-benzo[d]imidazol-2-yl)ethynyl)phenyl(methyl)carbamate (0.03 g, 35.3%). It was dissolved in acetonitrile (0.5 mL). To this solution was added a solution of 20% sulfuric acid (1.5 mL, 5.63 mmol). The resulting mixture was stirred at room temperature for 20 minutes, diluted with water (2.0 mL) and purified by preparative HPLC to afford T534 as TFA salt (0.004 g, 12.88%). $^{1}$H NMR (400 MHz, $CD_3CN$) δ 7.81-7.79 (m, 1H), 7.67-7.65 (m, 1H), 7.52-7.48 (m, 4H), 6.66-6.64 (m, 2H), 4.95-4.93 (m, 1H), 4.83-4.478 (m, 2H), 4.74-4.73 (m, 1H), 2.82 (s, 3H); MS (ESI): 294.1 ($M+H^+$).

Preparation of

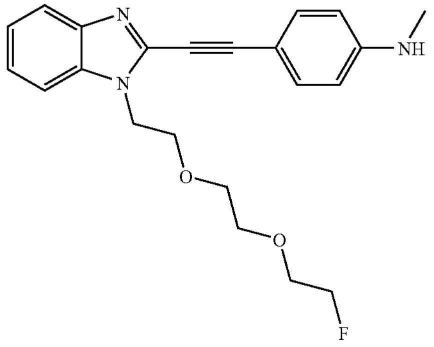 [SMILES: CNc1ccc(C#Cc2nc3ccccc3n2CCOCCOCCF)cc1]

T541 was prepared using general procedure B from 2-bromo-1-(2-(2-(2-fluoroethoxy)ethoxy)ethyl)-1H-benzo[d]imidazole and tert-butyl methyl-4-(ethynyl)phenylcarbamate. Reaction was performed on a 72 mgs scale of 2-bromo-1-(2-(2-(2-fluoroethoxy)ethoxy)ethyl)-1H-benzo[d]imidazole. The crude product was purified by ISCO column to afford tert-butyl 4-((1-(2-(2-(2-fluoroethoxy)ethoxy)ethyl)-1H-benzo[d]imidazol-2-yl)ethynyl)phenyl(methyl)carbamate (0.02 g, 19.21%). It was then dissolved in acetonitrile (1.0 mL). To this solution was added 20% Sulfuric acid (1.0 mL, 3.75 mmol). The reaction mixture was stirred at room temperature for 30 mins. The crude product was purified by prep HPLC to afford T541 TFA salt (0.004 g, 19.44%). $^{1}$H NMR (400 MHz, $CD_3CN$) δ 7.78-7.76 (m, 1H), 7.70-7.68 (m, 1H), 7.51-7.45 (m, 4H), 6.66-6.64 (m, 2H), 4.63-4.60 (m, 2H), 4.44-4.42 (m, 1H), 4.32-4.30 (m, 1H), 3.95-3.92 (m, 2H), 3.57-3.53 (m, 3H), 3.48-3.45 (m, 3H), 2.82 (m, 3H). MS (ESI): 382.1 ($M+H^+$).

Preparation of

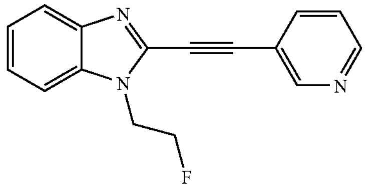 [SMILES: FCCn1c(C#Cc2cccnc2)nc2ccccc21]

T551 was prepared using general procedure B from 2-ethynyl-1-(2-fluoroethyl)-1H-benzo[d]imidazole and 3-bromopyridine. Reaction was performed on a 40 mgs scale of 2-ethynyl-1-(2-fluoroethyl)-1H-benzo[d]imidazole. The crude product was purified by prep HPLC to afford T551 TFA salt (0.006 g, 7.44%). NMR (400 MHz, $CD_3CN$): δ 8.92-8.91 (m, 1H), 8.70-8.69 (m, 1H), 8.14-8.11 (m, 1H), 7.79-7.77 (m, 1H), 7.64-7.62 (m, 1H), 7.55-7.40 (m, 3H), 4.94-4.92 (m, 1H), 4.82-4.80 (m, 2H), 4.76-4.73 (m, 1H); MS (ESI): 266.1 ($M+H^+$).

Preparation of

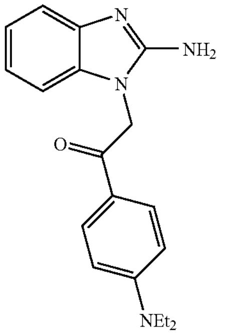

2-(2-amino-1H-benzo[d]imidazol-1-yl)-1-(4-(diethylamino)phenyl)ethanone: A solution of 2-aminobenzimidazole (197 mg, 1.5 mmol) and 2-Bromo-4'-(diethylamino)acetophenone (402 mg, 1.5 mmol) in MeOH (7 mL) was stirred at r.t. for 18 hours. The volatiles were removed in vacuo and $NaHCO_3$ (sat. aq., 30 mL) was added. The aqueous mixture was extracted with EtOAc (3×30 mL). The combined EtOAc extracts were dried with $MgSO_4$ and concentrated in vacuo. The residue was purified on silica gel eluting with a gradient up to 5:95 (MeOH:DCM) to isolate 2-(2-amino-1H-benzo[d]imidazol-1-yl)-1-(4-(diethylamino)phenyl)ethanone (176 mg, 36%) as a beige solid.

Preparation of

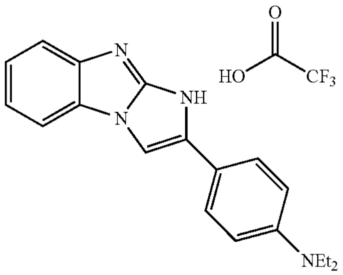

4-(1H-benzo[d]imidazo[1,2-a]imidazol-2-yl)-N,N-diethylaniline trifluoroacetate T506: A solution of 2-(2-amino-1H-benzo[d]imidazol-1-yl)-1-(4-(diethylamino)phenyl) ethanone (50 mg, 0.155 mmol) was heated to reflux in AcOH (2 mL) for several hours. The volatiles were removed in vacuo. The residue was dissolved in ACN and purified by semi-prep HPLC to isolate T506 (15 mg, 24%) as a beige solid. $^1H$ NMR (400 MHz, $CD_3OD$): δ 1.19 (t, 6H), 3.48 (q, 4H), 6.92 (m, 2H), 7.42-7.51 (m, 2H), 7.62 (m, 3H), 7.91 (m, 1H), 8.06 (s, 1H); MS (ESI): 305.1 ($M+H^+$).

Preparation of

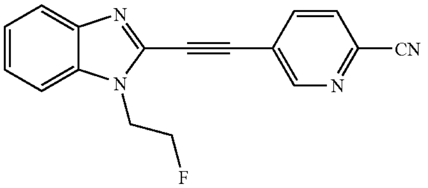 [SMILES: N#Cc1ccc(C#Cc2nc3ccccc3n2CCF)cn1]

T552 was prepared using general procedure B. Reaction was performed on a 40 mgs scale. The crude product was purified by prep HPLC to afford T552 TFA salt (0.006 g, 6.98%). $^1H$ NMR (400 MHz, $CD_3CN$) δ 9.08-9.07 (m, 1H), 8.42-8.40 (m, 1H), 8.19-8.16 (m, 1H), 7.71-7.67 (m, 2H), 7.40-7.29 (m, 2H), 4.86 (m, 2H), 4.79-4.74 (m, 2H); MS (ESI): 291.0 ($M+H^+$).

Preparation of

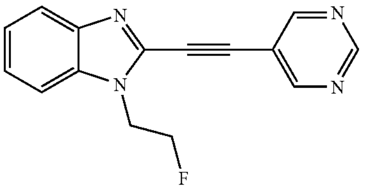 [SMILES: FCCn1c(C#Cc2cncnc2)nc2ccccc21]

T553 was prepared using general procedure B. Reaction was performed on a 40 mgs scale. The crude product was purified by prep HPLC to afford T553 TFA salt (0.006 g, 7.42%). $^1H$ NMR (400 MHz, $CD_3CN$) δ 9.23 (s, 1H), 9.05 (s, 2H), 7.82-7.79 (m, 1H), 7.67-7.65 (m, 1H), 7.52-7.43 (m, 2H), 4.94-4.92 (m, 1H), 4.84-4.80 (m, 2H), 4.78-4.75 (m, 1H); MS (ESI): 267.1 ($M+H^+$).

Preparation of

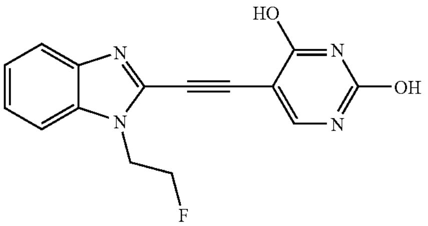 [SMILES: Oc1ncc(C#Cc2nc3ccccc3n2CCF)c(O)n1]

T554 was prepared using general procedure B. Reaction was performed on a 40 mgs scale. The crude product was purified by prep HPLC to afford T554 TFA salt (0.006 g, 6.85%). $^1H$ NMR (400 MHz, DMSO-$d_6$) δ 11.63-11.61 (m, 1H), 11.56 (s, 1H), 8.17-8.16 (m, 1H), 7.64-7.59 (m, 2H), 7.33-7.23 (m, 2H), 4.84-4.83 (m, 1H), 4.76-4.68 (m, 3H); MS (ESI): 299.6 ($M+H^+$).

Preparation of

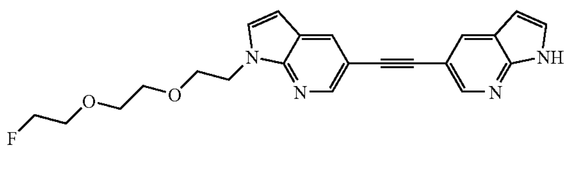 [SMILES: FCCOCCOCCn1ccc2cc(C#Cc3cnc4[nH]ccc4c3)cnc21]

T564 was prepared using general procedure B from 5-bromo-1-(2-(2-(2-fluoroethoxy)ethoxy)ethyl)-1H-pyrrolo[2,3-b]pyridine and tert-butyl 5-ethynyl-1H-pyrrolo[2,3-b]pyridine-1-carboxylate, followed by a hydrolysis with NaOH. The reaction was performed on a 85 mg scale of 5-bromo-1-(2-(2-(2-fluoroethoxy)ethoxy)ethyl)-1H-pyrrolo[2,3-b]pyridine. T564 TFA salt was isolated (0.007 g, 5.40%). $^1$H NMR (400 MHz, $CD_3CN$) δ 11.53 (s, 1H), 8.50-8.49 (m, 2H), 8.41-8.4 (m, 2H), 8.17 (m, 2H), 7.59-7.58 (m, 1H), 7.53-7.52 (m, 1H), 6.69-6.68 (m, 1H), 6.54-6.53 (m, 1H), 4.53-4.51 (m, 1H), 4.48-4.46 (m, 2H), 4.41-4.39 (m, 1H), 3.86-3.84 (m, 2H), 3.64-3.62 (m, 1H), 3.59-3.53 (m, 5H); MS (ESI): 393.5 ($M+H^+$).

Preparation of

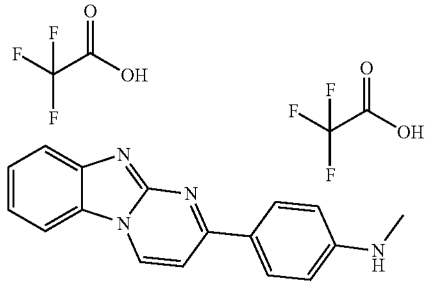

4-(Benzo[4,5]imidazo[1,2-a]pyrimidin-2-yl)-N-methylaniline bistrifluoroacetate T522: To a suspension of 4-(benzo[4,5]imidazo[1,2-a]pyrimin-2-yl)-aniline (25 mg, 0.10 mmol) in MeOH (3 mL) at r.t. was added paraformaldehyde (110 mg, 3.7 mmol) followed by $NaCNBH_3$ (40 mg, 0.63 mmol). The mixture was heated in a microwave reactor at 100° C. for 20 minutes. The volatiles were removed in vacuo. The residue was dissolved in EtOAc (15 mL), washed with $NaHCO_3$ (2×15 mL), and brine (15 mL). The EtOAc layer was dried with $MgSO_4$, filtered and evaporated to obtain an oil that was purified by semi-prep HPLC. 4-(benzo[4,5]imidazo[1,2-a]pyrimidin-2-yl)-N,N-dimethylaniline bistrifluoroacetate (2.0 mg, 4%) was obtained as an orange solid. $^1$H NMR (400 MHz, $CD_3OD$) δ 3.17 (s, 6H), 6.91 (m, 2H), 7.64 (m, 1H), 7.73-7.80 (m, 2H), 8.07 (d, J=7.6 Hz, 1H), 8.26 (m, 1H), 8.34 (m, 2H), 9.33 (d, J=7.6 Hz, 1H). MS (ESI): 275.1 ($M+H^+$).

Preparation of

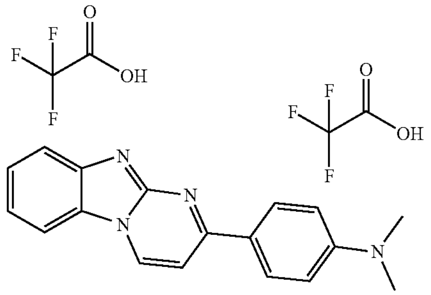

4-(Benzo[4,5]imidazo[1,2-a]pyrimidin-2-yl)-N,N-dimethylaniline bistrifluoroacetate T521 was also obtained from the preceding reaction (1 mg, 2%). $^1$H NMR (400 MHz, $CD_3OD$) δ 2.92 (s, 3H), 6.75 (m, 2H), 7.63 (m, 1H), 7.71-7.79 (m, 2H), 8.02 (d, J=7.6 Hz, 1H), 8.24-8.30 (m, 3H), 9.30 (d, J=7.6 Hz, 1H). MS (ESI): 289.1 ($M+H^+$)

Preparation of

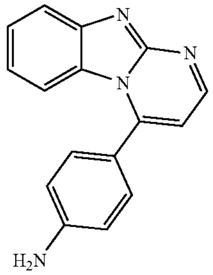 [SMILES: Nc1ccc(-c2ccnc3nc4ccccc4n23)cc1]

4-(Benzo[4,5]imidazo[1,2-a]pyrimidin-4-yl)aniline T520: To a solution of 4-(4-nitrophenyl)benzo[4,5]imidazo[1,2-a]pyrimidine (35 mg, 0.12 mmol) in MeOH:THF:H2O (1:1:3, 2 mL) was added a large excess of $Na_2S_2O_4$. The reaction was quenched with $NaHCO_3$ (sat. aq.) and extracted with EtOAc. The EtOAc layer was washed with $H_2O$ and then brine. The EtOAc layer was dried with MgSO4. The residue was purified by semi-prep HPLC to give T520 as TFA salt (3 mg, 7%). $^1$H NMR (400 MHz, DMSO-$d_6$) δ 6.81 (m, 2H), 7.27 (m, 1H), 7.36 (m, 2H), 7.45 (m, 2H), 7.67 (m, 1H), 7.88 (m, 1H), 9.01 (d, J=4.8 Hz, 1H). MS (ESI): 261.1 ($M+H^+$).

Preparation of

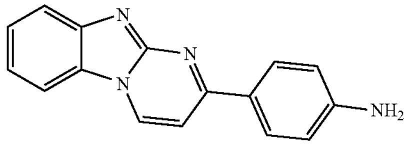 [SMILES: Nc1ccc(-c2ccn3c(n2)nc2ccccc23)cc1]

4-(Benzo[4,5]imidazo[1,2-a]pyrimidin-2-yl)aniline T518: To a suspension of 2-(4-nitrophenyl)benzo[4,5]imidazo[1,2-a]pyrimidine (58 mg, 0.20 mmol) in ethanol (3 mL) was added $SnCl_2.2H_2O$ (361 mg, 1.6 mmol). The solution was refluxed for 1.5 hours and then the volatiles were removed under vacuum. The residue was dissolved in DCM, washed with 1 N NaOH, and then $H_2O$. The DCM layer was dried with $MgSO_4$. The crude product was purified on flash chromatography (silica gel, 5% MeOH/DCM) to provide T518 as a yellow solid (35 mg, 67%). $^1H$ NMR (400 MHz, DMSO-$d_6$) δ 5.94 (s, 2H), 6.70 (m, 2H), 7.34 (m, 1H), 7.47 (m, 1H), 7.61 (d, J=7.6 Hz, 1H), 7.75 (m, 1H), 8.08 (m, 2H), 8.21 (m, 1H), 9.34 (d, J=7.6 Hz, 1H). MS (ESI): 261.1 (M+$H^+$).

Preparation of

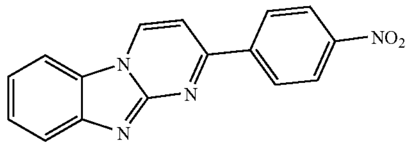 [SMILES: O=[N+]([O-])c1ccc(-c2ccn3c(n2)nc2ccccc23)cc1]

2-(4-Nitrophenyl)benzo[4,5]imidazo[1,2-a]pyrimidine T511: A solution of (E)-3-(dimethylamino)-1-(4-nitrophenyl)prop-2-en-1-one (410 mg, 1.9 mmol) and 1H-benzo[d]imidazol-2-amine (248 mg, 1.9 mmol) in AcOH (10 ml) was heated to reflux overnight. The volatiles were removed by rotary evaporation and the residue was partitioned between DCM and aqueous $NaHCO_3$. The mixture was filtered to obtain pure 2-(4-nitrophenyl)benzo[4,5]imidazo[1,2-a]pyrimidine (85 mg, 15%) as a yellow solid. $^1H$ NMR (400 MHz, DMSO-$d_6$) δ 7.47 (m, 1H), 7.59 (m, 1H), 7.90 (d, J=7.2 Hz, 1H), 7.96 (m, 1H), 8.38 (m, 1H), 8.44 (m, 2H), 8.61 (m, 2H), 9.72 (d, J=7.2 Hz, 1H). MS (ESI): 291.0 (M+$H^+$)

Preparation of

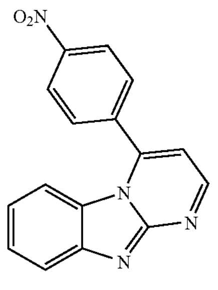 [SMILES: O=[N+]([O-])c1ccc(-c2ccnc3nc4ccccc4n23)cc1]

4-(4-Nitrophenyl)benzo[4,5]imidazo[1,2-a]pyrimidine T512: The DCM layer from the preceding reaction was washed with $H_2O$ and dried ($MgSO_4$). The residue was purified by flash chromatography (silica gel, 100% EtOAc) to give 4-(4-nitrophenyl)benzo[4,5]imidazo[1,2-a]pyrimidine (120 mg, 22%) as a yellow solid. $^1H$ NMR (400 MHz, DMSO-$d_6$) δ 6.65 (m, 1H), 7.09-7.14 (m, 2H), 7.47-7.52 (m, 1H), 7.90 (m, 1H), 8.08 (m, 2H), 8.54 (m, 2H), 8.91 (d, J=4.0 Hz, 1H). MS (ESI): 291.1 (M+$H^+$)

Preparation of

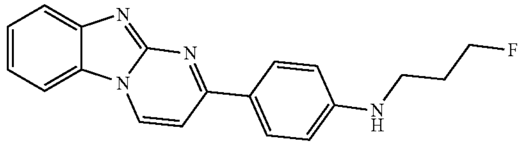 [SMILES: FCCCNc1ccc(-c2ccn3c(n2)nc2ccccc23)cc1]

4-(Benzo[4,5]imidazo[1,2-a]pyrimidin-2-yl)-N-(3-fluoropropyl)aniline T542: To 3-fluoropropan-1-ol (4 mg, 0.05 mmol) in 0.5 mL DCM was added Dess-Martin reagent (42 mg, 0.1 mmol). The mixture was stirred at rt for 1 h and filtered directly into a mixture of 4-(benzo[4,5]imidazo[1,2-a]pyrimidin-2-yl)aniline (4 mg, 0.015 mmol) and NaBH$(OAc)_3$ (43 mg, 0.2 mmol) with stirring. After vigorously stirred for 5 min, reaction was quenched by adding 0.5 M NaOH (2 mL). The mixture was extracted with EtOAc (3×10 mL) and the organic phase was dried over MgSO4 and concentrated. The crude product was purified by HPLC to afford 4-(Benzo[4,5]imidazo[1,2-a]pyrimidin-2-yl)-N-(3-fluoropropyl)aniline as a yellow solid (2.7 mg, 33%). $^1H$ NMR (400 MHz, $CDCl_3$): δ 8.76 (d, J=7.2 Hz, 1H), 7.88 (m, 4H), 7.55 (d, J=7.2 Hz, 1H), 7.53 (m, 1H), 7.40 (m, 1H), 6.47 (d, J=9.2 Hz, 1H), 4.68 (t, J=5.2 Hz, 1H), 4.56 (t, J=5.2 Hz, 1H), 3.34 (t, J=6.8 Hz, 2H), 2.09 (m, 1H), 2.02 (m, 1H); MS (ESI): 321 (M+$H^+$).

Preparation of

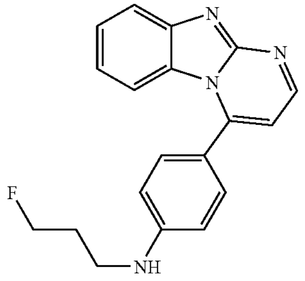 [SMILES: FCCCNc1ccc(-c2ccnc3nc4ccccc4n23)cc1]

4-(Benzo[4,5]imidazo[1,2-a]pyrimidin-4-yl)-N-(3-fluoropropyl)aniline T544 was prepared using the procedure for 4-(Benzo[4,5]imidazo[1,2-a]pyrimidin-2-yl)-N-(3-fluoropropyl)aniline from 4-(benzo[4,5]imidazo[1,2-a]pyrimidin-2-yl)aniline (10 mg, 0.038 mmol) and 3-fluoropropan-1-ol (8 mg, 0.1 mmol). The product T544 was obtained as a yellow solid (7 mg, 33%). $^1H$ NMR (400 MHz, $CDCl_3$): δ 8.93 (d, J=4.4 Hz, 1H), 8.19 (d, J=8.4 Hz, 1H), 7.65 (m, 1H), 7.45 (m, 2H), 7.35 (d, J=8.0 Hz, 1H), 7.29 (m, 1H), 7.17 (d, J=4.4 Hz, 1H), 6.83 (m, 2H), 4.73 (t, J=5.2 Hz, 1H), 4.61 (t, J=5.2 Hz, 1H), 3.47 (t, J=6.8 Hz, 2H), 2.16 (m, 1H), 2.08 (m, 1H); MS (ESI): 321 (M+$H^+$).

Preparation of

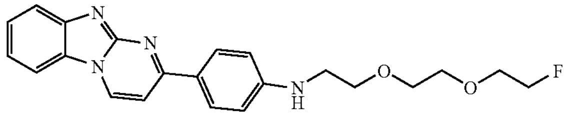 [SMILES: FCCOCCOCCNc1ccc(-c2ccn3c(n2)nc2ccccc23)cc1]

4-(Benzo[4,5]imidazo[1,2-a]pyrimidin-2-yl)-N-(2-(2-(2-fluoroethoxy)ethoxy)ethyl)-aniline T557: 4-(benzo[4,5]imidazo[1,2-a]pyrimidin-2-yl)-N-(2-(2-(2-fluoroethoxy)ethoxy)ethyl)aniline was prepared using the procedure for 4-(Benzo[4,5]imidazo[1,2-a]pyrimidin-2-yl)-N-(3-fluoropropyl)aniline from 4-(benzo[4,5]imidazo[1,2-a]pyrimidin-2-yl)aniline (10 mg, 0.038 mmol) and 2-(2-(2-hydroxyethoxy)ethoxy)ethyl 4-methylbenzenesulfonate (23 mg, 0.075 mmol). The product T557 was obtained as a yellow solid (1.2 mg, 5.1%). $^1$H NMR (400 MHz, $CDCl_3$): δ 9.31 (d, J=7.6 Hz, 1H), 8.25 (m, 2H), 8.02 (d, J=7.2 Hz, 1H), 7.78-7.75 (m, 1H), 7.72 (m, 1H), 7.61 (m, 1H), 6.80 (d, J=9.2 Hz, 2H), 4.56 (m, 1H), 4.45 (m, 1H), 3.75 (m, 1H), 3.71 (t, J=5.2 Hz, 2H), 3.69-3.65 (m, H), 3.47-3.43 (m, H); MS (ESI): 395 ($M+H^+$).

Preparation of

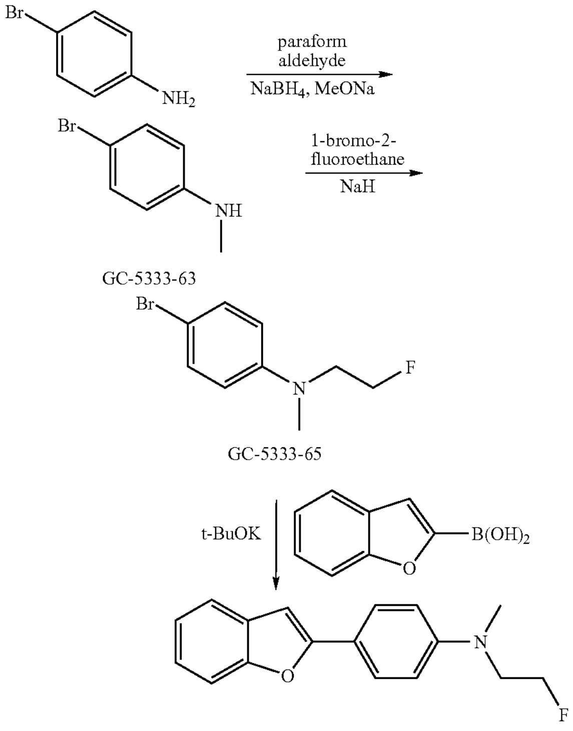

Synthesis of GC-5333-63: 4-Bromoaniline (10 g, 58 mmol) was dissolved in MeOH (20 ml). To the reaction mixture was added paraformaldehyde (5.18 ml, 174 mmol) and 25% sodium methoxide solution (48.3 ml, 291 mmol). The mixture was heated at 65° C. for 1 h and allowed to cool to room temperature. Sodium borohydride (6.17 ml, 174 mmol) was added into the reaction mixture portionwise. The reaction mixture was heated for another 2 h. The mixture was concentrated, diluted with water (50 mL), extracted with EtOAc (3×50 mL). The organic layers were combined, dried and concentrated in vacuo. The residue was purified on flash column chromatography (silica gel, 10% EtOAc/DCM) to afford GC-5333-63 (7.5 g, 69%). $^1$H-NMR (400 MHz, $CDCl_3$): δ 7.27-7.25 (m, 2H), 6.50-6.48 (m, 2H), 3.80. (br, 1H), 2.81 (s, 3H); MS (ESI): 186.1 ($M+H^+$).

GC-5333-65 was prepared using general procedure D. Reaction was performed on a 4 g scale. GC-5333-65 was eluted out in 20% EtOAc: Hexanes mixture in a gradient elution on a Biotage purification system (500 mg, 10%) as a colorless oil. $^1$H-NMR (400 MHz, $CDCl_3$): δ 7.31-7.29 (m, 2H), 6.59-5.58 (m, 2H), 4.59 (dt, J=47.2, 5.2 Hz, 2H), 3.62 (dt, J=24.8, 5.2 Hz, 2H), 2.99 (s, 3H); MS (ESI): 232.1 ($M+H^+$).

T478 was prepared using general procedure A. Reaction was performed on a 30 mg scale. T78 was isolated as a solid (8 mg, 23%). $^1$H-NMR (400 MHz, $CDCl_3$): δ 7.75-7.72 (m, 2H), 7.57-7.52 (m, 2H), 7.24-7.19 (m, 2H), 6.81-6.76 (m, 3H), 4.63 (dt, J=47.2, 5.2 Hz, 2H), 3.70 (dt, J=24.8, 5.2 Hz, 2H), 3.01 (s, 3H); MS (ESI): 270.1 ($M+H^+$).

3. Preparation of Radiolabeling Precursors

Preparation of

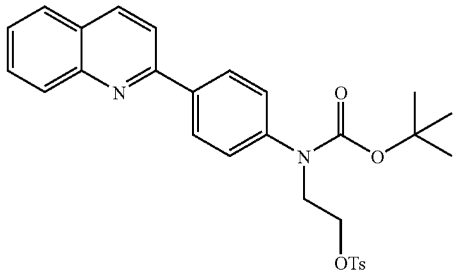 [SMILES: Cc1ccc(S(=O)(=O)OCCN(C(=O)OC(C)(C)C)c2ccc(-c3ccc4ccccc4n3)cc2)cc1]

2-((tert-Butoxycarbonyl)(4-(quinolin-2-yl)phenyl)amino)ethyl-4-methyl-benzene-sulfonate T411P was prepared using general procedure D. Reaction was performed on 0.187 g scale. T411P was isolated as an oil (0.014 g, 6%); $^1$H NMR (400 MHz, $CDCl_3$): δ 8.28-8.19 (m, 2H), 8.09 (dt, J=8.8, 2.4 Hz, 1H), 7.88-7.82 (m, 2H), 7.76-7.70 (m, 3H), 7.54 (ddd, J=8.0, 6.8, 0.8 Hz, 1H), 7.30-7.24 (m, 4H), 4.21 (t, J=5.6 Hz, 2H), 3.90 (t, J=5.6 Hz, 2H), 2.34 (s, 3H), 1.40 (s, 9H); MS (ESI): 519.1 [$M+H^+$], 541.1 ($M+Na^+$).

Preparation of

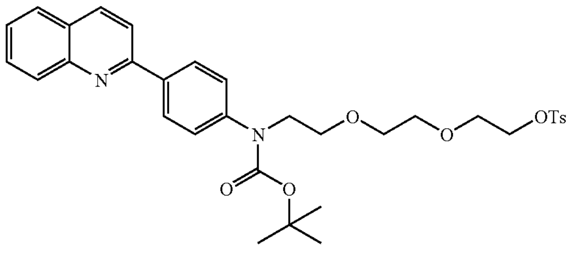 [SMILES: Cc1ccc(S(=O)(=O)OCCOCCOCCN(C(=O)OC(C)(C)C)c2ccc(-c3ccc4ccccc4n3)cc2)cc1]

2,2-Dimethyl-4-oxo-5-(4-(quinolin-2-yl)phenyl)3,8,11-trioxa-azamidecan-13-yl-4-methylbenzenesulfonate T442P was prepared using general procedure D.

Reaction performed on a 0.032 g scale. T442P was isolated as a light yellow oil (0.028 g, 46%); NMR (400 MHz, $CDCl_3$): δ 8.21 (d, J=8.4 Hz, 2H), 8.11 (d, J=8.8 Hz, 2H), 7.86 (d, J=8.8 Hz, 1H), 7.82 (d, J=8.0 Hz, 1H), 7.75 (dt, J=8.0, 2.0 Hz, 2H), 7.70 (d, J=6.8 Hz, 1H), 7.52 (t, J=8.0 Hz, 1H), 7.38 (d, J=8.4 Hz, 1H), 7.27 (d, J=8.0 Hz, 1H), 4.12 (t, J=4.8 Hz, 2H), 3.83 (t, J=4.8 Hz, 2H), 3.64-3.59 (m, 4H), 3.52 (s, 4H), 2.38 (s, 3H), 1.43 (s, 9H); MS (ESI): 607.2 $M+H^+$).

Preparation of

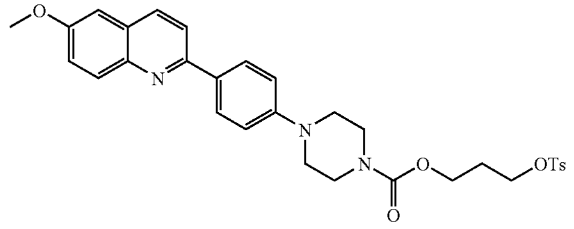 [SMILES: COc1ccc2nc(-c3ccc(N4CCN(C(=O)OCCCOS(=O)(=O)c5ccc(C)cc5)CC4)cc3)ccc2c1]

3-(Tosyloxy)propyl-4-(4-(6-methoxyquinolin-2-yl)phenyl)piperazine-1-carboxylate T498P was prepared using General experimental procedure E for N-alkylation using $Cs_2CO_3$ as the base (method E) was used. Reaction performed on a 0.032 g scale. Product eluted out in 20% EtOAc:DCM mixture in a gradient elution on a Combiflash purification system. T498P was isolated as a light yellow color solid (0.010 g, 18%). $^1$H NMR (400 MHz, $CDCl_3$): δ 8.06 (br t, J=8.8 Hz, 4H), 7.79 (dt, J=8.4 and 1.6 Hz, 2H), 7.77 (d, J=8.4 Hz, 1H), 7.36-7.32 (m, 3H), 7.06 (d, J=2.4 Hz, 1H), 7.00 (dt, J=8.8 and 1.6 Hz, 2H), 4.14 (q, J=7.2 Hz, 4H), 3.93 (s, 3H), 3.60 (br s, 4H), 3.22 (br s, 4H), 2.43 (s, 3H), 2.01 (q, J=8.0 Hz, 2H); LC-MS (ESI): $(M+H^+)$.

Preparation of

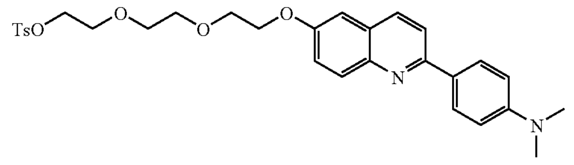 [SMILES: Cc1ccc(S(=O)(=O)OCCOCCOCCOc2ccc3nc(-c4ccc(N(C)C)cc4)ccc3c2)cc1]

2-(2-(2-((2-(4-(Dimethylamino)phenyl)quinolin-6-yl)oxy)ethoxy)ethoxy)ethyl-4-methylbenzenesulfonate T510P was prepared using general procedure E. Reaction performed on a 0.050 g scale. T510P was isolated as yellow solid (0.030 g, 29%). $^1$H NMR (400 MHz, $CDCl_3$): δ 8.05 (dt, J=8.0, 2.0 Hz, 2H), 7.98 (d, J=8.8 Hz, 2H), 7.77 (dt, J=8.8, 2.0 Hz, 2H), 7.76 (d, J=8.8 Hz, 1H), 7.33 (dd, J=9.2, 2.8 Hz, 1H), 7.28 (dd, J=8.4, 0.4 Hz, 2H), 7.04 (d, J=2.8 Hz, 1H), 6.81 (dt, J=8.8, 2.0 Hz), 4.21 (t, J=4.8 Hz, 2H), 4.15 (t, J=4.8 Hz, 2H), 3.88 (t, J=4.8 Hz, 2H), 3.70-3.66 (m, 3H), 3.63-3.60 (m, 3H), 3.01 (s, 3H), 3.39 (s, 6H); MS (ESI): 551.2 $(M+H^+)$, 324 $(M+Na^+)$.

Preparation of

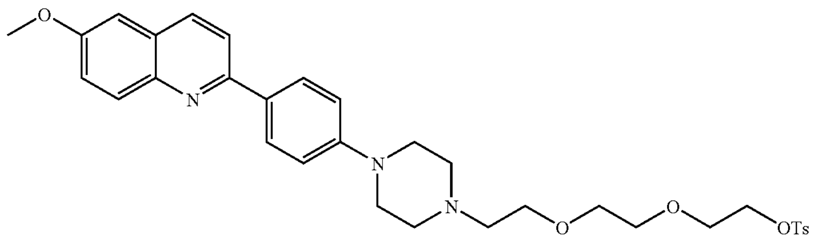 [SMILES: COc1ccc2nc(-c3ccc(N4CCN(CCOCCOCCOS(=O)(=O)c5ccc(C)cc5)CC4)cc3)ccc2c1]

2-(4-(4-(2-(6-Methoxyquinolin-2-yl)phenyl)piperazin-1-yl)ethoxy)ethoxy)ethyl-4-methylbenzenesulfonate T530P was prepared using general procedure E. Reaction was performed on a 0.1 g scale. T530P was isolated as off white oil (0.046 g, 24%). $^1$H NMR (400 MHz, $CDCl_3$): δ 7.99 (dt, J=8.8, 2.0 Hz, 2H), 8.01 (d, J=8.4 Hz, 1H), 7.97 (d, J=9.2 Hz, 1H), 7.73 (dt, J=8.4, 2.0 Hz, 1H), 7.71 (d, J=9.2 Hz, 1H), 7.29-7.25 (m, 2H), 6.99 (d, J=2.8 Hz, 1H), 6.95 (dt, J=8.8, 2.0 Hz, 2H), 4.09 (t, J=4.8 Hz, 2H), 3.86 (s, 3H), 3.64 (t, J=4.8 Hz, 2H), 3.61-3.52 (m, 6H), 3.25 (t, J=4.8 Hz, 4H), 2.64-2.60 (m, 6H); MS (ESI): 606.1 $(M+H^+)$.

Preparation of

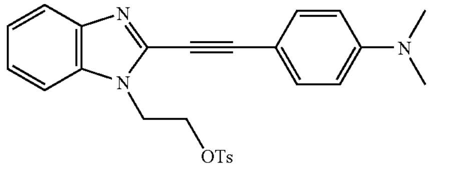 [SMILES: Cc1ccc(S(=O)(=O)OCCn2c(C#Cc3ccc(N(C)C)cc3)nc3ccccc32)cc1]

2-(2-((4-(Mimethylamino)phenyl)ethynyl)-1H-benzo imidazol-1-yl)ethyl-4-methylbenzenesulfonate: T482P was prepared using general procedure E. Reaction was performed on a 140 mg scale of T481. T482P was isolated as a white solid (135 mg, 55%). $^1$H NMR (400 MHz, $CDCl_3$): δ 7.67 (m, 1H), 7.44-7.48 (m, 4H), 7.25-7.27 (m, 3H), 7.05 (d, J=8.4 Hz, 2H), 6.68 (m, 2H), 4.57 (t, J=5.6 Hz, 2H), 4.43 (t, J=5.6 Hz, 2H), 3.04 (s, 6H), 2.33 (s, 3H); MS (ESI): 460 $(M+H^+)$.

Preparation of

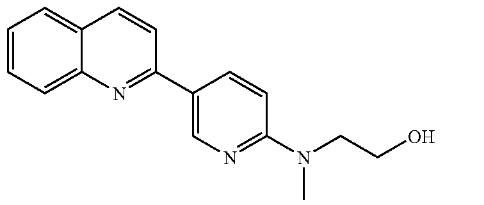 [SMILES: CN(CCO)c1ccc(-c2ccc3ccccc3n2)cn1]

2-(Methyl(5-(quinolin-2-yl)pyridin-2-yl)amino)ethanol: T491 was prepared using general procedure M. Reaction was performed on a 110 mg scale of T455. T491 was isolated as a light yellow solid (120 mg, 88%). $^1$H NMR (400 MHz, $CDCl_3$): δ 8.86 (dd, J=2.4, 0.8 Hz, 1H), 8.41 (dd, J=8.8, 2.4 Hz, 1H), 8.15 (d, J=8.4 Hz, 1H), 8.09 (dd, J=8.4, 0.8 Hz, 1H), 7.78 (m, 2H), 7.69 (m, 1H), 7.48 (m, 1H), 6.69 (dd, J=8.8, 0.8 Hz, 1H), 4.92 (br s, 1H), 3.90 (t, J=4.6 Hz, 2H), 3.81 (t, J=4.6 Hz, 2H), 3.15 (s, 3H); MS (ESI): 280 ($M+H^+$).

Preparation of

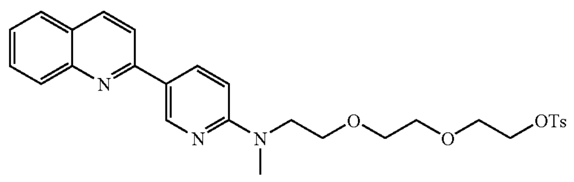 [SMILES: Cc1ccc(S(=O)(=O)OCCOCCOCCN(C)c2ccc(-c3ccc4ccccc4n3)cn2)cc1]

2-(2-(2-(Methyl(5-(quinolin-2-yl)pyridin-2-yl)amino)ethoxy)ethoxy)ethyl 4-methylbenzenesulfonate: T502P was prepared using general procedure D. Reaction was performed on a 94 mg scale of T491. T502P was isolated as light yellow oil (86 mg, 49%). $^1$H NMR (400 MHz, $CDCl_3$): δ 8.92 (dd, J=2.4, 0.8 Hz, 1H), 8.37 (dd, J=8.8, 2.4 Hz, 1H), 8.15 (d, J=8.8 Hz, 1H), 8.09 (dd, J=8.4, 1.0 Hz, 1H), 7.80 (m, 2H), 7.69 (m, 1H), 7.48 (m, 1H), 6.65 (dd, J=8.4, 0.8 Hz, 1H), 4.15 (m, 2H), 3.84 (t, J=6.2 Hz, 2H), 3.66-3.72 (m, 4H), 3.57 (t, J=1.4 Hz, 2H), 3.17 (s, 3H), 2.42 (s, 3H); MS (ESI): 522 ($M+H^+$).

Preparation of

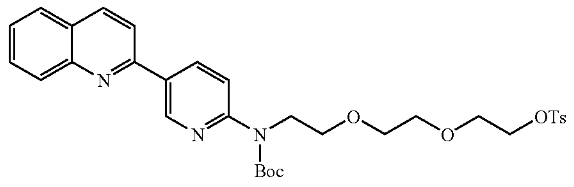 [SMILES: Cc1ccc(S(=O)(=O)OCCOCCOCCN(C(=O)OC(C)(C)C)c2ccc(-c3ccc4ccccc4n3)cn2)cc1]

2,2-Dimethyl-4-oxo-5-(5-(quinolin-2-yl)pyridin-2-yl)-3,8,11-trioxa-5-azamidecan-13-yl 4-methylbenzenesulfonate: T525P was prepared using general procedure D. Reaction was performed on a 67.0 mg scale of T503. T525P was isolated as colorless oil (80.5 mg, 65%). $^1$H NMR (400 MHz, $CDCl_3$): δ 9.10 (dd, J=2.8, 0.8 Hz, 1H), 8.44 (dd, J=4.6, 2.6 Hz, 1H), 8.22 (d, J=8.4 Hz, 1H), 8.14 (d, J=8.4 Hz, 1H), 7.71-7.86 (m, 6H), 7.54 (m, 1H), 7.29 (m, 2H), 4.22 (t, J=6.4 Hz, 2H), 4.10 (m, 2H), 3.70 (t, J=6.4 Hz, 2H), 3.61 (m, 2H), 3.53 (m, 2H), 3.49 (m, 2H), 2.40 (s, 3H); MS (ESI): 608 ($M+H^+$).

Preparation of

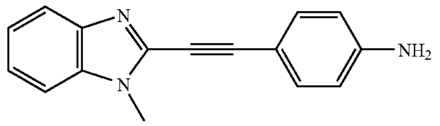 [SMILES: Cn1c(C#Cc2ccc(N)cc2)nc2ccccc21]

4-((1-Methyl-1H-benzo[d]imidazol-2-yl)ethynyl)aniline: CL-5311-144 Intermediate for T540P was prepared using general procedure E. Reaction was performed on a 277 mg scale of T464. CL-5311-144 was isolated as a light yellow solid (140 mg, 48%). $^1$H NMR (400 MHz, $CD_3OD$): δ 7.58 (m, 1H), 7.47 (m, 1H), 7.09-7.38 (m, 4H), 6.66 (m, 2H), 3.91 (s, 3H); MS (ESI): 248

Preparation of

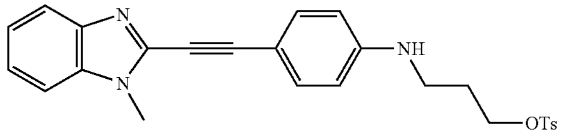 [SMILES: Cc1ccc(S(=O)(=O)OCCCNc2ccc(C#Cc3nc4ccccc4n3C)cc2)cc1]

3-(4-((1-Methyl-1H-benzo[d]imidazol-2-yl)ethynyl)phenylamino)propyl 4-methylbenzenesulfonate: T540P was prepared using general procedure Q. Reaction was performed on an 80.0 mg scale of CL-5311-144. T540P was isolated as a light yellow solid (83.0 mg, 56%). $^1$H NMR (400 MHz, $CD_2Cl_2$): δ 7.77 (m, 2H), 7.68 (m, 1H), 7.44 (m, 2H), 7.24-7.38 (m, 5H), 6.53 (m, 2H), 4.14 (t, J=6.0 Hz, 2H), 4.09 (br t, J=6.0 Hz, 2H), 3.89 (s, 3H), 3.24 (m, 2H), 2.44 (s, 3H), 1.95 (m, 2H); MS (ESI): 460 ($M+H^+$).

Preparation of

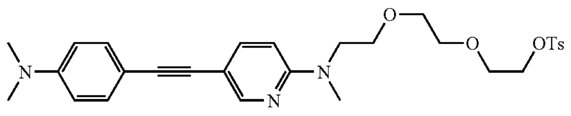 [SMILES: Cc1ccc(S(=O)(=O)OCCOCCOCCN(C)c2ccc(C#Cc3ccc(N(C)C)cc3)cn2)cc1]

2-(2-(2-((5-((4-(Dimethylamino)phenyl)ethynyl)pyridin-2-yl)(methyl)amino)ethoxy)ethoxy)ethyl 4-methylbenzenesulfonate: T546P was prepared using general D. Reaction was performed on a 35 mg scale of T526. T546P was isolated as a colorless gum (30.2 mg, 47%). $^1$H NMR (400 MHz, $CDCl_3$): δ 8.26 (dd, J=2.4, 0.8 Hz, 1H), 7.78 (m, 2H), 7.50 (dd, J=8.8, 2.4 Hz, 1H), 7.35 (m, 2H), 7.31 (m, 2H), 6.64 (m, 2H), 6.44 (d, J=8.8 Hz, 1H), 4.12 (t, J=4.8 Hz, 2H), 3.74 (t, J=5.6 Hz, 2H), 3.61-3.64 (m, 4H), 3.52-3.53 (m, 4H), 3.07 (s, 3H), 2.96 (s, 6H), 2.42 (s, 3H); MS (ESI): 538 ($M+H^+$).

Preparation of

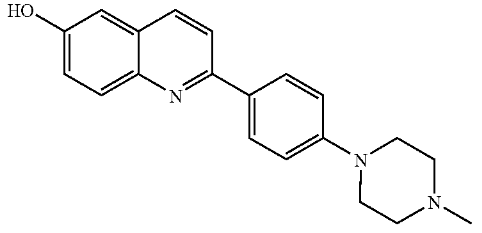 [SMILES: CN1CCN(c2ccc(-c3ccc4cc(O)ccc4n3)cc2)CC1]

2-(4-(4-Methylpiperazin-1-yl)phenyl)quinolin-6-ol: CL-5311-146 Intermediate for T550P was prepared using general procedure A. Reaction was performed on a 208 mg scale of 2-chloroquinolin-6-ol. CL-5311-146 was isolated as a grey solid (214 mg, 58%). $^1$H NMR (400 Hz, DMSO-$d_6$): δ 9.88 (s, 1H), 8.10 (d, J=8.8 Hz, 1H), 8.06 (m, 2H), 7.89 (d, J=8.8 Hz, 1H), 7.81 (d, J=9.2 Hz, 1H), 7.25 (dd, J=9.2, 2.8 Hz, 1H), 7.09 (d, J=2.8 Hz, 1H), 7.02 (m, 2H), 3.22 (br, 4H), 2.45 (br s, 4H), 2.22 (s, 3H); MS (ESI): 320 (M+H$^+$).

Preparation of

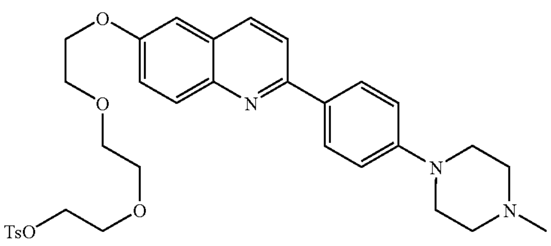 [SMILES: Cc1ccc(S(=O)(=O)OCCOCCOCCOc2ccc3nc(-c4ccc(N5CCN(C)CC5)cc4)ccc3c2)cc1]

2-(2-(2-(2-(4-(4-Methylpiperazin-1-yl)phenyl)quinolin-6-yloxy)ethoxy)-ethoxy)ethyl 4-methylbenzenesulfonate: T550P was prepared using general procedure C. Reaction was performed on a 101 mg scale of CL-5311-146. T550P was isolated as a white solid (90.0 mg, 47%). $^1$H NMR (400 MHz, $CDCl_3$): δ 7.97-8.08 (m, 4H), 7.75-7.79 (m, 3H), 7.35 (dd, J=9.2, 2.8 Hz, 1H), 7.29 (m, 2H), 7.06 (d, J=2.8 Hz, 1H), 7.02 (m, 2H), 4.24 (t, J=4.6 Hz, 2H), 4.15 (t, J=4.8 Hz, 2H), 3.89 (t, J=4.8 Hz, 2H), 3.67-3.70 (m, 4H), 3.61-3.64 (m, 2H), 3.35 (br s, 4H), 2.66 (br s, 4H), 2.40 (s, 3H), 2.39 (s, 3H); MS (ESI): 606 (M+H$^+$).

Preparation of

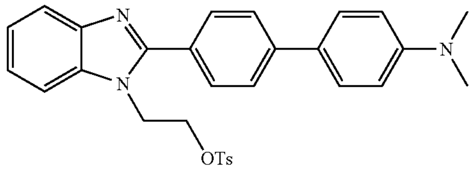 [SMILES: Cc1ccc(S(=O)(=O)OCCn2c(-c3ccc(-c4ccc(N(C)C)cc4)cc3)nc3ccccc32)cc1]

2-(2-(4'-(Dimethylamino)-[1,1'-biphenyl]-4-yl)-1H-benzo[d]imidazol-1-yl)ethyl-4-methylbenzenesulfonate T543P was prepared using general procedure E. Reaction was performed on a 0.082 g scale. T543P was isolated s a yellow solid (0.050 g, 38%). $^1$H NMR (400 MHz, $CDCl_3$): δ 7.78 (d, J=7.6 Hz, 1H), 7.62-7.71 (m, 4H), 7.56 (d, J=8.4 Hz, 2H), 7.39 (d J=8.4 Hz, 2H), 7.22-7.34 (m, 3H), 7.05 (d, J=8.8, Hz, 2H), 6.83 (d, J=8.8, Hz, 2H), 3.02 (s, 6H), 2.32 (s, 3H); MS (ESI): 512 (M+H$^+$).

Preparation of

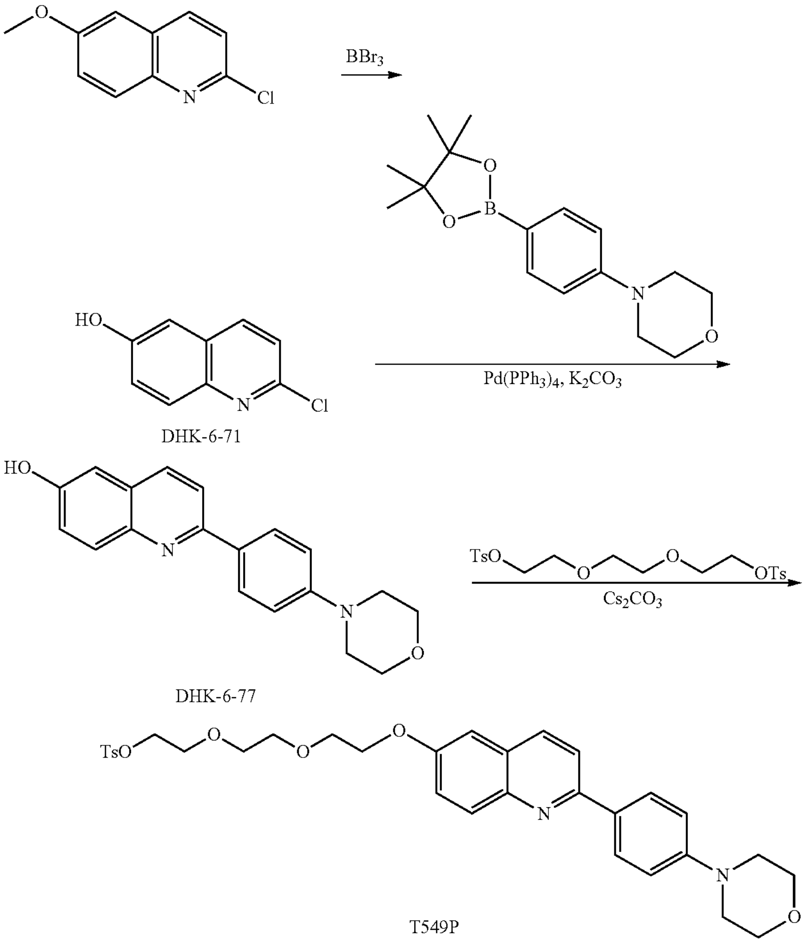

2-chloroquinolin-6-ol: DHK-6-71 was prepared using general procedure G. Reaction was performed on a 2 g scale. DHK-6-71 was isolated as yellow solid (1.72 g, 93%). MS (ESI): 180.0 (M+H$^+$).

2-(4-morpholinophenyl)quinolin-6-ol: DHK-6-77 was prepared using general procedure A. Reaction was performed on a 0.2 g scale. DHK-6-77 was isolated as yellow solid (0.31 g, 91%). MS (ESI): 307.1 (M+H$^+$).

2-(2-(2-((2-(4-morpholinophenyl)quinolin-6-yl)oxy) ethoxy)ethoxy)ethyl 4-methylbenzenesulfonate: T549P was prepared using general procedure C. Reaction was performed on a 0.19 g scale. T549P was isolated as white solid (0.1 g, 27%). $^1$H NMR (400 MHz, $CDCl_3$): δ 8.07 (d, J=8.8 Hz, 2H), 8.03 (d, J=8.8 Hz, 1H), 8.00 (d, J=9.2 Hz, 1H), 7.78 (d, J=8.0 Hz, 3H), 7.35 (dd, J=9.2, 2.8 Hz, 1H), 7.30 (d, J=8.0 Hz, 2H), 7.07 (d, J=3.2 Hz, 1H), 7.01 (d, J=8.8 Hz, 2H), 4.23 (t, J=4.8 Hz, 2H), 4.15 (t, J=4.4 Hz, H), 3.89 (t, J=4.8 Hz, 3H), 3.88 (t, J=4.8 Hz, 3H), 3.71-3.62 (m, 4H), 3.64-3.62 (m, 2H), 3.25 (t, J=4.8 Hz, 4H), 2.40 (s, 3H); MS (ESI): 593.1 (M+H$^+$).

Preparation of

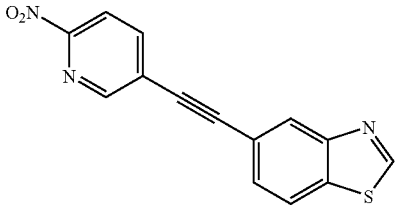 [SMILES: O=[N+]([O-])c1ccc(C#Cc2ccc3scnc3c2)cn1]

5-((6-Nitropyridin-3-yl)ethynyl)benzo[d]thiazole: T114P was prepared using general procedure A. Reaction was performed on a 0.04 g scale. T114P was isolated as yellow solid (0.070 g, 99%). $^1$H NMR (400 MHz, DMSO-$d_6$): δ 9.53 (s, 1H), 8.91 (d, J=1.6 Hz, 1H), 8.46-8.39 (m, 3H), 8.32 (d, J=8.0 Hz, 1H), 7.68 (dd, J=8.4, 1.2 Hz, 1H); MS (ESI): 282.0 (M+H$^+$).

Preparation of

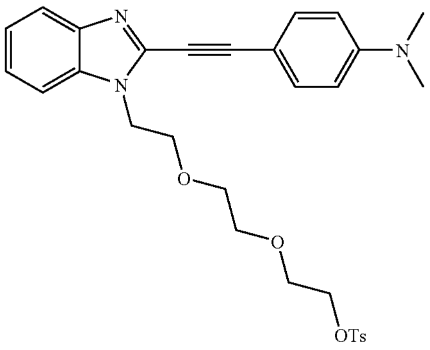 [SMILES: Cc1ccc(S(=O)(=O)OCCOCCOCCn2c(C#Cc3ccc(N(C)C)cc3)nc3ccccc32)cc1]

T508P was prepared using general procedure D. The reaction was performed on a 0.2 g scale. T508P was isolated as a solid (0.18 g, 42.9%). NMR (400 MHz, $CD_3CN$): δ 7.74-7.72 (m, 2H), 7.63-7.61 (m, 1H), 7.51-7.48 (m, 3H), 7.41-7.38 (m, 2H), 7.29-7.24 (m, 2H), 6.77-6.75 (m, 2H), 4.52-4.49 (m, 2H), 3.94-3.92 (m, 2H), 3.86-3.83 (m, 2H), 3.46-3.36 (m, 6H), 3.01 (s, 6H), 2.42 (s, 3H); MS (ESI): 548.1 (M+H$^+$).

Preparation of

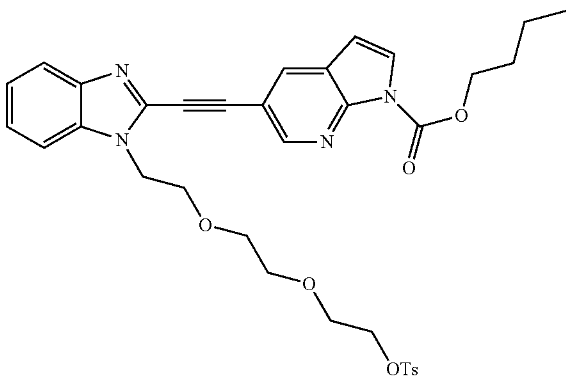 [SMILES: CCCCOC(=O)n1ccc2cc(C#Cc3nc4ccccc4n3CCOCCOCCOS(=O)(=O)c3ccc(C)cc3)cnc21]

T527P was prepared using general procedure D from butyl 5-((1H-benzo[d]imidazol-2-yl)ethynyl)-1H-pyrrolo[2,3-b]pyridine-1-carboxylate and 2,2'-(ethane-1,2-diylbis(oxy))bis(ethane-2,1-diyl)bis(4-methylbenzenesulfonate). The reaction was performed on a 0.21 g scale of butyl 5-((1H-benzo[d]imidazol-2-yl)ethynyl)-1H-pyrrolo[2,3-b]pyridine-1-carboxylate. T527P was isolated as a colorless oil (0.07 g, 18.53%). NMR (400 MHz, $CD_3CN$) δ 8.69 (m, 1H), 8.27-8.26 (m, 1H), 7.88-7.87 (m, 1H), 7.72-7.66 (m, 3H), 7.55-7.53 (m, 1H), 7.38-7.28 (m, 4H), 6.71-6.70 (m, 1H), 4.59-4.56 (m, 2H), 4.48-4.44 (m, 2H), 3.93-3.86 (m, 4H), 3.47-3.45 (m, 2H), 3.41-3.36 (m, 4H), 2.40 (s, 3H), 1.83-1.79 (m, 2H), 1.57-1.51 (m, 2H), 1.02-1.00 (m, 3H); MS (ESI): 645.0 (M+H$^+$).

Preparation of

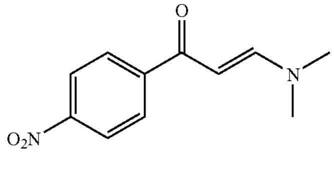 [SMILES: CN(C)/C=C/C(=O)c1ccc([N+](=O)[O-])cc1]

(E)-3-(Dimethylamino)-1-(4-nitrophenyl)prop-2-en-1-one: A solution of 1-(4-nitrophenyl)ethanone (2.2 g, 13 mmol) and N,N-dimethylformamide dimethyl acetal (25 ml) was heated to 120° C. in a sealed tube overnight. The volatiles were removed. The residue was dissolved in DCM and washed twice with $H_2O$. The DCM layer was dried with $MgSO_4$. The crude product was purified by flash chromatography (silica gel, 100% EtOAc) to isolate (E)-3-(dimethylamino)-1-(4-nitrophenyl)prop-2-en-1-one (2.2 g,) as a yellow solid. $^1$H NMR (400 MHz, $CDCl_3$) δ 2.99 (s, 3H), 3.23 (s, 3H), 5.70 (d, J=12.4 Hz, 1H), 7.94 (d, J=12.4 Hz, 1H), 8.03 (m, 2H), 8.26 (m, 2H). MS (ESI): 221 (M+H+)

Preparation of

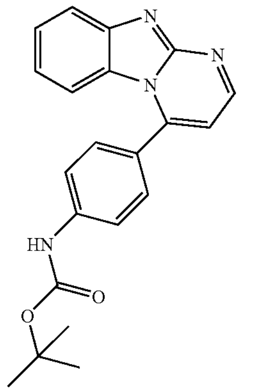 [SMILES: CC(C)(C)OC(=O)Nc1ccc(-c2ccnc3nc4ccccc4n23)cc1]

tert-Butyl(4-(benzo[4,5]imidazo[1,2-a]pyrimidin-4-yl) phenyl)carbamate: A solution of 4-(benzo[4,5]imidazo[1,2-a]pyrimidin-4-yl)aniline (350 mg, 1.3 mmol) in di-tert-butyl dicarbonate (4 mL) was heated in a sealed tube at 120° C. for 15 minutes. The reaction mixture was diluted with DCM and purified directly by flash chromatography (silica gel, 100% EtOAc) to give tert-butyl (4-(benzo[4,5]imidazo[1,2-a]pyrimidin-4-yl)phenyl)carbamate (249 mg, 53%) as an orange solid. $^1$H NMR (400 MHz, $CDCl_3$): δ 1.59 (s, 9H), 6.89 (m, 2H), 6.97 (m, 1H), 7.16 (m, 1H), 7.54-7.58 (m, 3H), 8.11 (m, 1H), 8.88 (d, J=4.4 Hz, 1H). MS (ESI): 361 (M+H+).

Preparation of

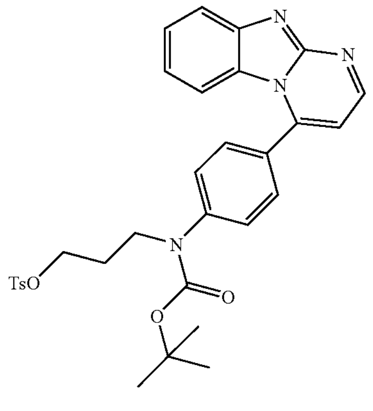 [SMILES: Cc1ccc(S(=O)(=O)OCCCN(C(=O)OC(C)(C)C)c2ccc(-c3ccnc4nc5ccccc5n34)cc2)cc1]

3-((4-(Benzo[4,5]imidazo[1,2-a]pyrimidin-4-yl)phenyl) (tert-butoxycarbonyl)amino)propyl 4-methylbenzenesulfonate T544P The title compound was prepared using general procedure D from 4-(benzo[4,5]imidazo[1,2-a] pyrimidin-4-yl)aniline and propane-1,3-diylbis(4-methylbenzenesulfonate). T554P was isolated as a solid (130 mg, 21%). $^1$H NMR (400 MHz, $CDCl_3$): δ 1.51 (s, 9H), 2.09 (m, 2H), 2.46 (s, 3H), 3.87-3.90 (m, 2H), 4.12-4.15 (m, 2H), 6.94 (m, 1H), 7.04 (bs, 1H), 7.19 (m, 1H), 7.35 (m, 1H), 7.52-7.65 (m, 5H), 7.77-7.79 (m, 2H), 8.18 (m, 1H), 8.97 (d, J=4.4 Hz, 1H). MS (ESI): 573.1 (M+H+).

Preparation of

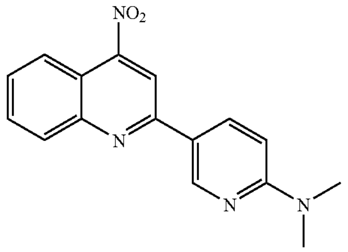

N,N-Dimethyl-5-(4-nitroquinolin-2-yl)pyridin-2-amine T480P was prepared using general procedure A from 2-Bromo-4-nitroquinoline (50 mg, 0.2 mmol) and (6-(dimethylamino)pyridin-3-yl)boronic acid (34 mg, 0.2 mmol). The product was obtained as a yellow solid (40 mg, 68%). $^1$H NMR (400 MHz, $CDCl_3$): δ 8.99 (d, J=2.4 Hz, 1H), 8.36-8.34 (m, 2H), 8.30 (s, 1H), 8.19 (m, 1H), 7.81 (m, 1H), 7.65 (m, 1H), 6.66 (d, J=9.0 Hz, 1H), 3.21 (s, 6H); MS (ESI): 295 (M+H+).

Preparation of

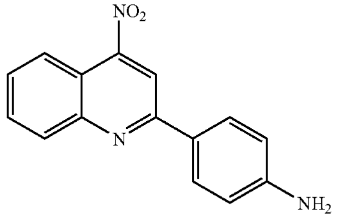

4-(4-Nitroquinolin-2-yl)aniline T492P was prepared by using general procedure A from 2-Bromo-4-nitroquinoline (50 mg, 0.2 mmol) and 4-(4,4,5,5-tetramethyl-1,3,2-dioxaborolan-2-yl)aniline (44 mg, 0.2 mmol). The product was obtained as a dark brown solid (31 mg, 58%). $^1$H NMR (400 MHz, $CDCl_3$): δ 8.36 (m, 1H), 8.32 (s, 1H), 8.20 (m, 1H), 8.06 (m, 2H), 7.80 (m, 1H), 7.65 (m, 1H), 6.81 (m, 2H), 3.99 (br s, 2H); MS (ESI): 266 (M+H+).

Preparation of

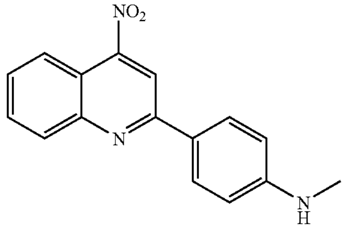 [SMILES: CNc1ccc(-c2cc([N+](=O)[O-])c3ccccc3n2)cc1]

N-Methyl-4-(4-nitroquinolin-2-yl)aniline T466P was prepared using general procedure A from 2-bromo-4-nitroquinoline (50 mg, 0.2 mmol) and N-methyl-4-(4,4,5,5-tetramethyl-1,3,2-dioxaborolan-2-yl)aniline (46 mg, 0.2 mmol). The product T466P was obtained as a brown solid (37 mg, 66%). NMR (400 MHz, $CDCl_3$): δ 8.34 (m, 1H), 8.32 (s, 1H), 8.19 (m, 1H), 8.09 (m, 2H), 7.79 (m, 1H), 7.63 (m, 1H), 6.72 (m, 2H), 2.93 (s, 3H); MS (ESI): 280 ($M+H^+$).

Preparation of

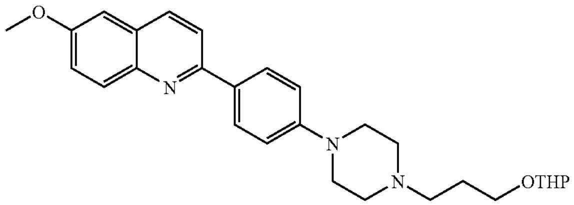

6-Methoxy-2-(4-(4-(3-((tetrahydro-2H-pyran-2-yl)oxy)propyl)piperazin-1-yl)-phenyl)quinoline AS-5332-79 was prepared using general procedure E. Reaction performed on a 0.032 g. AS-5332-79 was isolated as a off white solid (0.025 g, 54%). $^1H$ NMR (400 MHz, $CDCl_3$): δ 8.05 (dt, J=8.8, 2.8 Hz, 2H), 8.00 (d, J=10.4 Hz, 2H), 7.76 (d, J=8.8 Hz, 1H), 7.32 (dd, J=9.2, 2.8 Hz, 1H), 7.04 (d, J=2.8 Hz, 1H), 7.01 (dt, J=9.2, 2.8 Hz, 2H), 4.58 (t, J=4.4 Hz, 1H), 3.92 (s, 3H), 3.86-3.77 (m, 1H), 3.51-3.45 (m, 2H), 3.30 (t, J=4.8 Hz, 4H), 2.63 (t, J=4.8 Hz, 4H), 2.53-2.49 (m, 2H), 1.88-1.80 (m, 4H), 1.73-1.68 (m, 1H), 1.59-1.49 (m, 4H); MS (ESI): 462.4 ($M+H^+$).

Preparation of

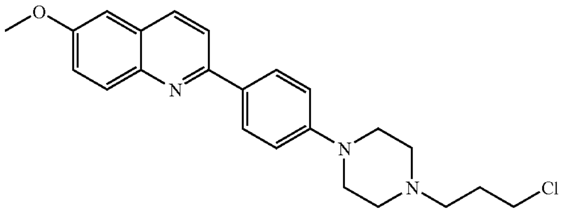 [SMILES: COc1ccc2nc(-c3ccc(N4CCN(CCCCl)CC4)cc3)ccc2c1]

2-(4-(4-(3-Chloropropyl)piperazin-1-yl)phenyl)-6-methoxyquinoline AS-5332-94, T499P (CI) was prepared using general procedure E. Reaction performed on a 0.025 g. T-99P (CI) was isolated as a off white solid (0.010 g, 32%). $^1H$-NMR (400 MHz, $CDCl_3$): δ 8.6-7.99 (m, 4H), 7.77 (d, J=8.8 Hz, 1H), 7.33 (dd, J=9.2, 2.8 Hz, 1H), 7.06-7.00 (m, 3H), 3.92 (s, 3H), 3.66 (t, J=6.4 Hz, 2H), 3.29 (t, J=5.2 Hz, 4H), 2.62 (t, J=4.8 Hz, 4H), 2.55 (t, J=7.6 Hz, 2H), 1.99 (m, 2H); MS (ESI): 396.1 ($M+H^+$).

4. General Procedures for Radiochemistry

Description of Radiolabeling Manufacturing Process and Process Controls

General Process for the Production of [F-18] Fluoride Ion 18F-Radiolabeling:

Aqueous [F-18] Fluoride ion produced in the cyclotron target, is passed through an anion exchange resin cartridge. The [O-18]H20 readily passes through the anion exchange resin while [F-18] fluoride is retained. The [F-18] fluoride is eluted from the column using a solution of potassium carbonate (3 mg) in water (0.4 mL) and is collected in a reaction vessel. Kryptofix® 222 (20 mg) dissolved in acetonitrile (1 mL) is added to the aqueous [F-18] fluoride mixture in the reaction vessel. The Kryptofix sequesters the potassium ions preventing the formation of strong K+/F on-pairs. This increases the chemical reactivity of the [F-18] fluoride ions. The mixture is dried by heating between 70-115° C. under a stream of inert gas and/or reduced pressure (250 mbar) and additional aliquots of acetonitrile may added to insure the fluoride mixture is completely dry. This evaporation step removes the water and converts the [F-18] to an anhydrous form, which is much more reactive than aqueous [F-18] fluoride.

Fluorine-18 [F-18] is produced by proton bombardment of the stable isotope, oxygen-18 (O-18) in water. For bombardment, the chemical form of the enriched O-18 is [O-18]$H_2O$. The [F-18] Fluorine produced is aqueous [F-18] fluoride ion. The target water is loaded into an approximately 1-2 mL target and pressurized to approximately 350 psi. The tantalum target body is outfitted with a high strength, durable metal foil. The foil is an alloy referred to as, "Havar®". The major components of Havar® are cobalt, nickel, chromium, and iron. This thin Havar® foil window permits entry of the protons, yet is sufficiently durable to withstand the pressurized water and proton irradiation. The facility utilizes two Siemens RDS-111 Eclipse cyclotron that produces 11 MeV protons with a 40-60 microamp beam current. Both targets are made of tantalum metal and are used exclusively for the production of F-18. After proton bombardment, the [O-18]$H_2O$ containing the [F-18] fluoride ion is transferred to a shielded enclosure ("hot cell"). The aqueous [F-18] Fluoride is then separated from the [O-18]$H_2O$.

Extraction of [F-18] Fluoride and Conversion to Anhydrous Form

Aqueous [F-18] Fluoride ion produced in the cyclotron target, as described in the preceding Section, is passed through an anion exchange resin cartridge. The [O-18]$H_2O$ readily passes through the anion exchange resin while [F-18] fluoride is retained. The [F-18] fluoride is eluted from the column using a solution of potassium carbonate (3 mg) in water (0.4 mL) and is collected in a reaction vessel. Kryptofix® 222 (20 mg) dissolved in acetonitrile (1 mL) is added to the aqueous [F-18] fluoride mixture in the reaction vessel. The Kryptofix sequesters the potassium ions preventing the formation of strong K+/F ion-pairs. This increases the chemical reactivity of the [F-18] fluoride ions.

The mixture is dried by heating between 70-115° C. under a stream of inert gas and/or reduced pressure (250 mbar) and additional aliquots of acetonitrile may added to insure the fluoride mixture is completely dry. This evaporation step removes the water and converts the [F-18] to an anhydrous form, which is much more reactive than aqueous [F-18] fluoride.

Reaction of Anhydrous [F-18] Fluoride with W366 Precursor

A solution of the nitro precursor, (1 to 20 mg), dissolved in anhydrous DMSO (0.5-2.5 mL) is added to the reaction vessel containing the anhydrous [F-18] Fluoride. The vessel is heated to approximately 150±10° C. for 15±5 minutes to induce displacement of the aromatic nitro leaving group by [F-18] fluoride as illustrated in the scheme below. The reaction mixture is then treated with 2N HCl (1 mL) and refluxed at 105° C. for 10 min.

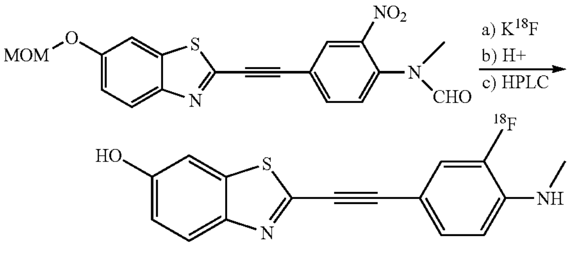

W366

HPLC Purification of [F-18]W366

The reaction mixture containing crude [F-18]W366 is cooled and first passes through an $Al_2O_3$ cartridge followed by a mixture of MeCN (1±0.5 mL) and $H_2O$ (2±1.0 mL). The final solution is then transferred to the HPLC sample loop and is purified via chromatographic separation using a semi-preparative HPLC column (Either ACE C18 Pyramid, 7μ, 250×10 mm, Phenomenex Luna, C18, 5μ, 10×250 mm or Phenomenex Synergi Hydro-RP C18, 250×10 mm, using a gradient system, up to 5.5 mL/min, however lower flow rates may be used if there is a high backpressure, or the system may start at a lower flow rate and then increase to the maximum flow rate). The first column uses a linear gradient starting at 5% MeCN (0.1% formic acid):95% H20 (0.1% formic acid) containing 100 mg/L of ascorbic acid and to a 95:5 mix of the solvents at 30 minutes. The column effluent is monitored using UV (220, 254 or 280 nm) and radiometric detectors connected in series. The purified [F-18]W366 is collected from the column at the retention time window determined for the W366 reference standard which coincides with the time that the radiometric detectors begin showing the main peak. After the product elutes, it is collected, loaded onto the HPLC load loop and purified again. (Either ACE C18 Pyramid, 7μ, 250×10 mm, Phenomenex Luna, C18, 5μ, 10×250 mm or Phenomenex Synergi Hydro-RP C18, 250×10 mm, using a isocratic solvent system suitable to purify W366, such as 40% MeCN: water with 0.1% formic acid and 100 mg/L of ascorbic acid, up to 5.5 mL/min, however lower flow rates may be used if there is a high backpressure, or the system may start at a lower flow rate and then increase to the maximum flow rate).

Formulation, Sterile Filtration and Aseptic Filling of Purified [F-18]W366

The purified [F-18]W366 fraction elutes from the second HPLC purification column, is diluted with water (40 100 mL) containing 5±5 mg/mL of ascorbic acid, and is captured onto a C18 SepPak cartridge. The C18 SepPak cartridge is washed with water (10 mL) containing 5±5 mg/mL ascorbic acid followed by eluting the product with 0.5-0.9 mL of EtOH. The sample is then diluted with sterile water (4.5-9.0 mL of water) containing 25±25 mg/mL of ascorbic acid affording a final formulation of [F-18]W366 in a maximum of 10% EtOH:water. The solution is then processed through a 0.45 μm sterile filter into the preloaded collection vial.

Biological Data

The disclosed compounds compete favorably for binding against 18F-PiB, as shown below. Briefly, 5 micron thick human brain slices from regions of the brain bearing high amyloid plaque and fibril burden were incubated with approximately 20 uCi of a radiolabeled tracer in 2.5%:2.5%: 95% DMSO:EtOH:PBS in the presence of blocker (2.5 and 0.25 uM total concentration) or absence of blocker (control). The slices were incubated at rt for 90 min. The slices were then quickly washed in PBS, followed by 70% EtOH:PBS for 2 min, then 30% EtOH:PBS for 2 min and then quickly washed with PBS. The slices were dried for 30 min and then exposed on autoradiographic film for 20 min. The brain slices were then removed from the slide and the radioactivity counted in a gamma counter. The counts are normalized and the percent blocking is determined in order to determine $IC_{50}$ values. The lower the number, the more effective the compounds displaced the tracer.

Reaction of Anhydrous [F-18] Fluoride with T114 Precursor

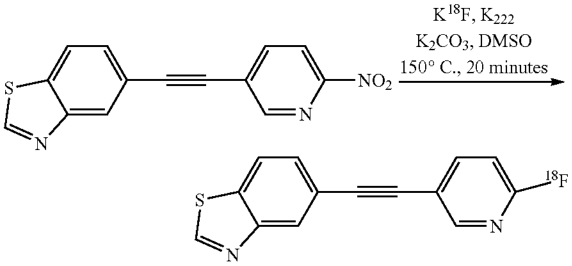

[F-18] Fluoride was prepared using $K_2CO_3$ and Kryptofix-2.2.2 according to the general procedure described above. A solution of T114P (10 mg) dissolved in anhydrous DMSO (1.0 mL) is added to the reaction vessel containing the anhydrous [F-18] Fluoride. The vessel is heated to approximately to 150° C. for 20 minutes. Reaction was loaded to a vial containing water (4 mL) and the resultant solution is then transferred to the HPLC sample loop (5 mL) and purified via chromatographic separation using a semi-preparative HPLC column (Phenomenex Gemini C18, 250×10 mm). This column uses a flow rate of 5 mL/min and an isocratic solvent system of 40% MeCN: 60% $H_2O$ containing 0.85 mL of 12N HCl per 1000 mL of water. The column effluent is monitored using UV (254 nM) and radiometric detectors connected in series. The purified [F-18] T114 is collected from the column at the retention time window determined for the T114 reference standard which coincides with the time that the radiometric detectors begin showing the main peak. The retention time of the [F-18] T114 in this system is approximately 39 minutes.

Formulation of Purified [F-18] T114

The purified [F-18] T114 fraction eluted from the HPLC purification column is diluted with water (50 mL) and filtered thru a C18 SepPak cartridge. The C18 SepPak cartridge is washed with water (10 mL) followed by elution of the product with 0.5 mL of ethyl alcohol. The sample is then diluted with 4.5 mL of water to afford a final formulation of [F-18] T114 in a maximum of 10% ethyl alcohol in water.

General Procedure for [F-18] Labeling of Aliphatic Tosylates

[F-18] Fluoride was prepared using $K_2CO_3$ and Kryptofix-2.2.2 according to the general procedure described above. After cooling, a solution of the tosylate precursor (5 mgs to 20 mgs) in anhydrous DMSO or MeCN (1 mL) was added to the residue of "dry" reactive [F-18] fluoride ion in the reaction vessel of the Explora RN synthesis module and the reaction was heated (80° C. to 110° C.) for 10 to 15 mins. The reaction was cooled to 70° C.

If the precursor contains an acid labile protecting group, 1N HCl (1 mL) was added to the reaction mixture and heated to 100° C. After 5 minutes, the reaction was cooled to room temperature and 2M NaOAc (0.5 mL) was added. The resulting mixture was added to a separate vial containing water (1.5 mL) and loaded to the HPLC sample loop to initiate purification.

If the precursor contains a basic labile protecting group, 1:1 MeOH: 1N NaOH (1 mL) was added to the reaction mixture and heated to 100° C. After 5 minutes, the reaction was added to a separate vial containing water (2 mL) and loaded to the HPLC sample loop to initiate purification.

If the precursor contains no protecting groups, the resulting reaction mixture is added to a separate vial containing water (3 mL) and loaded to the HPLC sample loop to initiate purification.

Purification was performed by semi-preparative HPLC (Phenomenex Gemini C18, 250×10 mm, flow rate 5 mL/min). The elution of the final product is initiated at 5% MeCN (0.05% TFA) in $H_2O$ (0.05% TFA) until the final concentration of MeCN (0.05% TFA) is reached within 15 to 20 minutes. Once the final concentration of the MeCN (0.05% TFA) is reached then the elution is allowed to run isocratic until the [F-18] product is collected. Once collected, the final formulation described above is followed.

TABLE 4
| Radiolabeling results of aliphatic tosylates | | | | | |
|---|---|---|---|---|---|
| Cmpd # Purity | Precursor | [F-18] Product | Yield (mCi) | Radio-chem. | HPLC conditions |
| T114 | 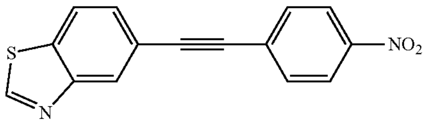 [SMILES: O=[N+]([O-])c1ccc(C#Cc2ccc3scnc3c2)cc1] | 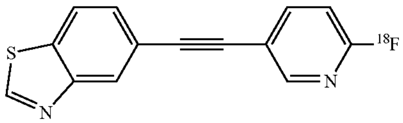 [SMILES: [18F]c1ccc(C#Cc2ccc3scnc3c2)cn1] | 48 | >98% | as described above |
| T442 | 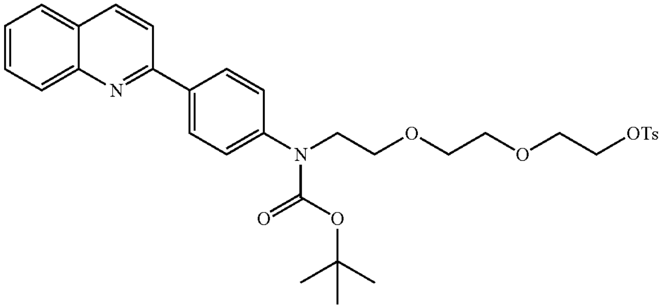 [SMILES: Cc1ccc(S(=O)(=O)OCCOCCOCCN(C(=O)OC(C)(C)C)c2ccc(-c3ccc4ccccc4n3)cc2)cc1] | 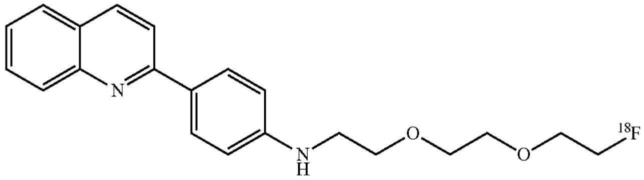 [SMILES: [18F]CCOCCOCCNc1ccc(-c2ccc3ccccc3n2)cc1] | 40 | >98% | Final conc: 25% MeCN (0.05% TFA) in water (0.05% TFA) |
| T482 | 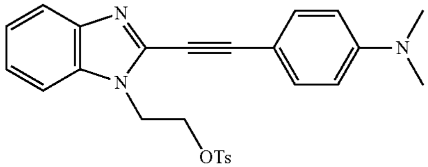 | 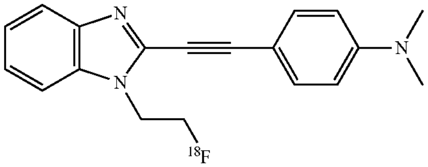 | 28 | >98% | Final conc: 30% MeCN (0.05% TFA) in water (0.05% TFA) |
| T510 | 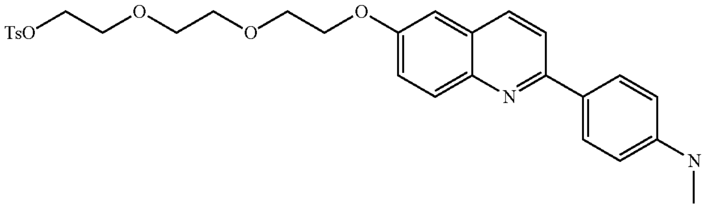 [SMILES: CNc1ccc(-c2ccc3cc(OCCOCCOCCOS(=O)(=O)c4ccc(C)cc4)ccc3n2)cc1] | 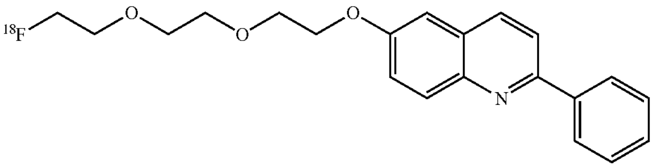 [SMILES: [18F]CCOCCOCCOc1ccc2nc(-c3ccccc3)ccc2c1] | 30 | >98% | Final conc: 30% MeCN (0.05% TFA) in water (0.05% TFA) |

TABLE 4-continued
Radiolabeling results of aliphatic tosylates
| Cmpd # Purity | Precursor | [F-18] Product | Yield (mCi) | Radio-chem. | HPLC conditions |
| --- | --- | --- | --- | --- | --- |
| T525 | 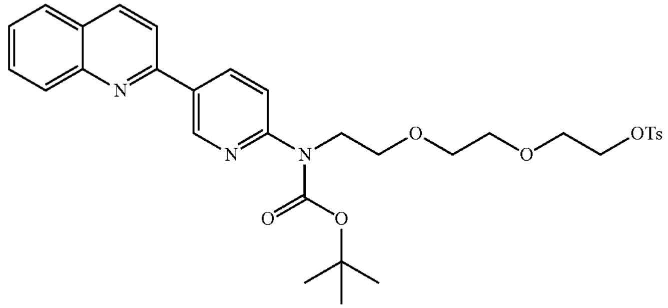 [SMILES: Cc1ccc(S(=O)(=O)OCCOCCOCCN(C(=O)OC(C)(C)C)c2ccc(-c3ccc4ccccc4n3)cn2)cc1] | 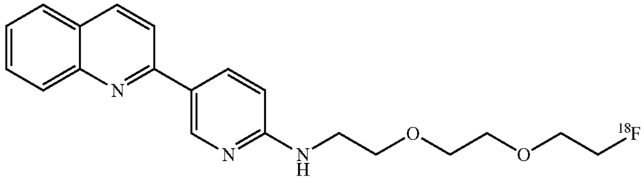 [SMILES: [18F]CCOCCOCCNc1ccc(-c2ccc3ccccc3n2)cn1] | 258 | >98% | Final conc: 20% MeCN (0.05% TFA) in water (0.05% TFA) |
| T527 | 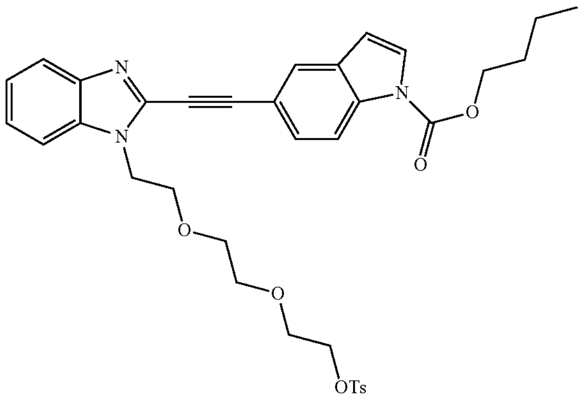 [SMILES: CCCCOC(=O)n1ccc2cc(C#Cc3nc4ccccc4n3CCOCCOCCOS(=O)(=O)c3ccc(C)cc3)ccc21] | 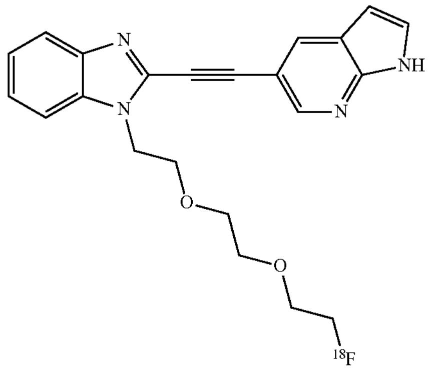 [SMILES: [18F]CCOCCOCCn1c(C#Cc2cnc3[nH]ccc3c2)nc2ccccc21] | 15 | >98% | Final conc: 25% MeCN in water (0.08% HCl) |
| T549 | 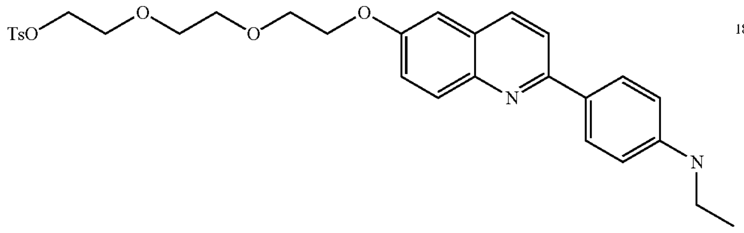 | 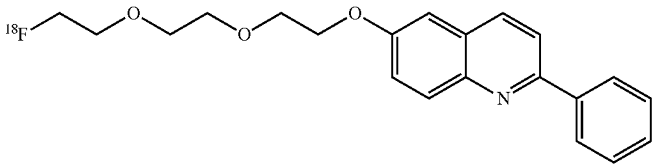 [SMILES: [18F]CCOCCOCCOc1ccc2nc(-c3ccccc3)ccc2c1] | 78 | >98% | Final conc: 25% MeCN (0.05% TFA) in water (0.05% TFA) |

Human AD Brain Section Autoradiography 5 micron thick human AD brain slices were first examined using antibodies for Aβ and Tau to determine whether the tested human brain contains Aβ and Tau. Thus, three types of human brain slices were selected for autoradiography: Aβ3+/Tau+; Aβ+/Tau−; and Aβ−/Tau−(control).

The Experimental Protocol is as Follows:

Pick one brain section for each type and air-dry in hood. A solution of diluted F-18 labeled tracer (40 μCi/mL, 500 μL) which was obtained from the dilution of F-18 tracer with 1×PBS containing 2.5% EtOH and 2.5% DMSO was applied onto each slides to cover the whole tissue section. The resulting slides were incubated at room temperature for 90 minutes, drained, and placed onto a slide holder. The slides were then washed sequentially with 1×PBS for 1 min; 70% EtOH in 1×PBS for 2 min; 30% EtOH in 1×PBS for 2 min; and 1×PBS for 1 min. The slides were dried in the hood for 30 min, and then placed on Fuji imaging plates and exposed overnight. The imaging plates were then scanned and the signal was measured using Fuji software to produce an autoradiography image of the brain section. (PBS—Phosphate Buffer Saline)

Protocol for Synthetic Beta-Amyloid and Tau Kds

Various concentrations solution of F-18 labeled and its parent cold compound in 1×PBS containing 5% Ethanol and 5% DMSO (pH 7.4) were incubated with synthetic beta-Amyloid or synthetic tau at room temperature in glass tubes for 90 min. The reaction mixture in each tube was filtered under vacuum through a microfiber filter. Each tube was washed with a solution of 20% EtOH in PBS. The PBS wash solution was filtered under vacuum through the filters. Each filter was then washed with a solution of 20% EtOH in PBS and then placed into a gamma counter vial for CPM counting. The data obtained was plotted for Kd determination.

Tau Fluorescent Compounds Staining on Human Brain Sections (Double or Triple Labeled with tau and β-Amyloid Immunohistochemistry (IHC))

Serial sections (6 μm thick) from OCT-embedded frozen blocks of front lobe were used for staining (OCT—optimal cutting temperature). After fixation and quenching of autofluorescence, tissue sections were incubated with in 100 μM of tau compound in 50% ethanol PBS for 60 min. Then sections were dipped briefly into water, rinsed in PBS, blocked with 5% normal horse serum in PBS for 1 hour at room temperature. After blocking, the tissue was incubated with tau or β-amyloid primary antibody at 4° C. overnight in a humid chamber. Next day, the sections were washed with PBS and then incubated with secondary antibody for 1 hour. The sections were washed and covered, and they were observed with a Nikon (Tokyo, Japan) Eclipse microscope equipped with violet, blue, and green filters.

Mouse and Rat Brain microPET Imaging

Wild type mice and rats were injected intravenously with the candidate tracers. Mice (weight range 25-45 g) were injected with doses between 180 and 300 μCi in 200 uL of saline solution. Rats (weight range 300-400 g) were injected with doses between 300 and 500 μCi of tracer in 400 μL of saline solution. Anesthesia was induced and maintained with Isoflurane. CT and PET scans were performed with a MM INVEON scanner (SIEMENS™). Acquisition for CT images preceded PET scanning and lasted 5 minutes. Only several minutes after the beginning of the PET acquisition, the radioactive dose was injected into the animal through the tail vein. Images were generated as dynamic scans that typically lasted 30 minutes. The initial image analysis consisted of determining whether there was uptake of the tracer in the brain which would establish its ability to cross the blood-brain barrier. All measurements were performed at the time point of 5 minutes following the injection of the tracer. The degree of uptake in the brain was estimated relative to the uptake of the traces in the region of neck muscles. The ratio between the percentage of injected dose per gram in the brain and that of the muscular neck region was provided as an estimate of brain uptake. Brain images of the representative tracers of formula (I) are shown in FIGS. 17-22.

Having thus descried in detail advantageous embodiments of the present invention, it is to be understood that the invention defined by the above paragraphs is not to be limited to particular details set forth in the above description as many apparent variations thereof are possible without departing from the spirit or scope of the present invention.

What is claimed:

1. A compound of Formula (I):

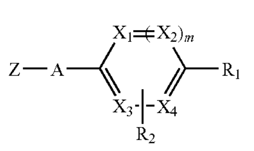

(I)

wherein

A is a bond, $(C_1\text{-}C_4)$alkyl, $(C_3\text{-}C_6)$cycloalkyl, $(C_2\text{-}C_4)$alkene, or $(C_2\text{-}C_4)$alkyne;

Z is:

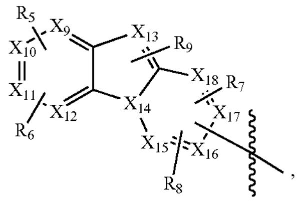

, wherein $X_1$ and $X_{13}$ are each independently C, CH, N, O, or S;

$X_2$-$X_4$, $X_9$-$X_{12}$ and $X_{14}$-$X_{18}$ are each independently C, CH or N;

$R_1$-$R_2$ are each independently H, halogen, hydroxy, nitro, cyano, amino, alkyl, alkoxy, $—(O—CH_2—CH_2)_n—$ (PEG), monoalkylamino, dialkylamino, monoarylamino, diarylamino, $NR_{10}$COOalkyl, $NR_{10}$ COOaryl, $NR_{10}$ COalkyl, $NR_{10}$ CO aryl, COOalkyl, COOaryl, COalkyl, COaryl, aryl, saturated heterocyclyl, wherein the last seventeen groups are unsubstituted or substituted by one or more radicals selected from the group consisting of halogen, alkyl, haloalkyl, cyano, hydroxyl, amino, monoalkylamino, dialkylamino, alkoxy, $R_{10}$, a radiolabel or alkyl substituted with a radiolabel;

$R_5$-$R_9$ are each independently H, halogen, hydroxy, nitro, cyano, amino, alkyl, alkoxy, $—(O—CH_2—CH_2)_n—$, monoalkylamino, dialkylamino, monoarylamino, diarylamino, $NR_{10}$COOalkyl, $NR_{10}$ COOaryl, $NR_{10}$ COalkyl, $NR_{10}$ CO aryl, COOalkyl, COOaryl, COalkyl, COaryl, aryl, heterocyclyl, wherein the last seventeen groups are unsubstituted or substituted by one or more radicals selected from the group consisting of halogen, alkyl, haloalkyl, cyano, hydroxyl, amino, monoalkylamino, dialkylamino, alkoxy, $R_{10}$, a radiolabel or alkyl substituted with a radiolabel;

$R_{10}$ is H, alkyl, alkene, aryl unsubstituted or substituted with halogen, hydroxyl, cyano, nitro, amino, —$OSO_2$alkyl, —$OSO_2$aryl, —OSi(alkyl)$_3$, —OTHP or a radiolabel;

n is 1, 2, or 3;

m is 1, wherein at least one of $R_1$-$R_2$ and $R_5$-$R_9$ comprises a radiolabel selected from the group consisting of $^{11}C$, $^{13}N$, $^{15}O$, $^{18}F$, $^{123}I$, $^{124}I$, $^{125}I$, $^{131}I$, $^{76}Br$ and $^{77}Br$, or a pharmaceutically acceptable salt thereof.

2. The compound of claim 1, wherein the radiolabel is $^{18}F$.

3. The compound of claim 1, wherein A is a bond.

4. The compound of claim 1, wherein at least one of $R_1$-$R_2$ and $R_5$-$R_9$ is —(O—$CH_2$—$CH_2$)$_2$—.

5. The compound of claim 1, wherein at least one of $X_9$-$X_{18}$ is nitrogen.

6. The compound of claim 5, wherein $X_{13}$ is N.

7. The compound of claim 6, wherein $X_1$-$X_4$ are independently C.

8. The compound of claim 7, wherein $X_{14}$ is N.

9. The compound of claim 8, wherein $X_{18}$ is N.

10. The compound of claim 9, wherein $X_9$-$X_{12}$ and $X_{15}$-$X_{17}$ are independently C.

11. The compound of claim 10, wherein $R_5$-$R_9$ are independently H.

12. The compound of claim 1, wherein $R_5$-$R_9$ are independently H.

13. The compound of claim 11, wherein $R_2$ is H.

14. The compound of claim 12, wherein $R_2$ is H.

15. The compound of claim 13, wherein $R_1$ is PEG.

16. The compound of claim 13, wherein $R_1$ is alkyl.

17. A compound of Formula

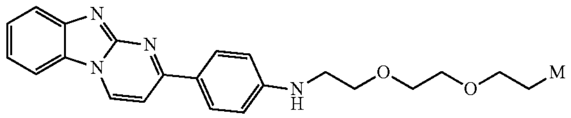

wherein M is selected from the group consisting of halo or a radionuclide.

18. The compound of claim 17, wherein M is $^{18}F$.

19. The compound of claim 5, wherein $X_1$-$X_4$ are independently CH.

20. The compound of claim 6, wherein $R_2$ is H.

* * * * *

UNITED STATES PATENT AND TRADEMARK OFFICE

CERTIFICATE OF CORRECTION

PATENT NO. : 8,491,869 B2
APPLICATION NO. : 12/661777
DATED : July 23, 2013
INVENTOR(S) : Umesh B. Gangadharmath et al.

It is certified that error appears in the above-identified patent and that said Letters Patent is hereby corrected as shown below:

Title Page, Col. 1, (Inventors), line 11, Delete "Vani P. Mocharia," and insert -- Vani P. Mocharla, --
Title Page, Col. 2, (Other Publications), line 7, Delete ""Polynnethylated" and insert -- "Polymethylated --
Title Page 2, Col. 1, (Other Publications), line 2, Delete "(Nphenylsulfony1)" and insert -- (N-phenylsulfonyl) --
Title Page 2, Col. 1, (Other Publications), line 23, Delete "benzimidaloses";" and insert -- benzimidazoles"; --
Title Page 2, Col. 1, (Other Publications), line 37, Delete "Radiotopes" and insert -- Radioisotopes --
Title Page 2, Col. 1, (Other Publications), line 44, Delete "Phamacotherapy" and insert -- Pharmacotherapy, --
Title Page 2, Col. 1, (Other Publications), line 61, Delete "Agnew Andte" and insert -- Angewandte --
Title Page 2, Col. 2, (Other Publications), line 18, Delete "and6,7" and insert -- and 6,7 --
Title Page 2, Col. 2, (Other Publications), line 24, Delete "meth ylchromene" and insert -- methylchromene --
Title Page 2, Col. 2, (Other Publications), line 27, Delete "[1311]" and insert -- [131I] --
Title Page 2, Col. 2, (Other Publications), line 46, Delete "Tetrahenron" and insert -- Tetrahedron --
Title Page 2, Col. 2, (Other Publications), line 48, Delete ""Radiolebeled" and insert -- "Radiolabeled --
Title Page 2, Col. 2, (Other Publications), line 51, Delete "biodistrubtion" and insert -- biodistribution --
Title Page 2, Col. 2, (Other Publications), line 56, Delete ""THe" and insert -- "The --
Title Page 2, Col. 2, (Other Publications), line 58, Delete "Isotops," and insert -- Isotopes, --
Title Page 3, Col. 1, (Other Publications), line 2, Delete "(3[8F]fluoropropy1)" and insert -- (3-[18F]fluoropropyl) --
Title Page 3, Col. 1, (Other Publications), line 6, Delete "Lipohilic" and insert -- Lipophilic --
Title Page 3, Col. 1, (Other Publications), line 6, Delete "Fluoralky1-21 nitroimidazoles" and insert -- Fluoroalkyl-2-nitroimidazoles --
Title Page 3, Col. 1, (Other Publications), line 10, Delete "Radiophaarmaceuticlas," and insert -- Radiopharmaceuticals, --

Signed and Sealed this
Fifteenth Day of October, 2013

Teresa Stanek Rea
*Deputy Director of the United States Patent and Trademark Office*

Title Page 3, Col. 2, (Other Publications), line 26, Delete “methoxybenzyI)” and insert -- methoxybenzyl) --

UNITED STATES PATENT AND TRADEMARK OFFICE

CERTIFICATE OF CORRECTION

PATENT NO. : 8,491,869 B2
APPLICATION NO. : 12/661777
DATED : July 23, 2013
INVENTOR(S) : Gangadharmath et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 354 days.

Signed and Sealed this
Sixth Day of January, 2015

Michelle K. Lee

Michelle K. Lee
*Deputy Director of the United States Patent and Trademark Office*